(12) United States Patent
Khaldi et al.

(10) Patent No.: US 10,463,591 B2
(45) Date of Patent: Nov. 5, 2019

(54) ANTI-INFLAMMATORY PEPTIDES, AND USES THEREOF

(71) Applicant: NURITAS LIMITED, South Dublin (IE)

(72) Inventors: Nora Khaldi, Dublin (IE); Cyril Lopez, Dublin (IE); Alessandro Adelfio, Dublin (IE)

(73) Assignee: NURITAS LIMITED, Dublin (IE)

( * ) Notice: Subject to any disclaimer, the term of this patent is extended or adjusted under 35 U.S.C. 154(b) by 0 days.

(21) Appl. No.: 15/744,304

(22) PCT Filed: Jul. 18, 2016

(86) PCT No.: PCT/EP2016/067090
§ 371 (c)(1),
(2) Date: Jan. 12, 2018

(87) PCT Pub. No.: WO2017/009484
PCT Pub. Date: Jan. 19, 2017

(65) Prior Publication Data
US 2019/0029939 A1     Jan. 31, 2019

(30) Foreign Application Priority Data

Jul. 16, 2015  (EP) .................................. 15177013
Jul. 16, 2015  (EP) .................................. 15177017

(51) Int. Cl.
| | | |
|---|---|---|
| *A61K 8/64* | (2006.01) | |
| *A61K 9/00* | (2006.01) | |
| *A61K 9/14* | (2006.01) | |
| *A61K 38/00* | (2006.01) | |
| *A61P 29/00* | (2006.01) | |
| *C07K 14/415* | (2006.01) | |

(52) U.S. Cl.
CPC ............. *A61K 8/64* (2013.01); *A61K 9/0014* (2013.01); *A61K 9/0053* (2013.01); *A61K 9/14* (2013.01); *A61P 29/00* (2018.01); *C07K 14/415* (2013.01); *A61K 38/00* (2013.01)

(58) Field of Classification Search
CPC .... A61K 38/00; A61K 9/0014; A61K 9/0053; A61K 9/14; A61K 8/64; A61P 29/00; C07K 14/415
See application file for complete search history.

(56) References Cited

U.S. PATENT DOCUMENTS

2004/0031072 A1    2/2004  La Rosa et al.
2004/0123343 A1*   6/2004  La Rosa ............. C07K 14/415
                                                          800/278

FOREIGN PATENT DOCUMENTS

| WO | 2004/042026 A2 | 5/2004 |
|---|---|---|
| WO | 2007/094570 A1 | 8/2007 |
| WO | 2009/026622 A1 | 3/2009 |

OTHER PUBLICATIONS

Kipp et al, Comparative Studies of High Mr Subunits of Rye and Wheat. II. Partial Amino Acid Sequences, Journal of Cereal Science, 1999, 30, pp. 303-313.*
Geneseq Database Accession No. ANM73492, "*Oryza sativa* amino acid sequence SEQ ID No. 187493", (2007).
Geneseq Database Accession No. AWH80057, "Human PHLDA1 protein PH domain peptide, SEQ ID 414", (2009).
Tong et al., "Rice α-globulin decreases serum cholesterol concentrations in rats fed a hypercholesterolemic diet and ameliorates atherosclerotic lesions in apolipoprotein E-deficient mice", Food Chemistry 132:194-200 (2012).
Uniprot Database Accession No. P29835 (1993).
Geneseq Database Acession No. AFP68974 XP-002789557 "Glycine max protein SEQ ID No. 160152" (2007).
Geneseq Database Acession No. AD043092 XP-002756637 "Cashew nut major allergen Ana o 2 peptide fragment" (2004).
Definition of Serum by Merriam-Webster, from https://merriam-webster.com/dictionary/serum, pp. 1-2 accessed May 8, 2019.
What is a humectant, from https://www.annmarieglanni.com/what-is-a-humectant-and-which-natural-ones-to-look-for-in-anti-aging-products/, pp. 1-7 accessed May 8, 2019.
Water, from http://biology-online.org/dictionary/Water, pp. 1-3 accessed Apr. 24, 2014.

(Continued)

*Primary Examiner* — Karlheinz R. Skowronek
*Assistant Examiner* — Li N Komatsu
(74) *Attorney, Agent, or Firm* — Nixon Peabody LLP; David S. Resnick; Ravinderjit S. Braich

(57) ABSTRACT

An anti-inflammatory peptide comprises an anti-inflammatory fragment of a protein selected from SEQUENCE ID NO's: 1 to 16, the anti-inflammatory fragment being 7 to 37 amino acids in length and having a charge of between −9 and +3; wherein the c-terminal amino acid is not cysteine (C) or methionine (M), and the n-terminal amino acid is not cysteine (C), histidine (H), proline (P) or threonine (T). The anti-inflammatory fragment does not contain cysteine (C). The anti-inflammatory fragment is from a region of the proteins of SEQUENCE ID NO's: 1 to 16, which region is characterised by being 17 to 109 amino acids in length and having a charge of between −6 and +4, wherein the c-terminal amino acid of the region is not aspartic acid (D), phenylalanine (F), methionine (M) or tryptophan (W), and the n-terminal amino acid of the region is not aspartic acid (D), histidine (H), methionine (M), proline (P) or tryptophan (W). Examples of peptides are provided in SEQUENCE ID NO's: 71 to 221.

5 Claims, 11 Drawing Sheets
Specification includes a Sequence Listing.

(56) References Cited

OTHER PUBLICATIONS

Human Ribosomal protein S6 kinase beta-1, from https://www.uniprot.org/uniprot/P23443, pp. 1-24 accessed May 2, 2019.
Wang et al., "Ana o 2, a Major Cashew (*Anacardium occidentals* L.) Nut Allergen of the Legumin Family" Int Arch Allergy Immunol 132(1): 27-39 (2003).

\* cited by examiner

SEQUENCE LISTING

<160> NUMBER OF SEQ ID NOS: 425

<210> SEQ ID NO 1
<211> LENGTH: 459
<212> TYPE: PRT
<213> ORGANISM: Pisum sativum

<400> SEQUENCE: 1

Met Ala Ala Thr Thr Met Lys Ala Ser Phe Pro Leu Leu Met Leu Met
1               5                   10                  15

```
Gly Ile Ser Phe Leu Ala Ser Val Cys Val Ser Ser Arg Ser Asp Pro
            20                  25                  30

Gln Asn Pro Phe Ile Phe Lys Ser Asn Lys Phe Gln Thr Leu Phe Glu
        35                  40                  45

Asn Glu Asn Gly His Ile Arg Leu Leu Gln Lys Phe Asp Gln Arg Ser
50                  55                  60

Lys Ile Phe Glu Asn Leu Gln Asn Tyr Arg Leu Leu Glu Tyr Lys Ser
65                  70                  75                  80

Lys Pro His Thr Ile Phe Leu Pro Gln His Thr Asp Ala Asp Tyr Ile
                85                  90                  95

Leu Val Val Leu Ser Gly Lys Ala Ile Leu Thr Val Leu Lys Pro Asp
            100                 105                 110

Asp Arg Asn Ser Phe Asn Leu Glu Arg Gly Asp Thr Ile Lys Leu Pro
        115                 120                 125

Ala Gly Thr Ile Ala Tyr Leu Val Asn Arg Asp Asp Asn Glu Glu Leu
    130                 135                 140

Arg Val Leu Asp Leu Ala Ile Pro Val Asn Arg Pro Gly Gln Leu Gln
145                 150                 155                 160

Ser Phe Leu Leu Ser Gly Asn Gln Asn Gln Asn Tyr Leu Ser Gly
            165                 170                 175

Phe Ser Lys Asn Ile Leu Glu Ala Ser Phe Asn Thr Asp Tyr Glu Glu
        180                 185                 190

Ile Glu Lys Val Leu Leu Glu His Glu Lys Glu Thr Gln His Arg
    195                 200                 205

Arg Ser Leu Lys Asp Lys Arg Gln Gln Ser Gln Glu Asn Val Ile
    210                 215                 220

Val Lys Leu Ser Arg Gly Gln Ile Glu Glu Leu Ser Lys Asn Ala Lys
225                 230                 235                 240

Ser Thr Ser Lys Lys Ser Val Ser Ser Glu Ser Glu Pro Phe Asn Leu
                245                 250                 255

Arg Ser Arg Gly Pro Ile Tyr Ser Asn Glu Phe Gly Lys Phe Phe Glu
            260                 265                 270

Ile Thr Pro Glu Lys Asn Pro Gln Leu Gln Asp Leu Asp Ile Phe Val
        275                 280                 285

Asn Ser Val Glu Ile Lys Glu Gly Ser Leu Leu Leu Pro His Tyr Asn
290                 295                 300

Ser Arg Ala Ile Val Ile Val Thr Val Asn Glu Gly Lys Gly Asp Phe
305                 310                 315                 320

Glu Leu Val Gly Gln Arg Asn Glu Asn Gln Glu Gln Arg Lys Glu
                325                 330                 335

Asp Asp Glu Glu Glu Gln Gly Glu Glu Ile Asn Lys Gln Val
            340                 345                 350

Gln Asn Tyr Lys Ala Lys Leu Ser Ser Gly Asp Val Phe Val Ile Pro
        355                 360                 365

Ala Gly His Pro Val Ala Val Lys Ala Ser Ser Asn Leu Asp Leu Leu
    370                 375                 380

Gly Phe Gly Ile Asn Ala Glu Asn Asn Gln Arg Asn Phe Leu Ala Gly
385                 390                 395                 400

Asp Glu Asp Asn Val Ile Ser Gln Ile Gln Arg Pro Val Lys Glu Leu
                405                 410                 415

Ala Phe Pro Gly Ser Ala Gln Glu Val Asp Arg Ile Leu Glu Asn Gln
            420                 425                 430
```

```
Lys Gln Ser His Phe Ala Asp Ala Gln Pro Gln Gln Arg Glu Arg Gly
            435                 440                 445

Ser Arg Glu Thr Arg Asp Arg Leu Ser Ser Val
    450                 455

<210> SEQ ID NO 2
<211> LENGTH: 124
<212> TYPE: PRT
<213> ORGANISM: Pisum sativum

<400> SEQUENCE: 2

Asp Arg Arg Gln Glu Leu Ser Asn Glu Asn Val Leu Val Lys Val Ser
1               5                   10                  15

Arg Arg Gln Leu Glu Glu Leu Ser Lys Asn Ala Lys Ser Ser Ser Arg
            20                  25                  30

Arg Ser Val Ser Ser Glu Ser Gly Pro Phe Asn Leu Arg Ser Glu Asp
        35                  40                  45

Pro Leu Tyr Ser Asn Asn Ser Gly Lys Phe Phe Glu Leu Thr Pro Glu
    50                  55                  60

Lys Asn Gln Gln Leu Gln Asp Leu Asp Leu Phe Val Asn Ser Val Asp
65                  70                  75                  80

Leu Lys Glu Gly Ser Leu Leu Leu Pro Asn Tyr Asn Ser Arg Ala Leu
                85                  90                  95

Leu Val Leu Val Leu Val Val Asn Glu Gly Lys Gly Asp Phe Glu Leu
            100                 105                 110

Val Gly Gln Arg Asn Glu Asn Gln Gly Lys Glu Asn
        115                 120

<210> SEQ ID NO 3
<211> LENGTH: 520
<212> TYPE: PRT
<213> ORGANISM: Pisum sativum

<400> SEQUENCE: 3

Met Ala Thr Lys Leu Leu Ala Leu Ser Leu Ser Phe Cys Phe Leu Leu
1               5                   10                  15

Leu Gly Gly Cys Phe Ala Leu Arg Glu Gln Pro Glu Gln Asn Glu Cys
            20                  25                  30

Gln Leu Glu Arg Leu Asn Ala Leu Glu Pro Asp Asn Arg Ile Glu Ser
        35                  40                  45

Glu Gly Gly Leu Ile Glu Thr Trp Asn Pro Asn Asn Lys Gln Phe Arg
    50                  55                  60

Cys Ala Gly Val Ala Leu Ser Arg Ala Thr Leu Gln His Asn Ala Leu
65                  70                  75                  80

Arg Arg Pro Tyr Tyr Ser Asn Ala Pro Gln Glu Ile Phe Ile Gln Gln
                85                  90                  95

Gly Asn Gly Tyr Phe Gly Met Val Phe Pro Gly Cys Pro Glu Thr Phe
            100                 105                 110

Glu Glu Pro Gln Glu Ser Glu Gln Gly Glu Gly Arg Arg Tyr Arg Asp
        115                 120                 125

Arg His Gln Lys Val Asn Arg Phe Arg Glu Gly Asp Ile Ile Ala Val
    130                 135                 140

Pro Thr Gly Ile Val Phe Trp Met Tyr Asn Asp Gln Asp Thr Pro Val
145                 150                 155                 160

Ile Ala Val Ser Leu Thr Asp Ile Arg Ser Ser Asn Asn Gln Leu Asp
                165                 170                 175
```

-continued

Gln Met Pro Arg Arg Phe Tyr Leu Ala Gly Asn His Glu Gln Glu Phe
            180                 185                 190

Leu Arg Tyr Gln His Gln Gln Gly Gly Lys Gln Glu Gln Glu Asn Glu
        195                 200                 205

Gly Asn Asn Ile Phe Ser Gly Phe Lys Arg Asp Phe Leu Glu Asp Ala
    210                 215                 220

Phe Asn Val Asn Arg His Ile Val Asp Arg Leu Gln Gly Arg Asn Glu
225                 230                 235                 240

Asp Glu Glu Lys Gly Ala Ile Val Lys Val Lys Gly Gly Leu Ser Ile
                245                 250                 255

Ile Ser Pro Pro Glu Lys Gln Ala Arg His Gln Arg Gly Ser Arg Gln
            260                 265                 270

Glu Glu Asp Glu Asp Glu Asp Glu Glu Arg Gln Pro Arg His Gln Arg
        275                 280                 285

Gly Ser Arg Gln Glu Glu Glu Asp Glu Asp Glu Glu Arg Gln Pro
    290                 295                 300

Arg His Gln Arg Arg Gly Glu Glu Glu Glu Asp Lys Lys Glu
305                 310                 315                 320

Arg Arg Gly Ser Gln Lys Gly Lys Ser Arg Arg Gln Gly Asp Asn Gly
                325                 330                 335

Leu Glu Glu Thr Val Cys Thr Ala Lys Leu Arg Leu Asn Ile Gly Pro
            340                 345                 350

Ser Ser Ser Pro Asp Ile Tyr Asn Pro Glu Ala Gly Arg Ile Lys Thr
        355                 360                 365

Val Thr Ser Leu Asp Leu Pro Val Leu Arg Trp Leu Lys Leu Ser Ala
    370                 375                 380

Glu His Gly Ser Leu His Lys Asn Ala Met Phe Val Pro His Tyr Asn
385                 390                 395                 400

Leu Asn Ala Asn Ser Ile Ile Tyr Ala Leu Lys Gly Arg Ala Arg Leu
                405                 410                 415

Gln Val Val Asn Cys Asn Gly Asn Thr Val Phe Asp Gly Glu Leu Glu
            420                 425                 430

Ala Gly Arg Ala Leu Thr Val Pro Gln Asn Tyr Ala Val Ala Ala Lys
        435                 440                 445

Ser Leu Ser Asp Arg Phe Ser Tyr Val Ala Phe Lys Thr Asn Asp Arg
    450                 455                 460

Ala Gly Ile Ala Arg Leu Ala Gly Thr Ser Ser Val Ile Asn Asn Leu
465                 470                 475                 480

Pro Leu Asp Val Val Ala Ala Thr Phe Asn Leu Gln Arg Asn Glu Ala
                485                 490                 495

Arg Gln Leu Lys Ser Asn Asn Pro Phe Lys Phe Leu Val Pro Ala Arg
            500                 505                 510

Gln Ser Glu Asn Arg Ala Ser Ala
        515                 520

<210> SEQ ID NO 4
<211> LENGTH: 613
<212> TYPE: PRT
<213> ORGANISM: Pisum sativum

<400> SEQUENCE: 4

Met Ala Thr Thr Ile Lys Ser Arg Phe Pro Leu Leu Leu Leu Leu Gly
1               5                   10                  15

Ile Ile Phe Leu Ala Ser Val Val Cys Val Thr Tyr Ala Asn Tyr Asp
            20                  25                  30

```
Glu Gly Ser Glu Pro Arg Val Pro Ala Gln Arg Glu Arg Gly Arg Gln
         35                  40                  45

Glu Gly Glu Lys Glu Glu Lys Arg His Gly Glu Trp Arg Pro Ser Tyr
         50                  55                  60

Glu Lys Glu Glu Asp Glu Glu Gly Gln Arg Glu Arg Gly Arg Gln
 65                  70                  75                  80

Glu Gly Glu Lys Glu Glu Lys Arg His Gly Trp Arg Pro Ser Tyr
                     85                  90                  95

Glu Lys Gln Glu Asp Glu Glu Lys Gln Lys Tyr Arg Tyr Gln Arg
                    100                 105                 110

Glu Lys Glu Asp Glu Glu Lys Gln Lys Tyr Gln Tyr Gln Arg Glu
                115                 120                 125

Lys Lys Glu Gln Lys Glu Val Gln Pro Gly Arg Glu Arg Trp Glu Arg
        130                 135                 140

Glu Glu Asp Glu Glu Gln Val Asp Glu Glu Trp Arg Gly Ser Gln Arg
145                 150                 155                 160

Arg Glu Asp Pro Glu Glu Arg Ala Arg Leu Arg His Arg Glu Glu Arg
                    165                 170                 175

Thr Lys Arg Asp Arg Arg His Gln Arg Glu Gly Glu Glu Glu Arg
                180                 185                 190

Ser Ser Glu Ser Gln Glu Arg Arg Asn Pro Phe Leu Phe Lys Ser Asn
        195                 200                 205

Lys Phe Leu Thr Leu Phe Glu Asn Glu Asn Gly His Ile Arg Leu Leu
        210                 215                 220

Gln Arg Phe Asp Lys Arg Ser Asp Leu Phe Glu Asn Leu Gln Asn Tyr
225                 230                 235                 240

Arg Leu Val Glu Tyr Arg Ala Lys Pro His Thr Ile Phe Leu Pro Gln
                    245                 250                 255

His Ile Asp Ala Asp Leu Ile Leu Val Val Leu Ser Gly Lys Ala Ile
                260                 265                 270

Leu Thr Val Leu Ser Pro Asn Asp Arg Asn Ser Tyr Asn Leu Glu Arg
        275                 280                 285

Gly Asp Thr Ile Lys Leu Pro Ala Gly Thr Thr Ser Tyr Leu Val Asn
        290                 295                 300

Gln Asp Asp Glu Glu Asp Leu Arg Leu Val Asp Leu Ile Pro Val
305                 310                 315                 320

Asn Gly Pro Gly Lys Phe Glu Ala Phe Asp Leu Ala Lys Asn Lys Asn
                    325                 330                 335

Gln Tyr Leu Arg Gly Phe Ser Lys Asn Ile Leu Glu Ala Ser Tyr Asn
                340                 345                 350

Thr Arg Tyr Glu Thr Ile Glu Lys Val Leu Leu Glu Glu Gln Glu Lys
        355                 360                 365

Asp Arg Lys Arg Arg Gln Gln Gly Glu Glu Thr Asp Ala Ile Val Lys
        370                 375                 380

Val Ser Arg Glu Gln Ile Glu Glu Leu Lys Lys Leu Ala Lys Ser Ser
385                 390                 395                 400

Ser Lys Lys Ser Leu Pro Ser Glu Phe Glu Pro Ile Asn Leu Arg Ser
                    405                 410                 415

His Lys Pro Glu Tyr Ser Asn Lys Phe Gly Lys Leu Phe Glu Ile Thr
                420                 425                 430

Pro Glu Lys Lys Tyr Pro Gln Leu Gln Asp Leu Asp Leu Phe Val Ser
        435                 440                 445
```

-continued

Cys Val Glu Ile Asn Glu Gly Ala Leu Met Leu Pro His Tyr Asn Ser
    450             455             460

Arg Ala Ile Val Val Leu Leu Val Asn Glu Gly Lys Gly Asn Leu Glu
465             470             475             480

Leu Leu Gly Leu Lys Asn Glu Gln Gln Glu Arg Glu Asp Arg Lys Glu
            485             490             495

Arg Asn Asn Glu Val Gln Arg Tyr Glu Ala Arg Leu Ser Pro Gly Asp
            500             505             510

Val Val Ile Ile Pro Ala Gly His Pro Val Ala Ile Thr Ala Ser Ser
            515             520             525

Asn Leu Asn Leu Gly Phe Gly Ile Asn Ala Glu Asn Asn Glu Arg
    530             535             540

Asn Phe Leu Ser Gly Ser Asp Asp Asn Val Ile Ser Gln Ile Glu Asn
545             550             555             560

Pro Val Lys Glu Leu Thr Phe Pro Gly Ser Val Gln Glu Ile Asn Arg
            565             570             575

Leu Ile Lys Asn Gln Lys Gln Ser His Phe Ala Asn Ala Glu Pro Glu
            580             585             590

Gln Lys Glu Gln Gly Ser Gln Gly Lys Arg Ser Pro Leu Ser Ser Ile
    595             600             605

Leu Gly Thr Phe Tyr
    610

<210> SEQ ID NO 5
<211> LENGTH: 438
<212> TYPE: PRT
<213> ORGANISM: Pisum sativum

<400> SEQUENCE: 5

Met Ala Ala Thr Pro Ile Lys Pro Leu Met Leu Leu Ala Ile Ala Phe
1               5               10              15

Leu Ala Ser Val Cys Val Ser Ser Arg Ser Asp Gln Glu Asn Pro Phe
            20              25              30

Ile Phe Lys Ser Asn Arg Phe Gln Thr Leu Tyr Glu Asn Glu Asn Gly
        35              40              45

His Ile Arg Leu Leu Gln Lys Phe Asp Lys Arg Ser Lys Ile Phe Glu
    50              55              60

Asn Leu Gln Asn Tyr Arg Leu Leu Glu Tyr Lys Ser Lys Pro Arg Thr
65              70              75              80

Leu Phe Leu Pro Gln Tyr Thr Asp Ala Asp Phe Ile Leu Val Val Leu
            85              90              95

Ser Gly Lys Ala Thr Leu Thr Val Leu Lys Ser Asn Asp Arg Asn Ser
            100             105             110

Phe Asn Leu Glu Arg Gly Asp Thr Ile Lys Leu Pro Ala Gly Thr Ile
        115             120             125

Ala Tyr Leu Ala Asn Arg Asp Asp Asn Glu Asp Leu Arg Val Leu Asp
    130             135             140

Leu Thr Ile Pro Val Asn Lys Pro Gly Gln Leu Gln Ser Phe Leu Leu
145             150             155             160

Ser Gly Thr Gln Asn Gln Pro Ser Leu Leu Ser Gly Phe Ser Lys Asn
            165             170             175

Ile Leu Glu Ala Ala Phe Asn Thr Asn Tyr Glu Glu Ile Glu Lys Val
        180             185             190

Leu Leu Glu Gln Gln Glu Gln Glu Pro Gln His Arg Arg Ser Leu Lys
    195             200             205

```
Asp Arg Arg Gln Glu Ile Asn Glu Glu Asn Val Ile Val Lys Val Ser
    210                 215                 220

Arg Glu Gln Ile Glu Glu Leu Ser Lys Asn Ala Lys Ser Ser Ser Lys
225                 230                 235                 240

Lys Ser Val Ser Glu Ser Gly Pro Phe Asn Leu Arg Ser Arg Asn
            245                 250                 255

Pro Ile Tyr Ser Asn Lys Phe Gly Lys Phe Glu Ile Thr Pro Glu
            260                 265                 270

Lys Asn Gln Gln Leu Gln Asp Leu Asp Ile Phe Val Asn Ser Val Asp
                275                 280                 285

Ile Lys Glu Gly Ser Leu Leu Pro Asn Tyr Asn Ser Arg Ala Ile
            290                 295                 300

Val Ile Val Thr Val Thr Glu Gly Lys Gly Asp Phe Glu Leu Val Gly
305                 310                 315                 320

Gln Arg Asn Glu Asn Gln Gly Lys Glu Asn Asp Lys Glu Glu Glu Gln
                325                 330                 335

Glu Glu Glu Thr Ser Lys Gln Val Gln Leu Tyr Arg Ala Lys Leu Ser
            340                 345                 350

Pro Gly Asp Val Phe Val Ile Pro Ala Gly His Pro Val Ala Ile Asn
            355                 360                 365

Ala Ser Ser Asp Leu Asn Leu Ile Gly Phe Gly Ile Asn Ala Glu Asn
370                 375                 380

Asn Glu Arg Asn Phe Leu Ala Gly Glu Glu Asp Asn Val Ile Ser Gln
385                 390                 395                 400

Val Glu Arg Pro Val Lys Glu Leu Ala Phe Pro Gly Ser Ser His Glu
                405                 410                 415

Val Asp Arg Leu Leu Lys Asn Gln Lys Gln Ser Tyr Phe Ala Asn Ala
            420                 425                 430

Gln Pro Leu Gln Arg Glu
        435

<210> SEQ ID NO 6
<211> LENGTH: 484
<212> TYPE: PRT
<213> ORGANISM: Oryza sativa

<400> SEQUENCE: 6

Met Ala Thr Thr Thr Ser Leu Leu Ser Ser Cys Leu Cys Ala Leu Leu
1               5                   10                  15

Leu Ala Pro Leu Phe Ser Gln Gly Val Asp Ala Trp Glu Ser Arg Gln
            20                  25                  30

Gly Ala Ser Arg Gln Cys Arg Phe Asp Arg Leu Gln Ala Phe Glu Pro
        35                  40                  45

Leu Arg Lys Val Arg Ser Glu Ala Gly Asp Thr Glu Tyr Phe Asp Glu
50                  55                  60

Arg Asn Glu Gln Phe Arg Cys Ala Gly Val Phe Val Ile Arg Arg Val
65                  70                  75                  80

Ile Glu Pro Gln Gly Leu Val Val Pro Arg Tyr Ser Asn Thr Pro Ala
                85                  90                  95

Leu Ala Tyr Ile Ile Gln Gly Lys Gly Tyr Val Gly Leu Thr Phe Pro
            100                 105                 110

Gly Cys Pro Ala Thr His Gln Gln Phe Gln Leu Phe Glu Gln Arg
        115                 120                 125

Gln Ser Asp Gln Ala His Lys Phe Arg Asp Glu His Gln Lys Ile His
```

```
              130                 135                 140
Glu Phe Arg Gln Gly Asp Val Ala Leu Pro Ala Ser Val Ala His
145                 150                 155                 160

Trp Phe Tyr Asn Gly Gly Asp Thr Pro Ala Val Val Tyr Val Tyr
                165                 170                 175

Asp Ile Lys Ser Phe Ala Asn Gln Leu Glu Pro Arg Gln Lys Glu Phe
            180                 185                 190

Leu Leu Ala Gly Asn Asn Gln Arg Gly Gln Gln Ile Phe Glu His Ser
                195                 200                 205

Ile Phe Gln His Ser Gly Gln Asn Ile Phe Ser Gly Phe Asn Thr Glu
    210                 215                 220

Val Leu Ser Glu Ala Leu Gly Ile Asn Thr Glu Ala Ser Lys Arg Leu
225                 230                 235                 240

Gln Ser Gln Asn Asp Gln Arg Gly Asp Ile Ile Arg Val Lys His Gly
                245                 250                 255

Leu Gln Leu Leu Lys Pro Thr Leu Thr Gln Arg Gln Glu His Arg
            260                 265                 270

Gln Tyr Gln Gln Val Gln Tyr Arg Glu Gly Gln Tyr Asn Gly Leu Asp
    275                 280                 285

Glu Asn Phe Cys Thr Ile Lys Ala Arg Val Asn Ile Glu Asn Pro Ser
290                 295                 300

Arg Ala Asp Tyr Tyr Asn Pro Arg Ala Gly Arg Ile Thr Leu Leu Asn
305                 310                 315                 320

Asn Gln Lys Phe Pro Ile Leu Asn Leu Ile Gly Met Gly Ala Ala Arg
                325                 330                 335

Val Asn Leu Tyr Gln Asn Ala Leu Leu Ser Pro Phe Trp Asn Ile Asn
                340                 345                 350

Ala His Ser Val Val Tyr Ile Ile Gln Gly Ser Val Arg Val Gln Val
            355                 360                 365

Ala Asn Asn Gln Gly Arg Ser Val Phe Asn Gly Val Leu His Gln Gly
                370                 375                 380

Gln Leu Leu Ile Ile Pro Gln Asn His Ala Val Ile Lys Lys Ala Glu
385                 390                 395                 400

His Asn Gly Cys Gln Tyr Val Ala Ile Lys Thr Ile Ser Asp Pro Thr
                405                 410                 415

Val Ser Trp Val Ala Gly Lys Asn Ser Ile Leu Arg Ala Leu Pro Val
                420                 425                 430

Asp Val Ile Ala Asn Ala Tyr Arg Ile Ser Arg Asp Glu Ala Arg Arg
            435                 440                 445

Leu Lys Asn Asn Arg Ala Asp Glu Ile Gly Pro Phe Thr Pro Arg Phe
450                 455                 460

Pro Gln Lys Ser Gln Arg Gly Tyr Gln Phe Leu Thr Glu Gly Leu Ser
465                 470                 475                 480

Leu Ile Gly Met

<210> SEQ ID NO 7
<211> LENGTH: 510
<212> TYPE: PRT
<213> ORGANISM: Oryza sativa

<400> SEQUENCE: 7

Met Ala Ser Met Ser Thr Ile Leu Pro Leu Cys Leu Gly Leu Leu Leu
1               5                   10                  15

Phe Phe Gln Val Ser Met Ala Gln Phe Ser Phe Gly Gly Ser Pro Leu
```

```
                    20                  25                  30
            Gln Ser Pro Arg Gly Phe Arg Gly Asp Gln Asp Ser Arg His Gln Cys
                        35                  40                  45
            Arg Phe Glu His Leu Thr Ala Leu Glu Ala Thr His Gln Gln Arg Ser
             50                  55                  60
            Glu Ala Gly Phe Thr Glu Tyr Tyr Asn Ile Glu Ala Arg Asn Glu Phe
             65                  70                  75                  80
            Arg Cys Ala Gly Val Ser Val Arg Arg Leu Val Val Glu Ser Lys Gly
                            85                  90                  95
            Leu Val Leu Pro Met Tyr Ala Asn Ala His Lys Leu Val Tyr Ile Val
                            100                 105                 110
            Gln Gly Arg Gly Val Phe Gly Met Ala Leu Pro Gly Cys Pro Glu Thr
                            115                 120                 125
            Phe Gln Ser Val Arg Ser Pro Phe Glu Gln Glu Val Ala Thr Ala Gly
                            130                 135                 140
            Glu Ala Gln Ser Ser Ile Gln Lys Met Arg Asp Glu His Gln Gln Leu
            145                 150                 155                 160
            His Gln Phe His Gln Gly Asp Val Ile Ala Val Pro Ala Gly Val Ala
                                165                 170                 175
            His Trp Leu Tyr Asn Asn Gly Asp Ser Pro Val Val Ala Phe Thr Val
                            180                 185                 190
            Ile Asp Thr Ser Asn Asn Ala Asn Gln Leu Asp Pro Lys Arg Arg Glu
                            195                 200                 205
            Phe Phe Leu Ala Gly Lys Pro Arg Ser Trp Gln Gln Gln Ser Tyr
                            210                 215                 220
            Ser Tyr Gln Thr Glu Gln Leu Ser Arg Asn Gln Asn Ile Phe Ala Gly
            225                 230                 235                 240
            Phe Ser Pro Asp Leu Leu Ser Glu Ala Leu Ser Val Ser Lys Gln Thr
                            245                 250                 255
            Val Leu Arg Leu Gln Gly Leu Ser Asp Pro Arg Gly Ala Ile Ile Arg
                            260                 265                 270
            Val Glu Asn Gly Leu Gln Ala Leu Gln Pro Ser Leu Gln Val Glu Pro
                            275                 280                 285
            Val Lys Glu Glu Gln Thr Gln Ala Tyr Leu Pro Thr Lys Gln Leu Gln
                            290                 295                 300
            Pro Thr Trp Leu Arg Ser Gly Gly Ala Cys Gly Gln Gln Asn Val Leu
            305                 310                 315                 320
            Asp Glu Ile Met Cys Ala Phe Lys Leu Arg Lys Asn Ile Asp Asn Pro
                            325                 330                 335
            Gln Ser Ser Asp Ile Phe Asn Pro His Gly Gly Arg Ile Thr Arg Ala
                            340                 345                 350
            Asn Ser Gln Asn Phe Pro Ile Leu Asn Ile Ile Gln Met Ser Ala Thr
                            355                 360                 365
            Arg Ile Val Leu Gln Asn Asn Ala Leu Leu Thr Pro His Trp Thr Val
                            370                 375                 380
            Asn Ala His Thr Val Met Tyr Val Thr Ala Gly Gln Gly His Ile Gln
            385                 390                 395                 400
            Val Val Asp His Arg Gly Arg Ser Val Phe Asp Gly Glu Leu His Gln
                            405                 410                 415
            Gln Gln Ile Leu Leu Ile Pro Gln Asn Phe Ala Val Val Val Lys Ala
                            420                 425                 430
            Arg Arg Glu Gly Phe Ala Trp Val Ser Phe Lys Thr Asn His Asn Ala
                            435                 440                 445
```

```
Val Asp Ser Gln Ile Ala Gly Lys Ala Ser Ile Leu Arg Ala Leu Pro
    450                 455                 460
Val Asp Val Val Ala Asn Ala Tyr Arg Leu Ser Arg Glu Asp Ser Arg
465                 470                 475                 480
His Val Lys Phe Asn Arg Gly Asp Glu Met Ala Val Phe Ala Pro Arg
                485                 490                 495
Arg Gly Pro Gln Gln Tyr Ala Glu Trp Gln Ile Asn Glu Lys
            500                 505                 510

<210> SEQ ID NO 8
<211> LENGTH: 386
<212> TYPE: PRT
<213> ORGANISM: Pisum sativum

<400> SEQUENCE: 8

Met Ala Thr Thr Ile Lys Ser Arg Phe Pro Leu Leu Leu Leu Leu Gly
1               5                   10                  15
Ile Ile Phe Leu Ala Ser Val Val Ser Val Thr Tyr Ala Asn Tyr Asp
                20                  25                  30
Glu Gly Ser Glu Pro Arg Val Pro Ala Gln Arg Glu Arg Gly Arg Gln
            35                  40                  45
Glu Gly Glu Lys Glu Glu Lys Arg His Gly Glu Trp Arg Pro Ser Tyr
        50                  55                  60
Glu Lys Glu Glu Asp Glu Glu Gly Gln Arg Glu Arg Gly Arg Gln
65                  70                  75                  80
Glu Gly Glu Lys Glu Glu Lys Arg His Gly Trp Gly Pro Ser Tyr
                85                  90                  95
Glu Lys Gln Glu Asp Glu Glu Lys Gln Lys Tyr Arg Tyr Gln Arg
            100                 105                 110
Glu Lys Glu Asp Glu Glu Lys Gln Lys Tyr Gln Tyr Gln Arg Glu
        115                 120                 125
Lys Lys Glu Gln Lys Glu Val Gln Pro Gly Arg Glu Arg Trp Glu Arg
130                 135                 140
Glu Glu Asp Glu Glu Gln Val Asp Glu Glu Trp Arg Gly Ser Gln Arg
145                 150                 155                 160
Arg Glu Asp Pro Glu Glu Arg Ala Arg Leu Arg His Arg Glu Glu Arg
                165                 170                 175
Thr Lys Arg Asp Arg Arg His Gln Arg Glu Gly Glu Glu Glu Arg
            180                 185                 190
Ser Ser Glu Ser Gln Glu Arg Arg Asn Pro Phe Leu Phe Lys Ser Asn
        195                 200                 205
Lys Phe Leu Thr Leu Phe Glu Asn Glu Asn Gly His Ile Arg Leu Leu
210                 215                 220
Gln Arg Phe Asp Lys Arg Ser Asp Leu Phe Glu Asn Leu Gln Asn Tyr
225                 230                 235                 240
Arg Leu Val Glu Tyr Arg Ala Lys Pro His Thr Ile Phe Leu Pro Gln
                245                 250                 255
His Ile Asp Ala Asp Leu Ile Leu Val Val Leu Ser Gly Lys Ala Ile
            260                 265                 270
Leu Thr Val Leu Ser Pro Asn Asp Arg Asn Ser Tyr Asn Leu Glu Arg
        275                 280                 285
Gly Asp Thr Ile Lys Leu Pro Ala Gly Thr Thr Ser Tyr Leu Val Asn
290                 295                 300
Gln Asp Asp Glu Glu Asp Leu Arg Leu Val Asp Leu Val Ile Pro Val
```

```
                 305                 310                 315                 320

Asn Gly Pro Gly Lys Phe Glu Ala Phe Asp Leu Ala Lys Asn Lys Asn
                325                 330                 335

Gln Tyr Leu Arg Gly Phe Ser Lys Asn Ile Leu Glu Ala Ser Tyr Asn
                340                 345                 350

Thr Arg Tyr Glu Thr Ile Glu Lys Val Leu Leu Glu Glu Gln Glu Lys
                355                 360                 365

Asp Arg Lys Arg Gln Gln Gly Glu Glu Thr Asp Ala Ile Val Lys
                370                 375                 380

Val Ser
385

<210> SEQ ID NO 9
<211> LENGTH: 386
<212> TYPE: PRT
<213> ORGANISM: Pisum sativum

<400> SEQUENCE: 9

Met Ala Thr Thr Ile Lys Ser Arg Phe Pro Leu Leu Leu Leu Leu Gly
1               5                   10                  15

Ile Ile Phe Leu Ala Ser Val Val Ser Val Thr Tyr Ala Asn Tyr Asp
                20                  25                  30

Glu Gly Ser Glu Pro Arg Val Pro Ala Gln Arg Glu Arg Gly Arg Gln
                35                  40                  45

Glu Gly Glu Lys Glu Glu Lys Arg His Gly Glu Trp Arg Pro Ser Tyr
                50                  55                  60

Glu Lys Glu Glu Asp Glu Glu Gly Gln Glu Arg Gly Arg Gln
65                  70                  75                  80

Glu Gly Glu Lys Glu Lys Arg His Gly Glu Trp Gly Pro Ser Tyr
                85                  90                  95

Glu Lys Gln Glu Asp Glu Glu Lys Gln Lys Tyr Arg Tyr Gln Arg
                100                 105                 110

Glu Lys Glu Asp Glu Glu Lys Gln Lys Tyr Gln Tyr Gln Arg Glu
                115                 120                 125

Lys Lys Glu Gln Lys Glu Val Gln Pro Gly Arg Glu Arg Trp Glu Arg
                130                 135                 140

Glu Glu Asp Glu Glu Gln Val Asp Glu Glu Trp Arg Gly Ser Gln Arg
145                 150                 155                 160

Arg Glu Asp Pro Glu Glu Arg Ala Arg Leu Arg His Arg Glu Glu Arg
                165                 170                 175

Thr Lys Arg Asp Arg Arg His Gln Arg Glu Gly Glu Glu Glu Arg
                180                 185                 190

Ser Ser Glu Ser Gln Glu Arg Arg Asn Pro Phe Leu Phe Lys Ser Asn
                195                 200                 205

Lys Phe Leu Thr Leu Phe Glu Asn Glu Asn Gly His Ile Arg Leu Leu
                210                 215                 220

Gln Arg Phe Asp Lys Arg Ser Asp Leu Phe Glu Asn Leu Gln Asn Tyr
225                 230                 235                 240

Arg Leu Val Glu Tyr Arg Ala Lys Pro His Thr Ile Phe Leu Pro Gln
                245                 250                 255

His Ile Asp Ala Asp Leu Ile Leu Val Val Leu Ser Gly Lys Ala Ile
                260                 265                 270

Leu Thr Val Leu Ser Pro Asn Asp Arg Asn Ser Tyr Asn Leu Glu Arg
                275                 280                 285
```

```
Gly Asp Thr Ile Lys Leu Pro Ala Gly Thr Thr Ser Tyr Leu Val Asn
            290                 295                 300

Gln Asp Asp Glu Glu Asp Leu Arg Leu Val Asp Leu Val Ile Pro Val
305                 310                 315                 320

Asn Gly Pro Gly Lys Phe Glu Ala Phe Asp Leu Ala Lys Asn Lys Asn
                325                 330                 335

Gln Tyr Leu Arg Gly Phe Ser Lys Asn Ile Leu Glu Ala Ser Tyr Asn
            340                 345                 350

Thr Arg Tyr Glu Thr Ile Glu Lys Val Leu Leu Glu Glu Gln Glu Lys
            355                 360                 365

Asp Arg Lys Arg Arg Gln Gln Gly Glu Glu Thr Asp Ala Ile Val Lys
370                 375                 380

Val Ser
385

<210> SEQ ID NO 10
<211> LENGTH: 499
<212> TYPE: PRT
<213> ORGANISM: Oryza sativa

<400> SEQUENCE: 10

Met Ala Ser Ser Val Phe Ser Arg Phe Ser Ile Tyr Phe Cys Val Leu
1               5                   10                  15

Leu Leu Cys His Gly Ser Met Ala Gln Leu Phe Asn Pro Ser Thr Asn
            20                  25                  30

Pro Trp His Ser Pro Arg Gln Gly Ser Phe Arg Glu Cys Arg Phe Asp
        35                  40                  45

Arg Leu Gln Ala Phe Glu Pro Leu Arg Lys Val Arg Ser Glu Ala Gly
50                  55                  60

Val Thr Glu Tyr Phe Asp Glu Lys Asn Glu Leu Phe Gln Cys Thr Gly
65                  70                  75                  80

Thr Phe Val Ile Arg Arg Val Ile Gln Pro Gln Gly Leu Leu Val Pro
                85                  90                  95

Arg Tyr Thr Asn Ile Pro Gly Val Val Tyr Ile Ile Gln Gly Arg Gly
            100                 105                 110

Ser Met Gly Leu Thr Phe Pro Gly Cys Pro Ala Thr Tyr Gln Gln Gln
        115                 120                 125

Phe Gln Gln Phe Ser Ser Gln Gly Gln Ser Gln Lys Phe Arg
130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Asp Gly Asp Ala Pro
                165                 170                 175

Ile Val Ala Val Tyr Val Tyr Asp Val Asn Asn Asn Ala Asn Gln Leu
            180                 185                 190

Glu Pro Arg Gln Lys Glu Phe Leu Leu Ala Gly Asn Asn Arg Ala
        195                 200                 205

Gln Gln Gln Gln Val Tyr Gly Ser Ser Ile Glu Gln His Ser Gly Gln
210                 215                 220

Asn Ile Phe Ser Gly Phe Gly Val Glu Met Leu Ser Glu Ala Leu Gly
225                 230                 235                 240

Ile Asn Ala Val Ala Ala Lys Arg Leu Gln Ser Gln Asn Asp Gln Arg
                245                 250                 255

Gly Glu Ile Ile His Val Lys Asn Gly Leu Gln Leu Leu Lys Pro Thr
            260                 265                 270
```

-continued

Leu Thr Gln Gln Gln Glu Gln Ala Gln Ala Gln Asp Gln Tyr Gln Gln
              275                 280                 285

Val Gln Tyr Ser Glu Arg Gln Gln Thr Ser Ser Arg Trp Asn Gly Leu
    290                 295                 300

Glu Glu Asn Phe Cys Thr Ile Lys Val Arg Val Asn Ile Glu Asn Pro
305                 310                 315                 320

Ser Arg Ala Asp Ser Tyr Asn Pro Arg Ala Gly Arg Ile Thr Ser Val
                325                 330                 335

Asn Ser Gln Lys Phe Pro Ile Leu Asn Leu Ile Gln Met Ser Ala Thr
                340                 345                 350

Arg Val Asn Leu Tyr Gln Asn Ala Ile Leu Ser Pro Phe Trp Asn Val
              355                 360                 365

Asn Ala His Ser Leu Val Tyr Met Ile Gln Gly Arg Ser Arg Val Gln
            370                 375                 380

Val Val Ser Asn Phe Gly Lys Thr Val Phe Asp Gly Val Leu Arg Pro
385                 390                 395                 400

Gly Gln Leu Leu Ile Ile Pro Gln His Tyr Ala Val Leu Lys Lys Ala
                405                 410                 415

Glu Arg Glu Gly Cys Gln Tyr Ile Ala Ile Lys Thr Asn Ala Asn Ala
                420                 425                 430

Phe Val Ser His Leu Ala Gly Lys Asn Ser Val Phe Arg Ala Leu Pro
            435                 440                 445

Val Asp Val Val Ala Asn Ala Tyr Arg Ile Ser Arg Glu Gln Ala Arg
450                 455                 460

Ser Leu Lys Asn Asn Arg Gly Glu Glu His Gly Ala Phe Thr Pro Arg
465                 470                 475                 480

Phe Gln Gln Gln Tyr Tyr Pro Gly Leu Ser Asn Glu Ser Glu Ser Glu
                485                 490                 495

Thr Ser Glu

<210> SEQ ID NO 11
<211> LENGTH: 499
<212> TYPE: PRT
<213> ORGANISM: Oryza sativa

<400> SEQUENCE: 11

Met Ala Ser Ile Asn Arg Pro Ile Val Phe Phe Thr Val Cys Leu Phe
1               5                   10                  15

Leu Leu Cys Asn Gly Ser Leu Ala Gln Gln Leu Leu Gly Gln Ser Thr
                20                  25                  30

Ser Gln Trp Gln Ser Ser Arg Arg Gly Ser Pro Arg Glu Cys Arg Phe
            35                  40                  45

Asp Arg Leu Gln Ala Phe Glu Pro Ile Arg Ser Val Arg Ser Gln Ala
        50                  55                  60

Gly Thr Thr Glu Phe Phe Asp Val Ser Asn Glu Gln Phe Gln Cys Thr
65                  70                  75                  80

Gly Val Ser Val Val Arg Arg Val Ile Glu Pro Arg Gly Leu Leu Leu
                85                  90                  95

Pro His Tyr Thr Asn Gly Ala Ser Leu Val Tyr Ile Ile Gln Gly Arg
                100                 105                 110

Gly Ile Thr Gly Pro Thr Phe Pro Gly Cys Pro Glu Ser Tyr Gln Gln
            115                 120                 125

Gln Phe Gln Gln Ser Gly Gln Ala Gln Leu Thr Glu Ser Gln Ser Gln
        130                 135                 140

Ser Gln Lys Phe Lys Asp Glu His Gln Lys Ile His Arg Phe Arg Gln
145                 150                 155                 160

Gly Asp Val Ile Ala Leu Pro Ala Gly Val Ala His Trp Cys Tyr Asn
                165                 170                 175

Asp Gly Glu Val Pro Val Val Ala Ile Tyr Val Thr Asp Leu Asn Asn
            180                 185                 190

Gly Ala Asn Gln Leu Asp Pro Arg Gln Arg Asp Phe Leu Leu Ala Gly
        195                 200                 205

Asn Lys Arg Asn Pro Gln Ala Tyr Arg Arg Glu Val Glu Glu Arg Ser
    210                 215                 220

Gln Asn Ile Phe Ser Gly Phe Ser Thr Glu Leu Leu Ser Glu Ala Leu
225                 230                 235                 240

Gly Val Ser Ser Gln Val Ala Arg Gln Leu Gln Cys Gln Asn Asp Gln
                245                 250                 255

Arg Gly Glu Ile Val Arg Val Glu His Gly Leu Ser Leu Leu Gln Pro
            260                 265                 270

Tyr Ala Ser Leu Gln Glu Gln Glu Gln Gly Gln Val Gln Ser Arg Glu
        275                 280                 285

Arg Tyr Gln Glu Gly Gln Tyr Gln Gln Ser Gln Tyr Gly Ser Gly Cys
    290                 295                 300

Ser Asn Gly Leu Asp Glu Thr Phe Cys Thr Leu Arg Val Arg Gln Asn
305                 310                 315                 320

Ile Asp Asn Pro Asn Arg Ala Asp Thr Tyr Asn Pro Arg Ala Gly Arg
                325                 330                 335

Val Thr Asn Leu Asn Thr Gln Asn Phe Pro Ile Leu Ser Leu Val Gln
            340                 345                 350

Met Ser Ala Val Lys Val Asn Leu Tyr Gln Asn Ala Leu Leu Ser Pro
        355                 360                 365

Phe Trp Asn Ile Asn Ala His Ser Val Val Tyr Ile Thr Gln Gly Arg
    370                 375                 380

Ala Arg Val Gln Val Val Asn Asn Asn Gly Lys Thr Val Phe Asn Gly
385                 390                 395                 400

Glu Leu Arg Arg Gly Gln Leu Leu Ile Ile Pro Gln His Tyr Ala Val
                405                 410                 415

Val Lys Lys Ala Gln Arg Glu Gly Cys Ala Tyr Ile Ala Phe Lys Thr
            420                 425                 430

Asn Pro Asn Ser Met Val Ser His Ile Ala Gly Lys Ser Ser Ile Phe
        435                 440                 445

Arg Ala Leu Pro Asn Asp Val Leu Ala Asn Ala Tyr Arg Ile Ser Arg
    450                 455                 460

Glu Glu Ala Gln Arg Leu Lys His Asn Arg Gly Asp Glu Phe Gly Ala
465                 470                 475                 480

Phe Thr Pro Ile Gln Tyr Lys Ser Tyr Gln Asp Val Tyr Asn Ala Ala
                485                 490                 495

Glu Ser Ser

<210> SEQ ID NO 12
<211> LENGTH: 499
<212> TYPE: PRT
<213> ORGANISM: Oryza sativa

<400> SEQUENCE: 12

Met Ala Ser Ile Asn Arg Pro Ile Val Phe Phe Thr Val Cys Leu Phe
1               5                   10                  15

```
Leu Leu Cys Asp Gly Ser Leu Ala Gln Gln Leu Leu Gly Gln Ser Thr
            20                  25                  30

Ser Gln Trp Gln Ser Ser Arg Arg Gly Ser Pro Arg Gly Cys Arg Phe
        35                  40                  45

Asp Arg Leu Gln Ala Phe Glu Pro Ile Arg Ser Val Arg Ser Gln Ala
 50                  55                  60

Gly Thr Thr Glu Phe Phe Asp Val Ser Asn Glu Leu Phe Gln Cys Thr
 65                  70                  75                  80

Gly Val Ser Val Val Arg Arg Val Ile Glu Pro Arg Gly Leu Leu Leu
                85                  90                  95

Pro His Tyr Thr Asn Gly Ala Ser Leu Val Tyr Ile Ile Gln Gly Arg
                100                 105                 110

Gly Ile Thr Gly Pro Thr Phe Pro Gly Cys Pro Glu Thr Tyr Gln Gln
            115                 120                 125

Gln Phe Gln Gln Ser Gly Gln Ala Gln Leu Thr Glu Ser Gln Ser Gln
130                 135                 140

Ser His Lys Phe Lys Asp Glu His Gln Lys Ile His Arg Phe Arg Gln
145                 150                 155                 160

Gly Asp Val Ile Ala Leu Pro Ala Gly Val Ala His Trp Cys Tyr Asn
                165                 170                 175

Asp Gly Glu Val Pro Val Val Ala Ile Tyr Val Thr Asp Ile Asn Asn
            180                 185                 190

Gly Ala Asn Gln Leu Asp Pro Arg Gln Arg Asp Phe Leu Leu Ala Gly
        195                 200                 205

Asn Lys Arg Asn Pro Gln Ala Tyr Arg Arg Glu Val Glu Glu Trp Ser
210                 215                 220

Gln Asn Ile Phe Ser Gly Phe Ser Thr Glu Leu Leu Ser Glu Ala Phe
225                 230                 235                 240

Gly Ile Ser Asn Gln Val Ala Arg Gln Leu Gln Cys Gln Asn Asp Gln
                245                 250                 255

Arg Gly Glu Ile Val Arg Val Glu Arg Gly Leu Ser Leu Leu Gln Pro
            260                 265                 270

Tyr Ala Ser Leu Gln Glu Gln Glu Gln Gly Gln Met Gln Ser Arg Glu
        275                 280                 285

His Tyr Gln Glu Gly Gly Tyr Gln Gln Ser Gln Tyr Gly Ser Gly Cys
290                 295                 300

Pro Asn Gly Leu Asp Glu Thr Phe Cys Thr Met Arg Val Arg Gln Asn
305                 310                 315                 320

Ile Asp Asn Pro Asn Arg Ala Asp Thr Tyr Asn Pro Arg Ala Gly Arg
                325                 330                 335

Val Thr Asn Leu Asn Ser Gln Asn Phe Pro Ile Leu Asn Leu Val Gln
            340                 345                 350

Met Ser Ala Val Lys Val Asn Leu Tyr Gln Asn Ala Leu Leu Ser Pro
        355                 360                 365

Phe Trp Asn Ile Asn Ala His Ser Ile Val Tyr Ile Thr Gln Gly Arg
370                 375                 380

Ala Gln Val Gln Val Val Asn Asn Asn Gly Lys Thr Val Phe Asn Gly
385                 390                 395                 400

Glu Leu Arg Arg Gly Gln Leu Leu Ile Val Pro Gln His Tyr Val Val
                405                 410                 415

Val Lys Lys Ala Gln Arg Glu Gly Cys Ala Tyr Ile Ala Phe Lys Thr
            420                 425                 430
```

Asn Pro Asn Ser Met Val Ser His Ile Ala Gly Lys Ser Ile Phe
            435                 440                 445

Arg Ala Leu Pro Thr Asp Val Leu Ala Asn Ala Tyr Arg Ile Ser Arg
450                 455                 460

Glu Glu Ala Gln Arg Leu Lys His Asn Arg Gly Asp Glu Phe Gly Ala
465                 470                 475                 480

Phe Thr Pro Leu Gln Tyr Lys Ser Tyr Gln Asp Val Tyr Asn Val Ala
                485                 490                 495

Glu Ser Ser

<210> SEQ ID NO 13
<211> LENGTH: 160
<212> TYPE: PRT
<213> ORGANISM: Oryza sativa

<400> SEQUENCE: 13

Met Ala Ser Asn Lys Val Val Phe Ser Val Leu Leu Ala Val Val
1               5                   10                  15

Ser Val Leu Ala Ala Thr Ala Thr Met Ala Glu Tyr His His Gln Asp
                20                  25                  30

Gln Val Val Tyr Thr Pro Gly Leu Cys Gln Pro Gly Met Gly Tyr
            35                  40                  45

Pro Met Tyr Pro Leu Pro Arg Cys Arg Ala Leu Val Lys Arg Gln Cys
50                  55                  60

Val Gly Arg Gly Thr Ala Ala Ala Glu Gln Val Arg Arg Asp Cys
65                  70                  75                  80

Cys Arg Gln Leu Ala Ala Val Asp Asp Ser Trp Cys Cys Glu Ala
                85                  90                  95

Ile Ser His Met Leu Gly Gly Ile Tyr Arg Glu Leu Gly Ala Pro Asp
                100                 105                 110

Val Gly His Pro Met Ser Glu Val Phe Arg Gly Cys Arg Arg Gly Asp
            115                 120                 125

Leu Glu Arg Ala Ala Ala Ser Leu Pro Ala Phe Cys Asn Val Asp Ile
130                 135                 140

Pro Asn Gly Gly Gly Val Cys Tyr Trp Leu Ala Arg Ser Gly Tyr
145                 150                 155                 160

<210> SEQ ID NO 14
<211> LENGTH: 500
<212> TYPE: PRT
<213> ORGANISM: Oryza sativa

<400> SEQUENCE: 14

Met Ala Thr Ile Ala Phe Ser Arg Leu Ser Ile Tyr Phe Cys Val Leu
1               5                   10                  15

Leu Leu Cys His Gly Ser Met Ala Gln Leu Phe Gly Pro Asn Val Asn
                20                  25                  30

Pro Trp His Asn Pro Arg Gln Gly Gly Phe Arg Glu Cys Arg Phe Asp
            35                  40                  45

Arg Leu Gln Ala Phe Glu Pro Leu Arg Arg Val Arg Ser Glu Ala Gly
50                  55                  60

Val Thr Glu Tyr Phe Asp Glu Lys Asn Glu Gln Phe Gln Cys Thr Gly
65                  70                  75                  80

Thr Phe Val Ile Arg Arg Val Ile Glu Pro Gln Gly Leu Leu Val Pro
                85                  90                  95

Arg Tyr Ser Asn Thr Pro Gly Met Val Tyr Ile Ile Gln Gly Arg Gly

```
            100                 105                 110
Ser Met Gly Leu Thr Phe Pro Gly Cys Pro Ala Thr Tyr Gln Gln Gln
            115                 120                 125

Phe Gln Gln Phe Leu Pro Glu Gly Gln Ser Gln Ser Gln Lys Phe Arg
            130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Ala Pro
                165                 170                 175

Val Val Ala Leu Tyr Val Phe Asp Leu Asn Asn Asn Ala Asn Gln Leu
            180                 185                 190

Glu Pro Arg Gln Lys Glu Phe Leu Leu Ala Gly Asn Asn Arg Glu
            195                 200                 205

Gln Gln Met Tyr Gly Arg Ser Ile Glu Gln His Ser Gly Gln Asn Ile
            210                 215                 220

Phe Ser Gly Phe Asn Asn Glu Leu Leu Ser Glu Ala Leu Gly Val Asn
225                 230                 235                 240

Ala Leu Val Ala Lys Arg Leu Gln Gly Gln Asn Asp Gln Arg Gly Glu
                245                 250                 255

Ile Ile Arg Val Lys Asn Gly Leu Lys Leu Leu Arg Pro Ala Phe Ala
                260                 265                 270

Gln Gln Gln Glu Gln Ala Gln Gln Glu Gln Ala Gln Ala Gln Tyr
            275                 280                 285

Gln Val Gln Tyr Ser Glu Glu Gln Gln Pro Ser Thr Arg Cys Asn Gly
            290                 295                 300

Leu Asp Glu Asn Phe Cys Thr Ile Lys Ala Arg Leu Asn Ile Glu Asn
305                 310                 315                 320

Pro Ser His Ala Asp Thr Tyr Asn Pro Arg Ala Gly Arg Ile Thr Arg
                325                 330                 335

Leu Asn Ser Gln Lys Phe Pro Ile Leu Asn Leu Val Gln Leu Ser Ala
                340                 345                 350

Thr Arg Val Asn Leu Tyr Gln Asn Ala Ile Leu Ser Pro Phe Trp Asn
            355                 360                 365

Val Asn Ala His Ser Leu Val Tyr Ile Val Gln Gly His Ala Arg Val
            370                 375                 380

Gln Val Val Ser Asn Leu Gly Lys Thr Val Phe Asn Gly Val Leu Arg
385                 390                 395                 400

Pro Gly Gln Leu Leu Ile Ile Pro Gln His Tyr Val Val Leu Lys Lys
                405                 410                 415

Ala Glu His Glu Gly Cys Gln Tyr Ile Ser Phe Lys Thr Asn Ala Asn
                420                 425                 430

Ser Met Val Ser His Leu Ala Gly Lys Asn Ser Ile Phe Arg Ala Met
            435                 440                 445

Pro Val Asp Val Ile Ala Asn Ala Tyr Arg Ile Ser Arg Glu Gln Ala
            450                 455                 460

Arg Ser Leu Lys Asn Asn Arg Gly Glu Glu Leu Gly Ala Phe Thr Pro
465                 470                 475                 480

Arg Tyr Gln Gln Gln Thr Tyr Pro Gly Phe Ser Asn Glu Ser Glu Asn
                485                 490                 495

Glu Ala Leu Glu
            500

<210> SEQ ID NO 15
```

<211> LENGTH: 609
<212> TYPE: PRT
<213> ORGANISM: Oryza sativa

<400> SEQUENCE: 15

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Leu Pro Pro Ala Met
            100                 105                 110

Ala Ala Asn Gly His Arg Val Met Val Ile Ser Pro Arg Tyr Asp Gln
            115                 120                 125

Tyr Lys Asp Ala Trp Asp Thr Ser Val Val Ala Glu Ile Lys Val Ala
130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
    370                 375                 380

Lys Glu Ala Leu Gln Ala Glu Ala Gly Leu Pro Val Asp Arg Lys Ile
```

```
            385                 390                 395                 400
Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asp Val Gln Ile
                420                 425                 430

Val Leu Leu Gly Thr Gly Lys Lys Phe Glu Lys Leu Leu Lys Ser
                435                 440                 445

Met Glu Glu Lys Tyr Pro Gly Lys Val Arg Ala Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
                500                 505                 510

Val Ile Glu Gly Lys Thr Gly Phe His Met Gly Arg Leu Ser Val Asp
        515                 520                 525

Cys Lys Val Val Glu Pro Ser Asp Val Lys Lys Val Ala Ala Thr Leu
        530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575

Trp Glu Asn Val Leu Leu Gly Leu Gly Val Ala Gly Ser Ala Pro Gly
                580                 585                 590

Ile Glu Gly Asp Glu Ile Ala Pro Leu Ala Lys Glu Asn Val Ala Ala
        595                 600                 605

Pro

<210> SEQ ID NO 16
<211> LENGTH: 336
<212> TYPE: PRT
<213> ORGANISM: Staphylococcus aureus

<400> SEQUENCE: 16

Met Lys Gly Lys Phe Leu Lys Val Ser Ser Leu Phe Val Ala Thr Leu
1               5                   10                  15

Thr Thr Ala Thr Leu Val Ser Ser Pro Ala Ala Asn Ala Leu Ser Ser
                20                  25                  30

Lys Ala Met Asp Asn His Pro Gln Gln Thr Gln Ser Ser Lys Gln Gln
            35                  40                  45

Thr Pro Lys Ile Gln Lys Gly Gly Asn Leu Lys Pro Leu Glu Gln Arg
        50                  55                  60

Glu His Ala Asn Val Ile Leu Pro Asn Asn Asp Arg His Gln Ile Thr
65                  70                  75                  80

Asp Thr Thr Asn Gly His Tyr Ala Pro Val Thr Tyr Ile Gln Val Glu
                85                  90                  95

Ala Pro Thr Gly Thr Phe Ile Ala Ser Gly Val Val Gly Lys Asp
                100                 105                 110

Thr Leu Leu Thr Asn Lys His Val Val Asp Ala Thr His Gly Asp Pro
            115                 120                 125

His Ala Leu Lys Ala Phe Pro Ser Ala Ile Asn Gln Asp Asn Tyr Pro
        130                 135                 140

Asn Gly Gly Phe Thr Ala Glu Gln Ile Thr Lys Tyr Ser Gly Glu Gly
```

```
                145                 150                 155                 160
Asp Leu Ala Ile Val Lys Phe Ser Pro Asn Glu Gln Asn Lys His Ile
                    165                 170                 175

Gly Glu Val Val Lys Pro Ala Thr Met Ser Asn Asn Ala Glu Thr Gln
                180                 185                 190

Val Asn Gln Asn Ile Thr Val Thr Gly Tyr Pro Gly Asp Lys Pro Val
                    195                 200                 205

Ala Thr Met Trp Glu Ser Lys Gly Lys Ile Thr Tyr Leu Lys Gly Glu
210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
                    245                 250                 255

Pro Asn Glu Phe Asn Gly Ala Val Phe Ile Asn Glu Asn Val Arg Asn
                260                 265                 270

Phe Leu Lys Gln Asn Ile Glu Asp Ile His Phe Ala Asn Asp Asp Gln
                    275                 280                 285

Pro Asn Asn Pro Asp Asn Pro Asp Asn Pro Asn Asn Pro Asp Asn Pro
                290                 295                 300

Asn Asn Pro Asp Glu Pro Asn Asn Pro Asp Asn Pro Asn Asn Pro Asp
305                 310                 315                 320

Asn Pro Asp Asn Gly Asp Asn Asn Ser Asp Asn Pro Asp Ala Ala
                    325                 330                 335

<210> SEQ ID NO 17
<211> LENGTH: 22
<212> TYPE: PRT
<213> ORGANISM: Artificial Sequence
<220> FEATURE:
<223> OTHER INFORMATION: Synthetic peptide

<400> SEQUENCE: 17

Pro Phe Asn Leu Arg Ser Arg Gly Pro Ile Tyr Ser Asn Glu Phe Gly
1               5                   10                  15

Lys Phe Phe Glu Ile Thr
            20

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide

<400> SEQUENCE: 18

Lys Pro Asp Asp Arg Asn Ser Phe Asn Leu Glu Arg Gly Asp Thr Ile
1               5                   10                  15

Lys

<210> SEQ ID NO 19
<211> LENGTH: 27
<212> TYPE: PRT
<213> ORGANISM: Artificial Sequence
<220> FEATURE:
<223> OTHER INFORMATION: Synthetic peptide

<400> SEQUENCE: 19

Tyr Leu Val Asn Arg Asp Asp Asn Glu Glu Leu Arg Val Leu Asp Leu
1               5                   10                  15
```

```
Ala Ile Pro Val Asn Arg Pro Gly Gln Leu Gln
        20                  25

<210> SEQ ID NO 20
<211> LENGTH: 51
<212> TYPE: PRT
<213> ORGANISM: Artificial Sequence
<220> FEATURE:
<223> OTHER INFORMATION: Synthetic peptide

<400> SEQUENCE: 20

Gln Glu Gln Arg Lys Glu Asp Asp Glu Glu Glu Gln Gly Glu Glu
1               5                   10                  15

Glu Ile Asn Lys Gln Val Gln Asn Tyr Lys Ala Lys Leu Ser Ser Gly
            20                  25                  30

Asp Val Phe Val Ile Pro Ala Gly His Pro Val Ala Val Lys Ala Ser
        35                  40                  45

Ser Asn Leu
    50

<210> SEQ ID NO 21
<211> LENGTH: 68
<212> TYPE: PRT
<213> ORGANISM: Artificial Sequence
<220> FEATURE:
<223> OTHER INFORMATION: Synthetic peptide

<400> SEQUENCE: 21

Ser Gly Phe Ser Lys Asn Ile Leu Glu Ala Ser Phe Asn Thr Asp Tyr
1               5                   10                  15

Glu Glu Ile Glu Lys Val Leu Leu Glu Glu His Glu Lys Glu Thr Gln
            20                  25                  30

His Arg Arg Ser Leu Lys Asp Lys Arg Gln Gln Ser Gln Glu Glu Asn
        35                  40                  45

Val Ile Val Lys Leu Ser Arg Gly Gln Ile Glu Leu Ser Lys Asn
    50                  55                  60

Ala Lys Ser Thr
65

<210> SEQ ID NO 22
<211> LENGTH: 74
<212> TYPE: PRT
<213> ORGANISM: Artificial Sequence
<220> FEATURE:
<223> OTHER INFORMATION: Synthetic peptide

<400> SEQUENCE: 22

Pro Phe Ile Phe Lys Ser Asn Lys Phe Gln Thr Leu Phe Glu Asn Glu
1               5                   10                  15

Asn Gly His Ile Arg Leu Leu Gln Lys Phe Asp Gln Arg Ser Lys Ile
            20                  25                  30

Phe Glu Asn Leu Gln Asn Tyr Arg Leu Leu Glu Tyr Lys Ser Lys Pro
        35                  40                  45

His Thr Ile Phe Leu Pro Gln His Thr Asp Ala Asp Tyr Ile Leu Val
    50                  55                  60

Val Leu Ser Gly Lys Ala Ile Leu Thr Val
65                  70

<210> SEQ ID NO 23
<211> LENGTH: 28
<212> TYPE: PRT
```

```
<213> ORGANISM: Artificial Sequence
<220> FEATURE:
<223> OTHER INFORMATION: Synthetic peptide

<400> SEQUENCE: 23

Gln Glu Val Asp Arg Ile Leu Glu Asn Gln Lys Gln Ser His Phe Ala
1               5                   10                  15

Asp Ala Gln Pro Gln Gln Arg Glu Arg Gly Ser Arg
            20                  25

<210> SEQ ID NO 24
<211> LENGTH: 35
<212> TYPE: PRT
<213> ORGANISM: Artificial Sequence
<220> FEATURE:
<223> OTHER INFORMATION: Synthetic peptide

<400> SEQUENCE: 24

Asn Asn Ser Gly Lys Phe Phe Glu Leu Thr Pro Glu Lys Asn Gln Gln
1               5                   10                  15

Leu Gln Asp Leu Asp Leu Phe Val Asn Ser Val Asp Leu Lys Glu Gly
            20                  25                  30

Ser Leu Leu
        35

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide

<400> SEQUENCE: 25

Lys Val Ser Arg Arg Gln Leu Glu Glu Leu Ser Lys Asn Ala Lys Ser
1               5                   10                  15

Ser

<210> SEQ ID NO 26
<211> LENGTH: 21
<212> TYPE: PRT
<213> ORGANISM: Artificial Sequence
<220> FEATURE:
<223> OTHER INFORMATION: Synthetic peptide

<400> SEQUENCE: 26

Gln Arg Gly Ser Arg Gln Glu Glu Asp Glu Asp Glu Asp Glu Asp Arg
1               5                   10                  15

Gln Pro Arg His Gln
            20

<210> SEQ ID NO 27
<211> LENGTH: 33
<212> TYPE: PRT
<213> ORGANISM: Artificial Sequence
<220> FEATURE:
<223> OTHER INFORMATION: Synthetic peptide

<400> SEQUENCE: 27

Gln Glu Phe Leu Arg Tyr Gln His Gln Gln Gly Gly Lys Gln Glu Gln
1               5                   10                  15

Glu Asn Glu Gly Asn Asn Ile Phe Ser Gly Phe Lys Arg Asp Phe Leu
            20                  25                  30

Glu
```

<210> SEQ ID NO 28
<211> LENGTH: 34
<212> TYPE: PRT
<213> ORGANISM: Artificial Sequence
<220> FEATURE:
<223> OTHER INFORMATION: Synthetic peptide

<400> SEQUENCE: 28

Tyr Asn Leu Glu Arg Gly Asp Thr Ile Lys Leu Pro Ala Gly Thr Thr
1               5                   10                  15

Ser Tyr Leu Val Asn Gln Asp Asp Glu Glu Asp Leu Arg Leu Val Asp
                20                  25                  30

Leu Val

<210> SEQ ID NO 29
<211> LENGTH: 80
<212> TYPE: PRT
<213> ORGANISM: Artificial Sequence
<220> FEATURE:
<223> OTHER INFORMATION: Synthetic peptide

<400> SEQUENCE: 29

Asn Gly Pro Gly Lys Phe Glu Ala Phe Asp Leu Ala Lys Asn Lys Asn
1               5                   10                  15

Gln Tyr Leu Arg Gly Phe Ser Lys Asn Ile Leu Glu Ala Ser Tyr Asn
                20                  25                  30

Thr Arg Tyr Glu Thr Ile Glu Lys Val Leu Leu Glu Glu Gln Glu Lys
            35                  40                  45

Asp Arg Lys Arg Arg Gln Gln Gly Glu Glu Thr Asp Ala Ile Val Lys
        50                  55                  60

Val Ser Arg Glu Gln Ile Glu Glu Leu Lys Lys Leu Ala Lys Ser Ser
65                  70                  75                  80

<210> SEQ ID NO 30
<211> LENGTH: 47
<212> TYPE: PRT
<213> ORGANISM: Artificial Sequence
<220> FEATURE:
<223> OTHER INFORMATION: Synthetic peptide

<400> SEQUENCE: 30

Arg Tyr Glu Ala Arg Leu Ser Pro Gly Asp Val Val Ile Ile Pro Ala
1               5                   10                  15

Gly His Pro Val Ala Ile Thr Ala Ser Ser Asn Leu Asn Leu Leu Gly
                20                  25                  30

Phe Gly Ile Asn Ala Glu Asn Asn Glu Arg Asn Phe Leu Ser Gly
            35                  40                  45

<210> SEQ ID NO 31
<211> LENGTH: 24
<212> TYPE: PRT
<213> ORGANISM: Artificial Sequence
<220> FEATURE:
<223> OTHER INFORMATION: Synthetic peptide

<400> SEQUENCE: 31

His Gly Glu Trp Arg Pro Ser Tyr Glu Lys Gln Glu Asp Glu Glu Glu
1               5                   10                  15

Lys Gln Lys Tyr Arg Tyr Gln Arg
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic peptide

<400> SEQUENCE: 32

Pro Ser Tyr Glu Lys Glu Glu Asp Glu Glu Gly Gln Arg Glu Arg
1               5                   10                  15

Gly Arg Gln

<210> SEQ ID NO 33
<211> LENGTH: 30
<212> TYPE: PRT
<213> ORGANISM: Artificial Sequence
<220> FEATURE:
<223> OTHER INFORMATION: Synthetic peptide

<400> SEQUENCE: 33

Lys Ser Lys Pro Arg Thr Leu Phe Leu Pro Gln Tyr Thr Asp Ala Asp
1               5                   10                  15

Phe Ile Leu Val Val Leu Ser Gly Lys Ala Thr Leu Thr Val
            20                  25                  30

<210> SEQ ID NO 34
<211> LENGTH: 22
<212> TYPE: PRT
<213> ORGANISM: Artificial Sequence
<220> FEATURE:
<223> OTHER INFORMATION: Synthetic peptide

<400> SEQUENCE: 34

Ser Gln Ser Gln Lys Phe Arg Asp Glu His Gln Lys Ile His Gln Phe
1               5                   10                  15

Arg Gln Gly Asp Ile Val
            20

<210> SEQ ID NO 35
<211> LENGTH: 23
<212> TYPE: PRT
<213> ORGANISM: Artificial Sequence
<220> FEATURE:
<223> OTHER INFORMATION: Synthetic peptide

<400> SEQUENCE: 35

Val Asn Ser Gln Lys Phe Pro Ile Leu Asn Leu Ile Gln Met Ser Ala
1               5                   10                  15

Thr Arg Val Asn Leu Tyr Gln
            20

<210> SEQ ID NO 36
<211> LENGTH: 40
<212> TYPE: PRT
<213> ORGANISM: Artificial Sequence
<220> FEATURE:
<223> OTHER INFORMATION: Synthetic peptide

<400> SEQUENCE: 36

Tyr Ile Ala Ile Lys Thr Asn Ala Asn Ala Phe Val Ser His Leu Ala
1               5                   10                  15

Gly Lys Asn Ser Val Phe Arg Ala Leu Pro Val Asp Val Ala Asn
            20                  25                  30

Ala Tyr Arg Ile Ser Arg Glu Gln
            35                  40

<210> SEQ ID NO 37
<211> LENGTH: 31
<212> TYPE: PRT
<213> ORGANISM: Artificial Sequence
<220> FEATURE:
<223> OTHER INFORMATION: Synthetic peptide

<400> SEQUENCE: 37

Ala Pro Ile Val Ala Val Tyr Val Tyr Asp Val Asn Asn Asn Ala Asn
1               5                   10                  15

Gln Leu Glu Pro Arg Gln Lys Glu Phe Leu Leu Ala Gly Asn Asn
            20                  25                  30

<210> SEQ ID NO 38
<211> LENGTH: 17
<212> TYPE: PRT
<213> ORGANISM: Artificial Sequence
<220> FEATURE:
<223> OTHER INFORMATION: Synthetic peptide

<400> SEQUENCE: 38

Glu Asn Pro Ser Arg Ala Asp Ser Tyr Asn Pro Arg Ala Gly Arg Ile
1               5                   10                  15

Thr

<210> SEQ ID NO 39
<211> LENGTH: 32
<212> TYPE: PRT
<213> ORGANISM: Artificial Sequence
<220> FEATURE:
<223> OTHER INFORMATION: Synthetic peptide

<400> SEQUENCE: 39

Gly Leu Gln Leu Leu Lys Pro Thr Leu Thr Gln Gln Gln Glu Gln Ala
1               5                   10                  15

Gln Ala Gln Asp Gln Tyr Gln Gln Val Gln Tyr Ser Glu Arg Gln Gln
            20                  25                  30

<210> SEQ ID NO 40
<211> LENGTH: 18
<212> TYPE: PRT
<213> ORGANISM: Artificial Sequence
<220> FEATURE:
<223> OTHER INFORMATION: Synthetic peptide

<400> SEQUENCE: 40

Cys Arg Phe Asp Arg Leu Gln Ala Phe Glu Pro Leu Arg Lys Val Arg
1               5                   10                  15

Ser Glu

<210> SEQ ID NO 41
<211> LENGTH: 48
<212> TYPE: PRT
<213> ORGANISM: Artificial Sequence
<220> FEATURE:
<223> OTHER INFORMATION: Synthetic peptide

<400> SEQUENCE: 41

Ile Leu Ser Pro Phe Trp Asn Val Asn Ala His Ser Leu Val Tyr Met
1               5                   10                  15

Ile Gln Gly Arg Ser Arg Val Gln Val Val Ser Asn Phe Gly Lys Thr

```
                 20                  25                  30

Val Phe Asp Gly Val Leu Arg Pro Gly Gln Leu Leu Ile Ile Pro Gln
         35                  40                  45

<210> SEQ ID NO 42
<211> LENGTH: 24
<212> TYPE: PRT
<213> ORGANISM: Artificial Sequence
<220> FEATURE:
<223> OTHER INFORMATION: Synthetic peptide

<400> SEQUENCE: 42

Ala Phe Thr Pro Arg Phe Gln Gln Gln Tyr Tyr Pro Gly Leu Ser Asn
1               5                  10                  15

Glu Ser Glu Ser Glu Thr Ser Glu
            20

<210> SEQ ID NO 43
<211> LENGTH: 31
<212> TYPE: PRT
<213> ORGANISM: Artificial Sequence
<220> FEATURE:
<223> OTHER INFORMATION: Synthetic peptide

<400> SEQUENCE: 43

Pro Arg Ala Gly Arg Val Thr Asn Leu Asn Thr Gln Asn Phe Pro Ile
1               5                  10                  15

Leu Ser Leu Val Gln Met Ser Ala Val Lys Val Asn Leu Tyr Gln
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Synthetic peptide

<400> SEQUENCE: 44

His Ser Val Val Tyr Ile Thr Gln Gly Arg Ala Arg Val Gln Val Val
1               5                  10                  15

Asn Asn Asn Gly Lys Thr Val Phe Asn Gly Glu Leu Arg Arg Gly Gln
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic peptide

<400> SEQUENCE: 45

His Ile Ala Gly Lys Ser Ser Ile Phe Arg Ala Leu Pro Asn Asp Val
1               5                  10                  15

Leu Ala Asn Ala Tyr Arg Ile Ser Arg Glu Glu Ala Gln Arg Leu Lys
            20                  25                  30

<210> SEQ ID NO 46
<211> LENGTH: 29
<212> TYPE: PRT
<213> ORGANISM: Artificial Sequence
<220> FEATURE:
<223> OTHER INFORMATION: Synthetic peptide

<400> SEQUENCE: 46
```

```
Val Pro Val Val Ala Ile Tyr Val Thr Asp Leu Asn Asn Gly Ala Asn
1               5                   10                  15

Gln Leu Asp Pro Arg Gln Arg Asp Phe Leu Leu Ala Gly
            20                  25
```

<210> SEQ ID NO 47
<211> LENGTH: 52
<212> TYPE: PRT
<213> ORGANISM: Artificial Sequence
<220> FEATURE:
<223> OTHER INFORMATION: Synthetic peptide

<400> SEQUENCE: 47

```
Thr Phe Cys Thr Met Arg Val Arg Gln Asn Ile Asp Asn Pro Asn Arg
1               5                   10                  15

Ala Asp Thr Tyr Asn Pro Arg Ala Gly Arg Val Thr Asn Leu Asn Ser
            20                  25                  30

Gln Asn Phe Pro Ile Leu Asn Leu Val Gln Met Ser Ala Val Lys Val
        35                  40                  45

Asn Leu Tyr Gln
    50
```

<210> SEQ ID NO 48
<211> LENGTH: 73
<212> TYPE: PRT
<213> ORGANISM: Artificial Sequence
<220> FEATURE:
<223> OTHER INFORMATION: Synthetic peptide

<400> SEQUENCE: 48

```
Tyr Ile Ala Phe Lys Thr Asn Pro Asn Ser Met Val Ser His Ile Ala
1               5                   10                  15

Gly Lys Ser Ser Ile Phe Arg Ala Leu Pro Thr Asp Val Leu Ala Asn
            20                  25                  30

Ala Tyr Arg Ile Ser Arg Glu Glu Ala Gln Arg Leu Lys His Asn Arg
        35                  40                  45

Gly Asp Glu Phe Gly Ala Phe Thr Pro Leu Gln Tyr Lys Ser Tyr Gln
    50                  55                  60

Asp Val Tyr Asn Val Ala Glu Ser Ser
65                  70
```

<210> SEQ ID NO 49
<211> LENGTH: 36
<212> TYPE: PRT
<213> ORGANISM: Artificial Sequence
<220> FEATURE:
<223> OTHER INFORMATION: Synthetic peptide

<400> SEQUENCE: 49

```
Ser Gln Ser His Lys Phe Lys Asp Glu His Gln Lys Ile His Arg Phe
1               5                   10                  15

Arg Gln Gly Asp Val Ile Ala Leu Pro Ala Gly Val Ala His Trp Cys
            20                  25                  30

Tyr Asn Asp Gly
        35
```

<210> SEQ ID NO 50
<211> LENGTH: 29
<212> TYPE: PRT
<213> ORGANISM: Artificial Sequence
<220> FEATURE:
<223> OTHER INFORMATION: Synthetic peptide

<400> SEQUENCE: 50

Thr Gln Gly Arg Ala Gln Val Gln Val Val Asn Asn Asn Gly Lys Thr
1               5                   10                  15

Val Phe Asn Gly Glu Leu Arg Arg Gly Gln Leu Leu Ile
            20                  25

<210> SEQ ID NO 51
<211> LENGTH: 24
<212> TYPE: PRT
<213> ORGANISM: Artificial Sequence
<220> FEATURE:
<223> OTHER INFORMATION: Synthetic peptide

<400> SEQUENCE: 51

Asn Gly Ala Ser Leu Val Tyr Ile Ile Gln Gly Arg Gly Ile Thr Gly
1               5                   10                  15

Pro Thr Phe Pro Gly Cys Pro Glu
            20

<210> SEQ ID NO 52
<211> LENGTH: 21
<212> TYPE: PRT
<213> ORGANISM: Artificial Sequence
<220> FEATURE:
<223> OTHER INFORMATION: Synthetic peptide

<400> SEQUENCE: 52

Cys Arg Phe Asp Arg Leu Gln Ala Phe Glu Pro Ile Arg Ser Val Arg
1               5                   10                  15

Ser Gln Ala Gly Thr
            20

<210> SEQ ID NO 53
<211> LENGTH: 40
<212> TYPE: PRT
<213> ORGANISM: Artificial Sequence
<220> FEATURE:
<223> OTHER INFORMATION: Synthetic peptide

<400> SEQUENCE: 53

Gln Asn Asp Gln Arg Gly Glu Ile Val Arg Val Glu Arg Gly Leu Ser
1               5                   10                  15

Leu Leu Gln Pro Tyr Ala Ser Leu Gln Glu Gln Glu Gln Gly Gln Met
            20                  25                  30

Gln Ser Arg Glu His Tyr Gln Glu
            35                  40

<210> SEQ ID NO 54
<211> LENGTH: 35
<212> TYPE: PRT
<213> ORGANISM: Artificial Sequence
<220> FEATURE:
<223> OTHER INFORMATION: Synthetic peptide

<400> SEQUENCE: 54

Pro Arg Gln Arg Asp Phe Leu Leu Ala Gly Asn Lys Arg Asn Pro Gln
1               5                   10                  15

Ala Tyr Arg Arg Glu Val Glu Glu Trp Ser Gln Asn Ile Phe Ser Gly
            20                  25                  30

Phe Ser Thr
            35

```
<210> SEQ ID NO 55
<211> LENGTH: 23
<212> TYPE: PRT
<213> ORGANISM: Artificial Sequence
<220> FEATURE:
<223> OTHER INFORMATION: Synthetic peptide

<400> SEQUENCE: 55

Gly Gly Ile Tyr Arg Glu Leu Gly Ala Pro Asp Val Gly His Pro Met
1               5                   10                  15

Ser Glu Val Phe Arg Gly Cys
            20

<210> SEQ ID NO 56
<211> LENGTH: 26
<212> TYPE: PRT
<213> ORGANISM: Artificial Sequence
<220> FEATURE:
<223> OTHER INFORMATION: Synthetic peptide

<400> SEQUENCE: 56

His Ser Leu Val Tyr Ile Val Gln Gly His Ala Arg Val Gln Val Val
1               5                   10                  15

Ser Asn Leu Gly Lys Thr Val Phe Asn Gly
            20                  25

<210> SEQ ID NO 57
<211> LENGTH: 23
<212> TYPE: PRT
<213> ORGANISM: Artificial Sequence
<220> FEATURE:
<223> OTHER INFORMATION: Synthetic peptide

<400> SEQUENCE: 57

Ala Arg Ser Leu Lys Asn Asn Arg Gly Glu Glu Leu Gly Ala Phe Thr
1               5                   10                  15

Pro Arg Tyr Gln Gln Gln Thr
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic peptide

<400> SEQUENCE: 58

Leu Asn Ser Gln Lys Phe Pro Ile Leu Asn Leu Val Gln Leu Ser Ala
1               5                   10                  15

Thr Arg Val Asn Leu Tyr Gln
            20

<210> SEQ ID NO 59
<211> LENGTH: 84
<212> TYPE: PRT
<213> ORGANISM: Artificial Sequence
<220> FEATURE:
<223> OTHER INFORMATION: Synthetic peptide

<400> SEQUENCE: 59

Gln Met Tyr Gly Arg Ser Ile Glu Gln His Ser Gly Gln Asn Ile Phe
1               5                   10                  15

Ser Gly Phe Asn Asn Glu Leu Leu Ser Glu Ala Leu Gly Val Asn Ala
            20                  25                  30
```

Leu Val Ala Lys Arg Leu Gln Gly Gln Asn Asp Gln Arg Gly Glu Ile
            35                  40                  45

Ile Arg Val Lys Asn Gly Leu Lys Leu Leu Arg Pro Ala Phe Ala Gln
 50                  55                  60

Gln Gln Glu Gln Ala Gln Gln Glu Gln Ala Gln Ala Gln Tyr Gln
65                  70                  75                  80

Val Gln Tyr Ser

<210> SEQ ID NO 60
<211> LENGTH: 24
<212> TYPE: PRT
<213> ORGANISM: Artificial Sequence
<220> FEATURE:
<223> OTHER INFORMATION: Synthetic peptide

<400> SEQUENCE: 60

Ala Gln Leu Phe Gly Pro Asn Val Asn Pro Trp His Asn Pro Arg Gln
 1               5                  10                  15

Gly Gly Phe Arg Glu Cys Arg Phe
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic peptide

<400> SEQUENCE: 61

Gly Val Ala His Trp Phe Tyr Asn Glu Gly Asp Ala Pro Val Val Ala
 1               5                  10                  15

Leu Tyr Val Phe Asp Leu Asn
            20

<210> SEQ ID NO 62
<211> LENGTH: 40
<212> TYPE: PRT
<213> ORGANISM: Artificial Sequence
<220> FEATURE:
<223> OTHER INFORMATION: Synthetic peptide

<400> SEQUENCE: 62

Tyr Ile Ser Phe Lys Thr Asn Ala Asn Ser Met Val Ser His Leu Ala
 1               5                  10                  15

Gly Lys Asn Ser Ile Phe Arg Ala Met Pro Val Asp Val Ile Ala Asn
            20                  25                  30

Ala Tyr Arg Ile Ser Arg Glu Gln
            35                  40

<210> SEQ ID NO 63
<211> LENGTH: 38
<212> TYPE: PRT
<213> ORGANISM: Artificial Sequence
<220> FEATURE:
<223> OTHER INFORMATION: Synthetic peptide

<400> SEQUENCE: 63

Lys Gly Pro Ala Lys Asn Trp Glu Asn Val Leu Leu Gly Leu Gly Val
 1               5                  10                  15

Ala Gly Ser Ala Pro Gly Ile Glu Gly Asp Glu Ile Ala Pro Leu Ala
            20                  25                  30

```
Lys Glu Asn Val Ala Ala
        35

<210> SEQ ID NO 64
<211> LENGTH: 31
<212> TYPE: PRT
<213> ORGANISM: Artificial Sequence
<220> FEATURE:
<223> OTHER INFORMATION: Synthetic peptide

<400> SEQUENCE: 64

Arg Ala Val Val Lys Phe Asn Ala Pro Leu Ala His Leu Ile Met Ala
1               5                   10                  15

Gly Ala Asp Val Leu Ala Val Pro Ser Arg Phe Glu Pro Cys Gly
            20                  25                  30

<210> SEQ ID NO 65
<211> LENGTH: 22
<212> TYPE: PRT
<213> ORGANISM: Artificial Sequence
<220> FEATURE:
<223> OTHER INFORMATION: Synthetic peptide

<400> SEQUENCE: 65

Lys Arg Ala Ile Lys Val Val Gly Thr Pro Ala Tyr Glu Glu Met Val
1               5                   10                  15

Arg Asn Cys Met Asn Gln
            20

<210> SEQ ID NO 66
<211> LENGTH: 55
<212> TYPE: PRT
<213> ORGANISM: Artificial Sequence
<220> FEATURE:
<223> OTHER INFORMATION: Synthetic peptide

<400> SEQUENCE: 66

Ala Pro Trp Ser Lys Thr Gly Gly Leu Gly Asp Val Leu Gly Gly Leu
1               5                   10                  15

Pro Pro Ala Met Ala Ala Asn Gly His Arg Val Met Val Ile Ser Pro
            20                  25                  30

Arg Tyr Asp Gln Tyr Lys Asp Ala Trp Asp Thr Ser Val Val Ala Glu
        35                  40                  45

Ile Lys Val Ala Asp Arg Tyr
        50                  55

<210> SEQ ID NO 67
<211> LENGTH: 109
<212> TYPE: PRT
<213> ORGANISM: Artificial Sequence
<220> FEATURE:
<223> OTHER INFORMATION: Synthetic peptide

<400> SEQUENCE: 67

Ile Asn Trp Met Lys Ala Gly Ile Leu Glu Ala Asp Arg Val Leu Thr
1               5                   10                  15

Val Ser Pro Tyr Tyr Ala Glu Glu Leu Ile Ser Gly Ile Ala Arg Gly
            20                  25                  30

Cys Glu Leu Asp Asn Ile Met Arg Leu Thr Gly Ile Thr Gly Ile Val
        35                  40                  45

Asn Gly Met Asp Val Ser Glu Trp Asp Pro Ser Lys Asp Lys Tyr Ile
        50                  55                  60
```

Thr Ala Lys Tyr Asp Ala Thr Thr Ala Ile Glu Ala Lys Ala Leu Asn
65                  70                  75                  80

Lys Glu Ala Leu Gln Ala Glu Ala Gly Leu Pro Val Asp Arg Lys Ile
                85                  90                  95

Pro Leu Ile Ala Phe Ile Gly Arg Leu Glu Glu Gln Lys
            100                 105

<210> SEQ ID NO 68
<211> LENGTH: 45
<212> TYPE: PRT
<213> ORGANISM: Artificial Sequence
<220> FEATURE:
<223> OTHER INFORMATION: Synthetic peptide

<400> SEQUENCE: 68

Arg Gly Val Asp Arg Val Phe Ile Asp His Pro Ser Phe Leu Glu Lys
1               5                   10                  15

Val Trp Gly Lys Thr Gly Glu Lys Ile Tyr Gly Pro Asp Thr Gly Val
                20                  25                  30

Asp Tyr Lys Asp Asn Gln Met Arg Phe Ser Leu Leu Cys
            35                  40                  45

<210> SEQ ID NO 69
<211> LENGTH: 21
<212> TYPE: PRT
<213> ORGANISM: Artificial Sequence
<220> FEATURE:
<223> OTHER INFORMATION: Synthetic peptide

<400> SEQUENCE: 69

Leu Glu Ala Pro Arg Ile Leu Asn Leu Asn Asn Pro Tyr Phe Lys
1               5                   10                  15

Gly Thr Tyr Gly Glu
            20

<210> SEQ ID NO 70
<211> LENGTH: 26
<212> TYPE: PRT
<213> ORGANISM: Artificial Sequence
<220> FEATURE:
<223> OTHER INFORMATION: Synthetic peptide

<400> SEQUENCE: 70

Tyr Ile Gln Val Glu Ala Pro Thr Gly Thr Phe Ile Ala Ser Gly Val
1               5                   10                  15

Val Val Gly Lys Asp Thr Leu Leu Thr Asn
                20                  25

<210> SEQ ID NO 71
<211> LENGTH: 12
<212> TYPE: PRT
<213> ORGANISM: Artificial Sequence
<220> FEATURE:
<223> OTHER INFORMATION: Synthetic peptide

<400> SEQUENCE: 71

Ser Arg Gly Pro Ile Tyr Ser Asn Glu Phe Gly Lys
1               5                   10

<210> SEQ ID NO 72
<211> LENGTH: 7
<212> TYPE: PRT
<213> ORGANISM: Artificial Sequence
<220> FEATURE:

<223> OTHER INFORMATION: Synthetic peptide

<400> SEQUENCE: 72

Asn Ser Phe Asn Leu Glu Arg
1               5

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Val Leu Asp Leu Ala Ile Pro Val Asn Arg
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Asp Asp Asn Glu Glu Leu Arg
1               5

<210> SEQ ID NO 75
<211> LENGTH: 18
<212> TYPE: PRT
<213> ORGANISM: Artificial Sequence
<220> FEATURE:
<223> OTHER INFORMATION: Synthetic peptide

<400> SEQUENCE: 75

Leu Ser Ser Gly Asp Val Phe Val Ile Pro Ala Gly His Pro Val Ala
1               5                   10                  15

Val Lys

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide

<400> SEQUENCE: 76

Glu Asp Asp Glu Glu Glu Glu Gln Gly Glu Glu Glu Ile Asn Lys
1               5                   10                  15

<210> SEQ ID NO 77
<211> LENGTH: 29
<212> TYPE: PRT
<213> ORGANISM: Artificial Sequence
<220> FEATURE:
<223> OTHER INFORMATION: Synthetic peptide

<400> SEQUENCE: 77

Asn Ile Leu Glu Ala Ser Phe Asn Thr Asp Tyr Glu Glu Ile Glu Lys
1               5                   10                  15

Val Leu Leu Glu Glu His Glu Lys Glu Thr Gln His Arg
            20                  25

<210> SEQ ID NO 78

-continued

```
<211> LENGTH: 24
<212> TYPE: PRT
<213> ORGANISM: Artificial Sequence
<220> FEATURE:
<223> OTHER INFORMATION: Synthetic peptide

<400> SEQUENCE: 78

Asn Ile Leu Glu Ala Ser Phe Asn Thr Asp Tyr Glu Glu Ile Glu Lys
1               5                   10                  15
Val Leu Leu Glu Glu His Glu Lys
            20

<210> SEQ ID NO 79
<211> LENGTH: 16
<212> TYPE: PRT
<213> ORGANISM: Artificial Sequence
<220> FEATURE:
<223> OTHER INFORMATION: Synthetic peptide

<400> SEQUENCE: 79

Asn Ile Leu Glu Ala Ser Phe Asn Thr Asp Tyr Glu Glu Ile Glu Lys
1               5                   10                  15

<210> SEQ ID NO 80
<211> LENGTH: 12
<212> TYPE: PRT
<213> ORGANISM: Artificial Sequence
<220> FEATURE:
<223> OTHER INFORMATION: Synthetic peptide

<400> SEQUENCE: 80

Arg Gln Gln Ser Gln Glu Glu Asn Val Ile Val Lys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic peptide

<400> SEQUENCE: 81

Gln Gln Ser Gln Glu Glu Asn Val Ile Val Lys
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic peptide

<400> SEQUENCE: 82

Leu Ser Arg Gly Gln Ile Glu Glu Leu Ser Lys
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide

<400> SEQUENCE: 83

Gly Gln Ile Glu Glu Leu Ser Lys
1               5
```

<210> SEQ ID NO 84
<211> LENGTH: 8
<212> TYPE: PRT
<213> ORGANISM: Artificial Sequence
<220> FEATURE:
<223> OTHER INFORMATION: Synthetic peptide

<400> SEQUENCE: 84

Val Leu Leu Glu Glu His Glu Lys
1               5

<210> SEQ ID NO 85
<211> LENGTH: 24
<212> TYPE: PRT
<213> ORGANISM: Artificial Sequence
<220> FEATURE:
<223> OTHER INFORMATION: Synthetic peptide

<400> SEQUENCE: 85

Ser Lys Pro His Thr Ile Phe Leu Pro Gln His Thr Asp Ala Asp Tyr
1               5                   10                  15

Ile Leu Val Val Leu Ser Gly Lys
            20

<210> SEQ ID NO 86
<211> LENGTH: 22
<212> TYPE: PRT
<213> ORGANISM: Artificial Sequence
<220> FEATURE:
<223> OTHER INFORMATION: Synthetic peptide

<400> SEQUENCE: 86

Pro His Thr Ile Phe Leu Pro Gln His Thr Asp Ala Asp Tyr Ile Leu
1               5                   10                  15

Val Val Leu Ser Gly Lys
            20

<210> SEQ ID NO 87
<211> LENGTH: 16
<212> TYPE: PRT
<213> ORGANISM: Artificial Sequence
<220> FEATURE:
<223> OTHER INFORMATION: Synthetic peptide

<400> SEQUENCE: 87

Ser Asn Lys Phe Gln Thr Leu Phe Glu Asn Glu Asn Gly His Ile Arg
1               5                   10                  15

<210> SEQ ID NO 88
<211> LENGTH: 11
<212> TYPE: PRT
<213> ORGANISM: Artificial Sequence
<220> FEATURE:
<223> OTHER INFORMATION: Synthetic peptide

<400> SEQUENCE: 88

Ser Lys Ile Phe Glu Asn Leu Gln Asn Tyr Arg
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 89

Ile Phe Glu Asn Leu Gln Asn Tyr Arg
1               5

<210> SEQ ID NO 90
<211> LENGTH: 18
<212> TYPE: PRT
<213> ORGANISM: Artificial Sequence
<220> FEATURE:
<223> OTHER INFORMATION: Synthetic peptide

<400> SEQUENCE: 90

Ile Leu Glu Asn Gln Lys Gln Ser His Phe Ala Asp Ala Gln Pro Gln
1               5                   10                  15

Gln Arg

<210> SEQ ID NO 91
<211> LENGTH: 24
<212> TYPE: PRT
<213> ORGANISM: Artificial Sequence
<220> FEATURE:
<223> OTHER INFORMATION: Synthetic peptide

<400> SEQUENCE: 91

Pro Gly Gln Leu Gln Ser Phe Leu Leu Ser Gly Asn Gln Asn Gln Gln
1               5                   10                  15

Asn Tyr Leu Ser Gly Phe Ser Lys
            20

<210> SEQ ID NO 92
<211> LENGTH: 25
<212> TYPE: PRT
<213> ORGANISM: Artificial Sequence
<220> FEATURE:
<223> OTHER INFORMATION: Synthetic peptide

<400> SEQUENCE: 92

Phe Phe Glu Leu Thr Pro Glu Lys Asn Gln Gln Leu Gln Asp Leu Asp
1               5                   10                  15

Leu Phe Val Asn Ser Val Asp Leu Lys
            20                  25

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide

<400> SEQUENCE: 93

Gln Leu Glu Glu Leu Ser Lys
1               5

<210> SEQ ID NO 94
<211> LENGTH: 11
<212> TYPE: PRT
<213> ORGANISM: Artificial Sequence
<220> FEATURE:
<223> OTHER INFORMATION: Synthetic peptide

<400> SEQUENCE: 94

Gln Glu Glu Asp Glu Asp Glu Asp Glu Glu Arg
1               5                   10
```

```
<210> SEQ ID NO 95
<211> LENGTH: 23
<212> TYPE: PRT
<213> ORGANISM: Artificial Sequence
<220> FEATURE:
<223> OTHER INFORMATION: Synthetic peptide

<400> SEQUENCE: 95

Tyr Gln His Gln Gln Gly Gly Lys Gln Glu Gln Glu Asn Glu Gly Asn
1               5                   10                  15

Asn Ile Phe Ser Gly Phe Lys
            20

<210> SEQ ID NO 96
<211> LENGTH: 24
<212> TYPE: PRT
<213> ORGANISM: Artificial Sequence
<220> FEATURE:
<223> OTHER INFORMATION: Synthetic peptide

<400> SEQUENCE: 96

Gly Asp Thr Ile Lys Leu Pro Ala Gly Thr Thr Ser Tyr Leu Val Asn
1               5                   10                  15

Gln Asp Asp Glu Glu Asp Leu Arg
            20

<210> SEQ ID NO 97
<211> LENGTH: 12
<212> TYPE: PRT
<213> ORGANISM: Artificial Sequence
<220> FEATURE:
<223> OTHER INFORMATION: Synthetic peptide

<400> SEQUENCE: 97

Arg Gln Gln Gly Glu Glu Thr Asp Ala Ile Val Lys
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic peptide

<400> SEQUENCE: 98

Val Leu Leu Glu Glu Gln Glu Lys Asp Arg Lys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide

<400> SEQUENCE: 99

Asn Ile Leu Glu Ala Ser Tyr Asn Thr Arg
1               5                   10

<210> SEQ ID NO 100
<211> LENGTH: 8
<212> TYPE: PRT
<213> ORGANISM: Artificial Sequence
<220> FEATURE:
<223> OTHER INFORMATION: Synthetic peptide

<400> SEQUENCE: 100
```

```
Phe Glu Ala Phe Asp Leu Ala Lys
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic peptide

<400> SEQUENCE: 101

Glu Gln Ile Glu Glu Leu Lys Lys
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Glu Gln Ile Glu Glu Leu Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 103

Asn Lys Asn Gln Tyr Leu Arg
1               5

<210> SEQ ID NO 104
<211> LENGTH: 37
<212> TYPE: PRT
<213> ORGANISM: Artificial Sequence
<220> FEATURE:
<223> OTHER INFORMATION: Synthetic peptide

<400> SEQUENCE: 104

Leu Ser Pro Gly Asp Val Val Ile Ile Pro Ala Gly His Pro Val Ala
1               5                   10                  15

Ile Thr Ala Ser Ser Asn Leu Asn Leu Leu Gly Phe Gly Ile Asn Ala
            20                  25                  30

Glu Asn Asn Glu Arg
        35

<210> SEQ ID NO 105
<211> LENGTH: 14
<212> TYPE: PRT
<213> ORGANISM: Artificial Sequence
<220> FEATURE:
<223> OTHER INFORMATION: Synthetic peptide

<400> SEQUENCE: 105

Pro Ser Tyr Glu Lys Gln Glu Asp Glu Glu Lys Gln Lys
1               5                   10

<210> SEQ ID NO 106
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 106

Glu Glu Asp Glu Glu Glu Gly Gln Arg
1               5

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide

<400> SEQUENCE: 107

Thr Leu Phe Leu Pro Gln Tyr Thr Asp Ala Asp Phe Ile Leu Val Val
1               5                   10                  15

Leu Ser Gly Lys
            20

<210> SEQ ID NO 108
<211> LENGTH: 24
<212> TYPE: PRT
<213> ORGANISM: Artificial Sequence
<220> FEATURE:
<223> OTHER INFORMATION: Synthetic peptide

<400> SEQUENCE: 108

Gly Tyr Val Gly Leu Thr Phe Pro Gly Cys Pro Ala Thr His Gln Gln
1               5                   10                  15

Gln Phe Gln Leu Phe Glu Gln Arg
            20

<210> SEQ ID NO 109
<211> LENGTH: 14
<212> TYPE: PRT
<213> ORGANISM: Artificial Sequence
<220> FEATURE:
<223> OTHER INFORMATION: Synthetic peptide

<400> SEQUENCE: 109

Arg Gly Pro Gln Gln Tyr Ala Glu Trp Gln Ile Asn Glu Lys
1               5                   10

<210> SEQ ID NO 110
<211> LENGTH: 21
<212> TYPE: PRT
<213> ORGANISM: Artificial Sequence
<220> FEATURE:
<223> OTHER INFORMATION: Synthetic peptide

<400> SEQUENCE: 110

Leu Val Asp Leu Val Ile Pro Val Asn Gly Pro Gly Lys Phe Glu Ala
1               5                   10                  15

Phe Asp Leu Ala Lys
            20

<210> SEQ ID NO 111
<211> LENGTH: 18
<212> TYPE: PRT
<213> ORGANISM: Artificial Sequence
<220> FEATURE:
<223> OTHER INFORMATION: Synthetic peptide

<400> SEQUENCE: 111
```

```
Lys Asn Pro Gln Leu Gln Asp Leu Asp Ile Phe Val Asn Tyr Val Glu
1               5                   10                  15

Ile Lys

<210> SEQ ID NO 112
<211> LENGTH: 10
<212> TYPE: PRT
<213> ORGANISM: Artificial Sequence
<220> FEATURE:
<223> OTHER INFORMATION: Synthetic peptide

<400> SEQUENCE: 112

Asp Glu His Gln Lys Ile His Gln Phe Arg
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113

Phe Arg Asp Glu His Gln Lys
1               5

<210> SEQ ID NO 114
<211> LENGTH: 13
<212> TYPE: PRT
<213> ORGANISM: Artificial Sequence
<220> FEATURE:
<223> OTHER INFORMATION: Synthetic peptide

<400> SEQUENCE: 114

Phe Pro Ile Leu Asn Leu Ile Gln Met Ser Ala Thr Arg
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic peptide

<400> SEQUENCE: 115

Thr Asn Ala Asn Ala Phe Val Ser His Leu Ala Gly Lys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic peptide

<400> SEQUENCE: 116

Ala Leu Pro Val Asp Val Val Ala Asn Ala Tyr Arg
1               5                   10

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 117

Tyr Val Tyr Asp Val Asn Asn Asn Ala Asn Gln Leu Glu Pro Arg Gln
1               5                   10                  15

Lys Glu Phe Leu
            20

<210> SEQ ID NO 118
<211> LENGTH: 21
<212> TYPE: PRT
<213> ORGANISM: Artificial Sequence
<220> FEATURE:
<223> OTHER INFORMATION: Synthetic peptide

<400> SEQUENCE: 118

Val Tyr Val Tyr Asp Val Asn Asn Asn Ala Asn Gln Leu Glu Pro Arg
1               5                   10                  15

Gln Lys Glu Phe Leu
            20

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Ala Asp Ser Tyr Asn Pro Arg
1               5

<210> SEQ ID NO 120
<211> LENGTH: 16
<212> TYPE: PRT
<213> ORGANISM: Artificial Sequence
<220> FEATURE:
<223> OTHER INFORMATION: Synthetic peptide

<400> SEQUENCE: 120

Lys Pro Thr Leu Thr Gln Gln Gln Glu Gln Ala Gln Ala Gln Asp Gln
1               5                   10                  15

<210> SEQ ID NO 121
<211> LENGTH: 13
<212> TYPE: PRT
<213> ORGANISM: Artificial Sequence
<220> FEATURE:
<223> OTHER INFORMATION: Synthetic peptide

<400> SEQUENCE: 121

Gln Ala Gln Ala Gln Asp Gln Tyr Gln Gln Val Gln Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic peptide

<400> SEQUENCE: 122

Gln Ala Gln Asp Gln Tyr Gln Gln Val Gln Tyr
1               5                   10

<210> SEQ ID NO 123
<211> LENGTH: 8

-continued

```
<212> TYPE: PRT
<213> ORGANISM: Artificial Sequence
<220> FEATURE:
<223> OTHER INFORMATION: Synthetic peptide

<400> SEQUENCE: 123

Leu Gln Ala Phe Glu Pro Leu Arg
1               5

<210> SEQ ID NO 124
<211> LENGTH: 11
<212> TYPE: PRT
<213> ORGANISM: Artificial Sequence
<220> FEATURE:
<223> OTHER INFORMATION: Synthetic peptide

<400> SEQUENCE: 124

Ser Arg Val Gln Val Val Ser Asn Phe Gly Lys
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic peptide

<400> SEQUENCE: 125

Trp Asn Val Asn Ala His Ser Leu Val Tyr
1               5                   10

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

Asn Val Asn Ala His Ser Leu Val Tyr
1               5

<210> SEQ ID NO 127
<211> LENGTH: 15
<212> TYPE: PRT
<213> ORGANISM: Artificial Sequence
<220> FEATURE:
<223> OTHER INFORMATION: Synthetic peptide

<400> SEQUENCE: 127

Ile Gln Gly Arg Ser Arg Val Gln Val Val Ser Asn Phe Gly Lys
1               5                   10                  15

<210> SEQ ID NO 128
<211> LENGTH: 14
<212> TYPE: PRT
<213> ORGANISM: Artificial Sequence
<220> FEATURE:
<223> OTHER INFORMATION: Synthetic peptide

<400> SEQUENCE: 128

Gly Lys Thr Val Phe Asp Gly Val Leu Arg Pro Gly Gln Leu
1               5                   10

<210> SEQ ID NO 129
<211> LENGTH: 15
<212> TYPE: PRT
```

```
<213> ORGANISM: Artificial Sequence
<220> FEATURE:
<223> OTHER INFORMATION: Synthetic peptide

<400> SEQUENCE: 129

Phe Gly Lys Thr Val Phe Asp Gly Val Leu Arg Pro Gly Gln Leu
1               5                   10                  15

<210> SEQ ID NO 130
<211> LENGTH: 19
<212> TYPE: PRT
<213> ORGANISM: Artificial Sequence
<220> FEATURE:
<223> OTHER INFORMATION: Synthetic peptide

<400> SEQUENCE: 130

Phe Gln Gln Gln Tyr Tyr Pro Gly Leu Ser Asn Glu Ser Glu Ser Glu
1               5                   10                  15

Thr Ser Glu

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide

<400> SEQUENCE: 131

Gln Gln Tyr Tyr Pro Gly Leu Ser Asn
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic peptide

<400> SEQUENCE: 132

Gln Gln Gln Tyr Tyr Pro Gly Leu Ser Asn
1               5                   10

<210> SEQ ID NO 133
<211> LENGTH: 21
<212> TYPE: PRT
<213> ORGANISM: Artificial Sequence
<220> FEATURE:
<223> OTHER INFORMATION: Synthetic peptide

<400> SEQUENCE: 133

Val Thr Asn Leu Asn Thr Gln Asn Phe Pro Ile Leu Ser Leu Val Gln
1               5                   10                  15

Met Ser Ala Val Lys
            20

<210> SEQ ID NO 134
<211> LENGTH: 19
<212> TYPE: PRT
<213> ORGANISM: Artificial Sequence
<220> FEATURE:
<223> OTHER INFORMATION: Synthetic peptide

<400> SEQUENCE: 134

Ile Thr Gln Gly Arg Ala Arg Val Gln Val Val Asn Asn Asn Gly Lys
1               5                   10                  15
```

Thr Val Phe

<210> SEQ ID NO 135
<211> LENGTH: 22
<212> TYPE: PRT
<213> ORGANISM: Artificial Sequence
<220> FEATURE:
<223> OTHER INFORMATION: Synthetic peptide

<400> SEQUENCE: 135

Ile Thr Gln Gly Arg Ala Arg Val Gln Val Val Asn Asn Asn Gly Lys
1               5                   10                  15

Thr Val Phe Asn Gly Glu
            20

<210> SEQ ID NO 136
<211> LENGTH: 21
<212> TYPE: PRT
<213> ORGANISM: Artificial Sequence
<220> FEATURE:
<223> OTHER INFORMATION: Synthetic peptide

<400> SEQUENCE: 136

Ile Thr Gln Gly Arg Ala Arg Val Gln Val Val Asn Asn Asn Gly Lys
1               5                   10                  15

Thr Val Phe Asn Gly
            20

<210> SEQ ID NO 137
<211> LENGTH: 13
<212> TYPE: PRT
<213> ORGANISM: Artificial Sequence
<220> FEATURE:
<223> OTHER INFORMATION: Synthetic peptide

<400> SEQUENCE: 137

Arg Val Gln Val Val Asn Asn Asn Gly Lys Thr Val Phe
1               5                   10

<210> SEQ ID NO 138
<211> LENGTH: 18
<212> TYPE: PRT
<213> ORGANISM: Artificial Sequence
<220> FEATURE:
<223> OTHER INFORMATION: Synthetic peptide

<400> SEQUENCE: 138

Arg Ala Leu Pro Asn Asp Val Leu Ala Asn Ala Tyr Arg Ile Ser Arg
1               5                   10                  15

Glu Glu

<210> SEQ ID NO 139
<211> LENGTH: 16
<212> TYPE: PRT
<213> ORGANISM: Artificial Sequence
<220> FEATURE:
<223> OTHER INFORMATION: Synthetic peptide

<400> SEQUENCE: 139

Ser Ile Phe Arg Ala Leu Pro Asn Asp Val Leu Ala Asn Ala Tyr Arg
1               5                   10                  15

<210> SEQ ID NO 140
<211> LENGTH: 15
<212> TYPE: PRT

```
<213> ORGANISM: Artificial Sequence
<220> FEATURE:
<223> OTHER INFORMATION: Synthetic peptide

<400> SEQUENCE: 140

Ser Ile Phe Arg Ala Leu Pro Asn Asp Val Leu Ala Asn Ala Tyr
1               5                   10                  15

<210> SEQ ID NO 141
<211> LENGTH: 13
<212> TYPE: PRT
<213> ORGANISM: Artificial Sequence
<220> FEATURE:
<223> OTHER INFORMATION: Synthetic peptide

<400> SEQUENCE: 141

Ser Ile Phe Arg Ala Leu Pro Asn Asp Val Leu Ala Asn
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthetic peptide

<400> SEQUENCE: 142

Ser Ser Ile Phe Arg Ala Leu Pro Asn Asp Val Leu Ala Asn Ala Tyr
1               5                   10                  15

Arg

<210> SEQ ID NO 143
<211> LENGTH: 21
<212> TYPE: PRT
<213> ORGANISM: Artificial Sequence
<220> FEATURE:
<223> OTHER INFORMATION: Synthetic peptide

<400> SEQUENCE: 143

Ser Ile Phe Arg Ala Leu Pro Asn Asp Val Leu Ala Asn Ala Tyr Arg
1               5                   10                  15

Ile Ser Arg Glu Glu
            20

<210> SEQ ID NO 144
<211> LENGTH: 9
<212> TYPE: PRT
<213> ORGANISM: Artificial Sequence
<220> FEATURE:
<223> OTHER INFORMATION: Synthetic peptide

<400> SEQUENCE: 144

Ser Ile Phe Arg Ala Leu Pro Asn Asp
1               5

<210> SEQ ID NO 145
<211> LENGTH: 19
<212> TYPE: PRT
<213> ORGANISM: Artificial Sequence
<220> FEATURE:
<223> OTHER INFORMATION: Synthetic peptide

<400> SEQUENCE: 145

Ile Tyr Val Thr Asp Leu Asn Asn Gly Ala Asn Gln Leu Asp Pro Arg
1               5                   10                  15
```

-continued

Gln Arg Asp

<210> SEQ ID NO 146
<211> LENGTH: 21
<212> TYPE: PRT
<213> ORGANISM: Artificial Sequence
<220> FEATURE:
<223> OTHER INFORMATION: Synthetic peptide

<400> SEQUENCE: 146

Val Thr Asn Leu Asn Ser Gln Asn Phe Pro Ile Leu Asn Leu Val Gln
1               5                   10                  15

Met Ser Ala Val Lys
            20

<210> SEQ ID NO 147
<211> LENGTH: 8
<212> TYPE: PRT
<213> ORGANISM: Artificial Sequence
<220> FEATURE:
<223> OTHER INFORMATION: Synthetic peptide

<400> SEQUENCE: 147

Gln Asn Ile Asp Asn Pro Asn Arg
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide

<400> SEQUENCE: 148

Ala Asp Thr Tyr Asn Pro Arg
1               5

<210> SEQ ID NO 149
<211> LENGTH: 21
<212> TYPE: PRT
<213> ORGANISM: Artificial Sequence
<220> FEATURE:
<223> OTHER INFORMATION: Synthetic peptide

<400> SEQUENCE: 149

Asn Ile Asp Asn Pro Asn Arg Ala Asp Thr Tyr Asn Pro Arg Ala Gly
1               5                   10                  15

Arg Val Thr Asn Leu
            20

<210> SEQ ID NO 150
<211> LENGTH: 25
<212> TYPE: PRT
<213> ORGANISM: Artificial Sequence
<220> FEATURE:
<223> OTHER INFORMATION: Synthetic peptide

<400> SEQUENCE: 150

Arg Val Arg Gln Asn Ile Asp Asn Pro Asn Arg Ala Asp Thr Tyr Asn
1               5                   10                  15

Pro Arg Ala Gly Arg Val Thr Asn Leu
            20                  25

<210> SEQ ID NO 151
<211> LENGTH: 18

-continued

```
<212> TYPE: PRT
<213> ORGANISM: Artificial Sequence
<220> FEATURE:
<223> OTHER INFORMATION: Synthetic peptide

<400> SEQUENCE: 151

Thr Asn Pro Asn Ser Met Val Ser His Ile Ala Gly Lys Ser Ser Ile
1               5                   10                  15

Phe Arg

<210> SEQ ID NO 152
<211> LENGTH: 16
<212> TYPE: PRT
<213> ORGANISM: Artificial Sequence
<220> FEATURE:
<223> OTHER INFORMATION: Synthetic peptide

<400> SEQUENCE: 152

His Asn Arg Gly Asp Glu Phe Gly Ala Phe Thr Pro Leu Gln Tyr Lys
1               5                   10                  15

<210> SEQ ID NO 153
<211> LENGTH: 12
<212> TYPE: PRT
<213> ORGANISM: Artificial Sequence
<220> FEATURE:
<223> OTHER INFORMATION: Synthetic peptide

<400> SEQUENCE: 153

Ser Tyr Gln Asp Val Tyr Asn Val Ala Glu Ser Ser
1               5                   10

<210> SEQ ID NO 154
<211> LENGTH: 8
<212> TYPE: PRT
<213> ORGANISM: Artificial Sequence
<220> FEATURE:
<223> OTHER INFORMATION: Synthetic peptide

<400> SEQUENCE: 154

Ile Ser Arg Glu Glu Ala Gln Arg
1               5

<210> SEQ ID NO 155
<211> LENGTH: 21
<212> TYPE: PRT
<213> ORGANISM: Artificial Sequence
<220> FEATURE:
<223> OTHER INFORMATION: Synthetic peptide

<400> SEQUENCE: 155

Ser Ile Phe Arg Ala Leu Pro Thr Asp Val Leu Ala Asn Ala Tyr Arg
1               5                   10                  15

Ile Ser Arg Glu Glu
                20

<210> SEQ ID NO 156
<211> LENGTH: 19
<212> TYPE: PRT
<213> ORGANISM: Artificial Sequence
<220> FEATURE:
<223> OTHER INFORMATION: Synthetic peptide

<400> SEQUENCE: 156

Tyr Arg Ile Ser Arg Glu Glu Ala Gln Arg Leu Lys His Asn Arg Gly
1               5                   10                  15
```

Asp Glu Phe

<210> SEQ ID NO 157
<211> LENGTH: 18
<212> TYPE: PRT
<213> ORGANISM: Artificial Sequence
<220> FEATURE:
<223> OTHER INFORMATION: Synthetic peptide

<400> SEQUENCE: 157

Tyr Arg Ile Ser Arg Glu Glu Ala Gln Arg Leu Lys His Asn Arg Gly
1               5                   10                  15

Asp Glu

<210> SEQ ID NO 158
<211> LENGTH: 10
<212> TYPE: PRT
<213> ORGANISM: Artificial Sequence
<220> FEATURE:
<223> OTHER INFORMATION: Synthetic peptide

<400> SEQUENCE: 158

Phe Lys Asp Glu His Gln Lys Ile His Arg
1               5                   10

<210> SEQ ID NO 159
<211> LENGTH: 14
<212> TYPE: PRT
<213> ORGANISM: Artificial Sequence
<220> FEATURE:
<223> OTHER INFORMATION: Synthetic peptide

<400> SEQUENCE: 159

Gln Gly Asp Val Ile Ala Leu Pro Ala Gly Val Ala His Trp
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Synthetic peptide

<400> SEQUENCE: 160

Thr Val Phe Asn Gly Glu Leu Arg Arg
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic peptide

<400> SEQUENCE: 161

Thr Val Phe Asn Gly Glu Leu Arg
1               5

<210> SEQ ID NO 162
<211> LENGTH: 13
<212> TYPE: PRT
<213> ORGANISM: Artificial Sequence
<220> FEATURE:
<223> OTHER INFORMATION: Synthetic peptide

<400> SEQUENCE: 162

```
Gln Val Gln Val Val Asn Asn Asn Gly Lys Thr Val Phe
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic peptide

<400> SEQUENCE: 163

Tyr Ile Ile Gln Gly Arg Gly Ile Thr Gly Pro Thr Phe
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Synthetic peptide

<400> SEQUENCE: 164

Val Tyr Ile Ile Gln Gly Arg Gly Ile Thr Gly Pro Thr Phe
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic peptide

<400> SEQUENCE: 165

Leu Gln Ala Phe Glu Pro Ile Arg Ser Val Arg
1               5                   10

<210> SEQ ID NO 166
<211> LENGTH: 22
<212> TYPE: PRT
<213> ORGANISM: Artificial Sequence
<220> FEATURE:
<223> OTHER INFORMATION: Synthetic peptide

<400> SEQUENCE: 166

Gly Leu Ser Leu Leu Gln Pro Tyr Ala Ser Leu Gln Glu Gln Glu Gln
1               5                   10                  15

Gly Gln Met Gln Ser Arg
            20

<210> SEQ ID NO 167
<211> LENGTH: 8
<212> TYPE: PRT
<213> ORGANISM: Artificial Sequence
<220> FEATURE:
<223> OTHER INFORMATION: Synthetic peptide

<400> SEQUENCE: 167

Gly Glu Ile Val Arg Val Glu Arg
1               5

<210> SEQ ID NO 168
<211> LENGTH: 13
<212> TYPE: PRT
<213> ORGANISM: Artificial Sequence
<220> FEATURE:
<223> OTHER INFORMATION: Synthetic peptide
```

```
<400> SEQUENCE: 168

Arg Gly Leu Ser Leu Leu Gln Pro Tyr Ala Ser Leu Gln
1               5                   10

<210> SEQ ID NO 169
<211> LENGTH: 15
<212> TYPE: PRT
<213> ORGANISM: Artificial Sequence
<220> FEATURE:
<223> OTHER INFORMATION: Synthetic peptide

<400> SEQUENCE: 169

Arg Gly Leu Ser Leu Leu Gln Pro Tyr Ala Ser Leu Gln Glu Gln
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Synthetic peptide

<400> SEQUENCE: 170

Arg Gly Leu Ser Leu Leu Gln Pro Tyr Ala Ser Leu Gln Glu Gln Glu
1               5                   10                  15

<210> SEQ ID NO 171
<211> LENGTH: 14
<212> TYPE: PRT
<213> ORGANISM: Artificial Sequence
<220> FEATURE:
<223> OTHER INFORMATION: Synthetic peptide

<400> SEQUENCE: 171

Arg Gly Leu Ser Leu Leu Gln Pro Tyr Ala Ser Leu Gln Glu
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Synthetic peptide

<400> SEQUENCE: 172

Arg Asn Pro Gln Ala Tyr Arg
1               5

<210> SEQ ID NO 173
<211> LENGTH: 13
<212> TYPE: PRT
<213> ORGANISM: Artificial Sequence
<220> FEATURE:
<223> OTHER INFORMATION: Synthetic peptide

<400> SEQUENCE: 173

Phe Leu Leu Ala Gly Asn Lys Arg Asn Pro Gln Ala Tyr
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 174

Glu Val Glu Glu Trp Ser Gln Asn Ile Phe
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Synthetic peptide

<400> SEQUENCE: 175

Leu Ala Gly Asn Lys Arg Asn Pro Gln Ala Tyr Arg
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic peptide

<400> SEQUENCE: 176

Phe Leu Leu Ala Gly Asn Lys Arg Asn Pro Gln Ala
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Synthetic peptide

<400> SEQUENCE: 177

Glu Leu Gly Ala Pro Asp Val Gly His Pro Met Ser Glu
1               5                   10

<210> SEQ ID NO 178
<211> LENGTH: 16
<212> TYPE: PRT
<213> ORGANISM: Artificial Sequence
<220> FEATURE:
<223> OTHER INFORMATION: Synthetic peptide

<400> SEQUENCE: 178

Ile Val Gln Gly His Ala Arg Val Gln Val Val Ser Asn Leu Gly Lys
1               5                   10                  15

<210> SEQ ID NO 179
<211> LENGTH: 14
<212> TYPE: PRT
<213> ORGANISM: Artificial Sequence
<220> FEATURE:
<223> OTHER INFORMATION: Synthetic peptide

<400> SEQUENCE: 179

Ile Val Gln Gly His Ala Arg Val Gln Val Val Ser Asn Leu
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Synthetic peptide

<400> SEQUENCE: 180

```
Ile Val Gln Gly His Ala Arg Val Gln Val Val Ser Asn
1               5                   10
```

<210> SEQ ID NO 181
<211> LENGTH: 13
<212> TYPE: PRT
<213> ORGANISM: Artificial Sequence
<220> FEATURE:
<223> OTHER INFORMATION: Synthetic peptide

<400> SEQUENCE: 181

```
Asn Asn Arg Gly Glu Glu Leu Gly Ala Phe Thr Pro Arg
1               5                   10
```

<210> SEQ ID NO 182
<211> LENGTH: 10
<212> TYPE: PRT
<213> ORGANISM: Artificial Sequence
<220> FEATURE:
<223> OTHER INFORMATION: Synthetic peptide

<400> SEQUENCE: 182

```
Gly Glu Glu Leu Gly Ala Phe Thr Pro Arg
1               5                   10
```

<210> SEQ ID NO 183
<211> LENGTH: 13
<212> TYPE: PRT
<213> ORGANISM: Artificial Sequence
<220> FEATURE:
<223> OTHER INFORMATION: Synthetic peptide

<400> SEQUENCE: 183

```
Phe Pro Ile Leu Asn Leu Val Gln Leu Ser Ala Thr Arg
1               5                   10
```

<210> SEQ ID NO 184
<211> LENGTH: 31
<212> TYPE: PRT
<213> ORGANISM: Artificial Sequence
<220> FEATURE:
<223> OTHER INFORMATION: Synthetic peptide

<400> SEQUENCE: 184

```
Ser Ile Glu Gln His Ser Gly Gln Asn Ile Phe Ser Gly Phe Asn Asn
1               5                   10                  15

Glu Leu Leu Ser Glu Ala Leu Gly Val Asn Ala Leu Val Ala Lys
            20                  25                  30
```

<210> SEQ ID NO 185
<211> LENGTH: 8
<212> TYPE: PRT
<213> ORGANISM: Artificial Sequence
<220> FEATURE:
<223> OTHER INFORMATION: Synthetic peptide

<400> SEQUENCE: 185

```
Leu Gln Gly Gln Asn Asp Gln Arg
1               5
```

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 186

Ser Gly Phe Asn Asn Glu Leu Leu Ser Glu Ala Leu Gly Val Asn Ala
1               5                   10                  15

Leu Val Ala Lys
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide

<400> SEQUENCE: 187

Pro Ala Phe Ala Gln Gln Gln Glu Gln Ala Gln Gln Glu Gln Ala
1               5                   10                  15

Gln Ala Gln Tyr
            20

<210> SEQ ID NO 188
<211> LENGTH: 15
<212> TYPE: PRT
<213> ORGANISM: Artificial Sequence
<220> FEATURE:
<223> OTHER INFORMATION: Synthetic peptide

<400> SEQUENCE: 188

Val Ala Lys Arg Leu Gln Gly Gln Asn Asp Gln Arg Gly Glu Ile
1               5                   10                  15

<210> SEQ ID NO 189
<211> LENGTH: 17
<212> TYPE: PRT
<213> ORGANISM: Artificial Sequence
<220> FEATURE:
<223> OTHER INFORMATION: Synthetic peptide

<400> SEQUENCE: 189

Ala Leu Val Ala Lys Arg Leu Gln Gly Gln Asn Asp Gln Arg Gly Glu
1               5                   10                  15

Ile

<210> SEQ ID NO 190
<211> LENGTH: 13
<212> TYPE: PRT
<213> ORGANISM: Artificial Sequence
<220> FEATURE:
<223> OTHER INFORMATION: Synthetic peptide

<400> SEQUENCE: 190

Leu Gln Gly Gln Asn Asp Gln Arg Gly Glu Ile Ile Arg
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic peptide

<400> SEQUENCE: 191

Pro Asn Val Asn Pro Trp His Asn Pro Arg Gln Gly Gly Phe
1               5                   10
```

```
<210> SEQ ID NO 192
<211> LENGTH: 13
<212> TYPE: PRT
<213> ORGANISM: Artificial Sequence
<220> FEATURE:
<223> OTHER INFORMATION: Synthetic peptide

<400> SEQUENCE: 192

Phe Tyr Asn Glu Gly Asp Ala Pro Val Val Ala Leu Tyr
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic peptide

<400> SEQUENCE: 193

Phe Tyr Asn Glu Gly Asp Ala Pro Val Val
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Synthetic peptide

<400> SEQUENCE: 194

Phe Tyr Asn Glu Gly Asp Ala Pro Val Val Ala Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Synthetic peptide

<400> SEQUENCE: 195

Phe Tyr Asn Glu Gly Asp Ala Pro Val Val Ala
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthetic peptide

<400> SEQUENCE: 196

Thr Asn Ala Asn Ser Met Val Ser His Leu Ala Gly Lys
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Synthetic peptide

<400> SEQUENCE: 197

Ala Met Pro Val Asp Val Ile Ala Asn Ala Tyr Arg
1               5                   10
```

```
<210> SEQ ID NO 198
<211> LENGTH: 28
<212> TYPE: PRT
<213> ORGANISM: Artificial Sequence
<220> FEATURE:
<223> OTHER INFORMATION: Synthetic peptide

<400> SEQUENCE: 198

Asn Trp Glu Asn Val Leu Leu Gly Leu Gly Val Ala Gly Ser Ala Pro
1               5                   10                  15

Gly Ile Glu Gly Asp Glu Ile Ala Pro Leu Ala Lys
            20                  25

<210> SEQ ID NO 199
<211> LENGTH: 19
<212> TYPE: PRT
<213> ORGANISM: Artificial Sequence
<220> FEATURE:
<223> OTHER INFORMATION: Synthetic peptide

<400> SEQUENCE: 199

Asn Val Leu Leu Gly Leu Gly Val Ala Gly Ser Ala Pro Gly Ile Glu
1               5                   10                  15

Gly Asp Glu

<210> SEQ ID NO 200
<211> LENGTH: 28
<212> TYPE: PRT
<213> ORGANISM: Artificial Sequence
<220> FEATURE:
<223> OTHER INFORMATION: Synthetic peptide

<400> SEQUENCE: 200

Asn Trp Glu Asn Val Leu Leu Gly Leu Gly Val Ala Gly Ser Ala Pro
1               5                   10                  15

Gly Ile Glu Gly Asp Glu Ile Ala Pro Leu Ala Lys
            20                  25

<210> SEQ ID NO 201
<211> LENGTH: 21
<212> TYPE: PRT
<213> ORGANISM: Artificial Sequence
<220> FEATURE:
<223> OTHER INFORMATION: Synthetic peptide

<400> SEQUENCE: 201

Phe Asn Ala Pro Leu Ala His Leu Ile Met Ala Gly Ala Asp Val Leu
1               5                   10                  15

Ala Val Pro Ser Arg
            20

<210> SEQ ID NO 202
<211> LENGTH: 10
<212> TYPE: PRT
<213> ORGANISM: Artificial Sequence
<220> FEATURE:
<223> OTHER INFORMATION: Synthetic peptide

<400> SEQUENCE: 202

Phe Asn Ala Pro Leu Ala His Leu Ile Met
1               5                   10

<210> SEQ ID NO 203
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 203

Phe Asn Ala Pro Leu Ala His Leu Ile Met Ala Gly Ala Asp Val Leu
1               5                   10                  15

Ala Val Pro Ser Arg
            20

<210> SEQ ID NO 204
<211> LENGTH: 12
<212> TYPE: PRT
<213> ORGANISM: Artificial Sequence
<220> FEATURE:
<223> OTHER INFORMATION: Synthetic peptide

<400> SEQUENCE: 204

Val Val Gly Thr Pro Ala Tyr Glu Glu Met Val Arg
1               5                   10

<210> SEQ ID NO 205
<211> LENGTH: 21
<212> TYPE: PRT
<213> ORGANISM: Artificial Sequence
<220> FEATURE:
<223> OTHER INFORMATION: Synthetic peptide

<400> SEQUENCE: 205

Thr Gly Gly Leu Gly Asp Val Leu Gly Gly Leu Pro Pro Ala Met Ala
1               5                   10                  15

Ala Asn Gly His Arg
            20

<210> SEQ ID NO 206
<211> LENGTH: 17
<212> TYPE: PRT
<213> ORGANISM: Artificial Sequence
<220> FEATURE:
<223> OTHER INFORMATION: Synthetic peptide

<400> SEQUENCE: 206

Tyr Asp Gln Tyr Lys Asp Ala Trp Asp Thr Ser Val Val Ala Glu Ile
1               5                   10                  15

Lys

<210> SEQ ID NO 207
<211> LENGTH: 12
<212> TYPE: PRT
<213> ORGANISM: Artificial Sequence
<220> FEATURE:
<223> OTHER INFORMATION: Synthetic peptide

<400> SEQUENCE: 207

Asp Ala Trp Asp Thr Ser Val Val Ala Glu Ile Lys
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Synthetic peptide

<400> SEQUENCE: 208
```

```
Val Met Val Ile Ser Pro Arg
1               5

<210> SEQ ID NO 209
<211> LENGTH: 22
<212> TYPE: PRT
<213> ORGANISM: Artificial Sequence
<220> FEATURE:
<223> OTHER INFORMATION: Synthetic peptide

<400> SEQUENCE: 209

Leu Thr Gly Ile Thr Gly Ile Val Asn Gly Met Asp Val Ser Glu Trp
1               5                   10                  15

Asp Pro Ser Lys Asp Lys
            20

<210> SEQ ID NO 210
<211> LENGTH: 18
<212> TYPE: PRT
<213> ORGANISM: Artificial Sequence
<220> FEATURE:
<223> OTHER INFORMATION: Synthetic peptide

<400> SEQUENCE: 210

Val Leu Thr Val Ser Pro Tyr Tyr Ala Glu Glu Leu Ile Ser Gly Ile
1               5                   10                  15

Ala Arg

<210> SEQ ID NO 211
<211> LENGTH: 14
<212> TYPE: PRT
<213> ORGANISM: Artificial Sequence
<220> FEATURE:
<223> OTHER INFORMATION: Synthetic peptide

<400> SEQUENCE: 211

Glu Ala Leu Gln Ala Glu Ala Gly Leu Pro Val Asp Arg Lys
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic peptide

<400> SEQUENCE: 212

Tyr Asp Ala Thr Thr Ala Ile Glu Ala Lys
1               5                   10

<210> SEQ ID NO 213
<211> LENGTH: 9
<212> TYPE: PRT
<213> ORGANISM: Artificial Sequence
<220> FEATURE:
<223> OTHER INFORMATION: Synthetic peptide

<400> SEQUENCE: 213

Ile Pro Leu Ile Ala Phe Ile Gly Arg
1               5

<210> SEQ ID NO 214
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 214

Ala Gly Ile Leu Glu Ala Asp Arg
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic peptide

<400> SEQUENCE: 215

Ile Pro Leu Ile Ala Phe Ile Gly Arg
1               5

<210> SEQ ID NO 216
<211> LENGTH: 11
<212> TYPE: PRT
<213> ORGANISM: Artificial Sequence
<220> FEATURE:
<223> OTHER INFORMATION: Synthetic peptide

<400> SEQUENCE: 216

Val Phe Ile Asp His Pro Ser Phe Leu Glu Lys
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Synthetic peptide

<400> SEQUENCE: 217

Gly Pro Asp Thr Gly Val Asp Tyr Lys Asp Asn Gln Met
1               5                   10

<210> SEQ ID NO 218
<211> LENGTH: 16
<212> TYPE: PRT
<213> ORGANISM: Artificial Sequence
<220> FEATURE:
<223> OTHER INFORMATION: Synthetic peptide

<400> SEQUENCE: 218

Ile Tyr Gly Pro Asp Thr Gly Val Asp Tyr Lys Asp Asn Gln Met Arg
1               5                   10                  15

<210> SEQ ID NO 219
<211> LENGTH: 11
<212> TYPE: PRT
<213> ORGANISM: Artificial Sequence
<220> FEATURE:
<223> OTHER INFORMATION: Synthetic peptide

<400> SEQUENCE: 219

Ile Tyr Gly Pro Asp Thr Gly Val Asp Tyr Lys
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 220

Ile Leu Asn Leu Asn Asn Asn Pro Tyr Phe Lys
1               5                   10

<210> SEQ ID NO 221
<211> LENGTH: 16
<212> TYPE: PRT
<213> ORGANISM: Artificial Sequence
<220> FEATURE:
<223> OTHER INFORMATION: Synthetic peptide

<400> SEQUENCE: 221

Ala Pro Thr Gly Thr Phe Ile Ala Ser Gly Val Val Gly Lys Asp
1               5                   10                  15

<210> SEQ ID NO 222
<211> LENGTH: 463
<212> TYPE: PRT
<213> ORGANISM: Vicia faba

<400> SEQUENCE: 222

Met Ala Ala Thr Thr Leu Lys Asp Ser Phe Pro Leu Leu Thr Leu Leu
1               5                   10                  15

Gly Ile Ala Phe Leu Ala Ser Val Cys Leu Ser Ser Arg Ser Asp Gln
                20                  25                  30

Asp Asn Pro Phe Val Phe Glu Ser Asn Arg Phe Gln Thr Leu Phe Glu
            35                  40                  45

Asn Glu Asn Gly His Ile Arg Leu Leu Gln Lys Phe Asp Gln His Ser
    50                  55                  60

Lys Leu Leu Glu Asn Leu Gln Asn Tyr Arg Leu Leu Glu Tyr Lys Ser
65                  70                  75                  80

Lys Pro His Thr Ile Phe Leu Pro Gln Gln Thr Asp Ala Asp Phe Ile
                85                  90                  95

Leu Val Val Leu Ser Gly Lys Ala Ile Leu Thr Val Leu Leu Pro Asn
            100                 105                 110

Asp Arg Asn Ser Phe Ser Leu Glu Arg Gly Asp Thr Ile Lys Leu Pro
        115                 120                 125

Ala Gly Thr Ile Gly Tyr Leu Val Asn Arg Asp Glu Glu Asp Leu
    130                 135                 140

Arg Val Leu Asp Leu Val Ile Pro Val Asn Arg Pro Gly Glu Pro Gln
145                 150                 155                 160

Ser Phe Leu Leu Ser Gly Asn Gln Asn Gln Pro Ser Ile Leu Ser Gly
                165                 170                 175

Phe Ser Lys Asn Ile Leu Glu Ala Ser Phe Asn Thr Asp Tyr Lys Glu
            180                 185                 190

Ile Glu Lys Val Leu Leu Glu His Gly Lys Glu Lys Tyr His Arg
        195                 200                 205

Arg Gly Leu Lys Asp Arg Gln Arg Gly Glu Glu Asn Val Ile
    210                 215                 220

Val Lys Ile Ser Arg Lys Gln Ile Glu Glu Leu Asn Lys Asn Ala Lys
225                 230                 235                 240

Ser Ser Ser Lys Lys Ser Thr Ser Glu Ser Glu Pro Phe Asn Leu
                245                 250                 255

Arg Ser Arg Glu Pro Ile Tyr Ser Asn Lys Phe Gly Lys Phe Phe Glu
            260                 265                 270

Ile Thr Pro Lys Arg Asn Pro Gln Leu Gln Asp Leu Asn Ile Phe Val

```
                275                 280                 285
Asn Tyr Val Glu Ile Asn Glu Gly Ser Leu Leu Pro His Tyr Asn
    290                 295                 300
Ser Arg Ala Ile Val Ile Val Thr Val Asn Glu Gly Lys Gly Asp Phe
305                 310                 315                 320
Glu Leu Val Gly Gln Arg Asn Glu Asn Gln Gln Gly Leu Arg Glu Glu
                325                 330                 335
Tyr Asp Glu Glu Lys Glu Gln Gly Glu Glu Ile Arg Lys Gln Val
            340                 345                 350
Gln Asn Tyr Lys Ala Lys Leu Ser Pro Gly Asp Val Leu Val Ile Pro
                355                 360                 365
Ala Gly Tyr Pro Val Ala Ile Lys Ala Ser Ser Asn Leu Asn Leu Val
            370                 375                 380
Gly Phe Gly Ile Asn Ala Glu Asn Asn Gln Arg Tyr Phe Leu Ala Gly
385                 390                 395                 400
Glu Glu Asp Asn Val Ile Ser Gln Ile His Lys Pro Val Lys Glu Leu
                405                 410                 415
Ala Phe Pro Gly Ser Ala Gln Glu Val Asp Thr Leu Leu Glu Asn Gln
            420                 425                 430
Lys Gln Ser His Phe Ala Asn Ala Gln Pro Arg Glu Arg Glu Arg Gly
                435                 440                 445
Ser Gln Glu Ile Lys Asp His Leu Tyr Ser Ile Leu Gly Ser Phe
            450                 455                 460

<210> SEQ ID NO 223
<211> LENGTH: 446
<212> TYPE: PRT
<213> ORGANISM: Cicer arietinum

<400> SEQUENCE: 223

Met Ala Ile Lys Ala Arg Phe Pro Leu Leu Val Leu Leu Gly Ile Val
1               5                   10                  15
Phe Leu Ala Ser Val Cys Ala Lys Ser Asp Lys Glu Asn Pro Phe Phe
                20                  25                  30
Phe Lys Ser Asn Asn Cys Gln Thr Leu Phe Glu Asn Glu Asn Gly His
            35                  40                  45
Val Arg Leu Leu Gln Arg Phe Asp Lys Arg Ser Gln Leu Phe Glu Asn
        50                  55                  60
Leu Gln Asn Tyr Arg Leu Met Glu Tyr Asn Ser Lys Pro His Thr Leu
65                  70                  75                  80
Phe Leu Pro Gln His Asn Asp Ala Asp Phe Ile Leu Val Val Leu Arg
                85                  90                  95
Gly Arg Ala Ile Leu Thr Val Leu Asn Pro Asn Asp Arg Asn Thr Phe
            100                 105                 110
Lys Leu Glu Arg Gly Asp Thr Ile Lys Leu Pro Ala Gly Thr Ile Ala
        115                 120                 125
Tyr Leu Ala Asn Arg Asp Asp Asn Glu Asp Leu Arg Val Leu Asp Leu
    130                 135                 140
Ala Ile Pro Val Asn Arg Pro Gly Gln Phe Gln Ser Phe Ser Leu Ser
145                 150                 155                 160
Gly Asn Glu Asn Gln Gln Ser Tyr Phe Gln Gly Phe Ser Lys Lys Ile
                165                 170                 175
Leu Glu Ala Ser Phe Asn Ser Asp Tyr Glu Glu Ile Glu Arg Val Leu
            180                 185                 190
```

```
Leu Glu Glu Gln Glu Gln Lys Pro Glu Gln Arg Arg Gly His Lys Gly
            195                 200                 205

Arg Gln Gln Ser Gln Glu Thr Asp Val Ile Val Lys Ile Ser Arg Glu
        210                 215                 220

Gln Ile Glu Glu Leu Ser Lys Asn Ala Lys Ser Asn Cys Lys Lys Ser
225                 230                 235                 240

Val Ser Ser Glu Ser Glu Pro Phe Asn Leu Arg Ser Arg Ser Pro Ile
                245                 250                 255

Tyr Ser Asn Arg Phe Gly Asn Phe Glu Ile Thr Pro Glu Lys Asn
            260                 265                 270

Pro Gln Leu Lys Asp Leu Asp Ile Phe Val Asn Ser Val Glu Ile Lys
        275                 280                 285

Glu Gly Ser Leu Leu Pro His Phe Asn Ser Arg Ala Thr Val Ile
290                 295                 300

Leu Val Val Asn Glu Gly Lys Gly Glu Val Glu Leu Val Gly Leu Arg
305                 310                 315                 320

Asn Glu Asn Glu Gln Glu Asn Lys Lys Glu Asp Glu Glu Glu Glu
            325                 330                 335

Asp Arg Asn Val Gln Val Gln Arg Phe Gln Ser Lys Leu Ser Ser Gly
        340                 345                 350

Asp Val Val Ile Pro Ala Ser His Pro Phe Ser Ile Asn Ala Ser
355                 360                 365

Ser Asp Leu Phe Leu Leu Gly Phe Gly Ile Asn Ala Gln Asn Asn Gln
        370                 375                 380

Arg Asn Phe Leu Ala Gly Glu Glu Asp Asn Val Ile Ser Gln Ile Gln
385                 390                 395                 400

Arg Pro Val Lys Glu Val Ala Phe Pro Gly Ser Ala Glu Glu Val Asp
                405                 410                 415

Arg Leu Leu Lys Asn Gln Arg Gln Ser His Phe Ala Asn Ala Gln Pro
            420                 425                 430

Gln Gln Lys Arg Lys Gly Ser Arg Ile Arg Ser Pro Phe
        435                 440                 445

<210> SEQ ID NO 224
<211> LENGTH: 418
<212> TYPE: PRT
<213> ORGANISM: Lens culinaris

<400> SEQUENCE: 224

Ser Arg Ser Asp Gln Glu Asn Pro Phe Ile Phe Lys Ser Asn Arg Phe
1               5                   10                  15

Gln Thr Ile Tyr Glu Asn Glu Asn Gly His Ile Arg Leu Leu Gln Arg
            20                  25                  30

Phe Asp Lys Arg Ser Lys Ile Phe Glu Asn Leu Gln Asn Tyr Arg Leu
        35                  40                  45

Leu Glu Tyr Lys Ser Lys Pro His Thr Ile Phe Leu Pro Gln Phe Thr
    50                  55                  60

Asp Ala Asp Phe Ile Leu Val Val Leu Ser Gly Lys Ala Ile Leu Thr
65                  70                  75                  80

Val Leu Asn Ser Asn Asp Arg Asn Ser Phe Asn Leu Glu Arg Gly Asp
                85                  90                  95

Thr Ile Lys Leu Pro Ala Gly Thr Ile Ala Tyr Leu Ala Asn Arg Asp
            100                 105                 110

Asp Asn Glu Asp Leu Arg Val Leu Asp Leu Ala Ile Pro Val Asn Arg
        115                 120                 125
```

Pro Gly Gln Leu Gln Ser Phe Leu Ser Gly Thr Gln Asn Gln Pro
        130                 135                 140

Ser Phe Leu Ser Gly Phe Ser Lys Asn Ile Leu Glu Ala Ala Phe Asn
145                 150                 155                 160

Thr Glu Tyr Glu Glu Ile Glu Lys Val Leu Leu Glu Glu Gln Glu Gln
                165                 170                 175

Lys Ser Gln His Arg Arg Ser Leu Arg Asp Lys Arg Gln Glu Ile Thr
            180                 185                 190

Asn Glu Asp Val Ile Val Lys Val Ser Arg Glu Gln Ile Glu Glu Leu
        195                 200                 205

Ser Lys Asn Ala Lys Ser Ser Lys Lys Ser Val Ser Ser Glu Ser
        210                 215                 220

Glu Pro Phe Asn Leu Arg Ser Arg Asn Pro Ile Tyr Ser Asn Lys Phe
225                 230                 235                 240

Gly Lys Phe Phe Glu Ile Thr Pro Glu Lys Asn Pro Gln Leu Gln Asp
                245                 250                 255

Leu Asp Ile Phe Val Asn Ser Val Glu Ile Lys Glu Gly Ser Leu Leu
            260                 265                 270

Leu Pro Asn Tyr Asn Ser Arg Ala Ile Val Ile Val Thr Val Asn Glu
        275                 280                 285

Gly Lys Gly Asp Phe Glu Leu Val Gly Gln Arg Asn Glu Asn Gln Gln
290                 295                 300

Glu Gln Arg Glu Glu Asn Asp Glu Glu Glu Gly Gln Glu Glu Glu Thr
305                 310                 315                 320

Thr Lys Gln Val Gln Arg Tyr Arg Ala Arg Leu Ser Pro Gly Asp Val
                325                 330                 335

Leu Val Ile Pro Ala Gly His Pro Val Ala Ile Asn Ala Ser Ser Asp
            340                 345                 350

Leu Asn Leu Ile Gly Phe Gly Ile Asn Ala Lys Asn Asn Gln Arg Asn
        355                 360                 365

Phe Leu Ala Gly Glu Glu Asp Asn Val Ile Ser Gln Ile Gln Arg Pro
370                 375                 380

Val Lys Glu Leu Ala Phe Pro Gly Ser Ser Arg Glu Val Asp Arg Leu
385                 390                 395                 400

Leu Thr Asn Gln Lys Gln Ser His Phe Ala Asn Ala Gln Pro Leu Gln
                405                 410                 415

Ile Glu

<210> SEQ ID NO 225
<211> LENGTH: 415
<212> TYPE: PRT
<213> ORGANISM: Lens culinaris

<400> SEQUENCE: 225

Ser Arg Ser Asp Gln Glu Asn Pro Phe Ile Phe Lys Ser Asn Arg Phe
1               5                   10                  15

Gln Thr Ile Tyr Glu Asn Glu Asn Gly His Ile Arg Leu Leu Gln Lys
            20                  25                  30

Phe Asp Lys Arg Ser Lys Ile Phe Glu Asn Leu Gln Asn Tyr Arg Leu
        35                  40                  45

Leu Glu Tyr Lys Ser Lys Pro His Thr Leu Phe Leu Pro Gln Tyr Thr
    50                  55                  60

Asp Ala Asp Phe Ile Leu Val Val Leu Ser Gly Lys Ala Val Leu Thr
65                  70                  75                  80

Val Leu Asn Ser Asn Asp Arg Asn Ser Phe Asn Leu Glu Arg Gly Asp
                85                  90                  95

Thr Ile Lys Leu Pro Ala Gly Thr Ile Ala Tyr Leu Ala Asn Arg Asp
            100                 105                 110

Asp Asn Glu Asp Leu Arg Val Leu Asp Leu Ala Ile Pro Val Asn Asn
        115                 120                 125

Pro Gly Gln Leu Glu Ser Phe Leu Leu Ser Gly Thr Gln Asn Gln Pro
    130                 135                 140

Ser Phe Leu Ser Gly Phe Asn Lys Ser Ile Leu Glu Ala Ala Phe Asn
145                 150                 155                 160

Thr Asp Tyr Glu Glu Ile Glu Lys Val Leu Leu Glu Asp Gln Glu Gln
                165                 170                 175

Glu Pro Gln His Arg Arg Ser Leu Arg Asp Arg Arg Gln Glu Ile Asn
            180                 185                 190

Lys Glu Asn Val Ile Val Lys Val Ser Arg Glu Gln Ile Lys Glu Leu
        195                 200                 205

Ser Lys Asn Ala Lys Ser Ser Lys Lys Ser Val Ser Ser Glu Ser
    210                 215                 220

Glu Pro Phe Asn Leu Arg Ser Arg Asn Pro Ile Tyr Ser Asn Lys Phe
225                 230                 235                 240

Gly Lys Phe Phe Glu Ile Thr Pro Glu Lys Asn Pro Gln Leu Gln Asp
                245                 250                 255

Leu Asp Ile Phe Val Asn Ser Val Glu Ile Lys Glu Gly Ser Leu Leu
            260                 265                 270

Leu Pro Asn Tyr Asn Ser Arg Ala Ile Val Ile Val Thr Val Asn Glu
        275                 280                 285

Gly Lys Gly Tyr Phe Glu Leu Val Gly Gln Arg Asn Glu Asn Gln Arg
    290                 295                 300

Glu Glu Asn Asp Asp Glu Glu Gln Glu Glu Glu Thr Ser Thr Gln
305                 310                 315                 320

Val Gln Arg Tyr Arg Ala Lys Leu Ser Pro Gly Asp Val Phe Val Val
                325                 330                 335

Pro Ala Gly His Pro Val Ala Ile Asn Ala Ser Ser Asp Leu Asn Leu
            340                 345                 350

Ile Gly Phe Gly Ile Asn Ala Lys Asn Asn Gln Arg Asn Phe Leu Ala
        355                 360                 365

Gly Glu Glu Asp Asn Val Ile Ser Gln Ile Gln Arg Pro Val Lys Glu
    370                 375                 380

Leu Ala Phe Pro Gly Ser Ser Arg Glu Val Asp Arg Leu Leu Thr Asn
385                 390                 395                 400

Gln Lys Gln Ser His Phe Ala Asn Ala Gln Pro Leu Gln Ile Glu
                405                 410                 415

<210> SEQ ID NO 226
<211> LENGTH: 463
<212> TYPE: PRT
<213> ORGANISM: Vicia narbonensis

<400> SEQUENCE: 226

Met Ala Ala Ile Thr Met Lys Val Ser Phe Pro Leu Leu Met Leu Leu
1               5                   10                  15

Gly Ile Ser Phe Leu Ala Ser Val Cys Val Ser Ser Arg Ser Asp Gln
            20                  25                  30

Glu Asn Pro Phe Ile Phe Lys Ser Asn Lys Phe Gln Thr Leu Phe Glu

-continued

```
                35                  40                  45
Asn Asp Asn Gly His Ile Arg Leu Leu Gln Lys Phe Asp Glu Arg Ser
 50                  55                  60
Lys Ile Leu Glu Asn Leu Gln Asn Tyr Arg Leu Leu Glu Tyr Lys Ser
 65                  70                  75                  80
Lys Pro Arg Thr Ile Phe Leu Pro Gln Gln Thr Asn Ala Asp Phe Ile
                 85                  90                  95
Leu Val Val Leu Ser Gly Lys Ala Ile Leu Thr Val Leu Lys Pro Asp
                100                 105                 110
Asp Arg Asn Ser Phe Asn Leu Glu Arg Gly Asp Thr Ile Lys Leu Pro
                115                 120                 125
Ala Gly Thr Ile Ala Tyr Leu Val Asn Lys Asp Asp Asn Glu Asp Leu
                130                 135                 140
Arg Val Leu Asp Leu Ala Ile Pro Val Asn Gly Pro Asp Gln Leu Gln
145                 150                 155                 160
Ser Phe Leu Leu Ser Gly Ser Glu Asn Gln Gln Ser Ile Leu Ser Gly
                165                 170                 175
Phe Ser Lys Ser Val Leu Glu Ala Ser Phe Asn Thr Gly Tyr Glu Glu
                180                 185                 190
Ile Glu Lys Val Leu Leu Glu Glu Arg Glu Lys Glu Thr Gln His Arg
                195                 200                 205
Arg Ser Leu Arg Asp Lys Arg Gln His Ser Gln Asp Glu Asp Val Ile
                210                 215                 220
Val Lys Leu Ser Arg Gly Gln Ile Glu Glu Leu Ser Arg Asn Ala Lys
225                 230                 235                 240
Ser Ser Ser Lys Lys Ser Val Ser Ser Glu Ser Glu Pro Phe Asn Leu
                245                 250                 255
Arg Ser Arg Asn Pro Ile Tyr Ser Asn Lys Phe Gly Lys Phe Phe Glu
                260                 265                 270
Ile Thr Pro Glu Lys Asn Pro Gln Leu Gln Asp Leu Asp Val Leu Val
                275                 280                 285
Asn Ser Val Glu Ile Lys Glu Gly Ser Leu Leu Leu Pro His Tyr Asn
                290                 295                 300
Ser Arg Ala Ile Val Ile Val Thr Val Asn Asp Gly Lys Gly Asp Phe
305                 310                 315                 320
Glu Ile Val Gly Gln Arg Asn Glu Asn Arg Gln Gly Gln Arg Lys Glu
                325                 330                 335
Asp Asp Glu Glu Glu Glu Gln Gly Asp Glu Asn Thr Asn Thr Gln Val
                340                 345                 350
Gln Asn Tyr Lys Ala Lys Leu Ser Arg Gly Asp Val Phe Val Ile Pro
                355                 360                 365
Ala Gly His Pro Val Ser Ile Lys Ala Ser Ser Asn Leu Asp Leu Leu
                370                 375                 380
Gly Phe Gly Ile Asn Ala Lys Asn Asn Gln Arg Asn Phe Leu Ala Gly
385                 390                 395                 400
Glu Glu Asp Asn Val Ile Ser Gln Ile Asp Arg Pro Val Lys Glu Leu
                405                 410                 415
Ala Phe Pro Gly Ser Ala Gln Glu Val Asp Arg Leu Leu Glu Asn Gln
                420                 425                 430
Lys Gln Ser His Phe Ala Asn Ala Gln Pro Gln Gln Arg Glu Arg Gly
                435                 440                 445
Ser His Glu Thr Arg Asp His Leu Ser Ser Ile Leu Asp Ala Phe
                450                 455                 460
```

```
<210> SEQ ID NO 227
<211> LENGTH: 396
<212> TYPE: PRT
<213> ORGANISM: Glycine max

<400> SEQUENCE: 227

Gln Tyr Gly His Val Arg Val Leu Gln Arg Phe Asn Lys Arg Ser Gln
1               5                   10                  15

Gln Leu Gln Asn Leu Arg Asp Tyr Arg Ile Leu Glu Phe Asn Ser Lys
            20                  25                  30

Pro Asn Thr Leu Leu Leu Pro His His Ala Asp Ala Asp Tyr Leu Ile
        35                  40                  45

Val Ile Leu Asn Gly Thr Ala Ile Leu Thr Leu Val Asn Asn Asp Asp
    50                  55                  60

Arg Asp Ser Tyr Asn Leu Gln Ser Gly Asp Ala Leu Arg Val Pro Ala
65                  70                  75                  80

Gly Thr Thr Tyr Tyr Val Val Asn Pro Asp Asn Asp Glu Asn Leu Arg
                85                  90                  95

Met Ile Thr Leu Ala Ile Pro Val Asn Lys Pro Gly Arg Phe Glu Ser
            100                 105                 110

Phe Phe Leu Ser Ser Thr Gln Ala Gln Gln Ser Tyr Leu Gln Gly Phe
        115                 120                 125

Ser Lys Asn Ile Leu Glu Ala Ser Tyr Asp Thr Lys Phe Glu Glu Ile
130                 135                 140

Asn Lys Val Leu Phe Gly Arg Glu Glu Gly Gln Gln Gln Gly Glu Glu
145                 150                 155                 160

Arg Leu Gln Glu Ser Val Ile Val Glu Ile Ser Lys Lys Gln Ile Arg
                165                 170                 175

Glu Leu Ser Lys His Ala Lys Ser Ser Ser Arg Lys Thr Ile Ser Ser
            180                 185                 190

Glu Asp Lys Pro Phe Asn Leu Arg Ser Arg Asp Pro Ile Tyr Ser Asn
        195                 200                 205

Lys Leu Gly Lys Leu Phe Glu Ile Thr Pro Glu Lys Asn Pro Gln Leu
    210                 215                 220

Arg Asp Leu Asp Val Phe Leu Ser Val Val Asp Met Asn Glu Gly Ala
225                 230                 235                 240

Leu Phe Leu Pro His Phe Asn Ser Lys Ala Ile Val Val Leu Val Ile
                245                 250                 255

Asn Glu Gly Glu Ala Asn Ile Glu Leu Val Gly Ile Lys Glu Gln Gln
            260                 265                 270

Gln Arg Gln Gln Gln Glu Glu Gln Pro Leu Glu Val Arg Lys Tyr Arg
        275                 280                 285

Ala Glu Leu Ser Glu Gln Asp Ile Phe Val Ile Pro Ala Gly Tyr Pro
    290                 295                 300

Val Val Val Asn Ala Thr Ser Asp Leu Asn Phe Phe Ala Phe Gly Ile
305                 310                 315                 320

Asn Ala Glu Asn Asn Gln Arg Asn Phe Leu Ala Gly Ser Lys Asp Asn
                325                 330                 335

Val Ile Ser Gln Ile Pro Ser Gln Val Gln Glu Leu Ala Phe Pro Gly
            340                 345                 350

Ser Ala Lys Asp Ile Glu Asn Leu Ile Lys Ser Gln Ser Glu Ser Tyr
        355                 360                 365

Phe Val Asp Ala Gln Pro Gln Gln Lys Glu Glu Gly Asn Lys Gly Arg
```

```
                     370                 375                 380

Lys Gly Pro Leu Ser Ser Ile Leu Arg Ala Phe Tyr
385                 390                 395

<210> SEQ ID NO 228
<211> LENGTH: 498
<212> TYPE: PRT
<213> ORGANISM: Vicia sativa

<400> SEQUENCE: 228

Met Ala Lys Leu Leu Ala Leu Ser Leu Ser Phe Cys Phe Leu Leu Phe
1               5                   10                  15

Ser Ser Cys Phe Ala Leu Arg Glu Gln Ser Gln Gln Asn Glu Cys Gln
            20                  25                  30

Leu Glu Arg Ile Asn Ala Leu Glu Pro Asp Asn Arg Ile Glu Ser Glu
        35                  40                  45

Gly Gly Leu Ile Glu Thr Trp Asn Pro Asn Asn Arg Gln Phe Arg Cys
    50                  55                  60

Ala Arg Val Ala Leu Ser Arg Ala Thr Leu Gln Arg Asn Ala Leu Arg
65                  70                  75                  80

Arg Pro Tyr Tyr Ser Asn Ala Pro Gln Glu Ile Tyr Ile Gln Gln Gly
                85                  90                  95

Asn Gly Tyr Phe Gly Met Val Phe Pro Gly Cys Pro Glu Thr His Glu
            100                 105                 110

Glu Pro Gln Gln Ser Glu Gln Gly Glu Gly Arg Arg Tyr Arg Asp Ser
        115                 120                 125

His Gln Lys Val Asn Arg Phe Arg Glu Gly Asp Ile Ile Ala Val Pro
    130                 135                 140

Thr Gly Ile Ala Phe Trp Met Tyr Asn Asp Gln Asp Thr Pro Val Ile
145                 150                 155                 160

Ala Ile Ser Leu Thr Asp Thr Gly Ser Ser Asn Asn Gln Leu Asp Gln
                165                 170                 175

Met Pro Arg Arg Phe Tyr Leu Ala Gly Asn Gln Glu Gln Glu Phe Leu
            180                 185                 190

Arg Tyr Gln His Gln Gly Gly Lys Gln Glu Gln Asp Asn Asp Gly
        195                 200                 205

Asn Asn Ile Phe Ser Gly Phe Lys Arg Asp Phe Leu Glu Asp Ala Phe
    210                 215                 220

Asn Val Asn Arg His Ile Val Asp Arg Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Ala Pro Pro Glu Arg Gln Ala Arg His Glu Arg Gly Ser Arg Gln Glu
            260                 265                 270

Glu Asp Glu Asp Glu Lys Glu Glu Arg Gln Pro Ser His His Lys Ser
        275                 280                 285

Arg Arg Asp Glu Asp Glu Asp Lys Glu Lys Arg His Ser Gln Lys
    290                 295                 300

Gly Gln Ser Arg Arg Gln Gly Asp Asn Gly Leu Glu Glu Thr Val Cys
305                 310                 315                 320

Thr Ala Lys Leu Arg Ala Asn Ile Gly Ser Ser Pro Ser Pro Asp Ile
                325                 330                 335

Tyr Asn Pro Gln Ala Gly Arg Ile Lys Thr Val Thr Ser Leu Asp Leu
            340                 345                 350
```

-continued

```
Pro Val Leu Arg Trp Leu Lys Leu Ser Ala Glu His Gly Ser Leu His
            355                 360                 365

Lys Asn Ala Met Phe Val Pro His Tyr Asn Leu Asn Ala Asn Ser Val
370                 375                 380

Ile Tyr Ala Leu Lys Gly Arg Ala Arg Leu Gln Val Val Asn Cys Asn
385                 390                 395                 400

Gly Asn Thr Val Phe Asp Gly Glu Leu Glu Ala Gly Arg Ala Leu Thr
                405                 410                 415

Val Pro Gln Asn Tyr Ala Val Ala Ala Lys Ser Leu Ser Glu Arg Phe
            420                 425                 430

Thr Tyr Val Ala Phe Lys Thr Asp Asp Arg Ala Ser Ile Ala Arg Leu
        435                 440                 445

Ala Gly Thr Ser Ser Val Ile Asp Asp Leu Pro Leu Asp Val Val Ala
    450                 455                 460

Ala Thr Phe Asn Met Gln Arg Asn Glu Ala Arg Gln Leu Lys Ser Asn
465                 470                 475                 480

Asn Pro Phe Lys Phe Leu Val Pro Pro Arg Gln Ser Glu Met Arg Ala
                485                 490                 495

Ser Ala

<210> SEQ ID NO 229
<211> LENGTH: 531
<212> TYPE: PRT
<213> ORGANISM: Medicago truncatula

<400> SEQUENCE: 229

Met Ala Lys Leu Leu Ala Leu Ser Leu Ser Leu Cys Phe Leu Leu Phe
1               5                   10                  15

Ser Gly Cys Phe Ala Ile Arg Glu His Gln Pro His Gln Lys Gln Gln
            20                  25                  30

Pro Gln Gln Asn Glu Cys Gln Leu Glu Gln Leu Asn Ala Leu Glu Pro
        35                  40                  45

Asp Asn Arg Ile Glu Ser Glu Gly Gly Ile Ile Glu Thr Trp Asn Pro
    50                  55                  60

Asn Asn Arg Gln Phe Arg Cys Ala Gly Val Ala Leu Ser Arg Cys Thr
65                  70                  75                  80

Leu Gln Arg Asn Ser Leu Arg Arg Pro Phe Tyr Ser Asn Ala Pro Gln
                85                  90                  95

Glu Ile Phe Ile Gln Gln Gly Ser Gly Tyr Phe Gly Met Val Phe Pro
            100                 105                 110

Gly Cys Pro Glu Thr Phe Glu Glu Pro Gln Glu Ser Glu Gln Arg Glu
        115                 120                 125

Ser Arg Arg Ile Arg Glu Ser Glu Gln Gly Glu Ser Arg Arg Ile Arg
    130                 135                 140

Glu Ser Glu Gln Gly Glu Gly Arg Arg Phe Arg Asp Ser His Gln Lys
145                 150                 155                 160

Val Asn Arg Phe Arg Glu Gly Asp Leu Ile Ala Val Pro Thr Gly Thr
                165                 170                 175

Val Phe Trp Met Tyr Asn Asp Gln Asp Thr Pro Val Ile Ala Val Ser
            180                 185                 190

Leu Ile Asp Thr Gly Ser Phe Gln Asn Gln Leu Asp Glu Met Pro Arg
        195                 200                 205

Arg Phe Tyr Leu Ala Gly Asn Gln Glu Gln Glu Phe Leu Gln Tyr Gln
    210                 215                 220
```

```
Gln Gln Gln Val Arg Gly Arg Gly Glu Gln Arg Gly Arg Glu Gln
225                 230                 235                 240

Gln Glu Asn Glu Gly Gly Asn Ile Phe Ser Gly Phe Lys Arg Asp Phe
                245                 250                 255

Leu Glu Asp Ala Leu Asn Val Asn Arg His Ile Val Asp Arg Leu Gln
            260                 265                 270

Gly Arg Asn Glu Asp Glu Glu Lys Gly Ala Ile Val Lys Val Arg Gly
        275                 280                 285

Gly Leu Ser Phe Val Thr Pro Pro Glu Arg Gln Ser Arg His Gln Gly
    290                 295                 300

Gly Ser Ile Ile Glu Glu Asp Glu Asp Glu Glu Asp Glu Trp Arg Arg
305                 310                 315                 320

Pro His His Gln Lys Ser Arg Arg Gly Glu Glu Glu Arg Pro Cys
                325                 330                 335

Arg Arg Gly Gln Lys Cys Glu Arg Ser Asn Gly Leu Glu Glu Thr Ile
            340                 345                 350

Cys Thr Ala Arg Leu Arg Gln Asn Ile Gly Ser Ser Ser Pro Asp
        355                 360                 365

Ile Tyr Asn Pro Glu Ala Gly Arg Ile Lys Thr Val Thr Ser Phe Asp
370                 375                 380

Leu Pro Ala Leu Arg Trp Leu Arg Leu Ser Ala Glu His Gly Thr Leu
385                 390                 395                 400

His Arg Asn Ala Met Phe Val Pro His Tyr Asn Leu Asn Ala Asn Ser
                405                 410                 415

Ala Ile Tyr Ala Leu Arg Gly Arg Ala Arg Leu Gln Val Val Asn Cys
            420                 425                 430

Asn Gly Asn Thr Val Phe Asp Gly Glu Leu Glu Ala Gly Arg Val Leu
        435                 440                 445

Ile Val Pro Gln Asn Phe Ala Val Ala Lys Ser Met Ser Asp Arg
    450                 455                 460

Phe Gln Tyr Val Ser Phe Lys Thr Asn Asp Asn Ala Ala Ile Ala Arg
465                 470                 475                 480

Leu Ala Gly Thr Gln Ser Thr Leu Ser Gly Val Pro Met Asp Val Leu
                485                 490                 495

Ala Ala Thr Tyr Asn Met Asp Arg Asn Glu Ala Arg Gln Leu Lys Asn
            500                 505                 510

Asn Asn Leu Tyr Lys Phe Leu Val Pro Pro Arg Glu Ser Glu Arg Arg
        515                 520                 525

Ala Ala Ala
    530

<210> SEQ ID NO 230
<211> LENGTH: 476
<212> TYPE: PRT
<213> ORGANISM: Lotus japonicus

<400> SEQUENCE: 230

Met Ala Tyr Lys Leu Phe Ala Leu Ser Leu Ser Phe Cys Phe Leu Leu
1               5                   10                  15

Phe Gly Gly Cys Phe Ala Ile Arg Gln Gln Ser Gln Gln Gln Asn Glu
            20                  25                  30

Cys Gln Leu Glu Arg Leu Asn Ala Leu Lys Pro Asp Asn Arg Ile Glu
        35                  40                  45

Ser Glu Ala Gly Tyr Ile Glu Thr Trp Asn Pro Thr Asn Asn Gln Phe
    50                  55                  60
```

```
Arg Cys Ala Gly Val Ala Leu Ser Arg Cys Thr Leu Arg Arg Asn Gly
 65                  70                  75                  80

Leu Lys Arg Pro Ser Tyr Ser Asn Ala Pro Gln Glu Ile Phe Ile Gln
                 85                  90                  95

Gln Gly Ser Gly Ile Phe Gly Met Ile Phe Pro Gly Cys Pro Glu Thr
            100                 105                 110

Val Glu Glu Pro Phe Glu Ser Asp Gln Gln Gly Arg Arg Asp Arg His
            115                 120                 125

Gln Lys Val Asn Arg Phe Arg Glu Gly Asp Val Ile Ala Val Pro Pro
        130                 135                 140

Gly Val Val Phe Trp Met Tyr Asn Glu Glu Thr Pro Val Ile Ala
145                 150                 155                 160

Val Ser Leu Ile Asp Thr Gly Ser Tyr Leu Asn Gln Leu Asp Gln Met
                165                 170                 175

Pro Arg Arg Phe Tyr Leu Ser Gly Asn Gln Glu Gln Glu Phe Leu Gln
            180                 185                 190

Tyr Gln Arg Gln Glu Val Arg Gly Arg Glu Glu Asn Gln Gly Gly
        195                 200                 205

Asn Ile Phe Ser Gly Phe Gly Glu Phe Leu Glu Asp Ala Leu Asn
210                 215                 220

Ile Asp Arg Asn Ile Val His Lys Leu Gln Gly Arg Asp Glu Glu Gln
225                 230                 235                 240

Asp Lys Gly Ala Ile Val Arg Val Lys Gly Gly Leu Ser Val Ile Thr
                245                 250                 255

Pro Pro Glu Arg Gln Ser His Arg Arg Gly Ser Glu Glu Glu Asp
            260                 265                 270

Glu Glu Glu Asp Arg Pro Ser Arg His Gln Ser Arg Gly Gly Ser Arg
            275                 280                 285

Arg Asn Gly Leu Glu Glu Thr Ile Cys Thr Val Arg Leu Arg Met Asn
    290                 295                 300

Ile Gly Lys Ser Ser Ser Pro Asp Ile Phe Asn Pro Gln Ala Gly Arg
305                 310                 315                 320

Ile Lys Thr Ala Thr Gly Phe Asp Phe Pro Ala Leu Arg Phe Leu Lys
                325                 330                 335

Leu Ser Ala Glu His Gly Ser Leu Asn Arg Asn Ala Met Val Val Pro
            340                 345                 350

His Tyr Asn Leu Asn Ala Asn Ser Ile Ile Tyr Ala Leu Arg Gly Arg
            355                 360                 365

Ala Trp Ile Gln Val Val Asn Cys Lys Gly Asn Arg Ile Phe Asp Gly
            370                 375                 380

Glu Leu Glu Glu Gly Gln Val Leu Ile Val Pro Gln Asn Phe Val Val
385                 390                 395                 400

Ala Ala Arg Ser Met Ser Asp Lys Phe Asn Tyr Val Ala Phe Lys Thr
                405                 410                 415

Asn Asp Met Pro Thr Met Ala Lys Leu Ala Gly Ala Thr Ser Glu Ile
            420                 425                 430

Gln Ala Met Pro Leu Glu Val Ile Gln Asn Ala Phe Asn Leu Glu Arg
        435                 440                 445

Glu Gln Ala Lys Gln Val Lys Phe Asn Asn Arg Phe Asn Phe Leu Val
        450                 455                 460

Pro Pro Arg Glu Gln Ser Gln Arg Arg Ala Ser Ala
465                 470                 475
```

```
<210> SEQ ID NO 231
<211> LENGTH: 526
<212> TYPE: PRT
<213> ORGANISM: PISUM ABYSSINICUM

<400> SEQUENCE: 231

Met Ala Thr Thr Val Glu Ser Arg Phe Pro Leu Leu Leu Phe Pro Gly
1               5                   10                  15

Ile Ile Phe Leu Ala Ser Val Cys Val Thr Tyr Ala Asn Tyr Asp Glu
                20                  25                  30

Gly Ser Glu Thr Arg Val Pro Gly Gln Arg Glu Arg Gly Arg Gln Glu
            35                  40                  45

Gly Glu Lys Glu Glu Lys Arg His Gly Glu Trp Arg Pro Ser Tyr Glu
        50                  55                  60

Lys Glu Glu Asp Glu Glu Glu Lys Gln Lys Tyr Arg Tyr Gln Arg Glu
65                  70                  75                  80

Lys Glu Asp Glu Glu Glu Lys Gln Lys Tyr Arg Tyr Gln Arg Glu Lys
                85                  90                  95

Lys Glu Glu Lys Glu Val Gln Pro Gly Arg Glu Arg Trp Glu Arg Glu
            100                 105                 110

Glu Asp Glu Glu Gln Val Asp Glu Glu Trp Arg Gly Ser Gln Arg Arg
        115                 120                 125

Gln Asp Pro Glu Glu Arg Ala Arg Leu Arg His Arg Glu Glu Arg Thr
130                 135                 140

Lys Arg Asp Arg Arg His Lys Arg Glu Gly Glu Glu Glu Glu Arg Ser
145                 150                 155                 160

Ser Glu Ser Gln Glu Gln Arg Asn Pro Phe Leu Phe Lys Ser Asn Lys
                165                 170                 175

Phe Leu Thr Leu Phe Glu Asn Glu Asn Gly His Ile Arg Arg Leu Gln
            180                 185                 190

Arg Phe Asp Lys Arg Ser Asp Leu Phe Glu Asn Leu Gln Asn Tyr Arg
        195                 200                 205

Leu Val Glu Tyr Arg Ala Lys Pro His Thr Ile Phe Leu Pro Gln His
210                 215                 220

Ile Asp Ala Asp Leu Ile Leu Val Val Leu Asn Gly Lys Ala Ile Leu
225                 230                 235                 240

Thr Val Leu Ser Pro Asn Asp Arg Asn Ser Tyr Asn Leu Glu Arg Gly
                245                 250                 255

Asp Thr Ile Lys Ile Pro Ala Gly Thr Thr Ser Tyr Leu Val Asn Gln
            260                 265                 270

Asp Asp Glu Glu Asp Leu Arg Val Val Asp Phe Val Ile Pro Val Asn
        275                 280                 285

Arg Pro Gly Lys Phe Glu Ala Phe Gly Leu Ser Glu Asn Lys Asn Gln
290                 295                 300

Tyr Leu Arg Gly Phe Ser Lys Asn Ile Leu Glu Ala Ser Leu Asn Thr
305                 310                 315                 320

Lys Tyr Glu Thr Ile Glu Lys Val Leu Leu Glu Glu Gln Lys Lys
                325                 330                 335

Pro Gln Gln Leu Arg Asp Arg Leu Arg Arg Gln Gly Gly Glu Arg
            340                 345                 350

Asp Ala Ile Ile Lys Val Ser Arg Glu Gln Ile Glu Glu Leu Arg Lys
        355                 360                 365

Leu Ala Lys Ser Ser Ser Lys Lys Ser Leu Pro Ser Glu Phe Glu Pro
370                 375                 380
```

```
Phe Asn Leu Arg Ser His Lys Pro Glu Tyr Ser Asn Lys Phe Gly Lys
385                 390                 395                 400

Leu Phe Glu Ile Thr Pro Glu Lys Lys Tyr Pro Gln Leu Gln Asp Leu
            405                 410                 415

Asp Ile Leu Val Ser Cys Val Glu Ile Asn Lys Gly Ala Leu Met Leu
        420                 425                 430

Pro His Tyr Asn Ser Arg Ala Ile Val Val Leu Leu Val Asn Glu Gly
                435                 440                 445

Lys Gly Asn Leu Glu Leu Leu Gly Leu Lys Asn Glu Gln Gln Glu Arg
450                 455                 460

Glu Asp Arg Lys Glu Arg Asn Asn Glu Val Gln Arg Tyr Glu Ala Arg
465                 470                 475                 480

Leu Ser Pro Gly Asp Val Val Ile Ile Pro Ala Gly His Pro Val Ala
                485                 490                 495

Ile Ser Ala Ser Ser Asn Leu Asn Leu Leu Gly Phe Gly Thr Asn Ala
            500                 505                 510

Glu Asn Asn Gln Arg Asn Phe Leu Ser Gly Ser Asp Asp Asn
515                 520                 525

<210> SEQ ID NO 232
<211> LENGTH: 541
<212> TYPE: PRT
<213> ORGANISM: LATHYRUS ANNUUS

<400> SEQUENCE: 232

Met Ala Thr Thr Ile Lys Ser Arg Phe Pro Leu Leu Leu Leu Leu Gly
1               5                   10                  15

Ile Ile Phe Leu Ala Ser Val Cys Val Thr Trp Ala Asn Tyr Asp Glu
            20                  25                  30

Gly Ser Glu Pro Arg Val Pro Gly Gln Arg Glu Arg Gly Arg Gln Glu
        35                  40                  45

Gly Glu Lys Glu Glu Lys Arg His Gly Glu Trp Arg Pro Ser Tyr Glu
50                  55                  60

Glu Tyr Asp Glu Gly Leu Glu Pro Lys Val Pro Gly Lys Arg Glu
65                  70                  75                  80

Arg Gly Arg Gln Glu Gly Glu Lys Glu Lys Arg His Glu Glu Trp
                85                  90                  95

Arg Pro Ser Tyr Glu Lys Glu Asp Glu Glu Lys Gln Lys Tyr
            100                 105                 110

Asn Tyr Gln Arg Glu Lys Lys Glu His Lys Glu Val Gln Pro Gly Arg
        115                 120                 125

Glu Arg Trp Glu Arg Lys Gln Asp Glu Lys Gln Val Glu Glu Asp Glu
130                 135                 140

Glu Pro Gly Glu Glu Gln Trp Arg Gly Ser Lys Arg His Glu Asp Pro
145                 150                 155                 160

Glu Glu Arg Ala Arg Leu Arg His Arg Glu Lys Thr Lys Ser Tyr
                165                 170                 175

Val Glu Asp Asn Glu Glu Thr Ser Ser Lys Glu Gly Arg Asn Pro Phe
            180                 185                 190

Leu Phe Lys Ser Asn Lys Phe Leu Thr Leu Phe Glu Asn Glu Asn Gly
        195                 200                 205

His Ile Arg Arg Leu Gln Arg Phe Asp Glu Arg Ser Asp Ile Phe Glu
    210                 215                 220

Asn Leu Gln Asn Tyr Arg Leu Val Glu Tyr Arg Ala Lys Pro His Thr
```

```
                225                 230                 235                 240
Met Phe Leu Pro Gln His Ile Asp Ala Asp Leu Ile Leu Val Val Leu
                    245                 250                 255

Asn Gly Lys Ala Ile Leu Thr Val Leu Ser Pro Asn Asp Arg Asn Ser
                    260                 265                 270

Tyr Asn Leu Glu Arg Gly Asp Thr Val Lys Leu Pro Ala Gly Thr Thr
                    275                 280                 285

Ser Tyr Leu Val Asn Gln Asp Glu Asp Leu Arg Val Val Asp
                290                 295                 300

Leu Ala Ile Pro Val Asn Arg Pro Gly Lys Phe Glu Ala Phe Gly Leu
305                 310                 315                 320

Ser Ala Asn Lys Asn Gln Tyr Leu Arg Gly Phe Ser Lys Asn Ile Leu
                    325                 330                 335

Glu Ala Ser Leu Asn Thr Lys Tyr Glu Thr Ile Glu Lys Val Leu Leu
                    340                 345                 350

Glu Glu Arg Arg Asp Gln Lys Gly Arg Gln Gly Gln Glu Thr Asn
                    355                 360                 365

Ala Ile Val Lys Val Ser Arg Glu Gln Ile Glu Glu Leu Arg Lys Leu
    370                 375                 380

Ala Lys Ser Ser Ser Lys Lys Ser Leu Leu Ser Glu Ser Glu Pro Leu
385                 390                 395                 400

Asn Leu Arg Ser Gln Asn Pro Lys Tyr Ser Asn Lys Phe Gly Lys Phe
                    405                 410                 415

Phe Glu Ile Thr Pro Gln Lys Lys Tyr Pro Gln Leu Gln Asp Leu Asp
                    420                 425                 430

Val Ser Ile Ser Cys Val Glu Ile Asn Lys Gly Ala Leu Leu Leu Pro
                435                 440                 445

His Tyr Asn Ser Arg Ser Ile Gly Ile Leu Leu Val Asn Glu Gly Lys
    450                 455                 460

Gly Asn Leu Glu Leu Val Gly Phe Lys Asn Glu Gln Gln Arg Gln Arg
465                 470                 475                 480

Glu Asn Glu Glu Thr Asn Lys Lys Leu Gln Arg Tyr Glu Ala Arg Leu
                    485                 490                 495

Ser Ser Gly Asp Val Val Ile Pro Glu Gly His Pro Val Ala Ile
                500                 505                 510

Ser Ala Ser Ser Asn Leu Asn Leu Leu Gly Phe Gly Ile Asn Ala Ala
                515                 520                 525

Asn Asn Gln Arg Asn Phe Leu Thr Gly Ser Asp Asp Asn
                530                 535                 540

<210> SEQ ID NO 233
<211> LENGTH: 589
<212> TYPE: PRT
<213> ORGANISM: Vicia villosa

<400> SEQUENCE: 233

Met Ala Thr Thr Ile Lys Ser Arg Phe Pro Val Leu Leu Leu Leu Gly
1               5                   10                  15

Ile Ile Phe Leu Thr Ser Val Cys Val Thr Tyr Ala Asn Tyr Asp Glu
                20                  25                  30

Gly Arg Glu Pro Ser Val Pro Gly Gln Arg Glu Arg Gly Arg Gln Glu
                35                  40                  45

Gly Glu Lys Glu Glu Lys Arg His Gly Glu Trp Arg Pro Ser Glu Glu
            50                  55                  60
```

```
Asp Glu Glu Lys Tyr Lys Tyr Glu Glu Gly Arg Val Pro Gly Gln
 65                  70                  75                  80

Arg Glu Arg Gly Arg Gln Glu Gly Glu Lys Glu Lys Arg His Gly
                 85                  90                  95

Lys Trp Arg Pro Ser Glu Glu Asp Glu Glu Lys Tyr Arg Tyr
                100                 105                 110

Glu Glu Gly Ser Glu Pro Arg Gly Pro Gly Gln Arg Glu Thr Gly Arg
                115                 120                 125

Gln Glu Gly Glu Lys Glu Lys Gln Arg Pro Glu Arg Glu Pro Ser Tyr
                130                 135                 140

Glu Lys Glu Glu Asp Glu Glu Lys Gln Lys Tyr Gln Tyr His Arg
145                 150                 155                 160

Glu Lys Lys Glu Gln Arg Glu Val Arg Pro Gly Arg Glu Arg Phe Glu
                165                 170                 175

Arg His Glu Asp Glu Glu Gln Trp Arg Gly Ile Gln Arg His Glu Asp
                180                 185                 190

Pro Glu Glu Arg Ala Arg Glu Arg Tyr Arg Ala Glu Ile Ala Lys Arg
                195                 200                 205

Gln Val Glu Glu Glu Arg Glu Glu Arg Asp Ile Pro His Glu Arg Glu
                210                 215                 220

Gln Arg Asn Pro Phe Leu Phe Lys Ser Asn Lys Phe Gln Thr Leu Phe
225                 230                 235                 240

Gln Asn Glu Asn Gly Tyr Ile Arg Arg Leu Gln Arg Phe Asp Lys Arg
                245                 250                 255

Ser Asp Leu Phe Glu Asn Leu Gln Asn Tyr Arg Leu Val Glu Tyr Arg
                260                 265                 270

Ala Lys Pro His Thr Ile Phe Leu Pro Gln His Ile Asp Ala Asp Leu
                275                 280                 285

Ile Ile Val Val Leu Ser Gly Arg Ala Ile Leu Thr Val Leu Ser Pro
                290                 295                 300

Asp Asp Arg Asn Ser Tyr Asn Leu Glu Arg Gly Asp Thr Ile Lys Leu
305                 310                 315                 320

Pro Ala Gly Thr Thr Ser Tyr Leu Val Asn Gln Asp Asp Glu Glu Asp
                325                 330                 335

Leu Arg Val Val Asp Leu Ala Ile Pro Val Asn Arg Pro Gly Lys Val
                340                 345                 350

Glu Ser Phe Leu Leu Ser Gly Asn Lys Asn Gln Tyr Leu Arg Gly Phe
                355                 360                 365

Ser Lys Asn Ile Leu Glu Ala Ser Phe Asn Thr Asn Tyr Glu Thr Ile
370                 375                 380

Glu Arg Val Leu Leu Glu Glu Gln Asp Lys Glu Ser Gln Gln Ser Ile
385                 390                 395                 400

Gly Gln Lys Arg Arg Ser Gln Arg Gln Glu Thr Asn Ala Leu Val Lys
                405                 410                 415

Val Ser Arg Glu Gln Leu Glu Asp Leu Lys Arg Leu Ala Lys Ser Ser
                420                 425                 430

Ser Gln Glu Gly Leu Ser Ser Gln Phe Glu Pro Ile Asn Leu Arg Ser
                435                 440                 445

Gln Asn Pro Lys Tyr Ser Asn Lys Phe Gly Lys Val Phe Glu Ile Thr
                450                 455                 460

Pro Glu Lys Lys Tyr Pro Gln Leu Gln Asp Leu Asp Leu Phe Val Ser
465                 470                 475                 480

Ser Val Asp Ile Lys Glu Gly Ala Leu Met Leu Pro His Tyr Asn Ser
```

```
                        485                 490                 495
Arg Ala Ile Val Val Leu Leu Val Asn Glu Gly Arg Gly Asn Leu Glu
            500                 505                 510

Leu Val Gly Leu Lys Asn Glu Gln Gln Glu Gln Arg Glu Lys Glu Asp
            515                 520                 525

Glu Gln Gln Glu Arg Asn Asn Gln Val Gln Arg Tyr Glu Ala Arg Leu
            530                 535                 540

Ser Pro Gly Asp Val Val Ile Ile Pro Ala Gly His Pro Val Ala Val
545                 550                 555                 560

Arg Ala Ser Ser Asp Leu Asn Leu Leu Ala Phe Gly Ile Asn Ala Glu
            565                 570                 575

Asn Asn Gln Arg Asn Phe Leu Ala Gly Ser Asp Asp Asn
            580                 585

<210> SEQ ID NO 234
<211> LENGTH: 463
<212> TYPE: PRT
<213> ORGANISM: Medicago truncatula

<400> SEQUENCE: 234

Met Ala Ile Lys Ala Pro Phe Gln Leu Leu Met Leu Leu Gly Ile Phe
1               5                   10                  15

Phe Leu Ala Ser Val Cys Val Ser Ser Arg Asp Asp Arg His Asp Gln
            20                  25                  30

Glu Asn Pro Phe Phe Phe Asn Ala Asn His Phe Gln Thr Leu Phe Glu
            35                  40                  45

Asn Glu Asn Gly His Ile Arg Leu Leu Gln Arg Phe Asp Lys Arg Ser
            50                  55                  60

Lys Ile Phe Glu Asn Leu Gln Asn Tyr Arg Leu Leu Glu Tyr His Ser
65                  70                  75                  80

Lys Pro His Thr Leu Phe Leu Pro Gln His Asn Asp Ala Asp Phe Ile
            85                  90                  95

Leu Ala Val Leu Ser Gly Lys Ala Ile Leu Thr Val Leu Asn Pro Asp
            100                 105                 110

Asn Arg Asn Ser Phe Asn Leu Glu Arg Gly Asp Thr Ile Lys Leu Pro
            115                 120                 125

Ala Gly Ser Ile Ala Tyr Leu Ala Asn Arg Asp Asp Asn Glu Asp Leu
            130                 135                 140

Arg Val Leu Asp Leu Ala Ile Pro Val Asn Arg Pro Gly Lys Phe Gln
145                 150                 155                 160

Ser Phe Ser Leu Ser Gly Ser Gln Asn Gln Gln Ser Phe Phe Ser Gly
            165                 170                 175

Phe Ser Lys Asn Ile Leu Glu Ala Ala Phe Asn Ala Asn Tyr Glu Glu
            180                 185                 190

Ile Glu Arg Val Leu Ile Glu Glu His Glu Gln Glu Pro Gln His Arg
            195                 200                 205

Arg Gly Leu Arg Lys Asp Arg Arg Gln Gln Ser Gln Asp Ser Asn Val
            210                 215                 220

Ile Val Lys Val Ser Arg Glu Gln Ile Glu Glu Leu Ser Arg His Ala
225                 230                 235                 240

Lys Ser Ser Ser Arg Arg Ser Gly Ser Ser Glu Ser Ala Pro Phe Asn
            245                 250                 255

Leu Arg Ser Arg Glu Pro Ile Tyr Ser Asn Glu Phe Gly Asn Phe Phe
            260                 265                 270
```

-continued

```
Glu Ile Thr Pro Glu Lys Asn Pro Gln Leu Lys Asp Leu Asp Ile Leu
            275                 280                 285

Val Asn Tyr Ala Glu Ile Arg Glu Gly Ser Leu Leu Leu Pro His Phe
290                 295                 300

Asn Ser Arg Ala Thr Val Ile Val Val Asp Glu Gly Lys Gly Glu
305                 310                 315                 320

Phe Glu Leu Val Gly Arg Asn Glu Asn Gln Gln Glu Gln Arg Glu
            325                 330                 335

Glu Asp Glu Gln Gln Glu Glu Arg Ser Gln Gln Val Gln Arg Tyr
            340                 345                 350

Arg Ala Arg Leu Ser Pro Gly Asp Val Tyr Val Ile Pro Ala Gly His
            355                 360                 365

Pro Thr Val Val Ser Ala Ser Ser Asp Leu Ser Leu Leu Gly Phe Gly
370                 375                 380

Ile Asn Ala Glu Asn Asn Glu Arg Asn Phe Leu Ala Gly Glu Glu Asp
385                 390                 395                 400

Asn Val Ile Ser Gln Ile Glu Arg Pro Val Lys Glu Val Ala Phe Pro
                405                 410                 415

Gly Ser Ala Gln Asp Val Glu Ser Leu Leu Lys Asn Gln Arg Gln Ser
            420                 425                 430

Tyr Phe Ala Asn Ala Gln Pro Gln Gln Arg Glu Arg Glu Glu Gly Arg
    435                 440                 445

Ser Gln Arg Gln Arg Glu Leu Ile Ser Ser Ile Leu Gly Val Phe
450                 455                 460

<210> SEQ ID NO 235
<211> LENGTH: 499
<212> TYPE: PRT
<213> ORGANISM: VICIA PEREGRINA

<400> SEQUENCE: 235

Met Ala Thr Thr Phe Lys Ser Arg Phe Ser Leu Leu Leu Leu Leu Gly
1               5                   10                  15

Ile Ile Phe Leu Ala Phe Val Cys Val Thr Cys Ala Asn Tyr Asp Glu
                20                  25                  30

Gly Ser Glu Pro Arg Val Pro Gly Gln Arg Glu Arg Gly Arg Gln Glu
            35                  40                  45

Gly Glu Lys Glu Glu Gln Ser Arg Glu Arg His Pro Gln Arg Glu Pro
        50                  55                  60

Ser Arg Glu Lys Glu Glu Asp Glu Glu Lys Gln Lys Tyr Asp Glu
65                  70                  75                  80

Gly Thr Glu Pro Arg Val Pro Gly Gln Arg Glu Arg Gly Arg Gln Glu
                85                  90                  95

Gly Glu Lys Glu Glu Gln Arg Arg Glu Arg His Pro Gly Gln Arg Glu
            100                 105                 110

Pro Ser Gln Glu Glu Asp Glu Glu Arg Glu Ser Asp Arg Arg Gln
        115                 120                 125

Glu Gly Ser Ser Lys Ser Glu Glu Gln Arg Asn Pro Phe Leu Phe Lys
130                 135                 140

Ser Asn Lys Phe Leu Thr Leu Phe Gln Asn Gly Asn Gly His Ile Arg
145                 150                 155                 160

Leu Leu Gln Arg Phe Asp Lys Arg Ser Asp Leu Phe Glu Asn Leu Gln
                165                 170                 175

Asn Tyr Arg Leu Leu Glu Tyr Arg Ala Lys Pro His Thr Ile Phe Leu
            180                 185                 190
```

```
Pro Gln His Ile Asp Ala Asp Leu Ile Leu Val Val Leu Ser Gly Arg
        195                 200                 205
Ala Ile Leu Thr Val Leu Ser Pro Asp Asp Arg Asn Ser Tyr Asn Leu
210                 215                 220
Glu Arg Gly Asp Thr Ile Lys Leu Pro Ala Gly Thr Thr Ser Tyr Pro
225                 230                 235                 240
Leu Asn Gln Asp Asp Glu Glu Asp Leu Arg Val Val Asp Leu Ala Ile
                245                 250                 255
Ser Val Asn Arg Pro Gly Lys Val Glu Ser Phe Asn Leu Ser Gly Asn
                260                 265                 270
Lys Asn Gln Tyr Leu Arg Gly Phe Ser Glu Asn Ile Leu Glu Ala Ser
                275                 280                 285
Phe Asn Thr Lys Tyr Glu Thr Ile Glu Lys Val Leu Leu Glu Glu Gln
                290                 295                 300
Asp Lys Glu Ser Gln Gln Pro Arg Gly Gln Arg Leu Gln Arg Gln Glu
305                 310                 315                 320
Thr Asn Ala Leu Val Lys Val Ser Arg Glu Gln Val Glu Glu Leu Lys
                325                 330                 335
Arg Leu Ala Arg Thr Ser Ser Lys Lys Gly Val Ser Glu Phe Glu
                340                 345                 350
Pro Phe Asn Leu Arg Ser His Gly Pro Lys Tyr Ser Asn Lys Phe Gly
                355                 360                 365
Lys Phe Phe Glu Ile Thr Pro Glu Lys Lys Tyr Pro Gln Leu Gln Asp
                370                 375                 380
Leu Asp Ile Ser Val Ser Ser Val Glu Ile Asn Glu Gly Ala Leu Phe
385                 390                 395                 400
Leu Pro His Tyr Asn Ser Arg Ala Ile Val Val Val Leu Val Asp Glu
                405                 410                 415
Gly Lys Gly Asn Leu Glu Leu Val Gly Phe Lys Asn Glu Gln Gln Glu
                420                 425                 430
Gln Arg Glu Lys Glu Asp Gln Glu Glu Arg Asn Lys Gln Val Gln
                435                 440                 445
Arg Tyr Glu Ala Lys Leu Ser Pro Gly Asp Val Ile Ile Pro Ala
                450                 455                 460
Gly His Pro Val Ala Val Ser Ala Ser Asn Leu Asn Leu Leu Gly
465                 470                 475                 480
Phe Gly Ile Asn Ala Glu Asn Asn Gln Arg Asn Phe Leu Thr Gly Ser
                485                 490                 495
Asp Asp Asn

<210> SEQ ID NO 236
<211> LENGTH: 515
<212> TYPE: PRT
<213> ORGANISM: VICIA LUTEA

<400> SEQUENCE: 236

Met Ala Thr Thr Ile Lys Leu Arg Phe Pro Leu Leu Leu Leu Gly
1               5                   10                  15
Val Ile Leu Leu Ala Ser Val Cys Val Thr Cys Ala Asn Tyr Asp Glu
                20                  25                  30
Gly Ser Glu Pro Arg Val Pro Gly Arg Pro Glu Gly Glu Lys Glu Glu
                35                  40                  45
Lys His Arg Gly Lys Leu Arg Pro Ser Tyr Glu Lys Glu Glu Asp Glu
50                  55                  60
```

-continued

```
Gly Glu Lys Gln Arg Tyr His Tyr Glu Lys Lys Gln Lys Glu Ala
65                  70                  75                  80

Gln Pro Arg Arg Glu Lys Lys Glu Gln Lys Glu Glu Lys Gln Val
                85                  90                  95

Glu Glu Glu Ser Arg Glu Ser Gln Arg Tyr Glu Asp Pro Gly Glu Arg
            100                 105                 110

Ala Arg Glu Arg Tyr Arg Ala Glu Ile Ile Lys Arg Gln Val Glu Lys
            115                 120                 125

Glu Arg Glu Glu Arg Asp Arg His Gln Arg Glu Gly Glu Glu Glu
130                 135                 140

Glu Gly Ser Ser Lys Ser Arg Asn Pro Phe Leu Phe Lys Ser Asn Asn
145                 150                 155                 160

Phe Leu Thr Leu Phe Glu Asn Glu Asn Gly His Ile Arg Leu Leu Gln
                165                 170                 175

Arg Phe Asp Lys Arg Ser Asp Leu Phe Glu Asn Leu Gln Asn Tyr Arg
                180                 185                 190

Leu Val Glu Tyr Arg Ala Lys Pro His Thr Ile Phe Leu Pro Gln His
            195                 200                 205

Ile Asp Ala Asp Leu Ile Leu Val Val Leu Ser Gly Lys Ala Ile Leu
210                 215                 220

Thr Val Leu Ser Pro Asn Asn Arg Asn Ser Tyr Asn Leu Lys Arg Gly
225                 230                 235                 240

Asp Thr Ile Lys Leu Pro Ala Gly Thr Thr Ser Tyr Leu Leu Asn Ser
                245                 250                 255

Asp Asp Glu Glu Asp Leu Arg Met Val Asp Leu Ala Ile Ser Val Asn
            260                 265                 270

Arg Pro Gly Lys Val Glu Ser Phe Asn Leu Ser Gly Asn Lys Asn Gln
            275                 280                 285

Tyr Leu Arg Gly Phe Ser Lys Asn Ile Leu Glu Ala Ser Phe Asn Thr
290                 295                 300

Lys Tyr Glu Thr Ile Glu Lys Val Leu Leu Glu Glu Gln Asp Lys Glu
305                 310                 315                 320

Ser Gln Gln Ser Ile Gly Gln Lys Arg Ile Ser Gln Arg Gln Glu Thr
                325                 330                 335

Asn Ala Leu Val Lys Val Ser Arg Glu Gln Ile Glu Glu Pro Lys Arg
            340                 345                 350

Leu Ala Arg Ser Ser Ser Arg Lys Gly Val Ser Ser Glu Phe Glu Pro
            355                 360                 365

Ile Asn Leu Arg Ser Gln Arg Pro Lys Tyr Ser Asn Lys Phe Gly Lys
370                 375                 380

Phe Tyr Glu Ile Ser Pro Glu Lys Lys Tyr Pro Gln Leu Gln Asp Leu
385                 390                 395                 400

Asp Val Ser Val Ser Ser Val Glu Ile Asn Glu Gly Ala Leu Leu Leu
                405                 410                 415

Pro His Tyr Asn Ser Arg Ala Ile Val Thr Val Leu Val Asn Glu Gly
            420                 425                 430

Lys Gly Asn Leu Glu Leu Ile Gly Phe Gln Asn Glu Gln Gln Gly Gln
            435                 440                 445

Arg Glu Lys Glu Asp Glu Gln Gln His Glu Arg Asn Lys Gln Val Gln
            450                 455                 460

Arg Tyr Asp Ala Arg Leu Ser Ser Gly Asp Val Val Ile Ile Pro Ala
465                 470                 475                 480
```

Gly His Pro Val Ala Val Ser Ala Ser Ser Asn Leu Asp Leu Leu Gly
            485                 490                 495

Phe Gly Ile Asn Ala Glu Asn Ser Gln Arg Asn Phe Leu Thr Gly Ser
            500                 505                 510

Asp Asp Asn
        515

<210> SEQ ID NO 237
<211> LENGTH: 494
<212> TYPE: PRT
<213> ORGANISM: Oryza brachyantha

<400> SEQUENCE: 237

Met Ala Thr Thr Thr Phe Ser Arg Phe Ser Ile Tyr Phe Cys Val Leu
1               5                   10                  15

Leu Leu Cys His Gly Ser Met Ala Gln Leu Phe Ser Pro Thr Leu Asn
                20                  25                  30

Pro Trp His Ser Ser Arg Arg Gly Gly Ser Arg Asp Cys Arg Phe Asp
            35                  40                  45

Arg Leu Gln Ala Phe Glu Pro Leu Arg Arg Val Arg Ser Glu Ala Gly
50                  55                  60

Val Thr Glu Tyr Phe Asp Glu Arg Asn Glu Gln Phe Gln Cys Thr Gly
65                  70                  75                  80

Thr Phe Val Ile Arg Arg Val Ile Glu Pro Gln Gly Leu Leu Val Pro
                85                  90                  95

Arg Tyr Thr Asn Thr Pro Gly Val Val Tyr Ile Met Gln Gly Arg Gly
            100                 105                 110

Ser Met Gly Leu Thr Phe Pro Gly Cys Pro Ala Thr Tyr Gln Gln Gln
        115                 120                 125

Phe Gln Gln Phe Leu Pro Glu Gly Gln Ser Gln Ser Gln Lys Phe Arg
    130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Thr Pro
                165                 170                 175

Val Val Ala Leu Tyr Val Phe Asp Ile Asn Asn Ser Ala Asn Gln Leu
            180                 185                 190

Glu Pro Arg Gln Lys Asp Phe Leu Leu Ala Gly Asn Asn Asn Arg Glu
        195                 200                 205

Gln Gln Val Tyr Gly Arg Ser Ile Glu Lys His Ser Gly Gln Asn Ile
    210                 215                 220

Phe Ser Gly Phe Asn His Glu Leu Leu Ser Glu Ala Leu Gly Ile Ser
225                 230                 235                 240

Thr Leu Ala Ala Lys Arg Leu Gln Gly Gln Asn Asp His Arg Gly Glu
                245                 250                 255

Ile Ile Arg Val Arg Asn Gly Leu Gln Leu Leu Lys Pro Thr Phe Thr
            260                 265                 270

Gln Gln Gln Glu Gln Ala Gln Ser Gln Tyr Gln Val Gln Tyr Ser Glu
        275                 280                 285

Lys Gln Gln Glu Ser Thr Arg Cys Asn Gly Leu Asp Glu Asn Phe Cys
    290                 295                 300

Thr Ile Asn Ala Arg Leu Asn Ile Glu Asn Pro Ser Arg Ala Asp Thr
305                 310                 315                 320

Tyr Asn Pro Arg Ala Gly Arg Ile Thr His Leu Asn Asn Gln Lys Phe
                325                 330                 335

Pro Ile Leu Asn Leu Val Gln Met Ser Ala Thr Arg Val Asn Leu Tyr
                340                 345                 350

Gln Asn Ala Ile Leu Ser Pro Tyr Trp Asn Val Asn Ala His Ser Leu
            355                 360                 365

Val Tyr Met Val Gln Gly His Ala Arg Val Gln Val Val Ser Asn Leu
        370                 375                 380

Gly Lys Thr Val Phe Asn Ser Val Leu Arg Pro Gly Gln Leu Leu Ile
385                 390                 395                 400

Ile Pro Gln His Tyr Val Val Leu Lys Lys Ala Glu Arg Glu Gly Cys
                405                 410                 415

Gln Tyr Ile Ala Phe Lys Thr Asn Ala Asn Ser Ile Val Ser Gln Leu
            420                 425                 430

Ala Gly Lys Asn Ser Ile Leu Arg Ala Met Pro Val Asp Val Val Ala
        435                 440                 445

Asn Ala Tyr Arg Ile Ser Arg Glu Gln Ala Arg Asp Leu Lys Asn Asn
450                 455                 460

Arg Gly Glu Glu Leu Gly Ala Phe Thr Pro Lys Phe Glu Gln Gln Ser
465                 470                 475                 480

Tyr Pro Gly Leu Ser Asn Glu Ser Glu Ser Glu Ala Ser Glu
                485                 490

<210> SEQ ID NO 238
<211> LENGTH: 515
<212> TYPE: PRT
<213> ORGANISM: Avena sativa

<400> SEQUENCE: 238

Met Ala Thr Thr Ser Phe Pro Ser Val Leu Phe Tyr Ser Cys Ile Phe
1               5                   10                  15

Leu Leu Tyr Asn Gly Ser Met Ala Gln Leu Phe Gly Gln Ser Phe Thr
            20                  25                  30

Pro Trp Gln Ser Ser Arg Gln Gly Gly Leu Lys Gly Cys Lys Phe Asp
        35                  40                  45

Arg Leu Gln Ala Phe Glu Pro Leu Arg Gln Val Arg Ser Gln Ala Gly
50                  55                  60

Val Thr Glu Tyr Phe Asp Glu Gln Asn Glu Gln Phe Arg Cys Thr Gly
65                  70                  75                  80

Val Phe Val Ile Arg Arg Val Ile Glu Pro Gln Gly Leu Leu Leu Pro
                85                  90                  95

Gln Tyr His Asn Ala Pro Gly Leu Val Tyr Ile Leu Gln Gly Arg Gly
            100                 105                 110

Tyr Thr Gly Leu Thr Phe Pro Gly Cys Pro Ala Thr Phe Gln Gln Gln
        115                 120                 125

Phe Gln Pro Phe Asp Gln Ala Gln Asp Gln Ser Gln Ser His Leu Lys
130                 135                 140

Asp Glu His Gln Arg Val His Arg Phe Lys Gln Gly Asp Val Ile Ala
145                 150                 155                 160

Leu Pro Ala Gly Ile Val His Trp Gly Tyr Asn Asp Gly Asp Ala Pro
                165                 170                 175

Val Val Ala Ile Tyr Val Phe Asp Asn Asn Ala Asn Gln Leu
            180                 185                 190

Glu Pro Arg Gln Lys Glu Phe Leu Ala Gly Asn Asn Lys Glu Asp
        195                 200                 205

Gln Gln Phe Gly Gln Asn Ile Phe Ser Gly Phe Asn Ile Gln Leu Leu

```
            210                 215                 220
Ser Glu Ala Leu Gly Ile Ser Gln Gln Ala Ala Gln Arg Ile Gln Ser
225                 230                 235                 240

Gln Lys Glu Gln Arg Gly Glu Ile Ile Arg Val Thr Gln Ala Leu Gln
                245                 250                 255

Phe Leu Lys Pro Thr Met Ser Gln Gln Glu Leu Val Glu His Gln Ala
                260                 265                 270

Tyr Gln Pro Ile Gln Ser Gln Glu Gly Gln Ser Thr Gln Tyr Gln Val
                275                 280                 285

Gly Gln Ser Thr Gln Tyr Gln Glu Gly Gln Ser Thr Gln Tyr Gln Ala
                290                 295                 300

Gly Gln Ser Gln Asp Arg Ser Phe Asn Gly Leu Glu Glu Asn Phe Cys
305                 310                 315                 320

Ser Leu Glu Ala Arg Gln Asn Ile Gly Asn Pro Lys Arg Ala Asp Thr
                325                 330                 335

His Asn Pro Arg Ala Gly Arg Ile Thr Arg Leu His Gly Gln Asn Phe
                340                 345                 350

Pro Ile Leu Asn Leu Val Gln Met Ser Ala Thr Arg Val Asn Leu Tyr
                355                 360                 365

Gln Asn Ala Ile Leu Ser Pro Phe Trp Asn Ile Asn Ala His Ser Val
370                 375                 380

Val Tyr Met Ile Gln Gly His Ala Gln Val Gln Val Asn Asn Asn
385                 390                 395                 400

Gly Gln Thr Val Phe Asn Asp Arg Leu Arg Gln Gly Gln Leu Leu Ile
                405                 410                 415

Val Pro Gln His Tyr Val Val Leu Lys Lys Ala Glu Arg Glu Gly Cys
                420                 425                 430

Gln Tyr Ile Ser Phe Lys Thr Asn Pro Asn Ser Met Val Ser His Ile
                435                 440                 445

Ala Gly Lys Ser Ser Ile Leu Arg Ala Leu Pro Val Asp Val Leu Ala
                450                 455                 460

Asn Ala Tyr Arg Ile Ser Arg Gln Glu Ala Arg Asn Leu Lys Asn Asn
465                 470                 475                 480

Arg Gly Gln Glu Ser Gly Val Phe Thr Pro Lys Phe Thr Gln Thr Ser
                485                 490                 495

Phe Gln Pro Tyr Pro Glu Gly Asp Glu Ser Ser Leu Thr Asn Lys
                500                 505                 510

Ala Ser Glu
        515

<210> SEQ ID NO 239
<211> LENGTH: 493
<212> TYPE: PRT
<213> ORGANISM: Brachypodium distachyon

<400> SEQUENCE: 239

Met Ala His Thr Ser Phe Ser Ser Val Leu Ser Tyr Phe Cys Ile Phe
1               5                   10                  15

Leu Leu Phe His Gly Ser Met Ala Gln Val Pro Gly Gln Gly Ser Thr
                20                  25                  30

Trp Gln Ser Pro Arg Gln Gly Gly Ser Arg Glu Cys Ser Phe Asp Arg
            35                  40                  45

Leu Gln Thr Ile Glu Pro Leu Thr Gln Val Arg Ser Gln Ala Gly Leu
        50                  55                  60
```

```
Thr Glu Tyr Phe Asp Glu Gln Asn Glu Gln Phe Arg Cys Ala Gly Val
 65                  70                  75                  80

Ser Val Ile Arg Arg Val Ile Glu Pro Arg Gly Leu Leu Pro Arg
             85                  90                  95

Tyr His Asn Thr Pro Gly Leu Val Tyr Ile Leu Glu Gly Ser Gly Phe
                100                 105                 110

Val Gly Leu Ala Phe Pro Gly Cys Pro Glu Thr Phe Leu Glu Gln Phe
            115                 120                 125

Gln Gln Ser Arg Gln Thr Gln Ser Thr Leu Gly Gln Ser Gln Cys Gln
        130                 135                 140

Ser Gln Ser Gln Lys Leu Gly Asp Val His Gln Arg Val His Gln Phe
145                 150                 155                 160

Thr Gln Gly Asp Val Ala Leu Pro Ala Gly Val Ala His Trp Phe
                165                 170                 175

Tyr Asn Gly Gly Asp Ala Pro Val Val Ala Val Tyr Val Phe Asp Val
                180                 185                 190

Asn Asn Asn Ala Asn Gln Leu Glu Pro Arg Gln Lys Glu Phe Leu Leu
            195                 200                 205

Ala Gly Asn Tyr Asn Gly Val Leu Gln Ser Gly Arg Asn Ile Leu Asn
        210                 215                 220

Gly Leu Asn Ala Gln Leu Leu Ser Gln Ala Phe Gly Ile Asn Glu Gln
225                 230                 235                 240

Thr Ser Arg Ile Ile Gln Asn Gln Asn Asp Gly Arg Gly Glu Ile Val
                245                 250                 255

Arg Val Glu Tyr Gly Leu Gln Phe Leu Thr Pro Val Val Thr Gln Gln
            260                 265                 270

Gln Gln Lys Gln Pro Phe Leu Pro Ile Glu Pro Gln Glu Gly Gln Ser
        275                 280                 285

Ser Arg Asn Gly Leu Glu Glu Asn Phe Cys Ser Leu Glu Pro Arg Gln
    290                 295                 300

Asn Ile Glu Asp Pro Asn Arg Ala Asp Thr Tyr Asn Pro Arg Ala Gly
305                 310                 315                 320

Ser Ile Ala Arg Leu Asn Gly Gln Asn Phe Pro Ile Leu Asn Leu Val
                325                 330                 335

Gln Met Ser Ala Thr Arg Val Asn Leu Gln Lys Asn Ala Ile Val Ser
            340                 345                 350

Pro Phe Trp Asn Ile Asn Ala His Ser Val Val Tyr Val Ile Gln Gly
        355                 360                 365

Gln Ala Ser Val Gln Val Val Asn Asn Gln Gly Arg Asn Val Phe Asn
    370                 375                 380

Gly Leu Leu Arg Arg Gly Gln Leu Leu Ile Ile Pro Gln Asn Tyr Val
385                 390                 395                 400

Val Leu Lys Lys Ala Glu Ser Glu Gly Tyr Gln Tyr Ile Ala Phe Lys
                405                 410                 415

Thr Asn Ala Asn Ser Met Val Ser His Ile Ala Gly Lys Asn Ser Ile
            420                 425                 430

Leu Arg Ala Leu Pro Val Asp Val Ile Ala Asn Ala Tyr Arg Ile Ser
        435                 440                 445

Arg Gln Glu Ala Gln Asn Leu Lys Asn Asn Arg Gly Glu Glu Ile Gly
    450                 455                 460

Val Leu Thr Pro Asn Phe Pro Gln Ser Ser Cys Gln Ser Tyr Pro Ile
465                 470                 475                 480

Gly Asp Val Asp Ser Ser Ser Thr Pro Lys Ala Gln Glu
```

485 490

<210> SEQ ID NO 240
<211> LENGTH: 489
<212> TYPE: PRT
<213> ORGANISM: Oryza sativa

<400> SEQUENCE: 240

Met Ala Gln Phe Ser Phe Gly Gly Ser Pro Leu Gln Ser Pro Arg Gly
1               5                   10                  15

Phe Arg Gly Asp Gln Asp Ser Arg His Gln Cys Arg Phe Glu His Leu
            20                  25                  30

Thr Ala Leu Glu Ala Thr His Gln Arg Ser Glu Ala Gly Phe Thr
        35                  40                  45

Glu Tyr Tyr Asn Ile Glu Ala Arg Asn Glu Phe Arg Cys Ala Gly Val
    50                  55                  60

Ser Val Arg Arg Leu Val Val Glu Ser Lys Gly Leu Val Leu Pro Met
65                  70                  75                  80

Tyr Ala Asn Ala His Lys Leu Val Tyr Ile Val Gln Gly Arg Gly Val
                85                  90                  95

Phe Gly Met Ala Leu Pro Gly Cys Pro Glu Thr Phe Gln Ser Val Arg
            100                 105                 110

Ser Pro Phe Glu Gln Glu Val Ala Thr Ala Gly Glu Ala Gln Ser Ser
        115                 120                 125

Ile Gln Lys Met Arg Asp Glu His Gln Gln Leu His Gln Phe His Gln
130                 135                 140

Gly Asp Val Ile Ala Val Pro Ala Gly Val Ala His Trp Leu Tyr Asn
145                 150                 155                 160

Asn Gly Asp Ser Pro Val Val Ala Phe Thr Val Ile Asp Thr Ser Asn
                165                 170                 175

Asn Ala Asn Gln Leu Asp Pro Lys Arg Arg Glu Phe Phe Leu Ala Gly
            180                 185                 190

Lys Pro Arg Ser Ser Trp Gln Gln Ser Tyr Ser Tyr Gln Thr Glu
        195                 200                 205

Gln Leu Ser Arg Asn Gln Asn Ile Phe Ala Gly Phe Ser Pro Asp Leu
210                 215                 220

Leu Ser Glu Ala Leu Ser Val Ser Lys Gln Thr Val Leu Arg Leu Gln
225                 230                 235                 240

Gly Leu Ser Asp Pro Arg Gly Ala Ile Ile Arg Val Glu Asn Gly Leu
                245                 250                 255

Gln Ala Leu Gln Pro Ser Leu Gln Val Glu Pro Val Lys Glu Glu Gln
            260                 265                 270

Thr Gln Ala Tyr Leu Pro Thr Lys Gln Leu Gln Pro Thr Trp Leu Arg
        275                 280                 285

Ser Gly Gly Ala Cys Gly Gln Gln Asn Val Leu Asp Glu Ile Met Cys
290                 295                 300

Ala Phe Lys Leu Arg Lys Asn Ile Asp Asn Pro Gln Ser Ser Asp Ile
305                 310                 315                 320

Phe Asn Pro His Gly Gly Arg Ile Thr Arg Ala Asn Ser Gln Asn Phe
                325                 330                 335

Pro Ile Leu Asn Ile Ile Gln Met Ser Ala Thr Arg Ile Val Leu Gln
            340                 345                 350

Asn Asn Ala Leu Leu Thr Pro His Trp Thr Val Asn Ala His Thr Val
        355                 360                 365

-continued

Met Tyr Val Thr Ala Gly Gln Gly His Ile Gln Val Val Asp His Arg
    370             375                 380

Gly Arg Ser Val Phe Asp Gly Glu Leu His Gln Gln Ile Leu Leu
385                 390                 395                 400

Ile Pro Gln Asn Phe Ala Val Val Lys Ala Arg Arg Glu Gly Phe
                    405                 410                 415

Ala Trp Val Ser Phe Lys Thr Asn His Asn Ala Val Asp Ser Gln Ile
                420             425                 430

Ala Gly Lys Ala Ser Ile Leu Arg Ala Leu Pro Val Asp Val Val Ala
            435                 440                 445

Asn Ala Tyr Arg Leu Ser Arg Glu Asp Ser Arg His Val Lys Phe Asn
    450                 455                 460

Arg Gly Asp Glu Met Ala Val Phe Ala Pro Arg Gly Pro Gln Gln
465                 470                 475                 480

Tyr Ala Glu Trp Gln Ile Asn Glu Lys
                485

<210> SEQ ID NO 241
<211> LENGTH: 489
<212> TYPE: PRT
<213> ORGANISM: Oryza sativa

<400> SEQUENCE: 241

Met Ala Gln Phe Ser Phe Gly Gly Ser Pro Leu Gln Ser Pro Arg Gly
1               5                   10                  15

Phe Arg Gly Asp Gln Asp Ser Arg His Gln Cys Arg Phe Glu His Leu
                20                  25                  30

Thr Ala Leu Glu Ala Thr His Gln Gln Arg Ser Glu Ala Gly Phe Thr
            35                  40                  45

Glu Tyr Tyr Asn Ile Glu Ala Arg Asn Glu Phe Arg Cys Ala Gly Val
    50                  55                  60

Ser Val Arg Arg Leu Val Val Glu Ser Lys Gly Leu Val Leu Pro Met
65                  70                  75                  80

Tyr Ala Asn Ala His Lys Leu Val Tyr Ile Val Gln Gly Arg Gly Val
                85                  90                  95

Phe Gly Met Ala Leu Pro Gly Cys Pro Glu Thr Phe Gln Ser Val Arg
                100                 105                 110

Ser Pro Phe Glu Gln Glu Val Ala Thr Ala Gly Glu Ala Gln Ser Ser
            115                 120                 125

Met Gln Lys Met Arg Asp Glu His Gln Gln Leu His Gln Phe His Gln
130                 135                 140

Gly Asp Val Ile Ala Val Pro Ala Gly Val Ala His Trp Leu Tyr Asn
145                 150                 155                 160

Asn Gly Asp Ser Pro Val Val Ala Phe Thr Val Ile Asp Thr Ser Asn
                165                 170                 175

Asn Ala Asn Gln Leu Asp Pro Lys Arg Arg Glu Phe Phe Leu Ala Gly
            180                 185                 190

Lys Pro Arg Ser Ser Trp Gln Gln Gln Ser Tyr Ser Tyr Gln Thr Glu
        195                 200                 205

Gln Leu Ser Arg Asn Gln Asn Ile Phe Ala Gly Phe Asn Pro Asp Leu
    210                 215                 220

Leu Ser Glu Ala Leu Ser Val Ser Lys Gln Thr Val Leu Arg Leu Gln
225                 230                 235                 240

Gly Leu Ser Asp Pro Arg Gly Ala Ile Ile Arg Val Glu Asn Gly Leu
                245                 250                 255

```
Gln Ala Leu Gln Pro Ser Leu Gln Val Glu Pro Val Lys Glu Glu Gln
                260                 265                 270

Thr Gln Ala Tyr Leu Pro Thr Lys Gln Leu Gln Pro Thr Trp Ser Arg
            275                 280                 285

Ser Gly Gly Ala Cys Gly Gln Gln Asn Gly Leu Asp Glu Ile Met Cys
290                 295                 300

Ala Phe Lys Leu Arg Lys Asn Ile Asp Asn Pro Gln Ser Ser Asp Ile
305                 310                 315                 320

Phe Asn Pro His Gly Gly Arg Ile Thr Arg Ala Asn Ser Gln Asn Phe
                325                 330                 335

Pro Ile Leu Asn Ile Ile Gln Met Ser Ala Thr Arg Ile Val Leu Gln
            340                 345                 350

Asn Asn Ala Leu Leu Thr Pro His Trp Thr Val Asn Ala His Thr Val
        355                 360                 365

Met Tyr Val Thr Ala Gly Gln Gly Arg Ile Gln Val Asp His Arg
370                 375                 380

Gly Arg Ser Val Phe Asp Gly Glu Leu His Gln Gln Ile Leu Leu
385                 390                 395                 400

Ile Pro Gln Asn Phe Ala Val Val Lys Ala Arg Arg Glu Gly Phe
                405                 410                 415

Ala Trp Val Ser Phe Lys Thr Asn His Asn Ala Val Asp Ser Gln Ile
            420                 425                 430

Ala Gly Lys Ala Ser Ile Leu Arg Ala Leu Pro Val Asp Val Val Ala
        435                 440                 445

Asn Ala Tyr Arg Leu Ser Arg Glu Asp Ser Arg Val Lys Phe Asn
    450                 455                 460

Arg Gly Asp Glu Met Ala Val Phe Ala Pro Arg Arg Gly Pro Gln Gln
465                 470                 475                 480

Tyr Ala Glu Trp Gln Ile Asn Glu Lys
                485

<210> SEQ ID NO 242
<211> LENGTH: 504
<212> TYPE: PRT
<213> ORGANISM: Oryza brachyantha

<400> SEQUENCE: 242

Met Val Asp Met Ser Ile Val Val Pro Val Cys Leu Thr Ile Phe Leu
1               5                   10                  15

Leu Ser Gln Val Cys Ile Ala Gln Val Ser Phe Asp Gly Ser Pro Leu
            20                  25                  30

Tyr Ser Ser Arg Gly Phe Arg Gly Gly Ser Ala Ser Gln Gln Gln Cys
        35                  40                  45

Arg Phe Glu His Leu Ala Ala Leu Glu Val Thr His Gln Glu Lys Ser
50                  55                  60

Glu Ala Gly Ser Ile Glu Tyr Tyr Asn Thr Glu Ala Arg Asp Glu Phe
65                  70                  75                  80

Arg Cys Ala Arg Val Ser Ala Arg Arg Leu Val Ile Glu Ser Arg Gly
                85                  90                  95

Leu Val Leu Pro Val Tyr Ala Asn Ala His Lys Leu Leu Tyr Ile Val
            100                 105                 110

Gln Gly Arg Gly Val Phe Gly Met Ala Leu Pro Gly Cys Pro Glu Thr
        115                 120                 125

Phe Gln Ser Val Arg Ser Ala Phe Glu Met Ala Thr Gly Asp Ala Glu
```

```
                130                 135                 140
Ser Ser Thr Arg Lys Leu Arg Asp Glu His Gln Lys Ile His Gln Phe
145                 150                 155                 160

Arg Gln Gly Asp Val Ile Ala Val Pro Pro Gly Val Ala His Trp Leu
                165                 170                 175

Tyr Asn Asn Gly Asp Ser Pro Val Val Ala Phe Ser Val Ile Asp Phe
                180                 185                 190

Gly Asn Asn Ala Asn Gln Leu Asp Pro Lys Pro Arg Glu Phe Phe Leu
                195                 200                 205

Ala Gly Lys Pro Trp Gly Trp Gln Gln Val Gln Tyr Ser Tyr Gln Ser
210                 215                 220

Glu Gln Gln Ser Lys His Gln Asn Ile Phe Ala Gly Phe Asn Pro Asp
225                 230                 235                 240

Leu Leu Ala Glu Ala Leu Ser Val Ser Arg Gln Thr Ala Met Arg Leu
                245                 250                 255

Gln Glu Leu Asn Asp Gln Arg Gly Ala Ile Ile Arg Val Glu Gln Gly
                260                 265                 270

Leu Gln Leu Ala Leu Asp Pro Ser Phe Gln Ala Glu Gln Glu Gln Glu
                275                 280                 285

Glu Gln Pro Gln Glu Tyr Leu Ser Ser Gln Gln Gln Gln Pro Thr Trp
                290                 295                 300

Ser Gln Arg Ser Gly Ala Cys Val Gln Asn Asn Gly Leu Asp Glu Ile
305                 310                 315                 320

Met Cys Ala Phe Lys Val Ser Lys Asn Ile Asn Ser Ala Gln Ser Thr
                325                 330                 335

Asp Ile Phe Asn Pro Arg Gly Gly Arg Ile Thr Arg Ala Asn Ser Gln
                340                 345                 350

Asn Phe Pro Val Leu Asn Ile Ile Gln Met Ser Ala Thr Arg Thr Val
                355                 360                 365

Leu Gln Asn Asn Ala Leu Leu Thr Pro His Trp Thr Val Asn Ala His
                370                 375                 380

Thr Val Met Tyr Val Thr Ala Gly Gln Gly Arg Ile Gln Val Val Asp
385                 390                 395                 400

His Arg Gly Arg Thr Val Phe Asp Gly Glu Leu Arg Gln Gln Gln Ile
                405                 410                 415

Leu Leu Ile Pro Gln Asn Phe Ala Val Ala Val Lys Ala Arg His Glu
                420                 425                 430

Gly Phe Ser Trp Val Ser Phe Lys Thr Ser His Asn Ala Ile Asp Ser
                435                 440                 445

Gln Ile Ala Gly Lys Gly Ser Ile Leu Arg Ala Leu Pro Val Asp Val
                450                 455                 460

Leu Ala Lys Ala Tyr Met Leu Ser Arg Glu Ser Arg Thr Leu Lys
465                 470                 475                 480

Tyr Asn Arg Ala Asp Glu Thr Leu Val Phe Ala Pro Arg Pro Glu Ile
                485                 490                 495

Gln Leu Tyr Ala Glu Ser Glu Lys
                500

<210> SEQ ID NO 243
<211> LENGTH: 543
<212> TYPE: PRT
<213> ORGANISM: Pisum fulvum

<400> SEQUENCE: 243
```

```
Met Ala Thr Thr Thr Lys Ser Arg Phe Pro Leu Leu Leu Leu Gly
1               5                   10                  15

Ile Ile Phe Leu Ala Ser Val Val Cys Val Thr Tyr Ala Asn Tyr Asp
            20                  25                  30

Glu Gly Ser Glu Pro Arg Val Pro Gly Arg Arg Glu Arg Gly Arg Gln
            35                  40                  45

Glu Gly Glu Lys Glu Glu Lys Arg His Gly Glu Trp Arg Pro Ser Tyr
50                  55                  60

Glu Lys Glu Glu Asp Glu Glu Gly Gln Arg Glu Arg Gly Arg Gln
65                  70                  75                  80

Glu Gly Glu Lys Glu Glu Lys Arg His Gly Glu Trp Gly Pro Ser Tyr
                85                  90                  95

Glu Lys Gln Glu Asp Glu Glu Glu Lys Gln Lys Tyr Arg Tyr Gln Arg
            100                 105                 110

Glu Lys Glu Asp Glu Glu Glu Lys Gln Lys Tyr Arg Tyr Gln Arg Glu
            115                 120                 125

Lys Lys Glu Gln Lys Glu Val Gln Pro Gly Arg Glu Arg Trp Glu Arg
            130                 135                 140

Glu Glu Asp Glu Glu His Val Asp Glu Glu Trp Arg Gly Ser Gln Arg
145                 150                 155                 160

His Glu Asp Pro Glu Glu Arg Ala Arg Leu Arg Tyr Arg Glu Glu Arg
                165                 170                 175

Thr Lys Arg Asp Arg Arg His Gln Arg Glu Gly Glu Glu Glu Arg
                180                 185                 190

Ser Ser Glu Ser Gln Glu Arg Arg Asn Pro Phe Leu Phe Lys Ser Asn
            195                 200                 205

Lys Phe Gln Thr Leu Phe Glu Asn Glu Asn Gly His Ile Arg Leu Leu
210                 215                 220

Gln Arg Phe Asp Lys Arg Ser Asp Leu Phe Glu Asn Leu Gln Asn Tyr
225                 230                 235                 240

Arg Leu Val Glu Tyr Arg Ala Lys Pro His Thr Ile Phe Leu Pro Gln
                245                 250                 255

His Ile Asp Ala Asp Leu Ile Leu Val Val Leu Ser Gly Lys Ala Ile
                260                 265                 270

Leu Thr Val Leu Ser Pro Asn Ala Arg Asn Ser Tyr Asn Leu Glu Arg
            275                 280                 285

Gly Asp Thr Ile Lys Leu Pro Ala Gly Thr Thr Ser Tyr Leu Val Asn
            290                 295                 300

Gln Asp Asp Glu Glu Asp Leu Arg Leu Val Asp Leu Val Ile Pro Val
305                 310                 315                 320

Asn Gly Pro Gly Lys Phe Glu Ala Phe Asp Leu Ser Lys Asn Lys Asn
                325                 330                 335

Gln Tyr Leu Arg Gly Phe Ser Lys Asn Ile Leu Glu Ala Ser Tyr Asn
            340                 345                 350

Thr Lys Tyr Glu Thr Ile Glu Lys Val Leu Leu Glu Glu Gln Glu Lys
            355                 360                 365

Thr Asp Ala Ile Val Lys Val Ser Arg Glu Gln Ile Glu Glu Leu Arg
370                 375                 380

Lys His Ala Lys Ser Ser Ser Lys Lys Ile Phe Pro Ser Glu Phe Glu
385                 390                 395                 400

Pro Ile Asn Leu Arg Asn His Lys Pro Glu Tyr Ser Asn Lys Phe Gly
                405                 410                 415

Lys Leu Phe Glu Ile Thr Pro Glu Lys Lys Tyr Pro Gln Leu Gln Asp
```

```
                     420                 425                 430
Leu Asp Ile Phe Val Ser Cys Val Glu Ile Asn Glu Gly Ala Leu Met
                435                 440                 445

Leu Pro His Tyr Asn Ser Arg Ala Ile Val Leu Leu Val Asn Glu
        450                 455                 460

Gly Lys Gly Asn Leu Glu Leu Gly Leu Glu Asn Glu Gln Gln Glu
465                 470                 475                 480

Arg Glu Asp Arg Lys Glu Arg Asn Asn Glu Val Gln Arg Tyr Glu Ala
                485                 490                 495

Arg Leu Ser Pro Gly Asp Val Val Ile Ile Pro Ala Gly His Pro Val
                500                 505                 510

Ala Ile Thr Ala Ser Ser Asn Leu Asn Leu Leu Ala Phe Gly Ile Asn
            515                 520                 525

Ala Glu Asn Asn Gln Arg Asn Phe Leu Ser Gly Ser Asp Asp Asn
        530                 535                 540

<210> SEQ ID NO 244
<211> LENGTH: 526
<212> TYPE: PRT
<213> ORGANISM: PISUM ABYSSINICUM

<400> SEQUENCE: 244

Met Ala Thr Thr Val Glu Ser Arg Phe Pro Leu Leu Phe Pro Gly
1               5                   10                  15

Ile Ile Phe Leu Ala Ser Val Cys Val Thr Tyr Ala Asn Tyr Asp Glu
                20                  25                  30

Gly Ser Glu Thr Arg Val Pro Gly Gln Arg Glu Arg Gly Arg Gln Glu
            35                  40                  45

Gly Glu Lys Glu Lys Arg His Gly Glu Trp Arg Pro Ser Tyr Glu
        50                  55                  60

Lys Glu Glu Asp Glu Glu Glu Lys Gln Lys Tyr Arg Tyr Gln Arg Glu
65                  70                  75                  80

Lys Glu Asp Glu Glu Glu Lys Gln Lys Tyr Arg Tyr Gln Arg Glu Lys
                85                  90                  95

Lys Glu Glu Lys Glu Val Gln Pro Gly Arg Glu Arg Trp Glu Arg Glu
            100                 105                 110

Glu Asp Glu Glu Gln Val Asp Glu Glu Trp Arg Gly Ser Gln Arg Arg
        115                 120                 125

Gln Asp Pro Glu Glu Arg Ala Arg Leu Arg His Arg Glu Glu Arg Thr
130                 135                 140

Lys Arg Asp Arg Arg His Lys Arg Glu Gly Glu Glu Glu Arg Ser
145                 150                 155                 160

Ser Glu Ser Gln Glu Gln Arg Asn Pro Phe Leu Phe Lys Ser Asn Lys
                165                 170                 175

Phe Leu Thr Leu Phe Glu Asn Glu Asn Gly His Ile Arg Arg Leu Gln
            180                 185                 190

Arg Phe Asp Lys Arg Ser Asp Leu Phe Glu Asn Leu Gln Asn Tyr Arg
        195                 200                 205

Leu Val Glu Tyr Arg Ala Lys Pro His Thr Ile Phe Leu Pro Gln His
    210                 215                 220

Ile Asp Ala Asp Leu Ile Leu Val Val Leu Asn Gly Lys Ala Ile Leu
225                 230                 235                 240

Thr Val Leu Ser Pro Asn Asp Arg Asn Ser Tyr Asn Leu Glu Arg Gly
                245                 250                 255
```

```
Asp Thr Ile Lys Ile Pro Ala Gly Thr Thr Ser Tyr Leu Val Asn Gln
                260                 265                 270

Asp Asp Glu Glu Asp Leu Arg Val Val Asp Phe Val Ile Pro Val Asn
            275                 280                 285

Arg Pro Gly Lys Phe Glu Ala Phe Gly Leu Ser Glu Asn Lys Asn Gln
        290                 295                 300

Tyr Leu Arg Gly Phe Ser Lys Asn Ile Leu Glu Ala Ser Leu Asn Thr
305                 310                 315                 320

Lys Tyr Glu Thr Ile Glu Lys Val Leu Leu Glu Gln Glu Lys Lys
                325                 330                 335

Pro Gln Gln Leu Arg Asp Arg Lys Arg Arg Gln Gln Gly Gly Glu Arg
            340                 345                 350

Asp Ala Ile Ile Lys Val Ser Arg Glu Gln Ile Glu Glu Leu Arg Lys
        355                 360                 365

Leu Ala Lys Ser Ser Ser Lys Lys Ser Leu Pro Ser Glu Phe Glu Pro
370                 375                 380

Phe Asn Leu Arg Ser His Lys Pro Glu Tyr Ser Asn Lys Phe Gly Lys
385                 390                 395                 400

Leu Phe Glu Ile Thr Pro Glu Lys Lys Tyr Pro Gln Leu Gln Asp Leu
                405                 410                 415

Asp Ile Leu Val Ser Cys Val Glu Ile Asn Lys Gly Ala Leu Met Leu
            420                 425                 430

Pro His Tyr Asn Ser Arg Ala Ile Val Leu Leu Val Asn Glu Gly
        435                 440                 445

Lys Gly Asn Leu Glu Leu Leu Gly Leu Lys Asn Glu Gln Gln Glu Arg
450                 455                 460

Glu Asp Arg Lys Glu Arg Asn Asn Glu Val Gln Arg Tyr Glu Ala Arg
465                 470                 475                 480

Leu Ser Pro Gly Asp Val Val Ile Pro Ala Gly His Pro Val Ala
                485                 490                 495

Ile Ser Ala Ser Ser Asn Leu Asn Leu Leu Gly Phe Gly Thr Asn Ala
            500                 505                 510

Glu Asn Asn Gln Arg Asn Phe Leu Ser Gly Ser Asp Asp Asn
        515                 520                 525

<210> SEQ ID NO 245
<211> LENGTH: 589
<212> TYPE: PRT
<213> ORGANISM: Vicia villosa

<400> SEQUENCE: 245

Met Ala Thr Thr Ile Lys Ser Arg Phe Pro Val Leu Leu Leu Leu Gly
1               5                   10                  15

Ile Ile Phe Leu Thr Ser Val Cys Val Thr Tyr Ala Asn Tyr Asp Glu
                20                  25                  30

Gly Arg Glu Pro Ser Val Pro Gly Gln Arg Glu Arg Gly Arg Gln Glu
            35                  40                  45

Gly Glu Lys Glu Glu Lys Arg His Gly Glu Trp Arg Pro Ser Glu Glu
        50                  55                  60

Asp Glu Glu Glu Lys Tyr Lys Tyr Glu Glu Gly Arg Val Pro Gly Gln
65                  70                  75                  80

Arg Glu Arg Gly Arg Gln Glu Gly Glu Lys Glu Lys Arg His Gly
                85                  90                  95

Lys Trp Arg Pro Ser Glu Glu Glu Asp Glu Glu Glu Lys Tyr Arg Tyr
            100                 105                 110
```

Glu Gly Ser Glu Pro Arg Gly Pro Gly Gln Arg Glu Thr Gly Arg
    115                 120                 125

Gln Glu Gly Glu Lys Glu Lys Gln Arg Pro Glu Arg Glu Pro Ser Tyr
130                 135                 140

Glu Lys Glu Glu Asp Glu Glu Lys Gln Lys Tyr Gln Tyr His Arg
145                 150                 155                 160

Glu Lys Lys Glu Gln Arg Glu Val Arg Pro Gly Arg Glu Arg Phe Glu
                165                 170                 175

Arg His Glu Asp Glu Glu Gln Trp Arg Gly Ile Gln Arg His Glu Asp
                180                 185                 190

Pro Glu Glu Arg Ala Arg Glu Arg Tyr Arg Ala Glu Ile Ala Lys Arg
                195                 200                 205

Gln Val Glu Glu Arg Glu Glu Arg Asp Ile Pro His Glu Arg Glu
    210                 215                 220

Gln Arg Asn Pro Phe Leu Phe Lys Ser Asn Lys Phe Gln Thr Leu Phe
225                 230                 235                 240

Gln Asn Glu Asn Gly Tyr Ile Arg Arg Leu Gln Arg Phe Asp Lys Arg
                245                 250                 255

Ser Asp Leu Phe Glu Asn Leu Gln Asn Tyr Arg Leu Val Glu Tyr Arg
            260                 265                 270

Ala Lys Pro His Thr Ile Phe Leu Pro Gln His Ile Asp Ala Asp Leu
            275                 280                 285

Ile Ile Val Val Leu Ser Gly Arg Ala Ile Leu Thr Val Leu Ser Pro
    290                 295                 300

Asp Asp Arg Asn Ser Tyr Asn Leu Glu Arg Gly Asp Thr Ile Lys Leu
305                 310                 315                 320

Pro Ala Gly Thr Thr Ser Tyr Leu Val Asn Gln Asp Asp Glu Glu Asp
            325                 330                 335

Leu Arg Val Val Asp Leu Ala Ile Pro Val Asn Arg Pro Gly Lys Val
            340                 345                 350

Glu Ser Phe Leu Leu Ser Gly Asn Lys Asn Gln Tyr Leu Arg Gly Phe
    355                 360                 365

Ser Lys Asn Ile Leu Glu Ala Ser Phe Asn Thr Asn Tyr Glu Thr Ile
    370                 375                 380

Glu Arg Val Leu Leu Glu Glu Gln Asp Lys Glu Ser Gln Gln Ser Ile
385                 390                 395                 400

Gly Gln Lys Arg Arg Ser Gln Arg Gln Glu Thr Asn Ala Leu Val Lys
            405                 410                 415

Val Ser Arg Glu Gln Leu Glu Asp Leu Lys Arg Leu Ala Lys Ser Ser
            420                 425                 430

Ser Gln Glu Gly Leu Ser Ser Gln Phe Glu Pro Ile Asn Leu Arg Ser
    435                 440                 445

Gln Asn Pro Lys Tyr Ser Asn Lys Phe Gly Lys Val Phe Glu Ile Thr
450                 455                 460

Pro Glu Lys Lys Tyr Pro Gln Leu Gln Asp Leu Asp Leu Phe Val Ser
465                 470                 475                 480

Ser Val Asp Ile Lys Glu Gly Ala Leu Met Leu Pro His Tyr Asn Ser
            485                 490                 495

Arg Ala Ile Val Val Leu Leu Val Asn Glu Gly Arg Gly Asn Leu Glu
            500                 505                 510

Leu Val Gly Leu Lys Asn Glu Gln Gln Glu Gln Arg Glu Lys Glu Asp
    515                 520                 525

```
Glu Gln Gln Glu Arg Asn Asn Gln Val Gln Arg Tyr Glu Ala Arg Leu
    530                 535                 540

Ser Pro Gly Asp Val Val Ile Ile Pro Ala Gly His Pro Val Ala Val
545                 550                 555                 560

Arg Ala Ser Ser Asp Leu Asn Leu Leu Ala Phe Gly Ile Asn Ala Glu
                565                 570                 575

Asn Asn Gln Arg Asn Phe Leu Ala Gly Ser Asp Asn
                580                 585

<210> SEQ ID NO 246
<211> LENGTH: 576
<212> TYPE: PRT
<213> ORGANISM: Lathyrus hirsutus

<400> SEQUENCE: 246

Met Ala Ile Ile Ile Lys Ser Arg Phe Pro Leu Leu Leu Leu Leu Gly
1               5                   10                  15

Ile Ile Phe Leu Ala Ser Val Cys Ala Thr Trp Ala Asn Tyr Asp Glu
                20                  25                  30

Gly Ser Glu Pro Arg Val Pro Gly Gln Arg Glu Arg Gly Arg Gln Glu
            35                  40                  45

Gly Glu Lys Ala Glu Lys Ser His Glu Lys Trp Arg Pro Ser Tyr Glu
50                  55                  60

Glu Glu Tyr Asp Glu Gly Ser Glu Pro Arg Val Pro Gly Lys Arg Glu
65                  70                  75                  80

Arg Gly Arg Gln Glu Gly Glu Lys Glu Lys Arg His Gly Glu Trp
                85                  90                  95

Arg Pro Ser His Glu Glu Tyr Asp Glu Gly Ser Glu Pro Arg Val
                100                 105                 110

Pro Thr His Gly Glu Arg Gly Arg Gln Glu Gly Glu Lys Glu Lys
            115                 120                 125

Arg His Glu Glu Trp Arg Pro Ser Tyr Glu Lys Glu Glu Asp Glu Glu
130                 135                 140

Glu Lys Glu Lys Tyr Lys Tyr Gln Arg Glu Lys Lys Glu Gln Lys Glu
145                 150                 155                 160

Val Gln Pro Gly Arg Glu Lys Trp Glu Arg Lys Gln Asp Glu Lys His
                165                 170                 175

Val Glu Glu Asp Glu Asp Gln Glu Glu Glu Gln Trp Arg Gly Ser Lys
                180                 185                 190

Arg Arg Glu Asp Pro Glu Glu Arg Ala Arg Leu Arg Tyr Arg Glu Glu
                195                 200                 205

Arg Thr Lys Ser Asn Val Glu Glu Thr Glu Glu Arg Arg Asn Pro
210                 215                 220

Phe Leu Phe Lys Ser Asn Lys Phe Leu Thr Leu Phe Glu Asn Glu Asn
225                 230                 235                 240

Gly His Ile Arg Arg Leu Gln Arg Phe Asp Glu Arg Ser Asp Ile Phe
                245                 250                 255

Glu Asn Leu Gln Asn Tyr Arg Leu Val Glu Tyr Lys Ala Lys Pro His
                260                 265                 270

Thr Met Phe Leu Pro Gln His Ile Asp Ala Asp Leu Ile Ile Val Val
            275                 280                 285

Leu Asn Gly Lys Ala Ile Leu Thr Val Leu Ser Pro Asn Asp Arg Asn
        290                 295                 300

Ser Tyr Asn Leu Glu Arg Gly Asp Thr Ile Lys Leu Pro Ala Gly Thr
305                 310                 315                 320
```

```
Thr Ser Tyr Leu Val Asn Gln Asp Glu Glu Asp Leu Arg Val Val
            325                 330                 335

Asp Leu Ala Ile Pro Val Asn Arg Pro Gly Lys Phe Glu Ala Phe Gly
            340                 345                 350

Leu Ser Ala Asn Lys Asn Gln Tyr Leu Arg Gly Phe Ser Lys Asn Ile
            355                 360                 365

Leu Glu Ala Phe Leu Asn Thr Lys Tyr Glu Thr Ile Glu Lys Val Leu
            370                 375                 380

Leu Glu Glu Gln Glu Arg Arg Asp Arg Lys Gly Arg Gln Gln Gly Gln
385                 390                 395                 400

Glu Thr Asn Ala Ile Val Lys Val Ser Arg Glu Gln Ile Glu Glu Leu
            405                 410                 415

Arg Lys Leu Ala Lys Ser Ser Lys Lys Ser Leu Leu Ser Glu Ser
            420                 425                 430

Glu Pro Ile Asn Leu Arg Ser Gln Asn Pro Lys Tyr Ser Asn Lys Phe
            435                 440                 445

Gly Lys Leu Phe Glu Ile Thr Pro Glu Lys Lys Tyr Pro Gln Leu Gln
            450                 455                 460

Asp Leu Asp Val Ser Ile Ser Cys Val Glu Ile Asn Glu Gly Ala Pro
465                 470                 475                 480

Leu Leu Pro His Tyr Asn Ser Arg Ala Ile Val Leu Leu Val Asn
            485                 490                 495

Glu Gly Lys Gly Asn Leu Glu Leu Val Gly Phe Lys Asn Glu Gln Gln
            500                 505                 510

Arg Gln Arg Glu Asn Glu Arg Asn Lys Lys Val Gln Arg Tyr Glu
            515                 520                 525

Ala Arg Leu Ser Pro Gly Asp Val Val Ile Pro Ala Gly His Pro
            530                 535                 540

Val Ala Ile Ser Ala Ser Leu Asn Leu Asn Leu Val Gly Phe Gly Val
545                 550                 555                 560

Asn Ala Glu Asn Asn Gln Arg Asn Phe Leu Thr Gly Ser Asp Asp Asn
            565                 570                 575

<210> SEQ ID NO 247
<211> LENGTH: 564
<212> TYPE: PRT
<213> ORGANISM: Lathyrus cicera

<400> SEQUENCE: 247

Met Ala Thr Ile Ile Lys Ser Arg Phe Pro Leu Leu Leu Leu Gly
1               5                   10                  15

Ile Ile Phe Leu Ala Ser Val Cys Val Thr Leu Ala Asn Tyr Asp Glu
            20                  25                  30

Gly Ser Glu Pro Arg Val Pro Ala Gln Arg Glu Arg Gly Arg Gln Glu
            35                  40                  45

Gly Glu Lys Glu Glu Lys Arg His Gly Glu Trp Arg Pro Ser His Glu
            50                  55                  60

Lys Glu Tyr Asp Glu Gly Ser Glu Pro Arg Val Pro Gly Arg Arg Glu
65                  70                  75                  80

Arg Gly Arg Gln Glu Gly Glu Lys Glu Lys Arg His Gly Glu Trp
            85                  90                  95

Arg Pro Ser Tyr Glu Lys Glu Tyr Asp Glu Gly Ser Glu Pro Arg Val
            100                 105                 110

Pro Gly Arg Arg Glu Arg Gly Arg Gln Glu Gly Glu Lys Glu Glu Lys
```

```
                115                 120                 125
        Arg His Gly Glu Trp Arg Pro Ser Tyr Glu Lys Glu Tyr Asp Glu Glu
            130                 135                 140
        Glu Lys Gln Lys Tyr Gln Tyr Glu Arg Glu Lys Glu Glu Gln Lys Glu
        145                 150                 155                 160
        Val Gln Pro Gly Arg Glu Arg Trp Glu Arg Lys Glu Asp Glu Glu Lys
                        165                 170                 175
        Glu Glu Asp Gln Trp Arg Gly Ser Gln Arg His Glu Asp Pro Glu Glu
                    180                 185                 190
        Arg Ala Arg Leu Arg Tyr Arg Lys Glu Arg Thr Lys Lys Tyr Val Glu
                        195                 200                 205
        Glu Asp Thr Glu Glu Thr Ser Ser Glu Ser Gln Gly Arg Arg Asn Pro
                    210                 215                 220
        Phe Leu Phe Lys Ser Asn Lys Phe Leu Thr Leu Phe Glu Asn Glu Asn
        225                 230                 235                 240
        Gly Tyr Ile Arg Arg Leu Gln Arg Phe Asp Glu Arg Ser Asp Ile Phe
                        245                 250                 255
        Glu Asn Leu Gln Asn Tyr Arg Leu Val Glu Tyr Arg Ala Lys Pro His
                    260                 265                 270
        Thr Ile Phe Leu Pro Gln His Ile Asp Ala Asp Leu Ile Leu Val Ile
                        275                 280                 285
        Leu Asn Gly Lys Ala Ile Leu Thr Val Leu Ser Pro Asn Asp Arg Asn
                    290                 295                 300
        Ser Tyr Asn Leu Glu Arg Gly Asp Thr Ile Lys Leu Pro Ala Gly Thr
        305                 310                 315                 320
        Thr Ser Tyr Leu Val Asn Glu Asp Asp Glu Glu Asp Leu Arg Val Val
                        325                 330                 335
        Asp Leu Val Ile Pro Val Asn Arg Pro Gly Lys Phe Glu Ala Phe Asp
                    340                 345                 350
        Leu Asn Gln Tyr Leu Gly Gly Phe Ser Lys Ser Val Leu Glu Ala Ser
                        355                 360                 365
        Leu Asn Thr Lys Tyr Glu Thr Ile Glu Lys Val Leu Leu Glu Glu Gln
                    370                 375                 380
        Gln Lys Gln Gly Gln Glu Thr Asn Ala Ile Val Lys Val Ser Arg Glu
        385                 390                 395                 400
        Gln Ile Glu Glu Leu Arg Lys Leu Ala Lys Ser Ser Lys Lys Ser
                        405                 410                 415
        Leu Leu Ser Glu Leu Glu Pro Val Asn Leu Arg Ser His Ser Pro Lys
                    420                 425                 430
        Tyr Ser Asn Lys Phe Gly Lys Phe Phe Glu Ile Thr Pro Glu Lys Lys
                    435                 440                 445
        Tyr Pro Gln Leu Gln Asp Leu Asp Val Ser Ile Ser Cys Val Glu Ile
                    450                 455                 460
        Asn Glu Gly Ala Leu Leu Leu Pro His Tyr Asn Ser Arg Ala Ile Val
        465                 470                 475                 480
        Val Val Leu Val Asn Glu Gly Lys Gly Asn Leu Glu Leu Leu Gly Val
                        485                 490                 495
        Gln Asn Glu Asp Glu Gln Glu Arg Lys Arg Asn Lys Glu Val
                    500                 505                 510
        Gln Arg Tyr Glu Ala Arg Leu Ser Pro Gly Asp Val Val Ile Ile Pro
                    515                 520                 525
        Ser Gly His Pro Val Ala Val Ser Ala Ser Ser Asn Leu Asn Leu Leu
        530                 535                 540
```

```
Gly Phe Gly Ile Asn Ala Glu Asn Asn Gln Arg Asn Phe Leu Ser Gly
545                 550                 555                 560

Ser Asp Asp Asn

<210> SEQ ID NO 248
<211> LENGTH: 527
<212> TYPE: PRT
<213> ORGANISM: Lathyrus sativus

<400> SEQUENCE: 248

Met Ala Thr Ile Ile Lys Ser Arg Phe Pro Leu Leu Leu Leu Leu Gly
1               5                   10                  15

Ile Ile Phe Leu Ala Ser Val Cys Val Thr Tyr Ala Asn Tyr Asp Glu
                20                  25                  30

Gly Ser Glu Pro Arg Val Pro Ala Gln Arg Glu Arg Gly Arg Gln Glu
            35                  40                  45

Gly Glu Lys Glu Glu Lys Arg His Gly Glu Trp Arg Pro Ser Ser Glu
50                  55                  60

Lys Glu Tyr Asp Glu Gly Ser Glu Pro Arg Val Pro Gly Arg Arg Glu
65                  70                  75                  80

Arg Gly Arg Gln Glu Gly Glu Lys Glu Lys Arg His Gly Glu Trp
                85                  90                  95

Arg Pro Ser Tyr Glu Lys Glu Tyr Asp Glu Glu Lys Gln Lys Tyr
            100                 105                 110

Gln Tyr Glu Arg Glu Lys Lys Glu Gln Lys Glu Val Glu Pro Gly Arg
        115                 120                 125

Glu Arg Trp Glu Arg Lys Glu Asp Glu Lys Glu Glu Asp Gln Trp
130                 135                 140

Arg Gly Ser Gln Arg His Glu Asp Pro Glu Glu Arg Ala Arg Leu Arg
145                 150                 155                 160

Tyr Arg Lys Glu Arg Thr Lys Lys Tyr Val Glu Glu Asp Thr Glu Glu
                165                 170                 175

Thr Ser Ser Glu Ser Gln Gly Arg Arg Asn Pro Phe Leu Phe Lys Ser
            180                 185                 190

Asn Lys Phe Leu Thr Leu Phe Glu Asn Glu Asn Gly Tyr Ile Arg Arg
        195                 200                 205

Leu Gln Arg Phe Asp Glu Arg Ser Asp Leu Phe Glu Asn Leu Gln Asn
    210                 215                 220

Tyr Arg Leu Val Glu Tyr Arg Ala Lys Pro His Thr Ile Phe Leu Pro
225                 230                 235                 240

Gln His Ile Asp Ala Asp Leu Ile Leu Val Ile Leu Asn Gly Lys Ala
                245                 250                 255

Ile Leu Thr Val Leu Ser Pro Asn Asp Arg Asn Ser Tyr Asn Leu Glu
            260                 265                 270

Arg Gly Asp Thr Ile Lys Leu Pro Ala Gly Thr Thr Ser Tyr Leu Val
        275                 280                 285

Asn Glu Asp Asp Glu Glu Asp Leu Arg Val Val Asp Leu Val Ile Pro
    290                 295                 300

Val Asn Arg Pro Gly Lys Phe Glu Ala Phe Asp Leu Asn Gln Tyr Leu
305                 310                 315                 320

Gly Gly Phe Ser Lys Ser Val Leu Lys Ala Ser Leu Asn Thr Lys Tyr
                325                 330                 335

Glu Thr Ile Glu Lys Val Leu Leu Glu Glu Gln Gln Lys Gln Gly Gln
            340                 345                 350
```

```
Glu Thr Asn Ala Ile Val Lys Val Ser Arg Glu Gln Ile Glu Glu Leu
        355                 360                 365

Arg Lys Leu Ala Lys Ser Ser Lys Lys Ser Leu Leu Ser Glu Leu
370                 375                 380

Glu Pro Val Asn Leu Arg Ser His Ser Pro Lys Tyr Ser Asn Lys Phe
385                 390                 395                 400

Gly Lys Phe Phe Glu Ile Thr Pro Gly Lys Lys Tyr Pro Gln Leu Gln
                405                 410                 415

Asp Leu Asp Val Ser Ile Ser Cys Val Glu Ile Asn Glu Gly Ala Leu
                420                 425                 430

Leu Leu Pro His Tyr Asn Ser Arg Ala Ile Val Val Leu Leu Val Asn
                435                 440                 445

Glu Gly Lys Gly Asn Leu Glu Leu Leu Gly Val Gln Asp Glu Asp Glu
        450                 455                 460

Gln Gln Glu Arg Lys Lys Arg Asn Lys Glu Val Gln Arg Tyr Glu Ala
465                 470                 475                 480

Arg Leu Ser Pro Ser Asp Val Val Ile Ile Pro Ala Gly His Pro Val
                485                 490                 495

Ala Val Ser Ala Ser Ser Asn Leu Asn Leu Leu Gly Phe Gly Ile Asn
                500                 505                 510

Ala Glu Asn Asn Glu Arg Asn Phe Leu Ser Gly Ser Asp Asp Asn
        515                 520                 525

<210> SEQ ID NO 249
<211> LENGTH: 495
<212> TYPE: PRT
<213> ORGANISM: Oryza brachyantha

<400> SEQUENCE: 249

Met Ala Thr Thr Val Phe Ser Arg Phe Ser Thr Tyr Phe Cys Val Leu
1               5                   10                  15

Leu Leu Cys His Gly Ser Met Ala Gln Leu Phe Asn Pro Ser Thr Asn
                20                  25                  30

Pro Trp His Asn Pro Arg Gln Gly Ser Ser Arg Glu Cys Arg Phe Asp
        35                  40                  45

Arg Leu Gln Pro Phe Glu Pro Leu Arg Lys Val Arg Ser Glu Ala Gly
    50                  55                  60

Val Thr Glu Tyr Phe Asp Glu Lys Asn Glu Leu Phe Gln Cys Thr Gly
65                  70                  75                  80

Thr Phe Val Ile Arg Arg Val Ile Gln Pro Gln Gly Leu Leu Val Pro
                85                  90                  95

Arg Tyr Thr Asn Ala Pro Gly Leu Val Tyr Ile Ile Gln Gly Arg Gly
                100                 105                 110

Ser Ile Gly Leu Thr Phe Pro Gly Cys Pro Ala Thr Tyr Gln Gln Gln
        115                 120                 125

Phe Gln Gln Phe Leu Pro Gln Glu Gln Ser Gln Ser Gln Lys Phe Arg
    130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Asp Gly Asp Ala Pro
                165                 170                 175

Val Val Ala Val Tyr Val Tyr Asp Val Lys Asn Ser Ala Asn Gln Leu
                180                 185                 190

Glu Pro Arg Gln Arg Glu Phe Leu Leu Gly Gly Asn Asn Met Arg Ala
```

```
              195                 200                 205
Gln Gln Val Tyr Gly Ser Ser Ala Glu Gln His Ser Arg Gln Asn Ile
        210                 215                 220
Phe Ser Gly Phe Gly Val Glu Ile Leu Ser Glu Ala Leu Gly Ile Ser
225                 230                 235                 240
Thr Val Thr Thr Lys Arg Leu Gln Ser Gln Asn Asp Gln Arg Gly Glu
                245                 250                 255
Ile Ile His Val Lys Asn Gly Leu Gln Phe Leu Lys Pro Thr Leu Thr
                260                 265                 270
Gln Gln Gln Glu Gln Ala Gln Ala Gln Tyr Gln Glu Val Gln Tyr Ser
                275                 280                 285
Glu Gln Gln Gln Thr Ser Ser Arg Trp Asn Gly Leu Asp Glu Asn Phe
290                 295                 300
Cys Thr Ile Lys Ala Arg Met Asn Ile Glu Asn Thr Ser Arg Ala Asp
305                 310                 315                 320
Thr Tyr Asn Pro Arg Ala Gly Arg Thr Thr Ser Leu Asn Ser Gln Lys
                325                 330                 335
Phe Pro Ile Leu Asn Leu Val Gln Met Ser Ala Thr Arg Val Asn Leu
                340                 345                 350
Tyr Gln Asn Ala Ile Leu Ser Thr Phe Trp Asn Val Asn Ala His Ser
                355                 360                 365
Leu Val Tyr Thr Ile Gln Gly Arg Ala Arg Val Gln Val Val Ser Asn
370                 375                 380
Phe Gly Lys Thr Val Phe Asp Gly Glu Leu Arg Pro Gly Gln Leu Leu
385                 390                 395                 400
Ile Ile Pro Gln His Tyr Val Val Leu Lys Lys Ala Gln Arg Glu Gly
                405                 410                 415
Phe Arg Tyr Ile Ala Ile Lys Thr Asn Ala Asn Ala Phe Val Ser Gln
                420                 425                 430
Leu Val Gly Lys Asn Ser Val Phe Arg Ser Leu Pro Val Asp Val Ile
                435                 440                 445
Ala Asn Val Tyr Arg Ile Ser Arg Glu Gln Ala Arg Ser Leu Lys Asn
450                 455                 460
Asn Arg Gly Glu Glu His Gly Ala Phe Ala Pro Arg Ser Gln Gln Gln
465                 470                 475                 480
Ser Tyr Pro Gly Phe Ser Asn Gln Ser Glu Ser Glu Thr Ser Glu
                485                 490                 495

<210> SEQ ID NO 250
<211> LENGTH: 494
<212> TYPE: PRT
<213> ORGANISM: Oryza brachyantha

<400> SEQUENCE: 250

Met Ala Thr Thr Thr Phe Ser Arg Phe Ser Ile Tyr Phe Cys Val Leu
1               5                   10                  15
Leu Leu Cys His Gly Ser Met Ala Gln Leu Phe Ser Pro Thr Leu Asn
                20                  25                  30
Pro Trp His Ser Ser Arg Arg Gly Gly Ser Arg Asp Cys Arg Phe Asp
                35                  40                  45
Arg Leu Gln Ala Phe Glu Pro Leu Arg Arg Val Arg Ser Glu Ala Gly
                50                  55                  60
Val Thr Glu Tyr Phe Asp Glu Arg Asn Glu Gln Phe Gln Cys Thr Gly
65                  70                  75                  80
```

```
Thr Phe Val Ile Arg Val Ile Glu Pro Gln Gly Leu Leu Val Pro
                85                  90                  95

Arg Tyr Thr Asn Thr Pro Gly Val Val Tyr Ile Met Gln Gly Arg Gly
            100                 105                 110

Ser Met Gly Leu Thr Phe Pro Gly Cys Pro Ala Thr Tyr Gln Gln Gln
        115                 120                 125

Phe Gln Gln Phe Leu Pro Glu Gly Gln Ser Gln Ser Gln Lys Phe Arg
    130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Thr Pro
                165                 170                 175

Val Val Ala Leu Tyr Val Phe Asp Ile Asn Asn Ser Ala Asn Gln Leu
            180                 185                 190

Glu Pro Arg Gln Lys Asp Phe Leu Leu Ala Gly Asn Asn Arg Glu
        195                 200                 205

Gln Gln Val Tyr Gly Arg Ser Ile Glu Lys His Ser Gly Gln Asn Ile
    210                 215                 220

Phe Ser Gly Phe Asn His Glu Leu Leu Ser Glu Ala Leu Gly Ile Ser
225                 230                 235                 240

Thr Leu Ala Ala Lys Arg Leu Gln Gly Gln Asn Asp His Arg Gly Glu
                245                 250                 255

Ile Ile Arg Val Arg Asn Gly Leu Gln Leu Leu Lys Pro Thr Phe Thr
            260                 265                 270

Gln Gln Gln Glu Gln Ala Gln Ser Gln Tyr Gln Val Gln Tyr Ser Glu
        275                 280                 285

Lys Gln Gln Glu Ser Thr Arg Cys Asn Gly Leu Asp Glu Asn Phe Cys
290                 295                 300

Thr Ile Asn Ala Arg Leu Asn Ile Glu Asn Pro Ser Arg Ala Asp Thr
305                 310                 315                 320

Tyr Asn Pro Arg Ala Gly Arg Ile Thr His Leu Asn Asn Gln Lys Phe
                325                 330                 335

Pro Ile Leu Asn Leu Val Gln Met Ser Ala Thr Arg Val Asn Leu Tyr
            340                 345                 350

Gln Asn Ala Ile Leu Ser Pro Tyr Trp Asn Val Asn Ala His Ser Leu
        355                 360                 365

Val Tyr Met Val Gln Gly His Ala Arg Val Gln Val Val Ser Asn Leu
    370                 375                 380

Gly Lys Thr Val Phe Asn Ser Val Leu Arg Pro Gly Gln Leu Leu Ile
385                 390                 395                 400

Ile Pro Gln His Tyr Val Val Leu Lys Lys Ala Glu Arg Glu Gly Cys
                405                 410                 415

Gln Tyr Ile Ala Phe Lys Thr Asn Ala Asn Ser Ile Val Ser Gln Leu
            420                 425                 430

Ala Gly Lys Asn Ser Ile Leu Arg Ala Met Pro Val Asp Val Val Ala
        435                 440                 445

Asn Ala Tyr Arg Ile Ser Arg Glu Gln Ala Arg Asp Leu Lys Asn Asn
    450                 455                 460

Arg Gly Glu Glu Leu Gly Ala Phe Thr Pro Lys Phe Glu Gln Gln Ser
465                 470                 475                 480

Tyr Pro Gly Leu Ser Asn Glu Ser Glu Ser Glu Ala Ser Glu
                485                 490
```

<210> SEQ ID NO 251
<211> LENGTH: 500
<212> TYPE: PRT
<213> ORGANISM: Zizania latifolia

<400> SEQUENCE: 251

```
Met Asn Met Ala Thr Ile Asn Gly Pro Thr Ile Phe Phe Thr Val Cys
1               5                   10                  15

Leu Phe Leu Leu Cys His Gly Ser Leu Ala Gln Leu Leu Gly Gln Ser
            20                  25                  30

Thr Ser Gln Trp Gln Ser Ser His Arg Gly Ser Ser Arg Gln Cys Arg
        35                  40                  45

Phe Asp Arg Leu Gln Ala Phe Glu Pro Val Arg Ser Val Arg Ser Gln
    50                  55                  60

Ala Gly Thr Thr Glu Phe Phe Asp Ala Ser Asn Glu Leu Phe Gln Cys
65                  70                  75                  80

Ala Gly Val Ser Ile Val Arg Arg Ile Ile Glu Pro Arg Gly Leu Leu
                85                  90                  95

Leu Pro Gln Tyr Thr Asn Gly Ala Thr Ile Met Tyr Ile Ile Gln Gly
            100                 105                 110

Arg Gly Ile Thr Gly Gln Thr Phe Pro Gly Cys Pro Glu Ser Tyr Gln
        115                 120                 125

Gln Gln Phe Gln Gln Ser Met Gln Ala Gln Leu Thr Gly Ser Gln Ser
    130                 135                 140

Gln Ser Gln Lys Phe Lys Asp Glu His Gln Lys Ile Asn Arg Phe Arg
145                 150                 155                 160

Gln Gly Asp Val Ile Ala Leu Pro Ala Gly Val Ala His Trp Cys Tyr
                165                 170                 175

Asn Asp Gly Glu Val Pro Val Val Ala Ile Tyr Val Ile Asp Ile Asn
            180                 185                 190

Asn Ala Ala Asn Gln Leu Asp Pro Arg Gln Arg Asp Phe Leu Leu Ala
        195                 200                 205

Gly Asn Met Arg Ser Pro Gln Ala Tyr Arg Arg Glu Val Glu Asn Gln
    210                 215                 220

Ser Gln Asn Ile Phe Ser Gly Phe Ser Ala Glu Leu Leu Ser Glu Ala
225                 230                 235                 240

Leu Gly Ile Ser Thr Gly Val Ala Arg Gln Leu Gln Cys Gln Asn Asp
                245                 250                 255

Gln Arg Gly Glu Ile Val Arg Val Glu His Gly Leu Ser Leu Leu Gln
            260                 265                 270

Pro Tyr Ala Ser Leu Gln Glu Gln Glu Lys Gln Glu Gln Pro Arg
        275                 280                 285

Glu Arg Tyr Gln Val Thr Gln His Gln Gln Ser Gln Tyr Gly Gly Gly
    290                 295                 300

Cys Ser Asn Gly Leu Asp Glu Thr Phe Cys Ala Met Arg Ile Trp Gln
305                 310                 315                 320

Asn Ile Asp Asn Pro Asn Leu Ala Asp Thr Tyr Asn Pro Arg Ala Gly
                325                 330                 335

Arg Val Thr Asn Leu Asn Ser Gln Lys Phe Pro Ile Leu Asn Leu Ile
            340                 345                 350

Gln Met Ser Ala Val Lys Val Asn Leu Tyr Gln Asn Ala Leu Leu Ser
        355                 360                 365

Pro Phe Trp Asn Ile Asn Ser His Ser Val Val Tyr Val Thr Gln Gly
    370                 375                 380
```

```
Cys Ala Arg Val Gln Val Asn Asn Asn Gly Lys Thr Val Phe Asn
385                 390                 395                 400

Gly Glu Leu Arg Arg Gly Gln Leu Leu Ile Ile Pro Gln His Tyr Val
            405                 410                 415

Val Val Lys Lys Ala Gln Arg Glu Gly Cys Ala Tyr Ile Ala Phe Lys
        420                 425                 430

Thr Asn Pro Asn Ser Met Val Ser His Ile Val Gly Lys Ser Ser Ile
            435                 440                 445

Phe Arg Ala Leu Pro Thr Asp Val Leu Ala Asn Ala Tyr Arg Ile Ser
450                 455                 460

Arg Glu Asp Ala Gln Arg Leu Lys His Asn Arg Gly Asp Glu Leu Gly
465                 470                 475                 480

Ala Phe Thr Pro Leu Gln Tyr Lys Ser Tyr Gln Asp Val Ser Ser Val
            485                 490                 495

Ala Ala Ser Ser
            500

<210> SEQ ID NO 252
<211> LENGTH: 454
<212> TYPE: PRT
<213> ORGANISM: Oryza sativa

<400> SEQUENCE: 252

Cys Arg Phe Asp Arg Leu Gln Ala Phe Glu Pro Ile Arg Ser Val Arg
1               5                   10                  15

Ser Gln Ala Gly Thr Thr Glu Phe Phe Asp Val Ser Asn Glu Gln Phe
            20                  25                  30

Gln Cys Thr Gly Val Ser Ala Val Arg Arg Val Ile Glu Pro Arg Gly
        35                  40                  45

Leu Leu Leu Pro His Tyr Thr Asn Gly Ala Ser Leu Val Tyr Ile Ile
    50                  55                  60

Gln Gly Arg Gly Ile Thr Gly Pro Thr Phe Pro Gly Cys Pro Glu Ser
65                  70                  75                  80

Tyr Gln Gln Gln Phe Gln Gln Ser Gly Gln Ala Gln Leu Thr Glu Ser
                85                  90                  95

Gln Ser Gln Ser His Lys Phe Lys Asp Glu His Gln Lys Ile His Arg
            100                 105                 110

Phe Arg Gln Gly Asp Val Ile Ala Leu Pro Ala Gly Val Ala His Trp
        115                 120                 125

Cys Tyr Asn Asp Gly Glu Val Pro Val Val Ala Ile Tyr Val Thr Asp
130                 135                 140

Leu Asn Asn Gly Ala Asn Gln Leu Asp Pro Arg Gln Arg Asp Phe Leu
145                 150                 155                 160

Leu Ala Gly Asn Lys Arg Asn Pro Gln Ala Tyr Arg Arg Glu Val Glu
                165                 170                 175

Glu Arg Ser Gln Asn Ile Phe Ser Gly Phe Ser Thr Glu Leu Leu Ser
            180                 185                 190

Glu Ala Leu Gly Val Ser Ser Gln Val Ala Arg Gln Leu Gln Cys Gln
        195                 200                 205

Asn Asp Gln Arg Gly Glu Ile Val Arg Val Glu His Gly Leu Ser Leu
210                 215                 220

Leu Gln Pro Tyr Ala Ser Leu Gln Gln Gln Gln Gly Gln Val Gln
225                 230                 235                 240

Ser Arg Glu Arg Tyr Gln Glu Gly Gln Tyr Gln Gln Ser Gln Tyr Gly
                245                 250                 255
```

```
Ser Gly Cys Ser Asn Gly Leu Asp Glu Thr Phe Cys Thr Met Lys Val
            260                 265                 270

Arg Gln Asn Ile Asp Asn Pro Asn Arg Ala Asp Thr Tyr Asn Pro Arg
            275                 280                 285

Ala Gly Arg Val Thr Asn Leu Asn Thr Gln Asn Phe Pro Ile Leu Asn
            290                 295                 300

Leu Val Gln Met Ser Ala Val Lys Val Asn Leu Tyr Gln Asn Ala Leu
305                 310                 315                 320

Leu Ser Pro Phe Trp Asn Ile Asn Ala His Ser Val Val Tyr Ile Thr
                325                 330                 335

Gln Gly Arg Ala Arg Val Gln Val Val Asn Asn Asn Gly Lys Thr Val
            340                 345                 350

Phe Asn Gly Glu Leu Arg Arg Gly Gln Leu Leu Ile Ile Pro Gln His
            355                 360                 365

Tyr Ala Val Val Lys Lys Ala Gln Arg Glu Gly Cys Ala Tyr Ile Ala
            370                 375                 380

Phe Lys Thr Asn Pro Asn Ser Met Val Ser His Ile Ala Gly Lys Ser
385                 390                 395                 400

Ser Ile Phe Arg Ala Leu Pro Asn Asp Val Leu Ala Asn Ala Tyr Arg
                405                 410                 415

Ile Ser Arg Glu Glu Ala Gln Arg Leu Lys His Asn Arg Gly Asp Glu
            420                 425                 430

Phe Gly Ala Phe Thr Pro Ile Gln Tyr Lys Ser Tyr Gln Asp Val Tyr
            435                 440                 445

Asn Ala Ala Glu Ser Ser
            450

<210> SEQ ID NO 253
<211> LENGTH: 500
<212> TYPE: PRT
<213> ORGANISM: Zizania latifolia

<400> SEQUENCE: 253

Met Asn Met Ala Thr Ile Asn Gly Pro Thr Ile Phe Phe Thr Val Cys
1               5                   10                  15

Leu Phe Leu Leu Cys His Gly Ser Leu Ala Gln Leu Leu Gly Gln Ser
            20                  25                  30

Thr Ser Gln Trp Gln Ser Ser His Arg Gly Ser Ser Arg Gln Cys Arg
            35                  40                  45

Phe Asp Arg Leu Gln Ala Phe Glu Pro Val Arg Ser Val Arg Ser Gln
        50                  55                  60

Ala Gly Thr Thr Glu Phe Phe Asp Ala Ser Asn Glu Leu Phe Gln Cys
65                  70                  75                  80

Ala Gly Val Ser Ile Val Arg Arg Ile Ile Glu Pro Arg Gly Leu Leu
                85                  90                  95

Leu Pro Gln Tyr Thr Asn Gly Ala Thr Ile Met Tyr Ile Ile Gln Gly
            100                 105                 110

Arg Gly Ile Thr Gly Gln Thr Phe Pro Gly Cys Pro Glu Ser Tyr Gln
            115                 120                 125

Gln Gln Phe Gln Gln Ser Met Gln Ala Gln Leu Thr Gly Ser Gln Ser
            130                 135                 140

Gln Ser Gln Lys Phe Lys Asp Glu His Gln Lys Ile Asn Arg Phe Arg
145                 150                 155                 160

Gln Gly Asp Val Ile Ala Leu Pro Ala Gly Val Ala His Trp Cys Tyr
```

```
            165                 170                 175
Asn Asp Gly Glu Val Pro Val Ala Ile Tyr Val Ile Asp Ile Asn
        180                 185                 190
Asn Ala Ala Asn Gln Leu Asp Pro Arg Gln Arg Asp Phe Leu Leu Ala
    195                 200                 205
Gly Asn Met Arg Ser Pro Gln Ala Tyr Arg Arg Glu Val Glu Asn Gln
    210                 215                 220
Ser Gln Asn Ile Phe Ser Gly Phe Ser Ala Glu Leu Leu Ser Glu Ala
225                 230                 235                 240
Leu Gly Ile Ser Thr Gly Val Ala Arg Gln Leu Gln Cys Gln Asn Asp
            245                 250                 255
Gln Arg Gly Glu Ile Val Arg Val Glu His Gly Leu Ser Leu Leu Gln
        260                 265                 270
Pro Tyr Ala Ser Leu Gln Glu Gln Glu Gln Lys Gln Glu Gln Pro Arg
    275                 280                 285
Glu Arg Tyr Gln Val Thr Gln His Gln Gln Ser Gln Tyr Gly Gly Gly
    290                 295                 300
Cys Ser Asn Gly Leu Asp Glu Thr Phe Cys Ala Met Arg Ile Trp Gln
305                 310                 315                 320
Asn Ile Asp Asn Pro Asn Leu Ala Asp Thr Tyr Asn Pro Arg Ala Gly
            325                 330                 335
Arg Val Thr Asn Leu Asn Ser Gln Lys Phe Pro Ile Leu Asn Leu Ile
        340                 345                 350
Gln Met Ser Ala Val Lys Val Asn Leu Tyr Gln Asn Ala Leu Leu Ser
    355                 360                 365
Pro Phe Trp Asn Ile Asn Ser His Ser Val Val Tyr Val Thr Gln Gly
    370                 375                 380
Cys Ala Arg Val Gln Val Val Asn Asn Asn Gly Lys Thr Val Phe Asn
385                 390                 395                 400
Gly Glu Leu Arg Arg Gly Gln Leu Leu Ile Ile Pro Gln His Tyr Val
            405                 410                 415
Val Val Lys Lys Ala Gln Arg Glu Gly Cys Ala Tyr Ile Ala Phe Lys
        420                 425                 430
Thr Asn Pro Asn Ser Met Val Ser His Ile Val Gly Lys Ser Ser Ile
    435                 440                 445
Phe Arg Ala Leu Pro Thr Asp Val Leu Ala Asn Ala Tyr Arg Ile Ser
    450                 455                 460
Arg Glu Asp Ala Gln Arg Leu Lys His Asn Arg Gly Asp Glu Leu Gly
465                 470                 475                 480
Ala Phe Thr Pro Leu Gln Tyr Lys Ser Tyr Gln Asp Val Ser Ser Val
            485                 490                 495
Ala Ala Ser Ser
        500

<210> SEQ ID NO 254
<211> LENGTH: 527
<212> TYPE: PRT
<213> ORGANISM: Avena sativa

<400> SEQUENCE: 254

Met Ala Thr Thr Ser Phe Pro Ser Met Leu Phe Tyr Phe Cys Ile Phe
1               5                   10                  15
Leu Leu Phe His Gly Ser Met Ala Gln Leu Phe Gly Gln Ser Ser Thr
            20                  25                  30
```

```
Pro Trp Gln Ser Ser Arg Gln Gly Gly Leu Arg Gly Cys Arg Phe Asp
             35                  40                  45
Arg Leu Gln Ala Phe Glu Pro Leu Arg Gln Val Arg Ser Gln Ala Gly
 50                  55                  60
Ile Thr Glu Tyr Phe Asp Glu Gln Asn Glu Gln Phe Arg Cys Thr Gly
 65                  70                  75                  80
Val Ser Val Ile Arg Arg Val Ile Glu Pro Gln Gly Leu Val Leu Pro
                 85                  90                  95
Gln Tyr His Asn Ala Pro Ala Leu Val Tyr Ile Leu Gln Gly Arg Gly
                100                 105                 110
Phe Thr Gly Leu Thr Phe Pro Gly Cys Pro Ala Thr Phe Gln Gln Gln
                115                 120                 125
Phe Gln Pro Phe Asp Gln Ser Gln Phe Ala Gln Gly Gln Arg Gln Ser
130                 135                 140
Gln Thr Ile Lys Asp Glu His Gln Arg Val Gln Arg Phe Lys Gln Gly
145                 150                 155                 160
Asp Val Val Ala Leu Pro Ala Gly Ile Val His Trp Cys Tyr Asn Asp
                165                 170                 175
Gly Asp Ala Pro Ile Val Ala Ile Tyr Val Phe Asp Val Asn Asn Asn
                180                 185                 190
Ala Asn Gln Leu Glu Pro Arg Gln Lys Glu Phe Leu Leu Ala Gly Asn
                195                 200                 205
Asn Lys Arg Glu Gln Gln Ser Gly Asn Asn Ile Phe Ser Gly Leu Ser
                210                 215                 220
Val Gln Leu Leu Ser Glu Ala Leu Gly Ile Ser Gln Gln Ala Ala Gln
225                 230                 235                 240
Arg Ile Gln Ser Gln Asn Asp Gln Arg Gly Glu Ile Ile Arg Val Ser
                245                 250                 255
Gln Gly Leu Gln Phe Leu Lys Pro Ile Val Ser Gln Val Pro Gly
                260                 265                 270
Glu Gln Gln Val Tyr Gln Pro Ile Gln Thr Gln Glu Gly Gln Ala Thr
                275                 280                 285
Gln Tyr Gln Val Gly Gln Ser Thr Gln Tyr Gln Val Gly Lys Ser Thr
                290                 295                 300
Pro Tyr Gln Gly Gly Gln Ser Ser Gln Tyr Gln Ala Gly Gln Ser Trp
305                 310                 315                 320
Asp Gln Ser Phe Asn Gly Leu Glu Glu Asn Phe Cys Ser Leu Glu Ala
                325                 330                 335
Arg Lys Asn Ile Glu Asn Pro Gln His Ala Asp Thr Tyr Asn Pro Arg
                340                 345                 350
Ala Gly Arg Ile Thr Arg Leu Asn Ser Lys Asn Phe Pro Ile Leu Asn
                355                 360                 365
Ile Val Gln Met Ser Ala Thr Arg Val Asn Leu Tyr Gln Asn Ala Ile
                370                 375                 380
Leu Ser Pro Phe Trp Asn Ile Asn Ala His Ser Val Ile Tyr Met Ile
385                 390                 395                 400
Gln Gly His Ala Arg Val Gln Val Val Asn Asn Asn Gly Gln Thr Val
                405                 410                 415
Phe Asn Asp Ile Leu Arg Arg Gly Gln Leu Leu Ile Val Pro Gln His
                420                 425                 430
Phe Val Val Leu Lys Lys Ala Glu Arg Glu Gly Cys Gln Tyr Ile Ser
                435                 440                 445
Phe Lys Thr Asn Pro Asn Ser Met Val Ser His Ile Ala Gly Lys Ser
```

```
               450                 455                 460
Ser Ile Leu Arg Ala Leu Pro Ile Asp Val Leu Ala Asn Ala Tyr Arg
465                 470                 475                 480

Ile Ser Arg Gln Glu Ala Arg Asn Leu Lys Asn Asn Arg Gly Glu Glu
                485                 490                 495

Phe Gly Ala Phe Thr Pro Lys Leu Thr Gln Lys Gly Phe Gln Ser Tyr
            500                 505                 510

Gln Asp Ile Glu Glu Gly Ser Ser Pro Val Arg Ala Ser Glu
        515                 520                 525
```

<210> SEQ ID NO 255
<211> LENGTH: 498
<212> TYPE: PRT
<213> ORGANISM: Oryza sativa

<400> SEQUENCE: 255

```
Met Ala Ser Thr Asn Arg Pro Ile Val Phe Phe Thr Val Cys Leu Phe
1               5                   10                  15

Leu Leu Cys Asp Gly Ser Leu Ala Gln Gln Leu Leu Gly Gln Ser Thr
                20                  25                  30

Ser Gln Trp Gln Ser Ser Arg Arg Gly Ser Pro Arg Gly Cys Arg Phe
            35                  40                  45

Asp Arg Leu Gln Ala Phe Glu Pro Ile Arg Ser Val Arg Ser Gln Ala
        50                  55                  60

Gly Thr Thr Glu Phe Phe Asp Val Ser Asn Glu Leu Phe Gln Cys Thr
65                  70                  75                  80

Gly Val Ser Val Val Arg Arg Val Ile Glu Pro Arg Gly Leu Leu Leu
                85                  90                  95

Pro His Tyr Thr Asn Gly Ala Ser Leu Val Tyr Ile Ile Gln Gly Arg
                100                 105                 110

Gly Ile Thr Gly Pro Thr Phe Pro Gly Cys Pro Glu Thr Tyr Gln Gln
            115                 120                 125

Gln Phe Gln Gln Ser Gly Gln Ala Gly Leu Thr Glu Ser Gln Ser Gln
        130                 135                 140

Ser His Lys Phe Lys Asp Glu His Gln Lys Ile His Arg Phe Arg Gln
145                 150                 155                 160

Gly Asp Val Ile Ala Leu Pro Ala Gly Val Ala His Trp Cys Tyr Asn
                165                 170                 175

Asp Cys Glu Val Pro Val Val Ala Ile Tyr Val Thr Asp Ile Asn Asn
            180                 185                 190

Gly Ala Asn Gln Leu Asp Pro Arg Gln Arg Asp Phe Leu Leu Ala Gly
        195                 200                 205

Asn Lys Arg Asn Pro Gln Ala Tyr Arg Arg Glu Val Glu Glu Trp Ser
210                 215                 220

Gln Asn Ile Phe Ser Gly Phe Ser Thr Glu Leu Leu Ser Glu Ala Phe
225                 230                 235                 240

Gly Ile Ser Asn Gln Val Ala Arg Gln Leu Gln Cys Gln Asn Asp Gln
                245                 250                 255

Lys Gly Glu Ile Val Arg Val Glu Arg Gly Leu Ser Leu Leu Gln Pro
            260                 265                 270

Tyr Ala Ser Leu Gln Glu Gln Glu Gln Gly Gln Met Gln Ser Arg Glu
        275                 280                 285

His Tyr Gln Glu Gly Gly Tyr Gln Gln Ser Gln Tyr Gly Ser Gly Cys
        290                 295                 300
```

```
Pro Asn Gly Leu Asp Glu Thr Phe Cys Val Asn Lys Val Arg Gln Asn
305                 310                 315                 320

Ile Asp Asn Pro Asn Arg Ala Asp Thr Tyr Asn Pro Arg Ala Gly Arg
                325                 330                 335

Val Thr Asn Leu Ser Gln Asn Phe Pro Ile Leu Asn Leu Val Gln Met
            340                 345                 350

Ser Ala Val Lys Val Asn Leu Tyr Gln Asn Thr Asp Thr Trp Ile Ser
        355                 360                 365

Met Gly Gln Glu Glu Asn Ala Leu Leu Ser Pro Phe Trp Asn Ile Asn
    370                 375                 380

Ala His Ser Ile Val Tyr Ile Thr Gln Gly Arg Ala Gln Val Gln Val
385                 390                 395                 400

Leu Arg Arg Gly Gln Leu Leu Ile Val Pro Gln His Tyr Val Val
                405                 410                 415

Lys Lys Ala Gln Arg Glu Gly Cys Ala Tyr Ile Ala Phe Lys Thr Asn
                420                 425                 430

Pro Asn Ser Met Val Ser His Ile Ala Gly Lys Ser Ser Ile Phe Arg
            435                 440                 445

Ala Leu Pro Thr Asp Val Leu Ala Asn Ala Tyr Arg Ile Ser Arg Glu
450                 455                 460

Glu Ala Gln Arg Leu Lys His Asn Arg Gly Asp Glu Phe Gly Ala Phe
465                 470                 475                 480

Thr Pro Leu Gln Tyr Lys Ser Tyr Gln Asp Val Tyr Asn Val Ala Glu
                485                 490                 495

Ser Ser

<210> SEQ ID NO 256
<211> LENGTH: 491
<212> TYPE: PRT
<213> ORGANISM: Oryza brachyantha

<400> SEQUENCE: 256

Met Lys Ser Ser Ile Val Phe Ser Thr Ile Cys Leu Val Leu Leu Cys
1               5                   10                  15

His Gly Ser Leu Ala Gln Leu Leu Ser Gln Ser Thr Ser Gln Trp Gln
                20                  25                  30

Ser Ser Arg Arg Gly Ser Pro Arg Gln Cys Arg Phe Asp Gln Leu Gln
            35                  40                  45

Ala Phe Glu Pro Ile Arg Thr Val Arg Ser Gln Ala Gly Val Thr Glu
        50                  55                  60

Phe Tyr Asp Val Ser Asn Glu Leu Phe Gln Cys Thr Gly Val Ser Val
65                  70                  75                  80

Val Arg Arg Val Ile Glu Pro Arg Gly Leu Leu Pro His Tyr Ser
                85                  90                  95

Asn Gly Ala Thr Leu Val Tyr Ile Ile Gln Gly Arg Gly Ile Thr Gly
                100                 105                 110

Pro Thr Phe Pro Gly Cys Pro Glu Thr Tyr Gln Gln Gln Phe Gln Gln
            115                 120                 125

Ser Gly Glu Ala Gln Pro Phe Glu Gly Gln Ser His Lys Phe Arg Asp
        130                 135                 140

Glu His Gln Lys Ile His Arg Phe Arg Gln Gly Asp Val Val Ala Leu
145                 150                 155                 160

Pro Ala Gly Val Ala His Trp Cys Tyr Asn Asp Gly Glu Val Pro Ile
                165                 170                 175
```

Val Ala Ile Tyr Val Thr Asp Ile Tyr Asn Ser Ala Asn Gln Leu Asp
                180                 185                 190

Pro Arg His Arg Asp Phe Phe Leu Ala Gly Asn Asn Lys Val Ala Gln
            195                 200                 205

Gln Leu Tyr Arg Ser Glu Ala Arg Glu Asn Ser Lys Asn Ile Phe Gly
        210                 215                 220

Gly Phe Ser Val Glu Leu Leu Ser Glu Ala Leu Gly Ile Ser Arg Gly
225                 230                 235                 240

Val Ala Arg Gln Leu Gln Cys Gln Asn Asp Gln Arg Gly Glu Ile Val
                245                 250                 255

Arg Val Glu His Gly Leu Ala Leu Leu Gln Pro Tyr Ala Ser Val Gln
            260                 265                 270

Glu Gln Gln Gln Glu Gln Val Gln Ser Arg Asp Tyr Glu Gln Thr Gln
        275                 280                 285

Tyr Gln Gln Lys Gln Pro Gln Gly Ser Cys Ser Asn Gly Leu Asp Glu
        290                 295                 300

Thr Phe Cys Thr Met Arg Leu Arg Gln Asn Ile Asp Asn Pro Asn Leu
305                 310                 315                 320

Ala Asp Thr Tyr Asn Pro Lys Ala Gly Arg Ile Thr Tyr Leu Asn Gly
                325                 330                 335

Gln Lys Phe Pro Ile Leu Asn Leu Val Gln Met Ser Ala Val Lys Val
            340                 345                 350

Asn Leu Tyr Gln Asn Ala Val Leu Ser Pro Phe Trp Asn Ile Asn Ala
        355                 360                 365

His Ser Val Val Tyr Ile Thr Gln Gly Arg Ala Arg Val Gln Val Val
        370                 375                 380

Asn Asn Asn Gly Lys Thr Val Phe Asp Gly Glu Leu Arg Gln Gly Gln
385                 390                 395                 400

Leu Leu Ile Ile Pro Gln His His Val Val Leu Lys Lys Ala Gln Arg
                405                 410                 415

Glu Gly Cys Ser Tyr Ile Ala Leu Lys Thr Asn Pro Asn Ser Ile Val
            420                 425                 430

Ser His Ile Ala Gly Lys Asn Ser Ile Phe Arg Ala Leu Pro Gly Asp
        435                 440                 445

Val Val Thr Asn Ala Tyr Arg Ile Ser Arg Glu Glu Ala Lys Arg Ile
450                 455                 460

Lys His Asn Arg Gly Asp Glu Ser Gly Val Phe Ala Pro Ser His Ala
465                 470                 475                 480

Tyr Arg Ser Tyr Gln Asp Met Ser Val Ala Ala
                485                 490

<210> SEQ ID NO 257
<211> LENGTH: 492
<212> TYPE: PRT
<213> ORGANISM: Brachypodium distachyon

<400> SEQUENCE: 257

Met Ala His Thr Ser Phe Ser Ser Phe Leu Ser Tyr Phe Cys Leu Phe
1               5                   10                  15

Leu Leu Phe His Gly Ser Met Ala Gln Val Leu Gly Gln Val Ser Thr
                20                  25                  30

Trp Gln Ser Ser Arg Gln Gly Gly Ser Arg Asp Cys Ser Phe Asp Arg
            35                  40                  45

Leu Gln Ala Ile Glu Pro Val Thr Gln Val Arg Ser Gln Ala Gly Leu
        50                  55                  60

-continued

```
Thr Glu Tyr Phe Asp Glu Gln Asn Glu Gln Phe Arg Cys Ala Gly Val
 65                  70                  75                  80

Phe Val Ile Arg Arg Val Ile Glu Pro Arg Gly Leu Leu Leu Pro Arg
                 85                  90                  95

Tyr His Asn Thr Pro Gly Leu Val Tyr Ile Leu Gln Gly Asn Gly Phe
                100                 105                 110

Val Gly Leu Thr Phe Pro Gly Cys Pro Glu Thr Phe Arg Glu Gln Phe
                115                 120                 125

Gln Gln Phe Arg Gln Thr Gln Ser Thr Leu Gly Gln Ser Gln Cys Gln
130                 135                 140

Ser Gln Lys Leu Gly Asp Val His Gln Arg Val His Gln Phe Thr Gln
145                 150                 155                 160

Gly Asp Val Val Ala Leu Pro Thr Gly Val Ala His Trp Ile Tyr Asn
                165                 170                 175

Gly Gly Asp Ala Pro Val Val Ile Val Tyr Val Phe Asp Val Asn Asn
                180                 185                 190

Asn Ala Asn Gln Leu Glu Pro Arg Gln Lys Glu Phe Leu Leu Gly Gly
            195                 200                 205

Asn Tyr Asn Gly Val Leu Gln Tyr Gly Gln Asn Ile Phe Ser Gly Phe
210                 215                 220

Asn Ala Gln Leu Leu Ser Gln Ala Phe Gly Ile Asn Glu Gln Thr Ser
225                 230                 235                 240

Gln Arg Ile Gln Asn Gln Asn Asp Gly Arg Gly Asp Ile Ile Arg Val
                245                 250                 255

Asp Asn Gly Leu Gln Phe Leu Lys Pro Val Val Thr Gln Gln Gln Pro
                260                 265                 270

Glu Gln Pro Phe Met Pro Ile Gln His Gln Thr Gly Gln Ser Ser Arg
                275                 280                 285

Asn Gly Leu Glu Glu Asn Phe Cys Ser Leu Glu Pro Arg Gln Asn Ile
            290                 295                 300

Glu Asp Pro Asn Arg Ala Asp Thr Tyr Asn Pro Arg Ala Gly Ser Ile
305                 310                 315                 320

Thr Arg Leu Asn Gly Gln Asn Phe Pro Ile Leu Asn Leu Val Gln Met
                325                 330                 335

Ser Ala Thr Arg Val Asn Leu Gln Lys Asn Ala Ile Leu Ser Pro Phe
                340                 345                 350

Trp Asn Ile Asn Ala His Ser Val Val Tyr Val Ile Gln Gly His Ala
                355                 360                 365

Leu Val Gln Val Val Asn Asn Gln Gly His Asn Val Phe Asn Gly Leu
                370                 375                 380

Leu His Arg Gly Gln Leu Leu Ile Ile Pro Gln Asn Tyr Val Val Leu
385                 390                 395                 400

Lys Lys Ala Glu Ser Glu Gly Tyr Gln Tyr Ile Ala Phe Lys Thr Asn
                405                 410                 415

Ala Asn Ser Met Val Ser His Ile Ala Gly Lys Asn Ser Ile Leu Arg
                420                 425                 430

Ala Leu Pro Val Asp Val Ile Ala Asn Ala Tyr Arg Ile Ser Arg Gln
                435                 440                 445

Glu Ala Gln Asn Leu Lys Asn Asn Arg Gly Glu Glu Thr Gly Val Leu
            450                 455                 460

Thr Pro Asn Phe Ser Gln Ser Thr Cys Gln Ser Tyr Gln Thr Glu Asp
465                 470                 475                 480
```

Val Gln Ser Leu Arg Pro Met Ser His Trp Ser Glu
            485                 490

<210> SEQ ID NO 258
<211> LENGTH: 166
<212> TYPE: PRT
<213> ORGANISM: Oryza sativa
<220> FEATURE:
<221> NAME/KEY: misc_feature
<222> LOCATION: (120)..(120)
<223> OTHER INFORMATION: Xaa can be any naturally occurring amino acid

<400> SEQUENCE: 258

Met Ala Ser Asn Lys Val Val Phe Ser Ala Leu Leu Ile Ile Val
1               5                   10                  15

Ser Val Leu Ala Ala Thr Ala Thr Met Ala Asp His His Lys Asp Gln
            20                  25                  30

Val Val Tyr Ser Leu Gly Glu Arg Cys Gln Pro Gly Met Gly Tyr Pro
        35                  40                  45

Met Tyr Ser Leu Pro Arg Cys Arg Ala Val Val Lys Arg Gln Cys Val
    50                  55                  60

Gly His Gly Ala Pro Gly Gly Ala Val Asp Glu Gln Leu Arg Gln Asp
65                  70                  75                  80

Cys Cys Arg Gln Leu Ala Ala Val Asp Asp Ser Trp Cys Arg Cys Ser
                85                  90                  95

Ala Leu Asn His Met Val Gly Gly Ile Tyr Arg Glu Leu Gly Ala Thr
            100                 105                 110

Asp Val Gly His Pro Met Ala Xaa Val Phe Pro Gly Cys Arg Arg Gly
        115                 120                 125

Asp Leu Glu Arg Ala Ala Ala Ser Leu Pro Ala Phe Cys Asn Val Asp
    130                 135                 140

Ile Pro Asn Gly Thr Gly Gly Val Cys Tyr Trp Leu Gly Tyr Pro Arg
145                 150                 155                 160

Thr Pro Arg Thr Gly His
                165

<210> SEQ ID NO 259
<211> LENGTH: 165
<212> TYPE: PRT
<213> ORGANISM: Oryza sativa

<400> SEQUENCE: 259

Met Ala Ser Asn Lys Val Val Phe Ser Ala Leu Leu Leu Ile Ile Val
1               5                   10                  15

Ser Val Leu Arg Arg Asp Gly Thr Met Ala Asp His His Lys Asp Gln
            20                  25                  30

Val Val Tyr Ser Leu Gly Glu Arg Cys Gln Pro Gly Met Gly Tyr Pro
        35                  40                  45

Met Tyr Ser Leu Pro Arg Cys Arg Ala Val Val Lys Arg Gln Cys Val
    50                  55                  60

Gly His Gly Ala Pro Gly Ala Val Asp Glu Gln Leu Arg Gln Asp Cys
65                  70                  75                  80

Cys Arg Gln Leu Ala Ala Val Asp Asp Ser Trp Cys Arg Cys Ser Ala
                85                  90                  95

Leu Asn His Met Val Gly Gly Ile Tyr Arg Glu Leu Gly Ala Thr Asp
            100                 105                 110

Val Gly His Pro Met Ala Glu Val Phe Pro Gly Cys Arg Arg Gly Asp
        115                 120                 125

Leu Glu Arg Ala Ala Ala Ser Leu Pro Ala Phe Cys Asn Val Asp Ile
            130                 135                 140

Pro Asn Gly Thr Gly Val Cys Tyr Trp Leu Gly Tyr Pro Arg Thr
145                 150                 155                 160

Pro Arg Thr Gly His
                165

<210> SEQ ID NO 260
<211> LENGTH: 157
<212> TYPE: PRT
<213> ORGANISM: Oryza sativa

<400> SEQUENCE: 260

Met Ala Ser Asn Lys Val Val Ile Ser Ala Leu Leu Val Val Val
1               5                   10                  15

Ser Val Leu Ala Ala Thr Thr Thr Met Ala Asp His His Gln Glu Gln
                20                  25                  30

Val Val Tyr Thr Pro Gly Gln Leu Cys Gln Pro Gly Ile Gly Tyr Pro
            35                  40                  45

Thr Tyr Pro Leu Pro Arg Cys Arg Ala Phe Val Lys Arg Gln Cys Val
50                  55                  60

Ala Pro Gly Thr Val Asp Glu Gln Val Arg Arg Gly Cys Cys Arg Gln
65                  70                  75                  80

Leu Ala Ala Ile Asp Ser Ser Trp Cys Arg Cys Asp Ala Leu Asn His
                85                  90                  95

Met Leu Arg Ile Ile Tyr Arg Glu Ser Gly Ala Ala Asp Ala Gly His
            100                 105                 110

Pro Met Ala Glu Val Phe Arg Gly Cys Arg Arg Gly Asp Ile Glu Arg
        115                 120                 125

Ala Ala Ala Ser Leu Pro Ala Phe Cys Asn Val Asp Ile Pro Asn Gly
    130                 135                 140

Val Gly Val Cys Tyr Trp Leu Pro Gly Thr Gly Tyr
145                 150                 155

<210> SEQ ID NO 261
<211> LENGTH: 495
<212> TYPE: PRT
<213> ORGANISM: Oryza sativa

<400> SEQUENCE: 261

Met Thr Ile Ser Val Phe Ser Arg Phe Ser Ile Tyr Phe Cys Val Leu
1               5                   10                  15

Leu Leu Cys Asn Gly Ser Met Ala Gln Leu Phe Asp Pro Ala Thr Asn
                20                  25                  30

Gln Trp Gln Thr His Arg Gln Gly Ser Phe Arg Glu Cys Arg Phe Glu
            35                  40                  45

Arg Leu Gln Ala Phe Glu Pro Leu Gln Asn Val Arg Ser Glu Ala Gly
        50                  55                  60

Val Thr Glu Tyr Phe Asp Glu Thr Asn Glu Leu Phe Gln Cys Thr Gly
65                  70                  75                  80

Thr Phe Val Ile Arg Arg Val Ile Gln Pro Gln Gly Leu Leu Ile Pro
                85                  90                  95

Arg Tyr Ala Asn Thr Pro Gly Met Val Tyr Ile Ile Gln Gly Arg Gly
            100                 105                 110

Ser Met Gly Leu Thr Phe Pro Gly Cys Pro Ala Thr Tyr Gln Gln Gln
        115                 120                 125

Ser Gln Gln Phe Leu Phe Gln Gly Glu Ser Gln Ser Gln Lys Phe Ile
130                 135                 140

Asp Glu His Gln Lys Ile His Gln Phe Arg Gln Gly Asp Ile Val Val
145                 150                 155                 160

Leu Pro Thr Gly Val Ala His Trp Phe Tyr Asn Asp Gly Asp Thr Pro
                165                 170                 175

Val Val Ala Leu Tyr Val Tyr Asp Ile Asn Asn Ser Ala Asn Gln Leu
            180                 185                 190

Glu Pro Arg His Arg Glu Phe Leu Leu Ala Gly Lys Asn Asn Arg Val
        195                 200                 205

Gln Gln Val Tyr Gly Arg Ser Ile Gln Gln His Ser Gly Gln Asn Ile
210                 215                 220

Phe Asn Gly Phe Ser Val Glu Pro Leu Ser Glu Ala Leu Asn Ile Asn
225                 230                 235                 240

Thr Val Thr Thr Lys Arg Leu Gln Ser Gln Asn Asp Gln Arg Gly Glu
                245                 250                 255

Ile Ile His Val Lys Asn Gly Leu Gln Leu Leu Lys Pro Thr Leu Thr
            260                 265                 270

Gln Arg Gln Glu Gln Glu Gln Ala Gln Tyr Gln Glu Val Gln Tyr Ser
        275                 280                 285

Glu Lys Pro Gln Thr Ser Ser Arg Trp Asn Gly Leu Glu Glu Asn Leu
290                 295                 300

Cys Thr Ile Lys Thr Arg Leu Asn Ile Glu Asn Pro Ser Arg Ala Asp
305                 310                 315                 320

Ser Tyr Asp Pro Arg Ala Gly Arg Ile Thr Ser Leu Asp Ser Gln Lys
                325                 330                 335

Phe Pro Ile Leu Asn Ile Ile Gln Met Ser Ala Thr Arg Val Asn Leu
            340                 345                 350

Tyr Gln Asn Ala Ile Leu Thr Pro Phe Trp Asn Val Asn Ala His Ser
        355                 360                 365

Leu Met Tyr Val Ile Arg Gly Arg Ala Arg Val Gln Val Val Ser Asn
370                 375                 380

Phe Gly Lys Thr Val Phe Asp Gly Val Leu Arg Pro Glu Gln Leu Leu
385                 390                 395                 400

Ile Ile Pro Gln Asn Tyr Val Val Leu Lys Lys Ala Gln His Glu Gly
                405                 410                 415

Cys Gln Tyr Ile Ala Ile Asn Thr Asn Ala Asn Ala Phe Val Ser His
            420                 425                 430

Leu Ala Gly Val Asp Ser Val Phe His Ala Leu Pro Val Asp Val Ile
        435                 440                 445

Ala Asn Ala Tyr Cys Ile Ser Arg Glu Glu Ala Arg Arg Leu Lys Asn
450                 455                 460

Asn Arg Gly Asp Glu Tyr Gly Pro Phe Pro Arg Leu Gln Gln Gln
465                 470                 475                 480

Ile Tyr Pro Glu Phe Ser Asn Glu Ser Lys Gly Glu Thr Ser Glu
                485                 490                 495

<210> SEQ ID NO 262
<211> LENGTH: 480
<212> TYPE: PRT
<213> ORGANISM: Oryza sativa

<400> SEQUENCE: 262

Leu Leu Cys His Gly Ser Met Ala Gln Ile Phe Ser Leu Gly Ile Asn

-continued

```
1               5                   10                  15
Pro Trp Gln Asn Pro Arg Gln Gly Gly Ser Arg Glu Cys Arg Phe Asp
            20                  25                  30

Arg Leu Gln Ala Phe Glu Pro Leu Arg Lys Val Arg His Glu Ala Gly
            35                  40                  45

Val Thr Glu Tyr Phe Asp Glu Lys Asn Glu Gln Phe Gln Cys Thr Gly
            50                  55                  60

Thr Leu Val Ile Arg Arg Ile Ile Glu Pro Gln Gly Leu Leu Leu Pro
65                  70                  75                  80

Arg Tyr Ser Asn Thr Pro Gly Leu Val Tyr Ile Ile Gln Gly Thr Gly
                85                  90                  95

Val Leu Gly Leu Thr Phe Pro Gly Cys Pro Ala Thr Tyr Gln Lys Gln
                100                 105                 110

Phe Arg His Phe Gly Leu Glu Gly Gly Ser Gln Arg Gln Gly Lys Lys
                115                 120                 125

Leu Arg Asp Glu Asn Gln Lys Ile His Gln Phe Arg Gln Gly Asp Val
            130                 135                 140

Val Ala Leu Pro Ser Gly Ile Pro His Trp Phe Tyr Asn Glu Gly Asp
145                 150                 155                 160

Thr Pro Val Val Ala Leu Phe Val Phe Asp Val Asn Asn Ala Asn
                165                 170                 175

Gln Leu Glu Pro Arg Gln Lys Glu Phe Leu Leu Ala Gly Asn Asn Ile
            180                 185                 190

Glu Gln Gln Val Ser Asn Pro Ser Ile Asn Lys His Ser Gly Gln Asn
            195                 200                 205

Ile Phe Asn Gly Phe Asn Thr Lys Leu Leu Ser Glu Ala Leu Gly Val
210                 215                 220

Asn Ile Glu Val Thr Arg Arg Leu Gln Ser Gln Asn Asp Arg Arg Gly
225                 230                 235                 240

Asp Ile Ile Arg Val Lys Asn Gly Leu Arg Leu Ile Lys Pro Thr Ile
                245                 250                 255

Thr Gln Gln Gln Glu Gln Thr Gln Asp Gln Tyr Gln Gln Ile Gln Tyr
                260                 265                 270

His Arg Glu Gln Arg Ser Thr Ser Lys Tyr Asn Gly Leu Asp Glu Asn
            275                 280                 285

Phe Cys Ala Ile Arg Ala Arg Leu Asn Ile Glu Asn Pro Asn His Ala
            290                 295                 300

Asp Thr Tyr Asn Pro Arg Ala Gly Arg Ile Thr Asn Leu Asn Ser Gln
305                 310                 315                 320

Lys Phe Ser Ile Leu Asn Leu Val Gln Met Ser Ala Thr Arg Val Asn
                325                 330                 335

Leu Tyr Gln Asn Ala Ile Leu Ser Pro Phe Trp Asn Ile Asn Ala His
            340                 345                 350

Ser Leu Val Tyr Thr Ile Gln Gly Arg Ala Arg Val Gln Val Val Ser
            355                 360                 365

Asn His Gly Lys Ala Val Phe Asn Gly Val Leu Arg Pro Gly Gln Leu
            370                 375                 380

Leu Ile Ile Pro Gln Asn Tyr Val Val Met Lys Lys Ala Glu Leu Glu
385                 390                 395                 400

Gly Phe Gln Phe Ile Ala Phe Lys Thr Asn Pro Asn Ala Met Val Asn
                405                 410                 415

His Ile Ala Gly Lys Asn Ser Val Leu Arg Ala Met Pro Val Asp Val
            420                 425                 430
```

```
Ile Ala Asn Ala Tyr Arg Ile Ser Arg Gln Glu Ala Arg Ser Leu Lys
        435                 440                 445

Asn Asn Arg Gly Glu Glu Ile Gly Ala Phe Thr Pro Arg Tyr Gln Gln
    450                 455                 460

Gln Lys Ile His Gln Glu Tyr Ser Asn Pro Asn Glu Ser Glu Thr Gln
465                 470                 475                 480
```

<210> SEQ ID NO 263
<211> LENGTH: 518
<212> TYPE: PRT
<213> ORGANISM: Avena sativa

<400> SEQUENCE: 263

```
Met Ala Thr Thr Arg Phe Pro Ser Leu Leu Phe Tyr Ser Cys Ile Phe
1               5                   10                  15

Leu Leu Cys Asn Gly Ser Met Ala Gln Leu Phe Gly Gln Ser Phe Thr
            20                  25                  30

Pro Trp Gln Ser Ser Arg Gln Gly Gly Leu Arg Gly Cys Arg Phe Asp
        35                  40                  45

Arg Leu Gln Ala Phe Glu Pro Leu Arg Gln Val Arg Ser Gln Ala Gly
    50                  55                  60

Ile Thr Glu Tyr Phe Asp Glu Gln Asn Glu Gln Phe Arg Cys Ala Gly
65                  70                  75                  80

Val Ser Val Ile Arg Arg Val Ile Glu Pro Gln Gly Leu Leu Leu Pro
                85                  90                  95

Gln Tyr His Asn Ala Pro Gly Leu Val Tyr Ile Leu Gln Gly Arg Gly
            100                 105                 110

Phe Thr Gly Leu Thr Phe Pro Gly Cys Pro Ala Thr Phe Gln Gln Gln
        115                 120                 125

Phe Gln Pro Phe Asp Gln Ala Arg Phe Ala Gln Gly Gln Ser Lys Ser
130                 135                 140

Gln Asn Leu Lys Asp Glu His Gln Arg Val His Ile Lys Gln Gly
145                 150                 155                 160

Asp Val Val Ala Leu Pro Ala Gly Ile Val His Trp Cys Tyr Asn Asp
                165                 170                 175

Gly Asp Ala Pro Ile Val Ala Val Tyr Val Phe Asp Val Asn Asn Asn
            180                 185                 190

Ala Asn Gln Leu Glu Pro Arg Gln Lys Glu Phe Leu Leu Ala Gly Asn
        195                 200                 205

Asn Lys Arg Glu Gln Gln Phe Gly Gln Asn Ile Phe Ser Gly Phe Ser
    210                 215                 220

Val Gln Leu Leu Ser Glu Ala Leu Gly Ile Ser Gln Gln Ala Ala Gln
225                 230                 235                 240

Lys Ile Gln Ser Gln Asn Asp Gln Arg Gly Glu Ile Ile Arg Val Ser
                245                 250                 255

Gln Gly Leu Gln Phe Leu Lys Pro Phe Val Ser Gln Gln Gly Pro Val
            260                 265                 270

Glu His Gln Ala Tyr Gln Pro Ile Gln Ser Gln Glu Gln Ser Thr
        275                 280                 285

Gln Tyr Gln Val Gly Gln Ser Pro Gln Tyr Gln Gly Gln Ser Thr
    290                 295                 300

Gln Tyr Gln Ser Gly Gln Ser Trp Asp Gln Ser Phe Asn Gly Leu Glu
305                 310                 315                 320

Glu Asn Phe Cys Ser Leu Glu Ala Arg Gln Asn Ile Glu Asn Pro Lys
```

```
                    325                 330                 335
Arg Ala Asp Thr Tyr Asn Pro Arg Ala Gly Arg Ile Thr His Leu Asn
            340                 345                 350

Ser Lys Asn Phe Pro Thr Leu Asn Leu Val Gln Met Ser Ala Thr Arg
            355                 360                 365

Val Asn Leu Tyr Gln Asn Ala Ile Leu Ser Pro Tyr Trp Asn Ile Asn
            370                 375                 380

Ala His Ser Val Met His Met Ile Gln Gly Arg Ala Arg Val Gln Val
385                 390                 395                 400

Val Asn Asn His Gly Gln Thr Val Phe Asn Asp Ile Leu Arg Arg Gly
                405                 410                 415

Gln Leu Leu Ile Ile Pro Gln His Tyr Val Val Leu Lys Lys Ala Glu
            420                 425                 430

Arg Glu Gly Cys Gln Tyr Ile Ser Phe Lys Thr Pro Asn Ser Met
            435                 440                 445

Val Ser Tyr Ile Ala Gly Lys Thr Ser Ile Leu Arg Ala Leu Pro Val
            450                 455                 460

Asp Val Leu Ala Asn Ala Tyr Arg Ile Ser Arg Gln Glu Ser Gln Asn
465                 470                 475                 480

Leu Lys Asn Asn Arg Gly Glu Glu Phe Gly Ala Phe Thr Pro Lys Phe
                485                 490                 495

Ala Gln Thr Gly Ser Gln Ser Tyr Gln Asp Glu Gly Ser Ser Ser
            500                 505                 510

Thr Glu Lys Ala Ser Glu
            515
```

<210> SEQ ID NO 264
<211> LENGTH: 605
<212> TYPE: PRT
<213> ORGANISM: Oryza rufipogon

<400> SEQUENCE: 264

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
        50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
            115                 120                 125

Tyr Lys Asp Ala Trp Asp Thr Ser Val Val Ala Glu Ile Lys Val Ala
        130                 135                 140

Asp Arg Tyr Glu Arg Val Arg Phe Phe His Cys Tyr Lys Arg Gly Val
145                 150                 155                 160

Asp Arg Val Phe Val Asp His Pro Ser Phe Leu Glu Lys Val Trp Gly
                165                 170                 175
```

```
Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Pro Arg Ile Leu
        195                 200                 205

Asn Leu Asn Asn Asn Pro Tyr Phe Lys Gly Thr Tyr Gly Glu Asp Val
    210                 215                 220

Val Phe Val Cys Asn Asp Trp His Thr Gly Pro Leu Ala Ser Tyr Leu
225                 230                 235                 240

Lys Asn Asn Tyr Gln Pro Asn Gly Ile Tyr Arg Asn Ala Lys Val Ala
                245                 250                 255

Phe Cys Ile His Asn Ile Ser Tyr Gln Gly Arg Phe Ala Phe Glu Asp
            260                 265                 270

Tyr Pro Glu Leu Asn Leu Ser Glu Arg Phe Arg Ser Phe Asp Phe
        275                 280                 285

Ile Asp Gly Tyr Asp Thr Pro Val Glu Gly Arg Lys Ile Asn Trp Met
    290                 295                 300

Lys Ala Gly Ile Leu Glu Ala Asp Arg Val Leu Thr Val Ser Pro Tyr
305                 310                 315                 320

Tyr Ala Glu Glu Leu Ile Ser Gly Ile Ala Arg Gly Cys Glu Leu Asp
                325                 330                 335

Asn Ile Met Arg Leu Thr Gly Ile Thr Gly Ile Val Asn Gly Met Asp
            340                 345                 350

Val Ser Glu Trp Asp Pro Ser Lys Asp Lys Tyr Ile Thr Ala Lys Tyr
        355                 360                 365

Asp Ala Thr Thr Ala Ile Glu Ala Lys Ala Leu Asn Lys Glu Ala Leu
    370                 375                 380

Gln Ala Glu Ala Gly Leu Pro Val Asp Arg Lys Ile Pro Leu Ile Ala
385                 390                 395                 400

Phe Ile Gly Arg Leu Glu Glu Gln Lys Gly Pro Asp Val Met Ala Ala
                405                 410                 415

Ala Ile Pro Glu Leu Met Gln Glu Asp Val Gln Ile Val Leu Leu Gly
            420                 425                 430

Thr Gly Lys Lys Lys Phe Glu Lys Leu Leu Lys Ser Met Glu Glu Lys
        435                 440                 445

Tyr Pro Gly Lys Val Arg Ala Val Lys Phe Asn Ala Pro Leu Ala
    450                 455                 460

His Leu Ile Met Ala Gly Ala Asp Val Leu Ala Val Pro Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Val Ile Glu Gly
            500                 505                 510

Lys Thr Gly Phe His Met Gly Arg Leu Ser Val Asp Cys Lys Val Val
        515                 520                 525

Glu Pro Ser Asp Val Lys Lys Val Ala Ala Thr Leu Lys Arg Ala Ile
    530                 535                 540

Lys Val Val Gly Thr Pro Ala Tyr Glu Glu Met Val Arg Asn Cys Met
545                 550                 555                 560

Asn Gln Asp Leu Ser Trp Lys Gly Pro Ala Lys Asn Trp Glu Asn Val
                565                 570                 575

Leu Leu Gly Leu Gly Val Ala Gly Ser Ala Pro Gly Ile Glu Gly Asp
            580                 585                 590

Glu Ile Ala Pro Leu Ala Lys Glu Asn Val Ala Ala Pro
```

<210> SEQ ID NO 265
<211> LENGTH: 609
<212> TYPE: PRT
<213> ORGANISM: ORYZA OFFICINALIS

<400> SEQUENCE: 265

Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Ser Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Leu Pro Pro Ala Met
            100                 105                 110

Ala Ala Asn Gly His Arg Val Met Val Ile Ser Pro Arg His Asp Gln
        115                 120                 125

Tyr Lys Asp Ala Trp Asp Thr Ser Val Val Ala Glu Ile Lys Val Ala
    130                 135                 140

Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Pro Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ser Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

```
Ala Ala Lys Tyr Asp Ala Thr Thr Ala Ile Glu Ala Lys Ala Leu Asn
        370                 375                 380
Lys Glu Ala Leu Gln Ala Glu Ala Gly Leu Pro Val Asp Arg Lys Ile
385                 390                 395                 400
Pro Leu Ile Ala Phe Ile Gly Arg Leu Glu Glu Gln Lys Gly Pro Asp
                405                 410                 415
Val Met Ala Ala Ala Ile Pro Glu Leu Met Gln Glu Asn Val Gln Ile
            420                 425                 430
Val Leu Leu Gly Thr Gly Lys Lys Lys Phe Glu Lys Leu Leu Lys Ser
        435                 440                 445
Met Glu Glu Lys Tyr Pro Gly Lys Val Arg Ala Val Lys Phe Asn
    450                 455                 460
Ala Pro Leu Ala His Leu Ile Met Ala Gly Ala Asp Val Leu Ala Val
465                 470                 475                 480
Pro Ser Arg Phe Glu Pro Cys Gly Leu Ile Gln Leu Gln Gly Met Arg
                485                 490                 495
Tyr Gly Thr Pro Cys Ala Cys Ala Ser Thr Gly Gly Leu Val Asp Thr
            500                 505                 510
Val Ile Glu Gly Lys Thr Gly Phe His Met Gly Arg Leu Ser Val Asp
        515                 520                 525
Cys Lys Val Val Glu Pro Ser Asp Val Gln Lys Val Ala Thr Thr Leu
    530                 535                 540
Lys Arg Ala Ile Lys Ile Val Gly Thr Pro Ala Tyr Asn Glu Met Val
545                 550                 555                 560
Arg Asn Cys Met Asn Gln Asp Leu Ser Trp Lys Gly Pro Ala Lys Asn
                565                 570                 575
Trp Glu Asn Val Leu Leu Gly Leu Gly Val Ala Gly Ser Ala Pro Gly
            580                 585                 590
Val Glu Gly Glu Glu Ile Ala Pro Leu Ala Lys Glu Asn Val Ala Ala
        595                 600                 605
Pro

<210> SEQ ID NO 266
<211> LENGTH: 603
<212> TYPE: PRT
<213> ORGANISM: Hordeum vulgare

<400> SEQUENCE: 266

Met Ala Ala Leu Ala Thr Ser Gln Leu Ala Thr Ser Gly Thr Val Leu
1               5                   10                  15
Gly Val Thr Asp Arg Phe Arg Arg Pro Gly Phe Gln Gly Leu Arg Pro
                20                  25                  30
Arg Asn Pro Ala Asp Ala Ala Leu Gly Met Arg Thr Ile Gly Ala Ser
            35                  40                  45
Ala Ala Pro Lys Gln Ser Arg Lys Ala His Arg Gly Ser Arg Arg Cys
        50                  55                  60
Leu Ser Val Val Val Arg Ala Thr Gly Ser Gly Met Asn Leu Val Phe
65                  70                  75                  80
Val Gly Ala Glu Met Ala Pro Trp Ser Lys Thr Gly Gly Leu Gly Asp
                85                  90                  95
Val Leu Gly Gly Leu Pro Pro Ala Met Ala Ala Asn Gly His Arg Val
                100                 105                 110
Met Val Val Ser Pro Arg Tyr Asp Gln Tyr Lys Asp Ala Trp Asp Thr
            115                 120                 125
```

```
Ser Val Ile Ser Glu Ile Lys Val Ala Asp Glu Tyr Glu Arg Val Arg
    130                 135                 140

Phe Phe His Cys Tyr Lys Arg Gly Val Asp Arg Val Phe Ile Asp His
145                 150                 155                 160

Pro Trp Phe Leu Glu Lys Val Arg Gly Lys Thr Lys Glu Lys Ile Tyr
                165                 170                 175

Gly Pro Asp Ala Gly Thr Asp Tyr Glu Asp Asn Gln Gln Arg Phe Ser
                180                 185                 190

Leu Leu Cys Gln Ala Ala Leu Glu Ala Pro Arg Ile Leu Asn Leu Asn
            195                 200                 205

Asn Asn Pro Tyr Phe Ser Gly Pro Tyr Gly Glu Asp Val Val Phe Val
210                 215                 220

Cys Asn Asp Trp His Thr Gly Leu Leu Ala Cys Tyr Leu Lys Ser Asn
225                 230                 235                 240

Tyr Gln Ser Asn Gly Ile Tyr Arg Thr Ala Lys Val Ala Phe Cys Ile
                245                 250                 255

His Asn Ile Ser Tyr Gln Gly Arg Phe Ser Phe Asp Asp Phe Ala Gln
            260                 265                 270

Leu Asn Leu Pro Asp Arg Phe Lys Ser Ser Phe Asp Phe Ile Asp Gly
        275                 280                 285

Tyr Asp Lys Pro Val Glu Gly Arg Lys Ile Asn Trp Met Lys Ala Gly
290                 295                 300

Ile Leu Gln Ala Asp Lys Val Leu Thr Val Ser Pro Tyr Tyr Ala Glu
305                 310                 315                 320

Glu Leu Ile Ser Asp Glu Ala Arg Gly Cys Glu Leu Asp Asn Ile Met
                325                 330                 335

Arg Leu Thr Gly Ile Thr Gly Ile Val Asn Gly Met Asp Val Ser Glu
            340                 345                 350

Trp Asp Pro Thr Lys Asp Lys Phe Leu Ala Val Asn Tyr Asp Ile Thr
        355                 360                 365

Thr Ala Leu Glu Ala Lys Ala Leu Asn Lys Glu Ala Leu Gln Ala Glu
    370                 375                 380

Val Gly Leu Pro Val Asp Arg Lys Val Pro Leu Val Ala Phe Ile Gly
385                 390                 395                 400

Arg Leu Glu Glu Gln Lys Gly Pro Asp Val Met Ile Ala Ala Ile Pro
                405                 410                 415

Glu Ile Leu Lys Glu Glu Asp Val Gln Ile Ile Leu Leu Gly Thr Gly
            420                 425                 430

Lys Lys Lys Phe Glu Lys Leu Leu Lys Ser Met Glu Glu Lys Phe Pro
        435                 440                 445

Gly Lys Val Arg Ala Val Val Arg Phe Asn Ala Pro Leu Ala His Gln
    450                 455                 460

Met Met Ala Gly Ala Asp Leu Leu Ala Val Thr Ser Arg Phe Glu Pro
465                 470                 475                 480

Cys Gly Leu Ile Gln Leu Gln Gly Met Arg Tyr Gly Thr Pro Cys Val
                485                 490                 495

Cys Ala Ser Thr Gly Gly Leu Val Asp Thr Ile Val Glu Gly Lys Thr
            500                 505                 510

Gly Phe His Met Gly Arg Leu Ser Val Asp Cys Asn Val Val Glu Pro
        515                 520                 525

Ala Asp Val Lys Lys Val Ala Thr Thr Leu Lys Arg Ala Val Lys Val
    530                 535                 540

Val Gly Thr Pro Ala Tyr Gln Glu Met Val Lys Asn Cys Met Ile Gln
```

```
            545                 550                 555                 560
Asp Leu Ser Trp Lys Gly Pro Ala Lys Asn Trp Glu Asp Val Leu Leu
                565                 570                 575

Glu Leu Gly Val Glu Gly Ser Glu Pro Gly Ile Val Gly Glu Glu Ile
                580                 585                 590

Ala Pro Leu Ala Met Glu Asn Val Ala Ala Pro
                595                 600

<210> SEQ ID NO 267
<211> LENGTH: 336
<212> TYPE: PRT
<213> ORGANISM: Staphylococcus aureus

<400> SEQUENCE: 267

Met Lys Gly Lys Phe Leu Lys Val Ser Ser Leu Phe Val Ala Thr Leu
1               5                   10                  15

Thr Thr Ala Thr Leu Val Ser Ser Pro Ala Ala Asn Ala Leu Ser Ser
                20                  25                  30

Lys Ala Met Asp Asn His Pro Gln Gln Ser Gln Ser Ser Lys Gln Gln
            35                  40                  45

Thr Pro Lys Ile Gln Lys Gly Gly Asn Leu Lys Pro Leu Glu Gln Arg
        50                  55                  60

Glu His Ala Asn Val Ile Leu Pro Asn Asn Asp Arg His Gln Ile Thr
65                  70                  75                  80

Asp Thr Thr Asn Gly His Tyr Ala Pro Val Thr Tyr Ile Gln Val Glu
                85                  90                  95

Ala Pro Thr Gly Thr Phe Ile Ala Ser Gly Val Val Gly Lys Asp
                100                 105                 110

Thr Leu Leu Thr Asn Lys His Val Val Asp Ala Thr His Gly Asp Pro
            115                 120                 125

His Ala Leu Lys Ala Phe Pro Ser Ala Ile Asn Gln Asp Asn Tyr Pro
    130                 135                 140

Asn Gly Gly Phe Thr Ala Glu Gln Ile Thr Lys Tyr Ser Gly Glu Gly
145                 150                 155                 160

Asp Leu Ala Ile Val Lys Phe Ser Pro Asn Glu Gln Asn Lys His Ile
                165                 170                 175

Gly Glu Val Val Lys Pro Ala Thr Met Ser Asn Asn Ala Glu Thr Gln
                180                 185                 190

Val Asn Gln Asn Ile Thr Val Thr Gly Tyr Pro Gly Asp Lys Pro Val
            195                 200                 205

Ala Thr Met Trp Glu Ser Lys Gly Lys Ile Thr Tyr Leu Lys Gly Glu
        210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
                245                 250                 255

Pro Asn Glu Phe Asn Gly Ala Val Phe Ile Asn Glu Asn Val Arg Asn
                260                 265                 270

Phe Leu Lys Gln Asn Ile Glu Asp Ile His Phe Ala Asn Asp Asp Gln
            275                 280                 285

Pro Asn Asn Pro Asp Asn Pro Asp Asn Pro Asn Asn Pro Asp Asn Pro
        290                 295                 300

Asn Asn Pro Asp Glu Pro Asn Asn Pro Asp Asn Pro Asn Asn Pro Asp
305                 310                 315                 320
```

```
Asn Pro Asp Asn Gly Asp Asn Asn Ser Asp Asn Pro Asp Ala Ala
            325                 330                 335
```

<210> SEQ ID NO 268
<211> LENGTH: 14
<212> TYPE: PRT
<213> ORGANISM: Artificial Sequence
<220> FEATURE:
<223> OTHER INFORMATION: Synthetic peptide

<400> SEQUENCE: 268

```
Arg Gly Pro Gln Gln Tyr Ala Glu Trp Gln Ile Asn Glu Arg
1               5                   10
```

<210> SEQ ID NO 269
<211> LENGTH: 14
<212> TYPE: PRT
<213> ORGANISM: Artificial Sequence
<220> FEATURE:
<223> OTHER INFORMATION: Synthetic peptide

<400> SEQUENCE: 269

```
Arg Gly Pro Gln Gln Tyr Ala Glu Trp Gln Ile Asn Asp Lys
1               5                   10
```

<210> SEQ ID NO 270
<211> LENGTH: 14
<212> TYPE: PRT
<213> ORGANISM: Artificial Sequence
<220> FEATURE:
<223> OTHER INFORMATION: Synthetic peptide

<400> SEQUENCE: 270

```
Arg Gly Pro Gln Gln Phe Ala Glu Trp Gln Ile Asn Glu Lys
1               5                   10
```

<210> SEQ ID NO 271
<211> LENGTH: 14
<212> TYPE: PRT
<213> ORGANISM: Artificial Sequence
<220> FEATURE:
<223> OTHER INFORMATION: Synthetic peptide

<400> SEQUENCE: 271

```
Lys Gly Pro Gln Gln Tyr Ala Glu Trp Gln Ile Asn Glu Lys
1               5                   10
```

<210> SEQ ID NO 272
<211> LENGTH: 14
<212> TYPE: PRT
<213> ORGANISM: Artificial Sequence
<220> FEATURE:
<223> OTHER INFORMATION: Synthetic peptide

<400> SEQUENCE: 272

```
Arg Gly Pro Glu Gln Tyr Ala Glu Trp Gln Ile Asn Glu Lys
1               5                   10
```

<210> SEQ ID NO 273
<211> LENGTH: 14
<212> TYPE: PRT
<213> ORGANISM: Artificial Sequence
<220> FEATURE:
<223> OTHER INFORMATION: Synthetic peptide

<400> SEQUENCE: 273

```
Arg Gly Pro Gln Glu Tyr Ala Glu Trp Gln Ile Asn Glu Lys
```

```
1               5                   10
```

<210> SEQ ID NO 274
<211> LENGTH: 14
<212> TYPE: PRT
<213> ORGANISM: Artificial Sequence
<220> FEATURE:
<223> OTHER INFORMATION: Synthetic peptide

<400> SEQUENCE: 274

```
Arg Gly Pro Gln Gln Tyr Ala Asp Trp Gln Ile Asn Glu Lys
1               5                   10
```

<210> SEQ ID NO 275
<211> LENGTH: 14
<212> TYPE: PRT
<213> ORGANISM: Artificial Sequence
<220> FEATURE:
<223> OTHER INFORMATION: Synthetic peptide

<400> SEQUENCE: 275

```
Arg Gly Pro Gln Gln Tyr Ala Glu Tyr Gln Ile Asn Glu Lys
1               5                   10
```

<210> SEQ ID NO 276
<211> LENGTH: 14
<212> TYPE: PRT
<213> ORGANISM: Artificial Sequence
<220> FEATURE:
<223> OTHER INFORMATION: Synthetic peptide

<400> SEQUENCE: 276

```
Lys Gly Pro Glu Gln Tyr Ala Glu Trp Gln Ile Asn Glu Lys
1               5                   10
```

<210> SEQ ID NO 277
<211> LENGTH: 14
<212> TYPE: PRT
<213> ORGANISM: Artificial Sequence
<220> FEATURE:
<223> OTHER INFORMATION: Synthetic peptide

<400> SEQUENCE: 277

```
Lys Gly Pro Gln Glu Tyr Ala Glu Trp Gln Ile Asn Glu Lys
1               5                   10
```

<210> SEQ ID NO 278
<211> LENGTH: 14
<212> TYPE: PRT
<213> ORGANISM: Artificial Sequence
<220> FEATURE:
<223> OTHER INFORMATION: Synthetic peptide

<400> SEQUENCE: 278

```
Lys Gly Pro Gln Gln Phe Ala Glu Trp Gln Ile Asn Glu Lys
1               5                   10
```

<210> SEQ ID NO 279
<211> LENGTH: 14
<212> TYPE: PRT
<213> ORGANISM: Artificial Sequence
<220> FEATURE:
<223> OTHER INFORMATION: Synthetic peptide

<400> SEQUENCE: 279

```
Arg Gly Pro Glu Gln Phe Ala Glu Trp Gln Ile Asn Glu Lys
1               5                   10
```

<210> SEQ ID NO 280
<211> LENGTH: 14
<212> TYPE: PRT
<213> ORGANISM: Artificial Sequence
<220> FEATURE:
<223> OTHER INFORMATION: Synthetic peptide

<400> SEQUENCE: 280

Lys Gly Pro Gln Gln Tyr Ala Glu Trp Gln Ile Asn Glu Arg
1               5                   10

<210> SEQ ID NO 281
<211> LENGTH: 14
<212> TYPE: PRT
<213> ORGANISM: Artificial Sequence
<220> FEATURE:
<223> OTHER INFORMATION: Synthetic peptide

<400> SEQUENCE: 281

Arg Gly Pro Gln Gln Tyr Ala Glu Trp Gln Ile Asn Asp Arg
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Synthetic peptide

<400> SEQUENCE: 282

Arg Gly Pro Gln Gln Tyr Ala Asp Trp Gln Ile Asn Asp Lys
1               5                   10

<210> SEQ ID NO 283
<211> LENGTH: 14
<212> TYPE: PRT
<213> ORGANISM: Artificial Sequence
<220> FEATURE:
<223> OTHER INFORMATION: Synthetic peptide

<400> SEQUENCE: 283

Arg Gly Pro Gln Gln Phe Ala Glu Trp Gln Ile Asn Glu Arg
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Synthetic peptide

<400> SEQUENCE: 284

Arg Gly Pro Gln Gln Tyr Ala Glu Trp Gln Val Asn Glu Lys
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Synthetic peptide

<400> SEQUENCE: 285

Arg Gly Pro Gln Gln Phe Ala Glu Trp Gln Ile Asn Glu Lys
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Synthetic peptide

<400> SEQUENCE: 286

Lys Gly Pro Gln Gln Phe Ala Glu Trp Gln Ile Asn Glu Arg
1               5                   10

<210> SEQ ID NO 287
<211> LENGTH: 14
<212> TYPE: PRT
<213> ORGANISM: Artificial Sequence
<220> FEATURE:
<223> OTHER INFORMATION: Synthetic peptide

<400> SEQUENCE: 287

Lys Gly Pro Gln Gln Phe Ala Glu Trp Gln Val Asn Glu Lys
1               5                   10

<210> SEQ ID NO 288
<211> LENGTH: 14
<212> TYPE: PRT
<213> ORGANISM: Artificial Sequence
<220> FEATURE:
<223> OTHER INFORMATION: Synthetic peptide

<400> SEQUENCE: 288

Arg Gly Pro Gln Gln Phe Ala Glu Trp Gln Val Asn Asp Lys
1               5                   10

<210> SEQ ID NO 289
<211> LENGTH: 14
<212> TYPE: PRT
<213> ORGANISM: Artificial Sequence
<220> FEATURE:
<223> OTHER INFORMATION: Synthetic peptide

<400> SEQUENCE: 289

Arg Gly Pro Gln Gln Tyr Ala Asp Trp Gln Ile Asn Asp Arg
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Synthetic peptide

<400> SEQUENCE: 290

Lys Gly Pro Gln Gln Tyr Ala Asp Trp Gln Ile Asn Asp Lys
1               5                   10

<210> SEQ ID NO 291
<211> LENGTH: 14
<212> TYPE: PRT
<213> ORGANISM: Artificial Sequence
<220> FEATURE:
<223> OTHER INFORMATION: Synthetic peptide

<400> SEQUENCE: 291

Arg Gly Pro Gln Gln Phe Ala Asp Tyr Gln Ile Asn Glu Lys
1               5                   10

```
<210> SEQ ID NO 292
<211> LENGTH: 14
<212> TYPE: PRT
<213> ORGANISM: Artificial Sequence
<220> FEATURE:
<223> OTHER INFORMATION: Synthetic peptide

<400> SEQUENCE: 292

Arg Gly Pro Gln Gln Tyr Ala Arg Trp Gln Ile Asn Glu Lys
 1               5                  10

<210> SEQ ID NO 293
<211> LENGTH: 14
<212> TYPE: PRT
<213> ORGANISM: Artificial Sequence
<220> FEATURE:
<223> OTHER INFORMATION: Synthetic peptide

<400> SEQUENCE: 293

Arg Gly Pro Gln Gln Tyr Ala Glu Trp Gln Ile Asn Glu Glu
 1               5                  10

<210> SEQ ID NO 294
<211> LENGTH: 14
<212> TYPE: PRT
<213> ORGANISM: Artificial Sequence
<220> FEATURE:
<223> OTHER INFORMATION: Synthetic peptide

<400> SEQUENCE: 294

His Gly Pro Gln Gln Tyr Ala Glu Trp Gln Ile Asn Glu Lys
 1               5                  10

<210> SEQ ID NO 295
<211> LENGTH: 14
<212> TYPE: PRT
<213> ORGANISM: Artificial Sequence
<220> FEATURE:
<223> OTHER INFORMATION: Synthetic peptide

<400> SEQUENCE: 295

Arg Gly Pro Tyr Gln Tyr Ala Glu Trp Gln Ile Asn Glu Lys
 1               5                  10

<210> SEQ ID NO 296
<211> LENGTH: 14
<212> TYPE: PRT
<213> ORGANISM: Artificial Sequence
<220> FEATURE:
<223> OTHER INFORMATION: Synthetic peptide

<400> SEQUENCE: 296

Arg Gly Pro Gln Gln Tyr Met Glu Trp Gln Ile Asn Glu Lys
 1               5                  10

<210> SEQ ID NO 297
<211> LENGTH: 14
<212> TYPE: PRT
<213> ORGANISM: Artificial Sequence
<220> FEATURE:
<223> OTHER INFORMATION: Synthetic peptide

<400> SEQUENCE: 297

Arg Gly Pro Gln Gln Tyr Ala Glu Trp Cys Ile Asn Glu Lys
 1               5                  10

<210> SEQ ID NO 298
```

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 298

Arg Gly Pro Gln Pro Tyr Ala Glu Trp Gln Ile Asn Glu Lys
1               5                   10

<210> SEQ ID NO 299
<211> LENGTH: 14
<212> TYPE: PRT
<213> ORGANISM: Artificial Sequence
<220> FEATURE:
<223> OTHER INFORMATION: Synthetic peptide

<400> SEQUENCE: 299

Arg Gly Gly Gln Gln Tyr Ala Glu Trp Gln Ile Asn Glu Asp
1               5                   10

<210> SEQ ID NO 300
<211> LENGTH: 14
<212> TYPE: PRT
<213> ORGANISM: Artificial Sequence
<220> FEATURE:
<223> OTHER INFORMATION: Synthetic peptide

<400> SEQUENCE: 300

Arg Gly Pro Gln Gln Tyr Ala Arg Trp Lys Ile Asn Glu Lys
1               5                   10

<210> SEQ ID NO 301
<211> LENGTH: 14
<212> TYPE: PRT
<213> ORGANISM: Artificial Sequence
<220> FEATURE:
<223> OTHER INFORMATION: Synthetic peptide

<400> SEQUENCE: 301

Arg Gly Gly Gln Gln Tyr Ala Glu Thr Gln Ile Asn Glu Lys
1               5                   10

<210> SEQ ID NO 302
<211> LENGTH: 14
<212> TYPE: PRT
<213> ORGANISM: Artificial Sequence
<220> FEATURE:
<223> OTHER INFORMATION: Synthetic peptide

<400> SEQUENCE: 302

Arg Gly Pro Leu Gln Tyr Ala Glu Trp Gln Asn Asn Glu Lys
1               5                   10

<210> SEQ ID NO 303
<211> LENGTH: 14
<212> TYPE: PRT
<213> ORGANISM: Artificial Sequence
<220> FEATURE:
<223> OTHER INFORMATION: Synthetic peptide

<400> SEQUENCE: 303

Glu Gly Pro Gln Gln Tyr Ala Glu Trp Gln Ile Asn Glu Asp
1               5                   10

<210> SEQ ID NO 304
<211> LENGTH: 14
```

<212> TYPE: PRT
<213> ORGANISM: Artificial Sequence
<220> FEATURE:
<223> OTHER INFORMATION: Synthetic peptide

<400> SEQUENCE: 304

Arg Gly Pro Gln Gln Tyr Ala Glu Trp Gln Ile Asn Leu Leu
1               5                   10

<210> SEQ ID NO 305
<211> LENGTH: 14
<212> TYPE: PRT
<213> ORGANISM: Artificial Sequence
<220> FEATURE:
<223> OTHER INFORMATION: Synthetic peptide

<400> SEQUENCE: 305

Arg Gly Pro Gln Gln Gly Gly Glu Trp Gln Ile Asn Glu Lys
1               5                   10

<210> SEQ ID NO 306
<211> LENGTH: 14
<212> TYPE: PRT
<213> ORGANISM: Artificial Sequence
<220> FEATURE:
<223> OTHER INFORMATION: Synthetic peptide

<400> SEQUENCE: 306

Arg Gly Pro Gln Gln Tyr Ala Glu Trp Gln Ile Gly Gly Gly
1               5                   10

<210> SEQ ID NO 307
<211> LENGTH: 14
<212> TYPE: PRT
<213> ORGANISM: Artificial Sequence
<220> FEATURE:
<223> OTHER INFORMATION: Synthetic peptide

<400> SEQUENCE: 307

Arg Gly Pro Gln Gln Lys Tyr Glu Trp Gln Ile Asn Glu Lys
1               5                   10

<210> SEQ ID NO 308
<211> LENGTH: 14
<212> TYPE: PRT
<213> ORGANISM: Artificial Sequence
<220> FEATURE:
<223> OTHER INFORMATION: Synthetic peptide

<400> SEQUENCE: 308

Arg Gly Pro Gln Ala Gln Tyr Glu Trp Gln Ile Asn Glu Lys
1               5                   10

<210> SEQ ID NO 309
<211> LENGTH: 14
<212> TYPE: PRT
<213> ORGANISM: Artificial Sequence
<220> FEATURE:
<223> OTHER INFORMATION: Synthetic peptide

<400> SEQUENCE: 309

Arg Pro His Gln Gln Tyr Ala Glu Trp Gln Ile Asn Glu Lys
1               5                   10

<210> SEQ ID NO 310
<211> LENGTH: 14
<212> TYPE: PRT

```
<213> ORGANISM: Artificial Sequence
<220> FEATURE:
<223> OTHER INFORMATION: Synthetic peptide

<400> SEQUENCE: 310

Arg Gly Pro Gln His His His Glu Trp Gln Ile Asn Glu Lys
1               5                   10

<210> SEQ ID NO 311
<211> LENGTH: 14
<212> TYPE: PRT
<213> ORGANISM: Artificial Sequence
<220> FEATURE:
<223> OTHER INFORMATION: Synthetic peptide

<400> SEQUENCE: 311

Arg Gly Pro Pro Gln Tyr Ala Pro Pro Gln Ile Asn Glu Lys
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Synthetic peptide

<400> SEQUENCE: 312

Arg Gly Pro Gln Cys Tyr Tyr Glu Trp Cys Ile Asn Glu Lys
1               5                   10

<210> SEQ ID NO 313
<211> LENGTH: 14
<212> TYPE: PRT
<213> ORGANISM: Artificial Sequence
<220> FEATURE:
<223> OTHER INFORMATION: Synthetic peptide

<400> SEQUENCE: 313

Arg Gly Pro Thr Gln Tyr Ala Glu Gly Gln Ile Asn Glu Gly
1               5                   10

<210> SEQ ID NO 314
<211> LENGTH: 15
<212> TYPE: PRT
<213> ORGANISM: Artificial Sequence
<220> FEATURE:
<223> OTHER INFORMATION: Synthetic peptide

<400> SEQUENCE: 314

Arg Gly Pro Gln Gln Tyr Ala Glu Trp Gln Ile Asn Glu Lys Gly
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Synthetic peptide

<400> SEQUENCE: 315

Arg Gly Pro Gln Gln Tyr Ala Glu Trp Gln Ile Asn Glu Lys Tyr
1               5                   10                  15

<210> SEQ ID NO 316
<211> LENGTH: 16
<212> TYPE: PRT
<213> ORGANISM: Artificial Sequence
```

```
<220> FEATURE:
<223> OTHER INFORMATION: Synthetic peptide

<400> SEQUENCE: 316

Arg Gly Pro Gln Gln Tyr Ala Phe Thr Glu Trp Gln Ile Asn Glu Lys
1               5                   10                  15

<210> SEQ ID NO 317
<211> LENGTH: 17
<212> TYPE: PRT
<213> ORGANISM: Artificial Sequence
<220> FEATURE:
<223> OTHER INFORMATION: Synthetic peptide

<400> SEQUENCE: 317

Arg Gly Pro Gln Ser Gln Tyr Ala Glu Trp Gln Ile Asn Glu Lys Pro
1               5                   10                  15

Met

<210> SEQ ID NO 318
<211> LENGTH: 16
<212> TYPE: PRT
<213> ORGANISM: Artificial Sequence
<220> FEATURE:
<223> OTHER INFORMATION: Synthetic peptide

<400> SEQUENCE: 318

Arg Gly Pro Gln Gln Tyr Ala Glu Trp Gln Ile Asn Glu Lys Lys Lys
1               5                   10                  15

<210> SEQ ID NO 319
<211> LENGTH: 17
<212> TYPE: PRT
<213> ORGANISM: Artificial Sequence
<220> FEATURE:
<223> OTHER INFORMATION: Synthetic peptide

<400> SEQUENCE: 319

Arg Arg Arg Arg Gly Pro Gln Gln Tyr Ala Glu Trp Gln Ile Asn Glu
1               5                   10                  15

Lys

<210> SEQ ID NO 320
<211> LENGTH: 13
<212> TYPE: PRT
<213> ORGANISM: Artificial Sequence
<220> FEATURE:
<223> OTHER INFORMATION: Synthetic peptide

<400> SEQUENCE: 320

Arg Gly Pro Gln Gln Tyr Ala Glu Trp Gln Ile Asn Glu
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Synthetic peptide

<400> SEQUENCE: 321

Arg Gly Pro Gln Gln Tyr Ala Glu Trp Gln Ile Asn
1               5                   10

<210> SEQ ID NO 322
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 322

Arg Gly Pro Gln Gln Tyr Ala Glu Trp Gln Ile
1               5                   10

<210> SEQ ID NO 323
<211> LENGTH: 13
<212> TYPE: PRT
<213> ORGANISM: Artificial Sequence
<220> FEATURE:
<223> OTHER INFORMATION: Synthetic peptide

<400> SEQUENCE: 323

Gly Pro Gln Gln Tyr Ala Glu Trp Gln Ile Asn Glu Lys
1               5                   10

<210> SEQ ID NO 324
<211> LENGTH: 12
<212> TYPE: PRT
<213> ORGANISM: Artificial Sequence
<220> FEATURE:
<223> OTHER INFORMATION: Synthetic peptide

<400> SEQUENCE: 324

Pro Gln Gln Tyr Ala Glu Trp Gln Ile Asn Glu Lys
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic peptide

<400> SEQUENCE: 325

Gln Gln Tyr Ala Glu Trp Gln Ile Asn Glu Lys
1               5                   10

<210> SEQ ID NO 326
<211> LENGTH: 8
<212> TYPE: PRT
<213> ORGANISM: Artificial Sequence
<220> FEATURE:
<223> OTHER INFORMATION: Synthetic peptide

<400> SEQUENCE: 326

Gln Gln Tyr Ala Glu Trp Gln Ile
1               5

<210> SEQ ID NO 327
<211> LENGTH: 11
<212> TYPE: PRT
<213> ORGANISM: Artificial Sequence
<220> FEATURE:
<223> OTHER INFORMATION: Synthetic peptide

<400> SEQUENCE: 327

Pro Gln Gln Tyr Ala Glu Trp Gln Ile Asn Glu
1               5                   10

<210> SEQ ID NO 328
<211> LENGTH: 10
```

-continued

```
<212> TYPE: PRT
<213> ORGANISM: Artificial Sequence
<220> FEATURE:
<223> OTHER INFORMATION: Synthetic peptide

<400> SEQUENCE: 328

Pro Gln Gln Tyr Ala Glu Trp Gln Ile Asn
1               5                   10

<210> SEQ ID NO 329
<211> LENGTH: 7
<212> TYPE: PRT
<213> ORGANISM: Artificial Sequence
<220> FEATURE:
<223> OTHER INFORMATION: Synthetic peptide

<400> SEQUENCE: 329

Arg Gly Pro Gln Gln Tyr Ala
1               5

<210> SEQ ID NO 330
<211> LENGTH: 7
<212> TYPE: PRT
<213> ORGANISM: Artificial Sequence
<220> FEATURE:
<223> OTHER INFORMATION: Synthetic peptide

<400> SEQUENCE: 330

Glu Trp Gln Ile Asn Glu Lys
1               5

<210> SEQ ID NO 331
<211> LENGTH: 7
<212> TYPE: PRT
<213> ORGANISM: Artificial Sequence
<220> FEATURE:
<223> OTHER INFORMATION: Synthetic peptide

<400> SEQUENCE: 331

Glu Trp Gln Ile Asn Glu Lys
1               5

<210> SEQ ID NO 332
<211> LENGTH: 7
<212> TYPE: PRT
<213> ORGANISM: Artificial Sequence
<220> FEATURE:
<223> OTHER INFORMATION: Synthetic peptide

<400> SEQUENCE: 332

Phe Leu Pro Gln His Thr Asp
1               5

<210> SEQ ID NO 333
<211> LENGTH: 13
<212> TYPE: PRT
<213> ORGANISM: Artificial Sequence
<220> FEATURE:
<223> OTHER INFORMATION: Synthetic peptide

<400> SEQUENCE: 333

Gly Pro Gln Gln Tyr Ala Glu Trp Gln Ile Asn Glu Lys
1               5                   10

<210> SEQ ID NO 334
<211> LENGTH: 12
<212> TYPE: PRT
```

```
<213> ORGANISM: Artificial Sequence
<220> FEATURE:
<223> OTHER INFORMATION: Synthetic peptide

<400> SEQUENCE: 334

Pro Gly Gln Leu Gln Ser Phe Leu Leu Ser Gly Asn
1               5                   10

<210> SEQ ID NO 335
<211> LENGTH: 22
<212> TYPE: PRT
<213> ORGANISM: Artificial Sequence
<220> FEATURE:
<223> OTHER INFORMATION: Synthetic peptide

<400> SEQUENCE: 335

Pro Gly Gln Leu Gln Ser Phe Leu Leu Ser Gly Asn Gln Asn Gln Gln
1               5                   10                  15

Asn Tyr Leu Ser Gly Phe
            20

<210> SEQ ID NO 336
<211> LENGTH: 8
<212> TYPE: PRT
<213> ORGANISM: Artificial Sequence
<220> FEATURE:
<223> OTHER INFORMATION: Synthetic peptide

<400> SEQUENCE: 336

Pro Gln Gln Tyr Ala Glu Trp Gln
1               5

<210> SEQ ID NO 337
<211> LENGTH: 22
<212> TYPE: PRT
<213> ORGANISM: Artificial Sequence
<220> FEATURE:
<223> OTHER INFORMATION: Synthetic peptide

<400> SEQUENCE: 337

Gln Leu Gln Ser Phe Leu Leu Ser Gly Asn Gln Asn Gln Gln Asn Tyr
1               5                   10                  15

Leu Ser Gly Phe Ser Lys
            20

<210> SEQ ID NO 338
<211> LENGTH: 12
<212> TYPE: PRT
<213> ORGANISM: Artificial Sequence
<220> FEATURE:
<223> OTHER INFORMATION: Synthetic peptide

<400> SEQUENCE: 338

Gln Asn Gln Gln Asn Tyr Leu Ser Gly Phe Ser Lys
1               5                   10

<210> SEQ ID NO 339
<211> LENGTH: 12
<212> TYPE: PRT
<213> ORGANISM: Artificial Sequence
<220> FEATURE:
<223> OTHER INFORMATION: Synthetic peptide

<400> SEQUENCE: 339

Gln Ser Phe Leu Leu Ser Gly Asn Gln Asn Gln Gln
1               5                   10
```

<210> SEQ ID NO 340
<211> LENGTH: 9
<212> TYPE: PRT
<213> ORGANISM: Artificial Sequence
<220> FEATURE:
<223> OTHER INFORMATION: Synthetic peptide

<400> SEQUENCE: 340

Gln Ser Phe Leu Leu Ser Gly Asn Gln
1               5

<210> SEQ ID NO 341
<211> LENGTH: 7
<212> TYPE: PRT
<213> ORGANISM: Artificial Sequence
<220> FEATURE:
<223> OTHER INFORMATION: Synthetic peptide

<400> SEQUENCE: 341

Arg Gly Pro Gln Gln Tyr Ala
1               5

<210> SEQ ID NO 342
<211> LENGTH: 8
<212> TYPE: PRT
<213> ORGANISM: Artificial Sequence
<220> FEATURE:
<223> OTHER INFORMATION: Synthetic peptide

<400> SEQUENCE: 342

Asp Ala Leu Glu Pro Asp Asn Arg
1               5

<210> SEQ ID NO 343
<211> LENGTH: 17
<212> TYPE: PRT
<213> ORGANISM: Artificial Sequence
<220> FEATURE:
<223> OTHER INFORMATION: Synthetic peptide

<400> SEQUENCE: 343

Ser Glu Glu Gly Tyr Tyr Gly Glu Gln Gln Gln Pro Gly Met Thr
1               5                   10                  15

Arg

<210> SEQ ID NO 344
<211> LENGTH: 14
<212> TYPE: PRT
<213> ORGANISM: Artificial Sequence
<220> FEATURE:
<223> OTHER INFORMATION: Synthetic peptide

<400> SEQUENCE: 344

Gly Tyr Tyr Gly Glu Gln Gln Gln Gln Pro Gly Met Thr Arg
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Synthetic peptide

<400> SEQUENCE: 345

Ile Asp Gly Tyr Asp Thr Pro Val Glu Gly Arg

```
1               5                  10
```

<210> SEQ ID NO 346
<211> LENGTH: 9
<212> TYPE: PRT
<213> ORGANISM: Artificial Sequence
<220> FEATURE:
<223> OTHER INFORMATION: Synthetic peptide

<400> SEQUENCE: 346

```
Asn Gly Val Leu Arg Pro Gly Gln Leu
1               5
```

<210> SEQ ID NO 347
<211> LENGTH: 9
<212> TYPE: PRT
<213> ORGANISM: Artificial Sequence
<220> FEATURE:
<223> OTHER INFORMATION: Synthetic peptide

<400> SEQUENCE: 347

```
Arg His Gly Glu Trp Gly Pro Ser Tyr
1               5
```

<210> SEQ ID NO 348
<211> LENGTH: 4
<212> TYPE: PRT
<213> ORGANISM: Artificial Sequence
<220> FEATURE:
<223> OTHER INFORMATION: Synthetic peptide

<400> SEQUENCE: 348

```
Phe Trp Met Ala
1
```

<210> SEQ ID NO 349
<211> LENGTH: 12
<212> TYPE: PRT
<213> ORGANISM: Artificial Sequence
<220> FEATURE:
<223> OTHER INFORMATION: Synthetic peptide

<400> SEQUENCE: 349

```
Thr Val Phe Asp Gly Val Leu Arg Pro Gly Gln Leu
1               5                  10
```

<210> SEQ ID NO 350
<211> LENGTH: 16
<212> TYPE: PRT
<213> ORGANISM: Artificial Sequence
<220> FEATURE:
<223> OTHER INFORMATION: Synthetic peptide

<400> SEQUENCE: 350

```
Arg Leu Gln Ser Gln Asn Asp Gln Arg Gly Glu Ile Ile His Val Lys
1               5                  10                  15
```

<210> SEQ ID NO 351
<211> LENGTH: 16
<212> TYPE: PRT
<213> ORGANISM: Artificial Sequence
<220> FEATURE:
<223> OTHER INFORMATION: Synthetic peptide

<400> SEQUENCE: 351

```
His Gly Pro Val Glu Met Pro Tyr Thr Leu Leu Tyr Pro Ser Ser Lys
1               5                  10                  15
```

<210> SEQ ID NO 352
<211> LENGTH: 9
<212> TYPE: PRT
<213> ORGANISM: Artificial Sequence
<220> FEATURE:
<223> OTHER INFORMATION: Synthetic peptide

<400> SEQUENCE: 352

Leu Asp Ala Leu Glu Pro Asp Asn Arg
1               5

<210> SEQ ID NO 353
<211> LENGTH: 186
<212> TYPE: PRT
<213> ORGANISM: Oryza sativa

<400> SEQUENCE: 353

Met Ala Ser Lys Val Val Phe Phe Ala Ala Ala Leu Met Ala Ala Met
1               5                   10                  15

Val Ala Ile Ser Gly Ala Gln Leu Ser Glu Ser Glu Met Arg Phe Arg
                20                  25                  30

Asp Arg Gln Cys Gln Arg Glu Val Gln Asp Ser Pro Leu Asp Ala Cys
            35                  40                  45

Arg Gln Val Leu Asp Arg Gln Leu Thr Gly Arg Glu Arg Phe Gln Pro
        50                  55                  60

Met Phe Arg Arg Pro Gly Ala Leu Gly Leu Arg Met Gln Cys Cys Gln
65                  70                  75                  80

Gln Leu Gln Asp Val Ser Arg Glu Cys Arg Cys Ala Ala Ile Arg Arg
                85                  90                  95

Met Val Arg Ser Tyr Glu Glu Ser Met Pro Met Pro Leu Glu Gln Gly
                100                 105                 110

Trp Ser Ser Ser Ser Glu Tyr Tyr Gly Glu Gly Ser Ser Ser
            115                 120                 125

Glu Gln Gly Tyr Tyr Gly Gly Ser Ser Glu Glu Gly Tyr Tyr Gly
        130                 135                 140

Glu Gln Gln Gln Gln Pro Gly Met Thr Arg Val Arg Leu Thr Arg Ala
145                 150                 155                 160

Arg Gln Tyr Ala Ala Gln Leu Pro Ser Met Cys Arg Val Glu Pro Gln
                165                 170                 175

Gln Cys Ser Ile Phe Ala Ala Gly Gln Tyr
            180                 185

<210> SEQ ID NO 354
<211> LENGTH: 517
<212> TYPE: PRT
<213> ORGANISM: Pisum sativum

<400> SEQUENCE: 354

Met Ala Lys Leu Leu Ala Leu Ser Leu Ser Phe Cys Phe Leu Leu Leu
1               5                   10                  15

Gly Gly Cys Phe Ala Leu Arg Glu Gln Pro Gln Gln Asn Glu Cys Gln
                20                  25                  30

Leu Glu Arg Leu Asp Ala Leu Glu Pro Asp Asn Arg Ile Glu Ser Glu
            35                  40                  45

Gly Gly Leu Ile Glu Thr Trp Asn Pro Asn Asn Lys Gln Phe Arg Cys
        50                  55                  60

Ala Gly Val Ala Leu Ser Arg Ala Thr Leu Gln Arg Asn Ala Leu Arg

```
            65                  70                  75                  80
Arg Pro Tyr Tyr Ser Asn Ala Pro Gln Glu Ile Phe Ile Gln Gln Gly
                    85                  90                  95

Asn Gly Tyr Phe Gly Met Val Phe Pro Gly Cys Pro Glu Thr Phe Glu
                100                 105                 110

Glu Pro Gln Glu Ser Glu Gln Glu Gly Arg Arg Tyr Arg Asp Arg
                115                 120                 125

His Gln Lys Val Asn Arg Phe Arg Glu Gly Asp Ile Ile Ala Val Pro
        130                 135                 140

Thr Gly Ile Val Phe Trp Met Tyr Asn Asp Gln Asp Thr Pro Val Ile
145                 150                 155                 160

Ala Val Ser Leu Thr Asp Ile Arg Ser Ser Asn Asn Gln Leu Asp Gln
                165                 170                 175

Met Pro Arg Arg Phe Tyr Leu Ala Gly Asn His Glu Gln Glu Phe Leu
            180                 185                 190

Gln Tyr Gln His Gln Gln Gly Gly Lys Gln Glu Gln Glu Asn Glu Gly
                195                 200                 205

Asn Asn Ile Phe Ser Gly Phe Lys Arg Asp Tyr Leu Glu Asp Ala Phe
        210                 215                 220

Asn Val Asn Arg His Ile Val Asp Arg Leu Gln Gly Arg Asn Glu Asp
225                 230                 235                 240

Glu Glu Lys Gly Ala Ile Val Lys Val Lys Gly Gly Leu Ser Ile Ile
                245                 250                 255

Ser Pro Pro Glu Lys Gln Ala Arg His Gln Arg Gly Ser Arg Gln Glu
            260                 265                 270

Glu Asp Glu Asp Glu Glu Lys Gln Pro Arg His Gln Arg Gly Ser Arg
        275                 280                 285

Gln Glu Glu Glu Glu Asp Glu Asp Glu Glu Arg Gln Pro Arg His Gln
        290                 295                 300

Arg Arg Arg Gly Glu Glu Glu Glu Asp Lys Lys Glu Arg Gly Gly
305                 310                 315                 320

Ser Gln Lys Gly Lys Ser Arg Arg Gln Gly Asp Asn Gly Leu Glu Glu
                325                 330                 335

Thr Val Cys Thr Ala Lys Leu Arg Leu Asn Ile Gly Pro Ser Ser Ser
            340                 345                 350

Pro Asp Ile Tyr Asn Pro Glu Ala Gly Arg Ile Lys Thr Val Thr Ser
        355                 360                 365

Leu Asp Leu Pro Val Leu Arg Trp Leu Lys Leu Ser Ala Glu His Gly
        370                 375                 380

Ser Leu His Lys Asn Ala Met Phe Val Pro His Tyr Asn Leu Asn Ala
385                 390                 395                 400

Asn Ser Ile Ile Tyr Ala Leu Lys Gly Arg Ala Arg Leu Gln Val Val
                405                 410                 415

Asn Cys Asn Gly Asn Thr Val Phe Asp Gly Glu Leu Glu Ala Gly Arg
            420                 425                 430

Ala Leu Thr Val Pro Gln Asn Tyr Ala Val Ala Ala Lys Ser Leu Ser
        435                 440                 445

Asp Arg Phe Ser Tyr Val Ala Phe Lys Thr Asn Asp Arg Ala Gly Ile
        450                 455                 460

Ala Arg Leu Ala Gly Thr Ser Ser Val Ile Asn Asn Leu Pro Leu Asp
465                 470                 475                 480

Val Val Ala Ala Thr Phe Asn Leu Gln Arg Asn Glu Ala Arg Gln Leu
                485                 490                 495
```

Lys Ser Asn Asn Pro Phe Lys Phe Leu Val Pro Ala Arg Glu Ser Glu
            500                 505                 510

Asn Arg Ala Ser Ala
        515

<210> SEQ ID NO 355
<211> LENGTH: 861
<212> TYPE: PRT
<213> ORGANISM: Pisum sativum

<400> SEQUENCE: 355

Met Phe Ser Gly Val Thr Gly Ile Leu Asn Arg Gly His Lys Ile Lys
1               5                   10                  15

Gly Thr Val Val Leu Met Arg Lys Asn Val Leu Asp Ile Asn Ser Leu
            20                  25                  30

Thr Thr Val Gly Gly Val Ile Gly Gln Gly Phe Asp Ile Leu Gly Ser
        35                  40                  45

Thr Val Asp Asn Leu Thr Ala Phe Leu Gly Arg Ser Val Ser Leu Gln
    50                  55                  60

Leu Ile Ser Ala Thr Lys Pro Asp Ala Thr Gly Lys Gly Lys Leu Gly
65                  70                  75                  80

Lys Ala Thr Phe Leu Glu Gly Ile Ile Ser Ser Leu Pro Thr Leu Gly
                85                  90                  95

Ala Gly Gln Ser Ala Phe Lys Ile His Phe Glu Trp Asp Asp Asp Met
            100                 105                 110

Gly Ile Pro Gly Ala Phe Tyr Ile Lys Asn Phe Met Gln Thr Glu Phe
        115                 120                 125

Phe Leu Val Ser Leu Thr Leu Asp Asp Ile Pro Asn His Gly Ser Ile
    130                 135                 140

Tyr Phe Val Cys Asn Ser Trp Ile Tyr Asn Ala Lys His His Lys Ile
145                 150                 155                 160

Asp Arg Ile Phe Phe Ala Asn Gln Thr Tyr Leu Pro Ser Glu Thr Pro
                165                 170                 175

Ala Pro Leu Val His Tyr Arg Glu Glu Glu Leu Asn Asn Leu Arg Gly
            180                 185                 190

Asp Gly Thr Gly Glu Arg Lys Glu Trp Glu Arg Ile Tyr Asp Tyr Asp
        195                 200                 205

Val Tyr Asn Asp Leu Gly Asn Pro Asp Ser Gly Glu Asn His Ala Arg
    210                 215                 220

Pro Val Leu Gly Gly Ser Glu Thr Tyr Pro Tyr Pro Arg Arg Gly Arg
225                 230                 235                 240

Thr Gly Arg Lys Pro Thr Arg Lys Asp Pro Asn Ser Glu Ser Arg Ser
                245                 250                 255

Asp Tyr Val Tyr Leu Pro Arg Asp Glu Ala Phe Gly His Leu Lys Ser
            260                 265                 270

Ser Asp Phe Leu Thr Tyr Gly Leu Lys Ala Val Ser Gln Asn Val Val
        275                 280                 285

Pro Ala Leu Glu Ser Val Phe Phe Asp Leu Asn Phe Thr Pro Asn Glu
    290                 295                 300

Phe Asp Ser Phe Asp Glu Val His Gly Leu Tyr Glu Gly Gly Ile Lys
305                 310                 315                 320

Leu Pro Thr Asn Ile Leu Ser Gln Ile Ser Pro Leu Pro Val Leu Lys
                325                 330                 335

Glu Ile Phe Arg Thr Asp Gly Glu Asn Thr Leu Lys Tyr Pro Pro Pro

-continued

```
                340             345             350
Lys Val Ile Gln Val Ser Arg Ser Gly Trp Met Thr Asp Glu Glu Phe
            355             360             365
Ala Arg Glu Met Leu Ala Gly Val Asn Pro Asn Val Ile Cys Cys Leu
        370             375             380
Gln Glu Phe Pro Pro Arg Ser Lys Leu Asp Ser Gln Ile Tyr Gly Asp
385             390             395             400
His Thr Ser Lys Ile Ser Lys Glu His Leu Glu Pro Asn Leu Glu Gly
                405             410             415
Leu Thr Val Glu Glu Ala Ile Gln Asn Lys Lys Leu Phe Leu Leu Asp
            420             425             430
His His Asp Ser Ile Met Pro Tyr Leu Arg Arg Ile Asn Ser Thr Ser
        435             440             445
Thr Lys Ala Tyr Ala Thr Arg Thr Ile Leu Phe Leu Asn Asn Asn Gln
    450             455             460
Asn Leu Lys Pro Leu Ala Ile Glu Leu Ser Leu Pro His Pro Gln Gly
465             470             475             480
Asp Glu His Gly Ala Val Ser Tyr Val Tyr Gln Pro Ala Leu Glu Gly
                485             490             495
Val Glu Ser Ser Ile Trp Leu Leu Ala Lys Ala Tyr Val Ile Val Asn
            500             505             510
Asp Ser Cys Tyr His Gln Leu Val Ser His Trp Leu Asn Thr His Ala
        515             520             525
Val Val Glu Pro Phe Val Ile Ala Thr Asn Arg His Leu Ser Cys Leu
    530             535             540
His Pro Ile Tyr Lys Leu Leu Tyr Pro His Tyr Arg Asp Thr Met Asn
545             550             555             560
Ile Asn Ser Leu Ala Arg Leu Ser Leu Val Asn Asp Gly Gly Ile Ile
                565             570             575
Glu Lys Thr Phe Leu Trp Gly Arg Tyr Ser Met Glu Met Ser Ser Lys
            580             585             590
Val Tyr Lys Asn Trp Val Phe Thr Glu Gln Ala Leu Pro Ala Asp Leu
        595             600             605
Ile Lys Arg Gly Met Ala Ile Glu Asp Pro Ser Ser Pro Cys Gly Val
    610             615             620
Lys Leu Val Val Glu Asp Tyr Pro Tyr Ala Val Asp Gly Leu Glu Ile
625             630             635             640
Trp Ala Ile Ile Lys Thr Trp Val Gln Asp Tyr Val Ser Leu Tyr Tyr
                645             650             655
Thr Ser Asp Glu Lys Leu Arg Gln Asp Ser Glu Leu Gln Ala Trp Trp
            660             665             670
Lys Glu Leu Val Glu Val Gly His Gly Asp Lys Lys Asn Glu Pro Trp
        675             680             685
Trp Pro Lys Met Gln Thr Arg Glu Asp Leu Ile Glu Val Cys Ser Ile
    690             695             700
Val Ile Trp Thr Ala Ser Ala Leu His Ala Ala Val Asn Phe Gly Gln
705             710             715             720
Tyr Ser Tyr Gly Gly Leu Ile Leu Asn Arg Pro Thr Leu Ser Arg Arg
                725             730             735
Phe Met Pro Glu Lys Gly Ser Ala Glu Phe Glu Glu Leu Val Lys Ser
            740             745             750
Pro Gln Lys Ala Tyr Leu Lys Thr Ile Thr Pro Lys Phe Gln Thr Leu
        755             760             765
```

```
Ile Asp Leu Ser Val Ile Glu Ile Leu Ser Arg His Ala Ser Asp Glu
        770                 775                 780

Leu Tyr Leu Gly Glu Arg Asp Asn Pro Asn Trp Thr Ser Asp Lys Arg
785                 790                 795                 800

Ala Leu Glu Ala Phe Lys Lys Phe Gly Asn Lys Leu Ala Glu Ile Glu
                805                 810                 815

Lys Lys Leu Thr Gln Arg Asn Asn Asp Glu Lys Leu Arg Asn Arg His
            820                 825                 830

Gly Pro Val Glu Met Pro Tyr Thr Leu Leu Tyr Pro Ser Ser Lys Glu
        835                 840                 845

Gly Leu Thr Phe Arg Gly Ile Pro Asn Ser Ile Ser Ile
    850                 855                 860

<210> SEQ ID NO 356
<211> LENGTH: 10
<212> TYPE: PRT
<213> ORGANISM: Artificial Sequence
<220> FEATURE:
<223> OTHER INFORMATION: Synthetic peptide

<400> SEQUENCE: 356

Lys Asn Pro Gln Leu Gln Asp Leu Asp Ile
1               5                   10

<210> SEQ ID NO 357
<211> LENGTH: 11
<212> TYPE: PRT
<213> ORGANISM: Artificial Sequence
<220> FEATURE:
<223> OTHER INFORMATION: Synthetic peptide

<400> SEQUENCE: 357

Gly Gln Ser Thr Ser Gln Trp Gln Ser Ser Arg
1               5                   10

<210> SEQ ID NO 358
<211> LENGTH: 10
<212> TYPE: PRT
<213> ORGANISM: Artificial Sequence
<220> FEATURE:
<223> OTHER INFORMATION: Synthetic peptide

<400> SEQUENCE: 358

Gln Ser Thr Ser Gln Trp Gln Ser Ser Arg
1               5                   10

<210> SEQ ID NO 359
<211> LENGTH: 10
<212> TYPE: PRT
<213> ORGANISM: Artificial Sequence
<220> FEATURE:
<223> OTHER INFORMATION: Synthetic peptide

<400> SEQUENCE: 359

Gln Ser Thr Ser Gln Trp Gln Ser Ser Arg
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 360

Glu Glu Glu Glu Gln Gly Glu Glu Ile Asn Lys
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Synthetic peptide

<400> SEQUENCE: 361

Pro Ser Thr Asn Pro Trp His Ser Pro Arg
1               5                   10

<210> SEQ ID NO 362
<211> LENGTH: 14
<212> TYPE: PRT
<213> ORGANISM: Artificial Sequence
<220> FEATURE:
<223> OTHER INFORMATION: Synthetic peptide

<400> SEQUENCE: 362

Ala Gln Ala Gln Asp Gln Tyr Gln Gln Val Gln Tyr Ser Glu
1               5                   10

<210> SEQ ID NO 363
<211> LENGTH: 26
<212> TYPE: PRT
<213> ORGANISM: Artificial Sequence
<220> FEATURE:
<223> OTHER INFORMATION: Synthetic peptide

<400> SEQUENCE: 363

Ser Glu Ala Gly Val Thr Glu Tyr Phe Asp Glu Lys Asn Glu Leu Phe
1               5                   10                  15

Gln Cys Thr Gly Thr Phe Val Ile Arg Arg
            20                  25

<210> SEQ ID NO 364
<211> LENGTH: 15
<212> TYPE: PRT
<213> ORGANISM: Artificial Sequence
<220> FEATURE:
<223> OTHER INFORMATION: Synthetic peptide

<400> SEQUENCE: 364

Gln Ala Gln Ala Gln Asp Gln Tyr Gln Gln Val Gln Tyr Ser Glu
1               5                   10                  15

<210> SEQ ID NO 365
<211> LENGTH: 13
<212> TYPE: PRT
<213> ORGANISM: Artificial Sequence
<220> FEATURE:
<223> OTHER INFORMATION: Synthetic peptide

<400> SEQUENCE: 365

Gly Ser Met Gly Leu Thr Phe Pro Gly Cys Pro Ala Thr
1               5                   10

<210> SEQ ID NO 366
<211> LENGTH: 14
<212> TYPE: PRT
<213> ORGANISM: Artificial Sequence
<220> FEATURE:
```

<223> OTHER INFORMATION: Synthetic peptide

<400> SEQUENCE: 366

Gly Ser Met Gly Leu Thr Phe Pro Gly Cys Pro Ala Thr Tyr
1               5                   10

<210> SEQ ID NO 367
<211> LENGTH: 8
<212> TYPE: PRT
<213> ORGANISM: Artificial Sequence
<220> FEATURE:
<223> OTHER INFORMATION: Synthetic peptide

<400> SEQUENCE: 367

Leu Gly Ala Phe Thr Pro Arg Tyr
1               5

<210> SEQ ID NO 368
<211> LENGTH: 10
<212> TYPE: PRT
<213> ORGANISM: Artificial Sequence
<220> FEATURE:
<223> OTHER INFORMATION: Synthetic peptide

<400> SEQUENCE: 368

Leu Gly Ala Phe Thr Pro Arg Tyr Gln Gln
1               5                   10

<210> SEQ ID NO 369
<211> LENGTH: 16
<212> TYPE: PRT
<213> ORGANISM: Artificial Sequence
<220> FEATURE:
<223> OTHER INFORMATION: Synthetic peptide

<400> SEQUENCE: 369

Ala Leu Gly Val Asn Ala Leu Val Ala Lys Arg Leu Gln Gly Gln Asn
1               5                   10                  15

<210> SEQ ID NO 370
<211> LENGTH: 9
<212> TYPE: PRT
<213> ORGANISM: Artificial Sequence
<220> FEATURE:
<223> OTHER INFORMATION: Synthetic peptide

<400> SEQUENCE: 370

Leu Gly Ala Phe Thr Pro Arg Tyr Gln
1               5

<210> SEQ ID NO 371
<211> LENGTH: 13
<212> TYPE: PRT
<213> ORGANISM: Artificial Sequence
<220> FEATURE:
<223> OTHER INFORMATION: Synthetic peptide

<400> SEQUENCE: 371

Gly Ser Met Gly Leu Thr Phe Pro Gly Cys Pro Ala Thr
1               5                   10

<210> SEQ ID NO 372
<211> LENGTH: 14
<212> TYPE: PRT
<213> ORGANISM: Artificial Sequence
<220> FEATURE:
<223> OTHER INFORMATION: Synthetic peptide

<400> SEQUENCE: 372

Gly Ser Met Gly Leu Thr Phe Pro Gly Cys Pro Ala Thr Tyr
1               5                   10

<210> SEQ ID NO 373
<211> LENGTH: 14
<212> TYPE: PRT
<213> ORGANISM: Artificial Sequence
<220> FEATURE:
<223> OTHER INFORMATION: Synthetic peptide

<400> SEQUENCE: 373

Ser Asn Asn Pro Phe Lys Phe Leu Val Pro Ala Arg Gln Ser
1               5                   10

<210> SEQ ID NO 374
<211> LENGTH: 9
<212> TYPE: PRT
<213> ORGANISM: Artificial Sequence
<220> FEATURE:
<223> OTHER INFORMATION: Synthetic peptide

<400> SEQUENCE: 374

Cys Ala Gly Val Phe Val Ile Arg Arg
1               5

<210> SEQ ID NO 375
<211> LENGTH: 10
<212> TYPE: PRT
<213> ORGANISM: Artificial Sequence
<220> FEATURE:
<223> OTHER INFORMATION: Synthetic peptide

<400> SEQUENCE: 375

Gly Ser Pro Leu Gln Ser Pro Arg Gly Phe
1               5                   10

<210> SEQ ID NO 376
<211> LENGTH: 9
<212> TYPE: PRT
<213> ORGANISM: Artificial Sequence
<220> FEATURE:
<223> OTHER INFORMATION: Synthetic peptide

<400> SEQUENCE: 376

Arg Ser Ser Trp Gln Gln Gln Ser Tyr
1               5

<210> SEQ ID NO 377
<211> LENGTH: 11
<212> TYPE: PRT
<213> ORGANISM: Artificial Sequence
<220> FEATURE:
<223> OTHER INFORMATION: Synthetic peptide

<400> SEQUENCE: 377

Ser Phe Gly Gly Ser Pro Leu Gln Ser Pro Arg
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Synthetic peptide

<400> SEQUENCE: 378

Tyr Leu Pro Thr Lys Gln Leu Gln Pro Thr Trp
1               5                   10

<210> SEQ ID NO 379
<211> LENGTH: 10
<212> TYPE: PRT
<213> ORGANISM: Artificial Sequence
<220> FEATURE:
<223> OTHER INFORMATION: Synthetic peptide

<400> SEQUENCE: 379

Gly Lys Pro Arg Ser Ser Trp Gln Gln Gln
1               5                   10

<210> SEQ ID NO 380
<211> LENGTH: 11
<212> TYPE: PRT
<213> ORGANISM: Artificial Sequence
<220> FEATURE:
<223> OTHER INFORMATION: Synthetic peptide

<400> SEQUENCE: 380

Phe Gly Gly Ser Pro Leu Gln Ser Pro Arg Gly
1               5                   10

<210> SEQ ID NO 381
<211> LENGTH: 14
<212> TYPE: PRT
<213> ORGANISM: Artificial Sequence
<220> FEATURE:
<223> OTHER INFORMATION: Synthetic peptide

<400> SEQUENCE: 381

Leu Asn Leu Leu Gly Phe Gly Ile Asn Ala Glu Asn Asn Glu
1               5                   10

<210> SEQ ID NO 382
<211> LENGTH: 9
<212> TYPE: PRT
<213> ORGANISM: Artificial Sequence
<220> FEATURE:
<223> OTHER INFORMATION: Synthetic peptide

<400> SEQUENCE: 382

Gly Ala Leu Met Leu Pro His Tyr Asn
1               5

<210> SEQ ID NO 383
<211> LENGTH: 11
<212> TYPE: PRT
<213> ORGANISM: Artificial Sequence
<220> FEATURE:
<223> OTHER INFORMATION: Synthetic peptide

<400> SEQUENCE: 383

Gly Ala Leu Met Leu Pro His Tyr Asn Ser Arg
1               5                   10

<210> SEQ ID NO 384
<211> LENGTH: 9
<212> TYPE: PRT
<213> ORGANISM: Artificial Sequence
<220> FEATURE:
<223> OTHER INFORMATION: Synthetic peptide

<400> SEQUENCE: 384

```
Val Phe Asp Gly Val Leu Arg Pro Gly
1               5
```

<210> SEQ ID NO 385
<211> LENGTH: 6
<212> TYPE: PRT
<213> ORGANISM: Artificial Sequence
<220> FEATURE:
<223> OTHER INFORMATION: Synthetic peptide

<400> SEQUENCE: 385

```
Leu Gln Ser Gln Asn Asp
1               5
```

<210> SEQ ID NO 386
<211> LENGTH: 11
<212> TYPE: PRT
<213> ORGANISM: Artificial Sequence
<220> FEATURE:
<223> OTHER INFORMATION: Synthetic peptide

<400> SEQUENCE: 386

```
Leu Gln Ser Gln Asn Asp Gln Arg Gly Glu Ile
1               5                   10
```

<210> SEQ ID NO 387
<211> LENGTH: 14
<212> TYPE: PRT
<213> ORGANISM: Artificial Sequence
<220> FEATURE:
<223> OTHER INFORMATION: Synthetic peptide

<400> SEQUENCE: 387

```
Gln Ser Gln Asn Asp Gln Arg Gly Glu Ile Ile His Val Lys
1               5                   10
```

<210> SEQ ID NO 388
<211> LENGTH: 8
<212> TYPE: PRT
<213> ORGANISM: Artificial Sequence
<220> FEATURE:
<223> OTHER INFORMATION: Synthetic peptide

<400> SEQUENCE: 388

```
Arg Gly Glu Ile Ile His Val Lys
1               5
```

<210> SEQ ID NO 389
<211> LENGTH: 8
<212> TYPE: PRT
<213> ORGANISM: Artificial Sequence
<220> FEATURE:
<223> OTHER INFORMATION: Synthetic peptide

<400> SEQUENCE: 389

```
Arg Leu Gln Ser Gln Asn Asp Gln
1               5
```

<210> SEQ ID NO 390
<211> LENGTH: 10
<212> TYPE: PRT
<213> ORGANISM: Artificial Sequence
<220> FEATURE:
<223> OTHER INFORMATION: Synthetic peptide

<400> SEQUENCE: 390

```
Arg Leu Gln Ser Gln Asn Asp Gln Arg Gly
1               5                   10

<210> SEQ ID NO 391
<211> LENGTH: 14
<212> TYPE: PRT
<213> ORGANISM: Artificial Sequence
<220> FEATURE:
<223> OTHER INFORMATION: Synthetic peptide

<400> SEQUENCE: 391

Arg Leu Gln Ser Gln Asn Asp Gln Arg Gly Glu Ile Ile His
1               5                   10

<210> SEQ ID NO 392
<211> LENGTH: 4
<212> TYPE: PRT
<213> ORGANISM: Artificial Sequence
<220> FEATURE:
<223> OTHER INFORMATION: Synthetic peptide

<400> SEQUENCE: 392

Met Pro Met Pro
1

<210> SEQ ID NO 393
<211> LENGTH: 4
<212> TYPE: PRT
<213> ORGANISM: Artificial Sequence
<220> FEATURE:
<223> OTHER INFORMATION: Synthetic peptide

<400> SEQUENCE: 393

Pro Met Pro Leu
1

<210> SEQ ID NO 394
<211> LENGTH: 6
<212> TYPE: PRT
<213> ORGANISM: Artificial Sequence
<220> FEATURE:
<223> OTHER INFORMATION: Synthetic peptide

<400> SEQUENCE: 394

Leu Glu Pro Asp Asn Arg
1               5

<210> SEQ ID NO 395
<211> LENGTH: 13
<212> TYPE: PRT
<213> ORGANISM: Artificial Sequence
<220> FEATURE:
<223> OTHER INFORMATION: Synthetic peptide

<400> SEQUENCE: 395

Gly Ile Ala Arg Leu Ala Gly Thr Ser Ser Val Ile Asn
1               5                   10

<210> SEQ ID NO 396
<211> LENGTH: 6
<212> TYPE: PRT
<213> ORGANISM: Artificial Sequence
<220> FEATURE:
<223> OTHER INFORMATION: Synthetic peptide

<400> SEQUENCE: 396

Arg Ser Gln Asn Ile Phe
```

```
1               5

<210> SEQ ID NO 397
<211> LENGTH: 4
<212> TYPE: PRT
<213> ORGANISM: Artificial Sequence
<220> FEATURE:
<223> OTHER INFORMATION: Synthetic peptide

<400> SEQUENCE: 397

Pro Asn Ser Met
1

<210> SEQ ID NO 398
<211> LENGTH: 4
<212> TYPE: PRT
<213> ORGANISM: Artificial Sequence
<220> FEATURE:
<223> OTHER INFORMATION: Synthetic peptide

<400> SEQUENCE: 398

Gly His Pro Met
1

<210> SEQ ID NO 399
<211> LENGTH: 4
<212> TYPE: PRT
<213> ORGANISM: Artificial Sequence
<220> FEATURE:
<223> OTHER INFORMATION: Synthetic peptide

<400> SEQUENCE: 399

His Pro Met Ser
1

<210> SEQ ID NO 400
<211> LENGTH: 7
<212> TYPE: PRT
<213> ORGANISM: Artificial Sequence
<220> FEATURE:
<223> OTHER INFORMATION: Synthetic peptide

<400> SEQUENCE: 400

Phe Leu Pro Gln His Thr Asp
1               5

<210> SEQ ID NO 401
<211> LENGTH: 7
<212> TYPE: PRT
<213> ORGANISM: Artificial Sequence
<220> FEATURE:
<223> OTHER INFORMATION: Synthetic peptide

<400> SEQUENCE: 401

Glu Trp Gln Ile Asn Glu Lys
1               5

<210> SEQ ID NO 402
<211> LENGTH: 13
<212> TYPE: PRT
<213> ORGANISM: Artificial Sequence
<220> FEATURE:
<223> OTHER INFORMATION: Synthetic peptide

<400> SEQUENCE: 402

Gly Pro Gln Gln Tyr Ala Glu Trp Gln Ile Asn Glu Lys
1               5                   10
```

<210> SEQ ID NO 403
<211> LENGTH: 8
<212> TYPE: PRT
<213> ORGANISM: Artificial Sequence
<220> FEATURE:
<223> OTHER INFORMATION: Synthetic peptide

<400> SEQUENCE: 403

Pro Gln Gln Tyr Ala Glu Trp Gln
1               5

<210> SEQ ID NO 404
<211> LENGTH: 7
<212> TYPE: PRT
<213> ORGANISM: Artificial Sequence
<220> FEATURE:
<223> OTHER INFORMATION: Synthetic peptide

<400> SEQUENCE: 404

Arg Gly Pro Gln Gln Tyr Ala
1               5

<210> SEQ ID NO 405
<211> LENGTH: 4
<212> TYPE: PRT
<213> ORGANISM: Artificial Sequence
<220> FEATURE:
<223> OTHER INFORMATION: Synthetic peptide

<400> SEQUENCE: 405

His Asn Pro Arg
1

<210> SEQ ID NO 406

<400> SEQUENCE: 406

000

<210> SEQ ID NO 407

<400> SEQUENCE: 407

000

<210> SEQ ID NO 408
<211> LENGTH: 4
<212> TYPE: PRT
<213> ORGANISM: Artificial Sequence
<220> FEATURE:
<223> OTHER INFORMATION: Synthetic peptide

<400> SEQUENCE: 408

His Pro Ser Phe
1

<210> SEQ ID NO 409
<211> LENGTH: 22
<212> TYPE: PRT
<213> ORGANISM: Artificial Sequence
<220> FEATURE:
<223> OTHER INFORMATION: Synthetic peptide

<400> SEQUENCE: 409

Pro Gly Gln Leu Gln Ser Phe Leu Leu Ser Gly Asn Gln Asn Gln Gln
1               5                   10                  15

Asn Tyr Leu Ser Gly Phe
            20

<210> SEQ ID NO 410
<211> LENGTH: 22
<212> TYPE: PRT
<213> ORGANISM: Artificial Sequence
<220> FEATURE:
<223> OTHER INFORMATION: Synthetic peptide

<400> SEQUENCE: 410

Gln Leu Gln Ser Phe Leu Leu Ser Gly Asn Gln Asn Gln Gln Asn Tyr
1               5                   10                  15

Leu Ser Gly Phe Ser Lys
            20

<210> SEQ ID NO 411
<211> LENGTH: 12
<212> TYPE: PRT
<213> ORGANISM: Artificial Sequence
<220> FEATURE:
<223> OTHER INFORMATION: Synthetic peptide

<400> SEQUENCE: 411

Gln Ser Phe Leu Leu Ser Gly Asn Gln Asn Gln Gln
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Synthetic peptide

<400> SEQUENCE: 412

Pro Gly Gln Leu Gln Ser Phe Leu Leu Ser Gly Asn
1               5                   10

<210> SEQ ID NO 413
<211> LENGTH: 9
<212> TYPE: PRT
<213> ORGANISM: Artificial Sequence
<220> FEATURE:
<223> OTHER INFORMATION: Synthetic peptide

<400> SEQUENCE: 413

Gln Ser Phe Leu Leu Ser Gly Asn Gln
1               5

<210> SEQ ID NO 414
<211> LENGTH: 12
<212> TYPE: PRT
<213> ORGANISM: Artificial Sequence
<220> FEATURE:
<223> OTHER INFORMATION: Synthetic peptide

<400> SEQUENCE: 414

Gln Asn Gln Gln Asn Tyr Leu Ser Gly Phe Ser Lys
1               5                   10

<210> SEQ ID NO 415
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 415

Tyr Leu Arg Gly Phe Ser
1               5

<210> SEQ ID NO 416
<211> LENGTH: 11
<212> TYPE: PRT
<213> ORGANISM: Artificial Sequence
<220> FEATURE:
<223> OTHER INFORMATION: Synthetic peptide

<400> SEQUENCE: 416

Pro Val Glu Met Pro Thr Leu Leu Tyr Pro Ser
1               5                   10

<210> SEQ ID NO 417
<211> LENGTH: 13
<212> TYPE: PRT
<213> ORGANISM: Artificial Sequence
<220> FEATURE:
<223> OTHER INFORMATION: Synthetic peptide

<400> SEQUENCE: 417

Arg Gly Pro Gln Gln Tyr Ala Glu Trp Gln Ile Asn Glu
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Synthetic peptide

<400> SEQUENCE: 418

Thr Val Phe Asp Gly Val Leu Arg Pro Gly Gln Leu
1               5                   10

<210> SEQ ID NO 419
<211> LENGTH: 9
<212> TYPE: PRT
<213> ORGANISM: Artificial Sequence
<220> FEATURE:
<223> OTHER INFORMATION: Synthetic peptide

<400> SEQUENCE: 419

Leu Asp Ala Leu Glu Pro Asp Asn Arg
1               5

<210> SEQ ID NO 420
<211> LENGTH: 16
<212> TYPE: PRT
<213> ORGANISM: Artificial Sequence
<220> FEATURE:
<223> OTHER INFORMATION: Synthetic peptide

<400> SEQUENCE: 420

Arg Leu Gln Ser Gln Asn Asp Gln Arg Gly Glu Ile Ile His Val Lys
1               5                   10                  15

<210> SEQ ID NO 421
<211> LENGTH: 14
<212> TYPE: PRT
<213> ORGANISM: Artificial Sequence
<220> FEATURE:
<223> OTHER INFORMATION: Synthetic peptide
```

```
<400> SEQUENCE: 421

Val Leu Asp Leu Ala Ile Pro Val Asn Arg Pro Gly Gln Leu
1               5                   10

<210> SEQ ID NO 422
<211> LENGTH: 16
<212> TYPE: PRT
<213> ORGANISM: Artificial Sequence
<220> FEATURE:
<223> OTHER INFORMATION: Synthetic peptide

<400> SEQUENCE: 422

His Gly Pro Val Glu Met Pro Tyr Thr Leu Leu Tyr Pro Ser Ser Lys
1               5                   10                  15

<210> SEQ ID NO 423
<211> LENGTH: 14
<212> TYPE: PRT
<213> ORGANISM: Artificial Sequence
<220> FEATURE:
<223> OTHER INFORMATION: Synthetic peptide

<400> SEQUENCE: 423

Gly Tyr Tyr Gly Glu Gln Gln Gln Gln Pro Gly Met Thr Arg
1               5                   10

<210> SEQ ID NO 424
<211> LENGTH: 17
<212> TYPE: PRT
<213> ORGANISM: Artificial Sequence
<220> FEATURE:
<223> OTHER INFORMATION: Synthetic peptide

<400> SEQUENCE: 424

Ser Glu Glu Gly Tyr Tyr Gly Glu Gln Gln Gln Gln Pro Gly Met Thr
1               5                   10                  15
Arg

<210> SEQ ID NO 425
<211> LENGTH: 6
<212> TYPE: PRT
<213> ORGANISM: Artificial Sequence
<220> FEATURE:
<223> OTHER INFORMATION: Synthetic peptide

<400> SEQUENCE: 425

Leu Arg Gly Phe Ser Lys
1               5
```

ANTI-INFLAMMATORY PEPTIDES, AND USES THEREOF

CROSS REFERENCE TO RELATED APPLICATIONS

This application is a 371 National Phase Entry of International Patent Application No. PCT/EP2016/067090 filed on Jul. 18, 2016 which claims benefit under 35 U.S.C. § 119(b) of EP Application No. 15177013.8 filed Jul. 16, 2015 and EP Application No. 15177017.9 filed Jul. 16, 2015, the contents of which are incorporated herein by reference in their entirety.

SEQUENCE LISTING

The sequence listing of the present application has been submitted electronically via EFS-Web as an ASCII formatted sequence listing with a file name "SEQTXT-1-048262-091330.txt", creation date of Oct. 5, 2018 and a size of 359,048 bytes. The sequence listing submitted via EFS-Web is part of the specification and is herein incorporated by reference in its entirety.

BACKGROUND TO THE INVENTION

It is estimated that a staggering 2 billion people worldwide suffer from some type of inflammation. Inflammation is a vast biological process and an integral part of our immune response. The inflammatory response may be acute (short lived) or chronic (longer lasting) and can occur in almost every part of the body whether it be internal or external. Interestingly as well, whatever the cause of inflammation, the biological changes that occur within the body due to the inflammation response are the same throughout the body, meaning the modes of reducing inflammation, which different anti-inflammatory agents carry are the same in all parts of the body.

Typically, inflammation is a natural response and a necessary one that rids the cells of injury causes, foreign attacks, or removes dead cells. However, excess inflammation has drastic and sometimes detrimental effects on the human body. Indeed, an inflammatory response can have long-lasting, negative consequences such as tissue damage. During an inflammatory response, the body releases lysosomal enzymes which can damage tissue and can even lead to a life-threatening hypersensitivity reaction. These conditions can have long-lasting effects both externally, with the development of acute skin rashes and eczema, and internally, triggering diseases such as inflammatory bowel disease. As a result, maintaining a normal level of inflammation is very important for our health and wellbeing, both inside and out. Unfortunately, inflammation is on the rise. One of the major factors of this increase comes from our exposure to an increasing variety of external agents that our bodies are not accustomed to.

Most anti-inflammatory treatments used today are drugs. There are two major types of anti-inflammatory drugs, corticosteroids and non-steroidal anti-inflammatory drugs (NSAIDs). These include: Immunosuppressives (methotrexate, ciclosporin); Specific biological drugs (mostly TNF-alpha inhibitors, but also inhibitors of cyclooxygenase enzyme for example); Cytotoxic drugs; and Oral retinoids (acitretin). Furthermore, topical treatments exist to specifically reduce skin inflammation. Examples include creams and ointment (mostly cortisone based), and physical treatments like UV radiations. These drugs however have drastic side-effects such as gastrointestinal toxicity and anaphylactoid reactions. They can even suppress the immune system to such a point that it is made vulnerable to other diseases and pathogens.

Therefore, there is a clear need for the identification of agents having anti-inflammatory activity that are not immunosuppressive and/or cause other undesirable side effects. To that end, very specific types of food are known to reduce inflammation (Kiecolt-Glaser J. K. et al. 2010, Middleton E. et al. 2000, Chatterjee M. et al. 2005). Indeed, particular components of these specific foods are in low concentrations, hidden, or locked away, and once identified and unlocked can be scaled to specifically target inflammation in a recognized way, as our bodies understand the components of food and are able to readily process these molecules. Indeed, these particular food molecules can reduce inflammation without completely blocking this immune system response which puts the body in a vulnerable state. For those with many food allergies as well, identifying and unlocking the particular components of a food that may reduce inflammation would allow for these individuals to gain the anti-inflammatory benefits of a food they would otherwise be allergic to.

It is an object of the invention to overcome at least one of the above-referenced problems.

STATEMENTS OF INVENTION

The pea genome codes for over 70,000 different proteins. The Applicant has identified seven of these proteins, each of which contains one or more anti-inflammatory fragments. Likewise, out of the more than 60,000 proteins encoded by the rice genome, the Applicant has identified eight proteins, each of which contains one or more anti-inflammatory fragments. The anti-inflammatory fragments of the sixteen identified proteins have been shown to have anti-inflammatory activity when incubated with LPS-stimulated human cells (FIGS. 1 to 19), do not cause human cell viability issues (FIG. 20) and are not toxic to human cells (FIG. 21). The specific plant proteins from which the natural peptides are derived are provided in SEQ ID NO: 1-15 and 353-355, especially from regions of the proteins provided in SEQ ID NO: 17-69. The specific pea proteins from which the peptides are derived are provided in SEQ ID NO: 1 to 5, 8 and 9, and the specific rice proteins from which the peptides are derived are provided in SEQ ID NO: 6, 7 and 10 to 15. Homologs of these proteins are described in SEQ ID NO: 222-267. The specific peptides initially identified in the pea proteins are shown in SEQ ID Nos: 71-107 and 110-111. The specific peptides initially identified in the rice proteins are shown in SEQ ID Nos: 108-109 and 112-220. Additional peptides of the invention identified in the pea and rice proteins are provided herein, for example in SEQ ID NO: 320, 331 to 352, and 356-424. The peptide of the invention encompasses peptides comprising or consisting of any of the afore-mentioned peptides.

```
                                          (SEQ ID 331)
EWQINEK - Fragment of rice protein of SEQ ID 7

(SEQ ID 332)
FLPQHTD - Fragment of pea protein of SEQ ID 1

(SEQ ID 333)
GPQQYAEWQINEK - Fragment of rice protein of SEQ
ID 7
```

-continued

PGQLQSFLLSGN - Fragment of pea protein of SEQ ID 1 (SEQ ID 334)

PGQLQSFLLSGNQNQQNYLSGF - Fragment of pea protein of SEQ ID 1 (SEQ ID 335)

PQQYAEWQ - Fragment of rice protein of SEQ ID 7 (SEQ ID 336)

QLQSFLLSGNQNQQNYLSGFSK - Fragment of pea protein of SEQ ID 1 (SEQ ID 337)

QNQQNYLSGFSK - Fragment of pea protein of SEQ ID 1 (SEQ ID 338)

QSFLLSGNQNQQ - Fragment of pea protein of SEQ ID 1 (SEQ ID 339)

QSFLLSGNQ - Fragment of pea protein of SEQ ID 1 (SEQ ID 340)

RGPQQYA - Fragment of rice protein of SEQ ID 7 (SEQ ID 341)

DALEPDNR - Fragment of pea protein of SEQ ID 354 (SEQ ID 342)

SEEGYYGEQQQQPGMTR - Fragment of rice protein of SEQ ID 353 (SEQ ID 343)

GYYGEQQQQPGMTR - Fragment of rice protein of SEQ ID 353 (SEQ ID 344)

IDGYDTPVEGR - Fragment of rice protein of SEQ ID 15 (SEQ ID 345)

NGVLRPGQL - Fragment of rice protein of SEQ ID 14 (SEQ ID 346)

RHGEWGPSY (SEQ ID 347)

FWM - Fragment of pea protein of SEQ ID 3 (SEQ ID 348)

TVFDGVLRPGQL - Fragment of rice protein of SEQ ID 10 [SEQ ID 349]

RLQSQNDQRGEIIHVK - Fragment of rice protein of SEQ ID 10 [SEQ ID 350]

HGPVEMPYTLLYPSSK - Fragment of pea protein of SEQ ID 355 [SEQ ID 351]

LDALEPDNR - Fragment of pea protein of SEQ ID 354 [SEQ ID 352]

RGPQQYAEWQINE - Fragment of rice protein SEQ ID 7 [SEQ ID 320]

The peptides of the invention are primarily useful for causing a decrease in inflammation, and therefore have utility in the prevention or treatment of inflammatory conditions and maintaining gut health in mammals.

In a first aspect, the invention provides a peptide, typically 3 to 50 amino acids in length, and comprising a fragment of a protein disclosed herein, for example selected from SEQ ID NOs: 1 to 16, 349 or 350, or a homolog thereof, or a variant or fragment of the peptide (hereafter "peptide of the invention"). In one embodiment, the peptide or variant or fragment thereof is bioactive. In one embodiment, the peptide or variant or fragment thereof has anti-inflammatory activity.

In one embodiment, the peptide of the invention comprises a sequence selected from SEQ ID NO: 17-220, 268-352, and 356-424.

In one embodiment, the peptide of the invention consists essentially of a sequence selected from SEQ ID NO: 17-220, 268-352, and 356-424.

In one embodiment, the peptide consists of 3-50 amino acids. In one embodiment, the peptide consists of 4-50 amino acids. In one embodiment, the peptide consists of 5-50 amino acids. In one embodiment, the peptide consists of 6-50 amino acids.

In one embodiment, the fragment has between 7 and 37 amino acids and a charge of between −9 and +3.

Preferably, the c-terminal amino acid is not cysteine (C) or methionine (M).

Preferably, the n-terminal amino acid is not cysteine (C), histidine (H), proline (P) or threonine (T)

Preferably, the c-terminal domain of the fragment does not contain cysteine (C).

Preferably, the n-terminal domain of the fragment does not contain cysteine (C).

Preferably, the fragment does not contain cysteine (C).

Preferably, the peptide does not contain cysteine (C).

Preferably, the fragment is from a region of the proteins of SEQ ID NOs: 1 to 16, which regions are characterised by the following features:
  17 to 109 amino acids in length;
  a charge of between −6 and +4;
  the c-terminal amino acid is not aspartic acid (D), phenylalanine (F), methionine (M) or tryptophan (W);
  the n-terminal amino acid is not aspartic acid (D), histidine (H), methionine (M), proline (P) or tryptophan (W).

Preferably, the c-terminal domain of the region does not contain tryptophan (W).

Preferably, the regions of the proteins of SEQ ID NOs: 1 to 7 are selected from the SEQ ID NOs: 17-33.

Preferably, the regions of the proteins of SEQ ID NOs: 8 to 16 are selected from the SEQ ID NOs: 34-70.

Preferably, the regions of the proteins of SEQ ID NOs: 1 to 16 are selected from the SEQ ID NOs: 17-70.

Preferably, the fragment is selected from SEQ ID NOs: 71 to 221, or a variant of the fragment.

Preferably, the peptide consists of a fragment selected from SEQ ID NOs: 71 to 221, or a variant of the fragment.

Preferably, the peptide consists of a sequence selected from SEQ ID NOs: 71 to 221.

In one embodiment, the peptide comprises a fragment of a pea protein, wherein the fragment is selected from SEQ ID NO: 71-107, 332, 334, 335, 337-340, 342, 348 and 351-352.

In one embodiment, the peptide comprises a fragment of a pea protein, wherein the fragment is selected from SEQ ID NO: 71-107, 332, 334, 335, 337-340, 342, 348 and 351-352.

In one embodiment, the fragment is selected from 339, 352, 351, 93, 92, 75, 76, 105.

In one embodiment, the peptide comprises a fragment of a rice protein, wherein the fragment is selected from SEQ ID NO: 108-109, 112-220, 320, 331, 333, 336, 341, 343-346, 349-350. In one embodiment, the fragment is selected from 341, 144, 320, 349, 350, 177, 343-346.

In one embodiment, the peptide is a modified peptide. In one embodiment the peptide is modified with a protecting group. In one embodiment, the peptide is modified to increase its lipophilicity. In none embodiment, the peptide is modified to increase its half-life. In one embodiment, an N or C-terminal amino acid of the peptide is modified. In one embodiment, the N or C-terminal amino acid of the peptide is modified with a protecting group.

The invention also provides a conjugate comprising a peptide of the invention conjugated to a binding partner. In one embodiment, the peptide of the invention is modified with a reactive group configured to allow conjugation to the binding partner.

[SEQ ID NO: 1 (Pea Protein 1)]

Preferably, the peptide comprises a bioactive fragment of the protein of SEQ ID NO: 1, or a homolog thereof, or a bioactive variant of the protein fragment.

Preferably, the peptide comprises a bioactive fragment of one of seven regions of SEQ ID NO: 1, namely SEQ ID NOS: 17 to 23, or a bioactive variant of the protein fragment.

Preferably, the peptide comprises a bioactive fragment selected from SEQ ID NOS: 71 to 91 or 360, or a bioactive variant of the protein fragment.

Preferably, the peptide comprises a fragment of the region of SEQ ID NO:17, for example SEQ ID NO: 71, or a bioactive variant of the protein fragment.

Preferably, the peptide comprises a bioactive fragment of the region of SEQ ID NO:18, for example SEQ ID NO: 72, or a bioactive variant of the fragment.

Preferably, the peptide comprises a bioactive fragment of the region of SEQ ID NO:19, for example either or both of SEQ ID NO: 73 or 74, or a bioactive variant of the fragment.

Preferably, the peptide comprises a bioactive fragment of the region of SEQ ID NO:20, for example either or both of SEQ ID NO: 75 or 76. or a bioactive variant of the fragment.

Preferably, the peptide comprises a bioactive fragment of the region of SEQ ID NO:21, for example one or more or all of SEQ ID NO: 77 to 84, or a bioactive variant of the fragment.

Preferably, the peptide comprises a bioactive fragment of the region of SEQ ID NO:22, for example one or more or all of SEQ ID NO: 85 to 89, or a bioactive variant of the fragment.

Preferably, the peptide comprises a bioactive fragment of the region of SEQ ID NO:23, for example SEQ ID NO: 90 or a bioactive variant of the fragment.

Preferably, the peptide comprises SEQ ID NO: 91, or a bioactive variant of the fragment.

The invention also provides a composition comprising at least one peptide of the invention, which peptide includes a fragment of SEQ ID NO: 1 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a different fragment of SEQ ID NO: 1 or a homolog thereof. Preferably, the peptide or peptides are bioactive. Preferably, the peptide or peptides are anti-inflammatory. Preferably, the composition comprises a first peptide of the invention that comprises a fragment of a first region selected from SEQ-ID NOS: 17 to 23, and a second peptide of the invention that comprises fragment of a second region selected from SEQ ID NOS: 17 to 23. Preferably, the composition comprises a first bioactive peptide comprising a first bioactive fragment selected from SEQ ID NO: 71 to 91 (or a bioactive variant of the fragment), and a second bioactive peptide comprising a second bioactive fragment selected from SEQ ID NO: 71 to 91 (or a bioactive variant of the fragment).

Homologs of Pea Protein 1 (SEQ-ID NO: 1) include *Vicia fabia, Cicer arietinum* and *Lens culinaris* homologs (SEQ ID NO: 222-224).

[SEQ ID NO: 2 (Pea Protein 2)]

Preferably, the peptide comprises a bioactive fragment of the protein of SEQ ID NO: 2, or a homolog thereof.

Preferably, the peptide comprises a bioactive fragment of one of two regions of SEQ ID NO: 2, namely SEQ ID NOS: 24 or 25.

Preferably, the peptide comprises a bioactive fragment of the region of SEQ ID NO:24, for example SEQ ID NO: 92, or a bioactive variant of the fragment.

Preferably, the peptide comprises a bioactive fragment of the region of SEQ ID NO:25, for example SEQ ID NO: 93, or a bioactive variant of the fragment.

The invention also provides a composition comprising at least one bioactive peptide of the invention, which peptide includes a bioactive fragment of SEQ ID NO: 2 or a homolog thereof. The invention also provides a composition comprising at least two bioactive peptides of the invention, each of which comprises a different bioactive fragment of SEQ ID NO: 2 or a homolog thereof. Preferably, the composition comprises a first bioactive peptide comprising a bioactive fragment of the region of SEQ ID NO 24, and a second bioactive peptide comprising a bioactive fragment of the region of SEQ-ID NO 25. Preferably, the composition comprises a first bioactive peptide comprising a bioactive fragment of SEQ ID NO 92, and a second bioactive peptide comprising a bioactive fragment of SEQ-ID NO 93.

Homologs of Pea Protein 2 (SEQ ID NO: 2) include *Lens culinaris, Vicia narbonensis* and *Glycine max* (SEQ ID NO: 225-227).

[SEQ-ID NO: 3 (Pea Protein 3)]

Preferably, the peptide comprises a bioactive fragment of the protein of SEQ ID NO: 3, or a homolog thereof.

Preferably, the peptide comprises a bioactive fragment of one of two regions of SEQ ID NO: 3, namely SEQ ID NOS: 26 or 27.

Preferably, the peptide comprises a bioactive fragment of the region of SEQ ID NO:26, for example SEQ ID NO: 94, or a bioactive variant the fragment.

Preferably, the peptide comprises a bioactive fragment of the region of SEQ ID NO:27, for example SEQ ID NO: 95, or a bioactive variant of the fragment.

The invention also provides a composition comprising at least bioactive peptides of the invention, which peptide includes a bioactive fragment of SEQ ID NO: 3 or a homolog thereof. The invention also provides a composition comprising at least two bioactive peptides of the invention, each of which comprises a different bioactive fragment of SEQ ID NO: 3 or a homolog thereof. Preferably, the composition comprises a first peptide comprising a bioactive fragment of the region of SEQ ID NO 26, and a second peptide comprising a bioactive fragment of SEQ-ID NO 27. Preferably, the composition comprises a first bioactive peptide comprising a bioactive fragment of SEQ ID NO 94 (or a bioactive variant of the fragment), and a second bioactive peptide comprising a bioactive fragment of SEQ ID NO 95 (or a bioactive variant of the fragment).

Homologs of Pea Protein 3 (SEQ ID NO: 3) include *Vicia sativa, Medicago truncatula*, and *Lotus japonicas* (SEQ ID NO: 228-230).

[SEQ ID NO: 4 (Pea Protein 4)]

Preferably, the peptide comprises a bioactive fragment of the protein of SEQ ID NO: 4, or a homolog thereof.

Preferably, the peptide comprises a bioactive fragment of one of five regions of SEQ-ID NO: 4, namely SEQ ID NOS: 28 to 32. Preferably, the region is SEQ ID NO: 28, preferably SEQ ID NO: 29, preferably SEQ ID NO: 30, preferably SEQ ID NO: 31, preferably SEQ ID NO: 32.

Preferably, the peptide comprises a bioactive fragment of the region of SEQ ID NO:28, for example SEQ ID NO: 96, or a bioactive variant of the fragment.

Preferably, the peptide comprises a bioactive fragment of the region of SEQ ID NO:29, for example SEQ ID NO: 97 to 103, or a bioactive variant of the fragment.

Preferably, the peptide comprises a bioactive fragment of the region of SEQ ID NO:30, for example SEQ ID NO: 104, or a bioactive variant of the fragment.

Preferably, the peptide comprises a bioactive fragment of the region of SEQ ID NO:31, for example SEQ ID NO: 105, or a bioactive variant of the fragment.

Preferably, the peptide comprises a bioactive fragment of the region of SEQ ID NO:32, for example SEQ ID NO: 106, or a bioactive variant of the fragment.

The invention also provides a composition comprising at least one bioactive peptide of the invention, which peptide includes a bioactive fragment of SEQ ID NO: 4 or a homolog thereof. The invention also provides a composition comprising at least 2, preferably 3, preferably 4, preferably 5, preferably 6, preferably 7, preferably 8, preferably 9, or preferably 10 peptides of the invention that comprise different bioactive fragments of SEQ ID NO: 4 or a homolog thereof. Preferably, the composition comprises a first peptide comprising a bioactive fragment of a first region selected from SEQ ID NOS: 28 to 32, and a second peptide that comprises a bioactive fragment of a second region selected from SEQ ID NOS: 28 to 32. Preferably, the composition comprises a first bioactive peptide comprising a first bioactive fragment selected from SEQ ID NO: 96 to 106 (or an a bioactive variant of the fragment), and a second bioactive peptide comprising a second bioactive fragment selected from SEQ ID NO 96 to 106 (or a bioactive variant of the fragment).

Homologs of Pea Protein 4 (SEQ ID NO: 4) include *Pisum abyssinicum, Lathyrus annuus*, and *Vicia villosa* (SEQ ID NOs: 231-233).

[SEQ ID NO: 5 (Pea Protein 5)]

Preferably, the peptide comprises a bioactive fragment of the protein of SEQ ID NO: 5, or a homolog thereof.

Preferably, the peptide comprises a bioactive fragment of a region of SEQ ID NO: 5, namely the region of SEQ ID NO 33, for example SEQ ID NO: 107, or a bioactive variant of the fragment.

The invention also provides a composition comprising at least one bioactive peptides of the invention, which peptide includes a bioactive fragment of SEQ ID NO: 5 or a homolog thereof. The invention also provides a composition comprising at least two peptides of the invention that comprise at least one bioactive fragment of SEQ ID NO: 5 or a homolog thereof, for example SEQ ID NO: 107.

Homologs of Pea Protein 5 (SEQ ID NO: 5) include *Medicago truncatula, Vicia peregrine*, and *Vicia lutea* (SEQ ID NO: 234-236).

[SEQ ID NO: 6 (Rice Protein 7—Q6K508)]

Preferably, the peptide comprises a bioactive fragment of the protein of SEQ ID NO: 6 or a homolog thereof.

Preferably, the peptide comprises a bioactive fragment of SEQ ID NO: 108, or a bioactive variant of the fragment.

The invention also provides a composition comprising at least one bioactive peptides of the invention, which peptide includes a bioactive fragment of SEQ ID NO: 6 or a homolog thereof. The invention also provides a composition comprising at least two peptides of the invention including at least one bioactive fragment of SEQ ID NO: 6 or a homolog thereof, for example SEQ ID NO: 108 (SP1).

Homologs of Rice Protein 7 (SEQ ID NO: 6) include *Oryza, brachyantha, Avena sativa*, and *Brachypodium distachyon* (SEQ ID NO: 237-239).

[SEQ ID NO: 7 (Rice Protein 8—Q6K7K6)]

Preferably, the peptide comprises a bioactive fragment of the protein of SEQ ID NO: 7 or a homolog thereof.

Preferably, the peptide comprises a bioactive fragment of SEQ ID NO: 109 (SP2), or a bioactive variant of the fragment.

The invention also provides a composition comprising at least one bioactive peptides of the invention, which peptide includes a bioactive fragment of SEQ ID NO: 7 or a homolog thereof. The invention also provides a composition comprising at least two peptides of the invention including at least one bioactive fragment of SEQ ID NO: 7 or a homolog thereof, for example SEQ ID NO: 109 (SP2).

Homologs of Rice Protein 8 (SEQ ID NO: 7) include *Oryza sativa Japonica* Group, *Oryza sativa* Indica Group, and *Oryza brachyantha* (SEQ ID NO: 240-242).

[SEQ ID NO: 8 (Pea Protein 6—P13919)]

Preferably, the peptide comprises a bioactive fragment of the protein of SEQ ID NO: 8 or a homolog thereof.

Preferably, the peptide comprises a bioactive fragment of SEQ ID NO: 110 (SP3), or a bioactive variant of the fragment.

The invention also provides a composition comprising at least one bioactive peptide of the invention, which peptide includes a bioactive fragment of SEQ ID NO: 8 or a homolog thereof. The invention also provides a composition comprising at least two peptides of the invention including at least one bioactive fragment of SEQ ID NO: 8 or a homolog thereof, for example SEQ ID NO: 110 (SP3).

Homologs of Pea Protein 8 (SEQ ID NO: 8) include *Pisum fulvum, Pisum abyssinicum* and *Vicia villosa* (SEQ ID NO: 243-245).

[SEQ ID NO: 9 (Pea Protein 7—P02855)]

Preferably, the peptide comprises a bioactive fragment of the protein of SEQ ID NO: 9 or a homolog thereof.

Preferably, the peptide comprises a bioactive fragment of SEQ ID NO: 111 (SP4), or a bioactive variant of the fragment.

The invention also provides a composition comprising at least one bioactive peptide of the invention, which peptide includes a bioactive fragment of SEQ ID NO: 9 or a homolog thereof. The invention also provides a composition comprising at least two peptides of the invention including at least one bioactive fragment of SEQ ID NO: 9 or a homolog thereof, for example SEQ ID NO: 111 (SP4).

Homologs of Pea Protein 9 (SEQ ID NO: 9) include *Lathyrus hirsutus, Lathyrus cicero, Lathyrus sativus* (SEQ ID NO: 246-248).

[SEQ ID NO: 10 (Rice Protein 1—P07728)]

Preferably, the peptide comprises a bioactive fragment of the protein of SEQ ID NO: 10 or a homolog thereof.

Preferably, the peptide comprises a fragment of one of nine regions of SEQ ID NO: 10, namely SEQ ID NOS: 34 to 42. Preferably, the region is SEQ ID NO: 34, preferably SEQ ID NO: 35, preferably SEQ ID NO: 36, preferably SEQ ID NO: 37, preferably SEQ ID NO: 38, preferably SEQ ID NO: 39, preferably SEQ ID NO: 40, preferably SEQ ID NO: 41, preferably SEQ ID NO: 42.

Preferably, the peptide comprises a bioactive fragment of the region of SEQ ID NO:34, for example SEQ ID NO: 112 or SEQ ID NO: 113 or a bioactive variant of the fragment.

Preferably, the peptide comprises a bioactive fragment of the region of SEQ ID NO:35, for example SEQ ID NO: 114, or a bioactive variant of the fragment.

Preferably, the peptide comprises a bioactive fragment of the region of SEQ ID NO:36, for example SEQ ID NO: 115 or SEQ ID NO: 116, or a bioactive variant of the fragment.

Preferably, the peptide comprises a bioactive fragment of the region of SEQ ID NO:37, for example SEQ ID NO: 117 or SEQ ID NO: 118, or a bioactive variant of the fragment.

Preferably, the peptide comprises a bioactive fragment of the region of SEQ ID NO:38, for example SEQ ID NO: 119, or a bioactive variant of the fragment.

Preferably, the peptide comprises a bioactive fragment of the region of SEQ ID NO:39, for example SEQ ID NO: 120, 121 or 122, or a bioactive variant of the fragment.

Preferably, the peptide comprises a bioactive fragment of the region of SEQ ID NO:40, for example SEQ ID NO: 123, or a bioactive variant of the fragment.

Preferably, the peptide comprises a bioactive fragment of the region of SEQ ID NO:41, for example SEQ ID NO: 124, 125, 126, 127, 128 or 129, or a bioactive variant of the fragment.

Preferably, the peptide comprises a fragment of the region of SEQ ID NO:42, for example SEQ ID NO: 130, 131 or 132, or a bioactive variant of the fragment.

The invention also provides a composition comprising at least one bioactive peptide of the invention, which peptide includes a bioactive fragment of SEQ ID NO: 10 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a different bioactive fragment of SEQ ID NO: 10 or a homolog thereof. Preferably, the composition comprises a first peptide that comprises a bioactive fragment of a first region selected from SEQ ID NOS: 34 to 42, and a second peptide that comprises a bioactive fragment of a second region selected from SEQ ID NOS: 34 to 42. Preferably, the composition comprises a first bioactive peptide comprising a first bioactive fragment selected from SEQ ID NO: 112 to 132 (or a bioactive variant of the fragment), and a second bioactive peptide comprising a second bioactive fragment selected from SEQ ID NO 112 to 132 (or a bioactive variant of the fragment).

Homologs of Rice Protein 1 (SEQ ID NO: 10) include *Oryza brachyantha*, and *Zizania latifolia* (SEQ ID NO: 249-251).

[SEQ ID NO: 11 (Rice Protein 2—P07728)]

Preferably, the peptide comprises a bioactive fragment of the protein of SEQ ID NO: 11 or a homolog thereof.

Preferably, the peptide comprises a bioactive fragment of one of four regions of SEQ ID NO: 11, namely SEQ ID NOS: 43 to 46. Preferably, the region is SEQ ID NO: 43, preferably SEQ ID NO: 44, preferably SEQ ID NO: 45, preferably SEQ ID NO: 46.

Preferably, the peptide comprises a bioactive fragment of the region of SEQ ID NO:43, for example SEQ ID NO: 133 or a bioactive variant of the fragment.

Preferably, the peptide comprises a bioactive fragment of the region of SEQ ID NO:44, for example SEQ ID NO: 134 to 137, or a bioactive variant of the fragment.

Preferably, the peptide comprises a bioactive fragment of the region of SEQ ID NO:45, for example SEQ ID NO: 138 to 144, or a bioactive variant of the fragment.

Preferably, the peptide comprises a bioactive fragment of the region of SEQ ID NO:46, for example SEQ ID NO:145, or a bioactive variant of the fragment.

The invention also provides a composition comprising at least one bioactive peptides of the invention, which peptide includes a bioactive fragment of SEQ ID NO:11 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a bioactive fragment of SEQ ID NO: 11 or a homolog thereof. Preferably, the composition comprises a first peptide that comprises a bioactive fragment of a first region selected from SEQ ID NOS: 43 to 46, and a second peptide that comprises a bioactive fragment of a second region selected from SEQ ID NOS: 43 to 46. Preferably, the composition comprises a first bioactive peptide comprising a first bioactive fragment selected from SEQ ID NO: 133 to 145 (or a bioactive variant of the fragment), and a second bioactive peptide comprising a second bioactive fragment selected from SEQ ID NO 133 to 145 (or a bioactive variant of the fragment).

Homologs of Rice Protein 2 (SEQ ID NO: 11) include *Oryza sativa* Indica Group, *Zizania latifolia*, *Avena sativa* (SEQ ID NO: 252-254).

[SEQ ID NO: 12 (Rice Protein 3—P07730)]

Preferably, the peptide comprises a bioactive fragment of the protein of SEQ ID NO: 12 or a homolog thereof.

Preferably, the peptide comprises a bioactive fragment of one of eight regions of SEQ ID NO: 12, namely SEQ ID NOS: 47 to 54. Preferably, the region is SEQ ID NO: 47, preferably SEQ ID NO: 48, preferably SEQ ID NO: 49, preferably SEQ ID NO: 50, preferably SEQ ID NO: 51, preferably SEQ ID NO: 52, preferably SEQ ID NO: 53, preferably SEQ ID NO: 54.

Preferably, the peptide comprises a bioactive fragment of the region of SEQ ID NO:47, for example one of SEQ ID NO: 146 to 150, or a bioactive variant of the fragment.

Preferably, the peptide comprises a bioactive fragment of the region of SEQ ID NO:48, for example one of SEQ ID NO: 151 to 157, or a bioactive variant of the fragment.

Preferably, the peptide comprises a bioactive fragment of the region of SEQ ID NO:49, for example one of SEQ ID NO: 158 or SEQ ID NO: 159, or a bioactive variant of the fragment.

Preferably, the peptide comprises a bioactive fragment of the region of SEQ ID NO:50, for example one of SEQ ID NO: 160 to 162, or a bioactive variant of the fragment.

Preferably, the peptide comprises a bioactive fragment of the region of SEQ ID NO:51, for example one of SEQ ID NO: 163 or 164, or a bioactive variant of the fragment.

Preferably, the peptide comprises a bioactive fragment of the region of SEQ ID NO:52, for example SEQ ID NO: 165, or a bioactive variant of the fragment.

Preferably, the peptide comprises a bioactive fragment of the region of SEQ ID NO:53, for example one of SEQ ID NO: 166 to 171, or a bioactive variant of the fragment.

Preferably, the peptide comprises a bioactive fragment of the region of SEQ ID NO:54, for example one of SEQ ID NO: 172 to 176, or a bioactive variant of the fragment.

The invention also provides a composition comprising at least one bioactive peptides of the invention, which peptide includes a bioactive fragment of SEQ ID NO: 12 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a bioactive fragment of SEQ ID NO: 12 or a homolog thereof. Preferably, the composition comprises a first peptide that comprises a bioactive fragment of a first region selected from SEQ ID NOS: 47 to 54, and a second peptide that comprises a bioactive fragment of a second region selected from SEQ ID NOS: 47 to 54. Preferably, the composition comprises a first bioactive peptide comprising a first bioactive fragment selected from SEQ ID NO: 146 to 172 (or a bioactive variant of the fragment), and a second bioactive peptide comprising a second anti-inflammatory fragment selected from SEQ ID NO 146 to 172 (or a bioactive variant of the fragment).

Homologs of Rice Protein 3 (SEQ ID NO: 12) include *Oryza brachyantha, Brachipodium distachyon* (SEQ ID NO: 255-257).

[SEQ ID NO: 13 (Rice Protein 4—Q0D7S0)]

Preferably, the peptide comprises a bioactive fragment of the protein of SEQ ID NO: 13 or a homolog thereof.

Preferably, the peptide comprises a bioactive fragment of a region of SEQ ID NO: 13, namely SEQ ID NO 55, for example SEQ ID NO: 177, or a bioactive variant of the fragment.

The invention also provides a composition comprising at least one bioactive peptide of the invention, which peptide includes a bioactive fragment of SEQ ID NO: 13 or a homolog thereof. The invention also provides a composition comprising at least 2 peptides of the invention, at least one of which comprises a bioactive fragment of SEQ ID NO: 13 or a homolog thereof, for example SEQ ID NO: 177, or a bioactive variant of the fragment.

Homologs of Rice Protein 4 (SEQ ID NO: 13) include *Oryza sativa* Indica Group, *Zizania latifolia, Avena sativa* (SEQ ID NO: 252-254).

[SEQ ID NO: 14 (Rice Protein 5—P14614)]

Preferably, the peptide comprises a fragment of the protein of SEQ ID NO: 14 or a homolog thereof.

Preferably, the peptide comprises a bioactive fragment of one of seven regions of SEQ ID NO: 14, namely SEQ ID NOS: 56 to 62. Preferably, the region is SEQ ID NO: 56, preferably SEQ ID NO: 57, preferably SEQ ID NO: 58, preferably SEQ ID NO: 59, preferably SEQ ID NO: 60, preferably SEQ ID NO: 61, preferably SEQ ID NO: 62.

Preferably, the peptide comprises a bioactive fragment of the region of SEQ ID NO:56, for example one of SEQ ID NO: 178 to 180 or a bioactive variant of the fragment.

Preferably, the peptide comprises a bioactive fragment of the region of SEQ ID NO:57, for example one of SEQ ID NO: 181 to 182, or a bioactive variant of the fragment.

Preferably, the peptide comprises a bioactive fragment of the region of SEQ ID NO:58, for example SEQ ID NO: 183, or a bioactive variant of the fragment.

Preferably, the peptide comprises a bioactive fragment of the region of SEQ ID NO:59, for example one of SEQ ID NO: 184 to 190, or a bioactive variant of the fragment.

Preferably, the peptide comprises a bioactive fragment of the region of SEQ ID NO:60, for example SEQ ID NO:191, or a bioactive variant of the fragment.

Preferably, the peptide comprises a bioactive fragment of the region of SEQ ID NO:61, for example one of SEQ ID NO: 192 to 195, or a bioactive variant of the fragment.

Preferably, the peptide comprises a bioactive fragment of the region of SEQ ID NO:62, for example one of SEQ ID NO: 196 to 197, or a bioactive variant of the fragment.

The invention also provides a composition comprising at least one bioactive peptides of the invention, which peptide includes a bioactive fragment of SEQ ID NO: 14 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a bioactive fragment of SEQ ID NO: 14 or a homolog thereof. Preferably, the composition comprises a first peptide that comprises a bioactive fragment of a first region selected from SEQ ID NOS: 56 to 62, and a second peptide that comprises a bioactive fragment of a second region selected from SEQ ID NOS: 56 to 62. Preferably, the composition comprises a first bioactive peptide comprising a first bioactive fragment selected from SEQ ID NO: 178 to 197 (or a bioactive variant of the fragment), and a second bioactive peptide comprising a second bioactive fragment selected from SEQ ID NO 178 to 197 (or a bioactive variant of the fragment).

Homologs of Rice Protein 5 (SEQ ID NO: 14) include *Oryza sativa Japonica* Group, *Brachipodium distachyon* (SEQ ID NO: 261-263).

[SEQ ID NO: 15 (Rice Protein 6—Q0DEV5)]

Preferably, the peptide comprises a bioactive fragment of the protein of SEQ ID NO: 15 or a homolog thereof.

Preferably, the peptide comprises a bioactive fragment of one of seven regions of SEQ ID NO: 15, namely SEQ ID NOS: 63 to 67. Preferably, the region is SEQ ID NO: 63, preferably SEQ ID NO: 64, preferably SEQ ID NO: 65, preferably SEQ ID NO: 66, preferably SEQ ID NO: 67.

Preferably, the peptide comprises a fragment of the region of SEQ ID NO:63, for example one of SEQ ID NO: 198 to 200, or a bioactive variant of the fragment.

Preferably, the peptide comprises a fragment of the region of SEQ ID NO:64, for example one of SEQ ID NO: 201 to 203 or a bioactive variant of the fragment.

Preferably, the peptide comprises a fragment of the region of SEQ ID NO:65, for example SEQ ID NO: 204 or a bioactive variant of the fragment.

Preferably, the peptide comprises a fragment of the region of SEQ ID NO:66, for example one of SEQ ID NO: 205 to 208 or a bioactive variant of the fragment.

Preferably, the peptide comprises a fragment of the region of SEQ ID NO:67, for example one of SEQ ID NO:209 to 215 or a bioactive variant of the fragment.

Preferably, the peptide comprises a fragment of the region of SEQ ID NO:68, for example one of SEQ ID NO: 216 to 219, or a bioactive variant of the fragment.

Preferably, the peptide comprises a fragment of the region of SEQ ID NO:69, for example SEQ ID NO: 220, or a bioactive variant of the fragment.

The invention also provides a composition comprising at least one bioactive peptide of the invention, which peptide includes a bioactive fragment of SEQ ID NO: 15 or a homolog thereof. The invention also provides a composition comprising at least 2, preferably 3, preferably 4, preferably 5, preferably 6, preferably 7, preferably 8, preferably 9, or preferably 10 peptides of the invention, each of which comprises a bioactive fragment of SEQ ID NO: 15 or a homolog thereof. Preferably, the composition comprises a first peptide that comprises a bioactive fragment of a first region selected from SEQ ID NOS: 63 to 69, and a second peptide that comprises a bioactive fragment of a second region selected from SEQ ID NOS: 63 to 69. Preferably, the composition comprises a first bioactive peptide comprising a first bioactive fragment selected from SEQ ID NO: 198 to 220 (or a bioactive variant of the fragment), and a second bioactive peptide comprising a second bioactive fragment selected from SEQ ID NO 198 to 220 (or a bioactive variant of the fragment).

Homologs of Rice Protein 6 (SEQ ID NO: 15) include *Oryza rufipogon, Oryza officinalis, Hordeum vulgare* subsp. *vulgare* (SEQ ID NO: 264-266).

[SEQ ID NO: 16 (Bacterial Protein 1—POC1U8)]

Preferably, the peptide comprises a bioactive fragment of the protein of SEQ ID NO: 16 or a homolog thereof.

Preferably, the peptide comprises a bioactive fragment of a region of SEQ ID NO: 16, namely the region of SEQ ID NO 70. Typically, the peptide is SEQ ID NO 221, or a bioactive variant of the fragment.

The invention also provides a composition comprising at least one bioactive peptides of the invention, which peptide includes a bioactive fragment of SEQ ID NO: 16 or a homolog thereof. The invention also provides a composition comprising at least 2 peptides of the invention, at least one of which comprises a fragment of SEQ ID NO: 16 or a homolog thereof, for example SEQ ID NO: 212 or a bioactive variant of the fragment.

Homologs of Bacterial Protein 1 (SEQ ID NO: 16) include:

Preferably, the composition comprises at least seven distinct peptides of the invention.

Preferably, the composition comprises at least eight distinct peptides of the invention.

Preferably, the composition comprises at least nine distinct peptides of the invention.

Preferably, the composition comprises at least ten distinct peptides of the invention.

In one embodiment, the invention comprises a composition comprises one or more of SEQ ID NO: 71-107 and 110-111, or anti-inflammatory variants of the fragments, or a mixture of the anti-inflammatory fragments and variants.

In one embodiment, the composition comprises at least one, two, three, four, five or all of SEQ ID NOS 75, 91, 92, 93, 110 and 111.

In one embodiment, the composition comprises substantially all of fragments SEQ ID NO: 71-107 and 110-111.

In one embodiment, the invention comprises a composition comprises one or more of SEQ ID NO: 108-109 and 112 to 220, or anti-inflammatory variants of the fragments, or a mixture of the anti-inflammatory fragments and variants.

In one embodiment, the composition comprises at least one, two or three of SEQ ID NOS 108, 109 and 144.

>gi|580560623|gb|EVF84961.1| glutamyl endopeptidase [*Staphylococcus aureus* COAS6020]
>gi|580687002|gb|EVH10169.1| glutamyl endopeptidase [*Staphylococcus aureus* UCIM6080]
>gi|751815683|gb|KIN24957.1| glutamyl endopeptidase [*Staphylococcus aureus* MRSA_CVM43477]
>gi|781884797|dbj|BAR08486.1| glutamyl endopeptidase precursor [*Staphylococcus aureus* subsp. *aureus*]
>gi|781887762|dbj|BAR11210.1| glutamyl endopeptidase precursor [*Staphylococcus aureus* subsp. *aureus*]

The invention also provides bioactive composition comprising at least one and preferably a plurality of bioactive peptides of the invention, wherein each of the peptides of the invention comprises a bioactive fragment of a protein described herein. In one embodiment the protein is selected from SEQ ID NO: 1 to 16. Typically, the or each peptide of the invention is selected from, or comprises a bioactive fragment selected from, SEQ ID NO: 71-220, or a bioactive variant of the fragment.

In one embodiment, the composition comprises a peptide of the invention, which peptide comprises a sequence selected from SEQ ID NO: 17-220, 268-352, and 356-424.

In one embodiment, the composition comprises peptide of the invention, which peptide consists essentially of a sequence selected from SEQ ID NO: 17-220, 268-352, and 356-424.

Typically, the or each peptide of the invention is selected from, or comprises a bioactive fragment selected from, SEQ ID NO: 71-107 and 110-111, or a bioactive variant of the fragment.

Typically, the or each peptide of the invention is selected from, or comprises an anti-inflammatory fragment selected from, SEQ ID NO: 108-109 and 112 to 220, or an anti-inflammatory variant of the fragment.

In embodiment, the bioactive peptide, variant or fragment of the invention is anti-inflammatory.

Preferably, the composition comprises at least two distinct peptides of the invention.

Preferably, the composition comprises at least three distinct peptides of the invention.

Preferably, the composition comprises at least four distinct peptides of the invention.

Preferably, the composition comprises at least five distinct peptides of the invention.

Preferably, the composition comprises at least six distinct peptides of the invention.

In one embodiment, the composition of the invention is enriched in peptides having a molecular weight of less than 10 KD. In one embodiment, the composition is depleted of cell debris.

In one embodiment, the composition of the invention is a powder.

In one embodiment, the invention comprises a composition comprising substantially all of fragments SEQ ID NO: 108-109 and 112 to 220, or anti-inflammatory variants of the fragments, or a mixture of the anti-inflammatory fragments and variants.

In one embodiment the composition is edible (comestible). In one embodiment, the composition is a food or beverage. In one embodiment, the composition is a personal care composition. In one embodiment, the composition is a pharmaceutical composition. In one embodiment, the composition is nutritional supplement. In one embodiment, the composition is solid. In one embodiment, the composition is semi-solid (i.e. a cream, gel or lotion). In one embodiment, the composition is liquid.

The invention also relates to a comestible product comprising a peptide of the invention. Preferably the comestible product is man-made.

The invention also relates to a comestible product comprising a composition of peptides of the invention. Preferably the comestible product is man-made.

Preferably, the comestible product is a food product for human or animal (mammalian) consumption.

In one embodiment the man-made comestible product is a beverage. In one embodiment the man-made comestible product is a bakery product. In one embodiment the man-made comestible product is a dairy product. In one embodiment the man-made comestible product is a snack product. In one embodiment the man-made comestible product is a baked extruded food product. In one embodiment the man-made comestible product is powdered milk. In one embodiment the man-made comestible product is an infant formula product. In one embodiment the man-made comestible product is a confectionary product. In one embodiment the man-made comestible product is a yoghurt. In one embodiment the man-made comestible product is a yoghurt drink. In one embodiment the man-made comestible product is an ice cream product. In one embodiment the man-made comestible product is a frozen food product. In one embodiment the man-made comestible product is a breakfast cereal. In one embodiment the man-made comestible product is a bread. In one embodiment the man-made comestible product is a flavoured milk drink. In one embodiment the man-made comestible product is a confectionary bar. In one embodiment the man-made comestible product is a tea or tea product. In one embodiment the man-made comestible product is a based extruded snack product. In one embodiment the man-made comestible product is a fried snack product. In one embodiment the man-made comestible product is a nutritional supplement. In one embodiment the man-made comestible product is a sports nutritional product. In one embodiment the man-made comestible product is a baby food product. In one embodiment the man-made comestible product is a speciality food product for immunocompromised individuals. In one embodiment the man-made comestible product is a food for geriatric patients.

The invention also relates to a man-made personal care composition comprising a peptide of the invention.

The invention also relates to a man-made personal care composition comprising a composition of peptides of the invention.

In one embodiment the personal care composition is a skincare product. In one embodiment the personal care composition is a haircare product. In one embodiment the personal care composition is a dentrifice product. In one embodiment the personal care composition is a perfumery product. In one embodiment the personal care composition is a deodorant product. In one embodiment the personal care composition is an anti-perspirant product. In one embodiment the personal care composition is a soap. In one embodiment the personal care composition is a liquid soap. In one embodiment the personal care composition is a cream. In one embodiment the personal care composition is a lotion. In one embodiment the personal care composition is a gel. In one embodiment the personal care composition is a powder.

The invention also relates to a peptide of the invention for use in treatment or prevention of inflammation in a mammal.

The invention also relates to a composition of peptides of the invention for use in treatment or prevention of inflammation in a mammal.

The invention also relates to a peptide of the invention for use in treatment or prevention of an inflammatory disorder in a mammal.

The invention also relates to a composition of peptides of the invention for use in treatment or prevention of an inflammatory disorder in a mammal.

In one embodiment the inflammation is symptomatic inflammation.

In one embodiment the inflammatory disorder is an inflammatory disorder of the joints. In one embodiment the inflammatory disorder is an inflammatory disorder of the cardiovascular system. In one embodiment the inflammatory disorder is an autoimmune disease. In one embodiment the inflammatory disorder is a lung and airway inflammatory disorder. In one embodiment the inflammatory disorder is an intestinal inflammatory disorder. In one embodiment the inflammatory disorder is dermatitis. In one embodiment the inflammatory disorder is acne vulgaris. In one embodiment the inflammatory disorder is psoriasis. In one embodiment the inflammatory disorder is rheumatoid arthritis. In one embodiment the inflammatory disorder is cardiovascular disease. In one embodiment the inflammatory disorder is atherosclerosis. In one embodiment the inflammatory disorder is Type I diabetes. In one embodiment the inflammatory disorder is Graves disease. In one embodiment the inflammatory disorder is Guillain-Barre disease. In one embodiment the inflammatory disorder is Lupus. In one embodiment the inflammatory disorder is Psoriatic arthritis. In one embodiment the inflammatory disorder is Ulcerative colitis. In one embodiment the inflammatory disorder is asthma. In one embodiment the inflammatory disorder is cystic fibrosis. In one embodiment the inflammatory disorder is COPD. In one embodiment the inflammatory disorder is emphysema. In one embodiment the inflammatory disorder is acute respiratory distress syndrome. In one embodiment the inflammatory disorder is colitis. In one embodiment the inflammatory disorder is inflammatory bowel disease.

The invention also relates to a peptide of the invention for use in treatment or prevention of pain in a mammal.

The invention also relates to a composition of peptides of the invention for use in treatment or prevention of pain in a mammal.

The invention also relates to a peptide of the invention for use in treatment or prevention of a metabolic disorder in a mammal.

The invention also relates to a composition of peptides of the invention for use in treatment or prevention of a metabolic disorder in a mammal.

In one embodiment, the metabolic disorder is pre-diabetes. In one embodiment, the metabolic disorder is diabetes. In one embodiment, the metabolic disorder is Type-1 diabetes. In one embodiment, the metabolic disorder is Type-2 diabetes. In one embodiment, the metabolic disorder is metabolic syndrome. In one embodiment, the metabolic disorder is obesity. In one embodiment, the metabolic disorder is diabetic dyslipidemia. In one embodiment, the metabolic disorder is hyperlipidemia. In one embodiment, the metabolic disorder is hypertension. In one embodiment, the metabolic disorder is hypertriglyceridemia. In one embodiment, the metabolic disorder is hyperfattyacidemia. In one embodiment, the metabolic disorder is hypercholerterolemia. In one embodiment, the metabolic disorder is hyperinsulinemia. In one embodiment, the metabolic disorder is MODY The invention also relates to a peptide of the invention for use in maintaining or restoring gut health in a mammal.

The invention also relates to a composition of peptides of the invention for use in maintaining or restoring gut health in a mammal.

The invention also relates to a peptide of the invention for use in maintaining or restoring muscle health (for example lean tissue mass) in a mammal.

The invention also relates to a composition of peptides of the invention for use in maintaining or restoring muscle health (for example lean tissue mass) in in a mammal.

The invention also relates to a pharmaceutical composition comprising a peptide of the invention in combination with a pharmaceutically acceptable carrier.

The invention also relates to a pharmaceutical composition comprising a composition of peptides of the invention in combination with a pharmaceutically acceptable carrier.

Such peptides can be used in personal care, supplement, food and pharmaceutical products to treat and maintain healthy levels of inflammation throughout the body. The present invention meets the huge need for food-derived specific peptides and peptide compositions that reduces inflammation in a way that is able to be processed by the body without completely blocking the immune response and causing autoimmune issues and other undesirable side effects. The invention is ultimately helping the 2 billion people suffering from inflammation.

The invention also relates to a comestible product, for example a food product comprising a composition of the invention, for example a dairy or non-dairy product, a solid food or a beverage, a food additive or supplement. The dairy product may be a milk, a cheese, or yoghurt. In one embodiment, the food product is a snack bar. The food product may comprise any amount of the composition of the invention, for example from 0.1% to 30% (w/w).

The peptides of the invention are used in the topical cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight). Ideally, the peptides of the present invention are preferably used from about 0.00001% w/w to about 0.5% w/w [0.1 to 5000 ppm], and more preferably from 0.00005 w/w to about 0.05 w/w [0.5 to 500 ppm], and most preferably from about 0.0001 w/w to about 0.01 w/w of the composition [1 to 100 ppm]. Ideally, the peptides of the present invention are preferably used from about 0.0001% w/w to about 0.004% w/w of the composition.

For compositions of peptides of the invention, a typical daily dosage may be 0.2 g to 100 g.

The dosage of compositions of the invention for use in food products and food supplements (i.e. comestible compositions) will be broadly in the 0.2-100 g/day range. In one embodiment, the daily dosage is 1-10 g/day, ideally about 3-8 g/day. In one embodiment, the daily dosage is 10-20 g/day. In one embodiment, the daily dosage is 20-30 g/day. In one embodiment, the daily dosage is 30-40 g/day. In one embodiment, the daily dosage is 10-100 g/day. In one embodiment, the daily dosage is about 5 g/day, ideally about 3-8 g/day. In one embodiment, the dosage is 2-1000 mg/day/kg body weight. In one embodiment, the dosage is 10-500 mg/day/kg body weight. In one embodiment, the dosage is 10-100 mg/day/kg body weight. In one embodiment, the dosage is 30-70 mg/day/kg body weight. The dosage of peptides of the invention for food supplements may be 0.00001 mg-0.01 mg per day or dose.

The food product may be a Food for Specific Medicinal Purposes (FSMP) which is defined as foods that are specifically formulated, processed and intended for the dietary management of diseases, disorders or medical conditions of individuals who are being treated under medical supervision. These foods are intended for the exclusive or partial feeding of people whose nutritional requirements cannot be met by normal foods. The dose may be 50-500 g per day depending on the age and condition of the patient. When administered as a food for special medicinal purpose, or medical food, the daily dosage may be 50-500 g per day.

The peptides and compositions of the invention may also be employed in the non-therapeutic treatment of inflammation. Examples of non-therapeutic treatment of inflammation include use to relieve normal, non-pathological, inflammation, for example inflammation in the muscles and joints following exercise.

The invention also provides topical composition comprising a peptide of the invention. It will be appreciated that the topical composition may comprise a plurality of peptides, fragments and/or variants. In one embodiment, the topical composition comprises substantially all the peptides. In one embodiment, the topical composition comprises substantially all the variants. The topical composition of the invention may be presented in a formulation selected from the group comprising creams, multiple emulsions, anhydrous compositions, aqueous dispersions, oils, milks, balsams, foams, lotions, gels, cream gels, hydro-alcoholic solutions, hydro-glycolic solutions, cosmetic, personal care product, hydrogels, liniments, sera, soaps, dusting powder, paste, semi solid formulations, liniments, serums, shampoo, conditioner, ointments, any rinse off formulation, talc, mousses, powders, sprays, aerosols, solutions, suspensions, emulsions, syrups, elixirs, polysaccharide films, patches, gel patches, bandages, an adhesive system, water-in-oil emulsions, oil-in-water emulsions, and silicone emulsions.

In an embodiment of the current invention, the emulsion contains a lipid or oil. The emulsion may be, but is not limited to, oil-in-water, water-in-oil, water-in-oil-in-water and oil-in-water-in-silcone emulsions. The emulsion may contain a humectant. The emulsion may contain an anti-foaming agent, such as silicone. The emulsion may have any suitable viscosity. Emulsions may further contain an emulsifier and/or an anti-foaming agent. Methods of preparing an emulsion are known to a person skilled in the art.

The topical composition of the invention may be incorporated into a medical device for administration. Such a device can include but is not limited to a fabric, patch, bandage, gauge, sock, tight, underwear, dressing, glove, mask, adhesive patches, non-adhesive patches, occlusive patches and microelectric patches or suitable adhesive system. In such an embodiment, the device is in direct contact with the keratinous layer such as the skin, thus releasing the peptides of the invention. It will be understood that the topical composition may be incorporated in any suitable form as detailed herein. For example, the topical composition or peptides of the invention can be incorporated into the device or be present on the surface of the device or can be in a cream, gel or wax formulation or any suitable formulation defined herein and incorporated into the device or on the surface of the device. The device may be adapted for adhesion or attachment to the skin.

In one embodiment the device is adapted to release a constant quantity of the composition or the peptides of the invention. It will be understood that the amount of the composition contained in the sustained release system will depend, for example, on where the composition is to be administered, the kinetics and duration of the release of the composition of the invention, as well as the nature of the condition, disorder and/or disease to be treated and/or cared for. The device may be such that the composition is released by biodegradation of the device, or by friction between the device and the body, due to bodily moisture, the skin's pH or body temperature.

In an embodiment of the invention the topical composition may further comprise at least one cosmetically or pharmaceutically acceptable excipient. Excipient may be used interchangeably with functional ingredient or additive. It will be understood that although the topical compositions of the current invention can be administered alone, they will generally be administered in admixture with a cosmetic or pharmaceutical excipient. Cosmetically or pharmaceutically acceptable excipient are well known in the art and any known excipient, may be used provided that it is suitable for topical administration and is dermatologically acceptable without undue toxicity, incompatibility and/or allergic reaction.

Preferably any excipient included is present in trace amounts. The amount of excipient included will depend on numerous factors, including the type of excipient used, the nature of the excipient, the component(s) of the topical composition, the amount of active or peptide in the topical composition and/or the intended use of the topical composition. The nature and amount of any excipient should not unacceptably alter the benefits of the peptides of this invention.

In an embodiment of the invention the excipient may be a suitable diluent, carrier, binder, lubricant, suspending agent, coating agent, preservative, stabilisers, dyes, vehicle, solubilising agent, base, emollient, emulsifying agent, fragrance, humectant, and/or surfactants.

Examples of suitable diluents include, but are not limited to, any diluent disclosed in disclosed in US2014120131 or US2004132667. Examples include ethanol, glycerol and water.

Examples of suitable carriers include, but are not limited to, lactose, starch, glucose, methyl cellulose, magnesium stearate, mannitol, sorbitol and any suitable carrier disclosed in US2014120131 or US2004132667.

Examples of suitable binders include, but are not limited to, starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol and any suitable binder disclosed in US2014120131 or US2004132667.

Examples of suitable lubricants include, but are not limited to, sodium oleate, sodium stearate, magnesium stearate, sodium benzoate, sodium acetate, and sodium chloride and any suitable lubricant disclosed in US2014120131 or US2004132667.

The carrier may be any suitable carried known in the art or disclosed in US2014120131 or US2004132667. In some embodiments, the carrier may include, but is not limited to, a liquid, such as water, oils or surfactants, including those of petroleum, animal, plant or synthetic origin, polymer, oil, such as peanut oil, mineral oil, castor oil, soybean oil, alcohol, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, or digitonin. It will be understood that the carrier will be dermatologically acceptable. Preferred carriers contain an emulsion such as oil-in-water, water-in-oil, water-in-oil-in-water and oil-in-water-in-silicone emulsions. Emulsions may further contain an emulsifier and/or an anti-foaming agent.

In an embodiment of the invention, the topical composition may further comprise one or more additional ingredients. The topical composition of the invention may be administered consecutively, simultaneously or sequentially with the one or more other additional agents. Such additional ingredients may be those of benefit to include in a topical composition, or of benefit depending on the intended use of the topical composition. The additional ingredient may be active or functional or both.

Examples of such additional ingredients include, but are not limited to, one or more of cleaning agents, conditioning agents, sunscreen, pigment, moisturiser, thickening agents, gelling agents, essential oil, astringents, pigments, anti-caking agent, anti-foaming agent, binders, additives, buffers, chelating agents, external analgesics, film formers or materials, bulking agents, polymers, opacifying agents, pH adjusters, propellants, reducing agents, sequestrants, skin bleaching and lightening agents, skin conditioning agents, aloe vera, healing agents, soothing agents, smoothing agents, pantothenic acid, treating agents, thickeners, vitamins. colourants, pharmaceuticals, antiseptic agents, anti-foaming agents, buffering agents, astringents, polymers, pH adjuster, deodorant or any other dermatologically acceptable carrier or surfactant.

It is to be understood that additional ingredients listed may provide more than one benefit. The classification given herein is for clarity and convenience only and not intended to limit the additional ingredient to that particular application or category listed.

Any additional ingredients should be suitable for application to the skin without undue toxicity, incompatibility and/or allergic reaction.

In some embodiments, the additional ingredient has glucose transport activity or aids glucose transport activity. In some embodiments, the additional ingredient has anti-inflammatory activity or aids anti-inflammatory activity. In some embodiments, the additional ingredient has anti-aging activity or aids anti-aging activity. In some embodiments, the additional ingredient is for keratinous layer health and/or development, skin health and/or development, and/or muscle health, recovery and/or development. The active agent may be a pharmacological enhancer. Such active agents are known and available on the market. In such cases, the topical composition of the invention may be administered consecutively, simultaneously or sequentially with the one or more other active agents.

In some embodiments, the additional ingredient may be farnesol ([2E, 6E], -3, 7, 11,-trimethyl-2, 6, 10, dodecatrien-1-ol), phytantriol (3, 7, 11, 15, tetramethylhexadecane-1, 2, 3, -triol), desquamation actives, enzymes, enzyme inhibitors, enzyme activators, botanical extracts and marine extracts, anti-acne actives, anti-wrinkle or anti atrophy actives, anti-oxidant/radical scavengers, chelators, flavonoids, anti-inflammatory agents, anti-cellulite agents, topical anaesthetics, tanning actives, skin lightening agents, skin healing agents, bisabolol, antimicrobial or antifungal active, sunscreen actives, particulate material, conditioning agents, structuring agents, thickening agent, The desquamation active may be any suitable agent that enhances the skin appearance or texture of the skin and is as disclosed in US2014120131 or US2004132667.

Examples of anti-acne actives are as disclosed in US2014120131 or US2004132667 and include, resorcinol, salicylic acid, erythromycin, zine, sulfur, benzoyl peroxides.

Examples of thickening agents are as disclosed in US2014120131 or US2004132667 and include carboxylic acid polymers, crosslinked polyacrylate polymers, polyacrylamide polymers, polysaccharides.

Examples of conditioning agents are as disclosed in US2014120131 or US2004132667 and include humectants, moisturiser or skin conditioner.

Examples of structuring agents are as disclosed in US2014120131 or US2004132667 and include any agent that provide rheological characteristics to the composition and contributes to the stability of the composition.

Any suitable antimicrobial or antifungal active may be used and examples are as disclosed in US2014120131 or US2004132667. Such actives are capable of destroying microbes, preventing growth or action of microbes.

Examples include but are not limited to β-lactam drugs, quinolone drugs, tetracycline, erythromycin, streptomycin sulfate, salicylic acid, benzoyl peroxide.

Examples of a particulate material include metallic oxide. Examples of anti-cellulite agents include xanthine agents. Examples of tanning actives includes 1, 3-dihydroxy-2-propanone and those disclosed in US2014120131 or US2004132667. Examples of topical anaesthetics include benzocaine, lidocaine and bupivacaine and those disclosed in US2014120131 or US2004132667.

Examples of skin lightening agents include any agent known in the art such as kojic acid, ascorbic acid and those disclosed in US2014120131 or US2004132667.

Examples of sunscreen actives include any suitable organic or inorganic sunscreen active. Examples include metallic oxides, 2-ethylhexyl-p-methoxycinnamate and those disclosed in US2014120131 or US2004132667.

Examples of skin healing agents includes panthenoic acid as disclosed in US2014120131 or US2004132667.

Examples of anti-inflammatory agents include any agent that enhances the skin appearance, tone or colour and include but are not limited to corticosteroids, hydrocortisone, non-steroidal agents such as ibuprofen and aspirin and those disclosed in US2014120131 or US2004132667.

Examples of flavonoids includes flavanones, methoxy flavonones, unsubstituted chalcone and mixtures thereof and those disclosed in US2014120131 or US2004132667.

Examples of enzymes include lipases, proteases, catalase, super oxide-dismutase, amylase, peroxidase, glucuronidase, ceramidases, hyaluronidases. Examples of enzyme inhibitors include trypsine inhibitors, Bowmann Birk inhibitors, chymotrypsin inhibitors, botanical extracts, flavonoids, quercetin chalcone and those disclosed in US2014120131 or US2004132667 and mixtures thereof. Examples of enzyme activators include coenzyme A, Q10 (ubiquinone), glycyrrhizin, berberine, chrysin and those disclosed in US2014120131 or US2004132667 and mixtures thereof Examples of anti-wrinkle or anti atrophy actives include sulfur containing D and L amino acids, particular, N-acyl derivatives such as N-acetyl-L-cysteine, hydroxyl acids, phytic acid, lipoic acid, lysophosphatidic acid, skin peel agents, vitamin $B_3$, retinoids and those disclosed in US2014120131 or US2004132667 and mixtures thereof.

The anti-oxidant/radical scavenger agent may be any agent that is useful for providing protection against UV radiation or other environmental agents which may cause skin damage such as those disclosed in US2014120131 or US2004132667. Examples of anti-oxidant/radical scavengers include ascorbic acid, its salts and derivatives (vitamin C), tocopherol its salts and derivatives (vitamin E), butylated hydroxyl benzoic acids and their salts, peroxides, gallic acids and alkyl esters, sorbic acid, lipoic acid, amines, lycine pidolate, arginine pilolate, nordihydroguaiaretic acid, bioflavonoids, curcumin, lysine, methionine, proline, superoxide dismutase, silymarin, tea extracts and mixtures thereof.

Examples of chelators include EDTA, NTA, hydoxamic acids, phytic acid, lactoferrin and those disclosed in US2014120131 or US2004132667 and mixtures thereof. A chelator means an agent capable of removing a metal ion by forming a complex so that the metal ion cannot participate in or catalyse chemical reactions. A chelator is useful for protection against UV radiation or other environmental agents that can cause skin damage.

It will be appreciated that a plurality of additional ingredients may be added. The amount of the additional ingredient may be from about 0.001% to about 50% weight of the composition, preferably, about 0.01% to about 20%, preferably about 0.1% to about 10%, about 0.5% to about 10%, about 1% to about 5%, preferably 2% weight of the composition. The amount of additional ingredient included will depend on numerous factors, including the type of additional ingredient used, the nature of the additional ingredient, the component(s) of the topical composition, the amount of active or peptide in the topical composition and/or the intended use of the topical composition. The nature and amount of any additional ingredient should not unacceptably alter the benefits of the peptides of this invention.

The topical composition may be alcohol free.

In some embodiments of the invention, the composition further comprises one or more additional active agents, in addition to the peptide of the invention (also known as the active of the composition). In addition, or alternatively, the composition may be administered with one or more other additional active agents. Typical said additional active agent is present in trace amounts only. In some embodiments, there may be no additional active agent present in the composition. The amount of additional active agent included will depend on numerous factors, including the type of additional active agent used, the nature of the additional active agent, the component(s) of the topical composition, the amount of active or peptide in the topical composition and/or the intended use of the topical composition. The nature and amount of any additional active agent should not unacceptably alter the benefits of the peptides of this invention.

It is to be understood that an ingredient that is considered to be an "active" ingredient in one product may be a "functional" or "excipient" ingredient in another and vice versa. It will also be appreciated that some ingredients play a dual role as both an active ingredient and as a functional or excipient ingredient.

Examples of the additional active agents include glucose transport promoting drugs, skin supplement, agent for treatment and/or care of the skin, anti-inflammatory agent, an anti-aging agent, a cellular growth promoting agent and pharmacological enhancers. Such agents are well known in the art and it will be appreciated that any suitable additional active agent may be used. Additional active agents for treatment and/or care of the skin may include collagen synthesis agents, retinoids, exfoliating agents, anti-cellulite agents, elastase inhibiting agents, melanin synthesis stimulating or inhibiting agents, self-tanning agents, antiaging agents, antimicrobial agents, antifungal agents, fungistatic agents, bactericidal agents, and healing agents. Active agents also include anti-inflammatory agents.

Any additional active agent should be suitable for application to the skin without undue toxicity, incompatibility and/or allergic reaction.

It will be understood that the classification given herein is for clarity and convenience only and not intended to limit the additional ingredient, excipient, or active to that particular application or category listed.

In a particularly preferred embodiment, the methods and uses of the invention involve administration of a peptide or composition of the invention in combination with one or more other active agents, for example, existing growth promoting drugs or pharmacological enhancers available on the market. In such cases, the compounds of the invention may be administered consecutively, simultaneously or sequentially with the one or more other active agents.

The effect of the current invention is accomplished by topical application or administration of the topical composition of the invention described herein to a person, animal or a patient in need of treatment or care. Topical delivery preferably means delivery to a keratinous layer such as the skin, hair and/or nails, but can also mean delivery to a body lumen lined with epithelial cells, for example the lungs or airways, the gastrointestinal tract, the buccal cavity. The effect may be confined to the surface of the skin or may be within the skin or a combination of both.

The topical composition of the invention is administered in a cosmetically or pharmaceutically effective amount. In other words, in an amount that is non-toxic but sufficient amount to provide the desired effect. It will be appreciated that a person skilled in the art would be capable of determining an appropriate dose of the topical compositions of the invention to administer without undue experimentation. Alternatively, a physician will determine the actual dose that is most suitable for a patient depending on the particular condition, disease or disorder to be treated or cared for and the age, body weight and/or health of the person. It will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can, of course, be individual instances where higher or lower dosage ranges are merited, and such are within the scope of this invention. For example, the composition may be administered at a dose of from 0.01 to 50 mg/kg body weight, such as from 0.1 to 30 mg/kg, more preferably from 0.1 to 20 mg/kg body weight, more preferably from 0.1 to 10 mg/kg body weight, preferably 0.1 to 5 mg/kg body weight. In an exemplary embodiment, one or more doses of 10 to 300 mg/day or more preferably, 10 to 150 mg/day, will be administered to the patient. The amount and the frequency is as best suited to the purpose. The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

In preferred embodiments, repeated use of the topical composition is provided.

The topical composition may be applied by, but not limited to, rubbing, or massaging into the keratinous tissue, skin or area of the body to be treated or cared for. In some embodiments, the composition is left on or not removed from the area of the body. In other embodiments, the composition is removed after a period of time, such as, but not limited to, from about 2 minutes to 60 minutes, from about 5 minutes to about 30 minutes, preferably from about 10 minutes to about 20 minutes. The composition may be removed immediately after application. In some embodiments of the current invention, the composition of the invention may be applied to an area to be treated by means to achieve a greater penetration of the composition and/or peptide of the invention, such as, but not limited to, iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof.

The peptides of the invention are used in the topical cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

In some embodiments of the current invention, the composition may be delivered via any one of liposomes, mixed liposomes, oleosomes, niosomes, ethosomes, millicapsules, capsules, macrocapsules, nanocapsules, nanostructured lipid carriers, sponges, cyclodextrins, vesicles, micelles, mixed micelles of surfactants, surfactant-phospholipid mixed micelles, milli spheres, spheres, lipospheres, particles, nanospheres, nanoparticles, milliparticles, solid nanopartciles as well as microemulsions including water-in-oil microemulsions with an internal structure of reverse micelle and nanoemulsions microspheres, microparticles.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

These delivery systems may be adapted to achieve a greater penetration of the compound and/or peptides of the invention. This may improve pharmacokinetic and pharmacodynamics properties. The delivery system may be a sustained release system wherein the compound or peptide of the invention is gradually released during a period of time and preferably with a constant release rate over a period of time. The delivery systems are prepared by methods known in the art. The amount of peptide contained in the sustained release system will depend on where the composition is to be delivered and the duration of the release as well as the type of the condition, disease and/or disorder to be treated or cared for.

The topical composition of the invention may be for human or animal usage in human and veterinary medicine.

The topical composition of the invention may be used for pharmaceutical, personal care and/or cosmetic uses.

The composition can be used to treat or care for any disease, disorder or condition of the skin, including but not limited to, psoriasis, dermatitis, allergic dermatitis, eczema, spongiosis, edema, skin cancer, ulcers, acne, scars, cellulitis, elastosis, keratosis, rosacea, varicose veins, inflammatory disorders.

The topical composition may be used to for treating or caring for visible signs of aging including but not limited to wrinkles, stretch marks and dark circles, dryness, fine lines, age spots, red blotches, sagging skin, and conditions caused by sun exposure including sunburn, stress, pollution and/ diet. The topical composition may also be used for delaying, slowing or inhibiting the skins or the onset of aging. The composition may be administered by a medical device, such as a plaster or a patch as described herein.

The topical composition may be used to treat or care for a wound in a mammal. In another embodiment, the topical composition is for use in the treatment or prevention of a disease or condition characterised by damaged epithelial cells or tissue, and/or damaged dermal or epithelial cells or tissue. The disease may be but is not limited to cancer and trauma.

The topical composition may be used to treat or care for any muscle condition, to improve, muscle status in a mammal, to promote recovery of muscle, typically following exercise, to maintain or restore muscle health (for example lean tissue mass) in a mammal, to enhance physical performance, in treatment or prevention of a disease or condition characterised by lethargy or low energy levels.

The topical composition may be used to promote growth of a tissue, promote growth of epithelial tissue, promote growth of skin, promote growth of an organ, promote growth of an organism. The skin can have a normal pathology and/or an abnormal pathology.

The topical composition may also be used to treat or care for any inflammatory disorder.

A further aspect of the invention relates to a pharmaceutical composition comprising a peptide of the invention or a composition of peptides of the invention, admixed with one or more pharmaceutically acceptable diluents, excipients or carriers. Even though the peptides and compositions of the present invention can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, $2^{nd}$ Edition, (1994), Edited by A Wade and P J Weller. In particular, formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The peptide or composition of the invention may be adapted for topical, oral, rectal, parenteral, intramuscular, intraperitoneal, intra-arterial, intrabronchial, subcutaneous, intradermal, intravenous, nasal, vaginal, buccal or sublingual routes of administration. For oral administration, particular use is made of compressed tablets, pills, tablets, gellules, drops, and capsules. Preferably, these compositions contain from 1 to 250 mg and more preferably from 10-100 mg, of active ingredient per dose. Other forms of administration comprise solutions or emulsions which may be injected intravenously, intra-arterial, subcutaneously, intradermally, intraperitoneally or intramuscularly, and which are prepared from sterile or sterilisable solutions. The pharmaceutical compositions of the present invention may also be in form of suppositories, vaginal rings, pessaries, suspensions, emulsions, lotions, ointments, creams, gels, sprays, solutions or dusting powders. The composition of the invention may be formulated for topical delivery. Topical delivery generally means delivery to the skin, but can also mean delivery to a body lumen lined with epithelial cells, for example the lungs or airways, the gastrointestinal tract, the buccal cavity. In particular, formulations for topical delivery are described in Topical drug delivery formulations edited by David Osborne and Antonio Aman, Taylor & Francis, the complete contents of which are incorporated herein by reference. Compositions or formulations for delivery to the airways are described in O'Riordan et al (Respir Care, 2002, November 47), EP2050437, WO2005023290, US2010098660, and US20070053845. Composition and formulations for delivering active agents to the iluem, especially the proximal iluem, include microparticles and microencapsulates where the active agent is encapsulated within a protecting matrix formed of polymer or dairy protein that is acid resistant but prone to dissolution in the more alkaline environment of the ileum. Examples of such delivery systems are described in EP1072600.2 and EP13171757.1. An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. Depending upon the need, the agent may be administered at a dose of from 0.01 to 30 mg/kg body weight, such as from 0.1 to 10 mg/kg, more preferably from 0.1 to 1 mg/kg body weight. In an exemplary embodiment, one or more doses of 10 to 300 mg/day or more preferably, 10 to 150 mg/day, will be administered to the patient for the treatment of an inflammatory disorder.

In a particularly preferred embodiment, the methods and uses of the invention involve administration of a peptide or composition of the invention in combination with one or more other active agents, for example, existing anti-inflammatory drugs or pharmacological enhancers available on the market. In such cases, the compounds of the invention may be administered consecutively, simultaneously or sequentially with the one or more other active agents.

In one embodiment of the invention, the peptide of the invention may be administered in the form of a conjugate comprising the peptide, and may optionally include a linker, and a partner molecule, for example a protein such as an antibody molecule intended to increase the half-life of the conjugate in-vivo. In one embodiment, the peptide may be modified to substitute one or more amino acids with amino acids employed to attach partner molecules. For example, an amino acid may be substituted with a lysine residue for the purpose of conjugating a partner molecule such as a PEG molecule.

Definitions

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

The term "mammal" should be understood to mean a higher mammal, especially a human. However, the term also includes non-mammalian animals such as fish.

The term "peptide" used herein refers to a polymer composed of up to 50 amino acid monomers typically via peptide bond linkage. The peptide may be 3-50 amino acids in length. The peptide may be 4 to 50 amino acids in length. The peptide may be 5-50 amino acids in length. The peptide may be 7 to 50 amino acids in length. Peptides (including fragments and variants thereof) of and for use in the invention may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984). When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids.

"Modified peptide": In an embodiment of the invention the peptide is a modified peptide. The term modified peptide is used interchangeably with the term derivative of the peptide. The modified peptide includes a peptide which has been substituted with one or more groups as defined herein. The modification may be any modified that provides the peptides and or the composition of the invention with an increased ability to penetrate a cell. The modification may be any modification that increases the half-life of the composition or peptides of the invention. In one embodiment, the group is a protecting group. The protecting group may be an N-terminal protecting group, a C-terminal protecting group or a side-chain protecting group. The peptide may have one or more of these protecting groups. The person skilled in the art is aware of suitable techniques to react amino acids with these protecting groups. These groups can be added by preparation methods known in the art, for example the methods as outlined in paragraphs [0104] to [0107] of US2014120141. The groups may remain on the peptide or may be removed. The protecting group may be added during synthesis. In an embodiment of the invention the peptides may be substituted with a group selected from one or more straight chain or branched chain, long or short chain, saturated, or unsaturated, substituted with a hydroxyl, amino, amino acyl, sulfate or sulphide group or unsubstituted having from 1 to 29 carbon atoms. N-acyl derivatives include acyl groups derived from acetic acid, capric acid, lauric acid, myristic acid, octanoic acid, palmitic acid, stearic acid, behenic acid, linoleic acid, linolenic acid, lipoic acid, oleic acid, isosteric acid, elaidoic acid, 2-ethylhexaneic acid, coconut oil fatty acid, tallow fatty acid, hardened tallow fatty acid, palm kernel fatty acid, lanolin fatty acid or similar acids. These may be substituted or unsubstituted. When substituted they are preferably substituted with hydroxyl, or sulphur containing groups such as but not limited to $SO_3H$, SH, or S—S. In an embodiment of the current invention, the peptide is $R_1$—X—$R_2$. $R_1$ and/or $R_2$ groups respectively bound to the amino-terminal (N-terminal) and carboxyl-terminal (C-terminal) of the peptide sequence. In one embodiment, the peptide is $R_1$—X. Alternatively, the peptide is X—$R_2$. Preferably, $R_1$ is H, $C_{1-4}$ alkyl, acetyl, benzoyl or trifluoroacetyl; X is the peptide of the invention; $R_2$ is OH or $NH_2$. In an embodiment, $R_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, Tert-butyloxycarbonyl, 9-fluorenylmethyloxycarbonyl (Fmoc) and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; $R_2$ is selected from the group formed by —$NR_3R_4$, —$OR_3$ and —$SR_3$, wherein $R_3$ and $R_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids. In accordance with another preferred embodiment, $R_2$ is —$NR_3R_4$, —$OR_3$ or —$SR_3$ wherein $R_3$ and $R_4$ are independently selected from the group formed by H, substituted or unsubstituted $C_1$-$C_{24}$ alkyl, substituted or unsubstituted $C_2$-$C_{24}$ alkenyl, Tert-butyloxycarbonyl, 9-fluorenylmethyloxycarbonyl (Fmoc), substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl of 3-10 members, substituted or unsubstituted heteroarylalkyl with a ring of 3 to 10 members and an alkyl chain of 1 to 6 carbon atoms. More preferably $R_3$ and $R_4$ are selected from the group formed by H, methyl, ethyl, hexyl, dodecyl, or hexadecyl. Even more preferably $R_3$ is H and $R_4$ is selected from the group formed by H, methyl, ethyl, hexyl, dodecyl, or hexadecyl. In accordance with an even more preferred embodiment, $R_2$ is selected from —OH and —$NH_2$. In accordance with another embodiment of this invention $R_1$ is selected from the group formed by H, acetyl, lauroyl, myristoyl or palmitoyl, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. In a preferred embodiment, the acyl group is bound to the N-terminal end of at least one amino acid of the peptide. In an embodiment of the invention, the peptide is modified to comprise a side chain protecting group. The side chain protecting group may be one or more of the group comprising benzyl or benzyl based groups, t-butyl-based groups, benzyloxy-carbonyl (Z) group, and allyloxycarbonyl (alloc) protecting group. The side chain protecting group may be derived from an achiral amino acid such as achiral glycine. The use of an achiral amino acid helps to stabilise the resultant peptide and also facilitate the facile synthesis route of the present invention. Preferably, the peptide further comprises a modified C-terminus, preferably an amidated C-terminus. The achiral residue may be alpha-aminoisobutyric acid (methylalaine). It will be appreciated that the specific side chain protecting groups used will depend on the sequence of the peptide and the type of N-terminal protecting group used.

"Conjugate": In one embodiment of the invention the peptide is conjugated, linked or fused to a binding partner, for example one or more polyethylene glycol polymers or other compounds, such as molecular weight increasing compounds or lipophilic groups. The molecular weight increasing compound is any compound that will increase the molecular weight, typically by 10% to 90%, or 20% to 50% of the resulting conjugate and may have a molecular weight of between 200 and 20, 000, preferably between 500 and 10, 000. The molecular weight increasing compound may be PEG, any water-soluble (amphiphilic or hydrophilic) polymer moiety, homo or co-polymers of PEG, a monomethyl-substituted polymer of PEG (mPEG) and polyoxyethylene glycerol (POG), polyamino acids such as poly-lysine, poly-glutamic acid, poly-aspartic acid, particular those of L conformation, pharmacologically inactive proteins such as albumin, gelatin, a fatty acid, olysaccharide, a lipid amino acid and dextran. The polymer moiety may be straight chained or branched and it may have a molecular weight of 500 to 40000 Da, 5000 to 10000 Da, 10000 to 5000, Da. The compound (binding partner) may be any suitable cell penetrating compound, such as that peptide, penetratin, pep-1. The compound (binding partner) may be an antibody molecule. The compound (binding partner) may be a lipophilic moiety or a polymeric moiety. The lipophilic substituent and polymeric substituents are known in the art. The lipophilic substituent includes an acyl group, a sulphonyl group, an N atom, an O atom or an S atom which forms part of the ester, sulphonyl ester, thioester, amide or sulphonamide. The lipophilic moiety may include a hydrocarbon chain having 4 to 30 C atoms, preferably between 8 and 12 C atoms. It may be linear or branched, saturated or unsaturated. The hydrocarbon chain may be further substituted. It may be cycloalkane or heterocycloalkane. The peptide may be modified at the N-terminal, C-terminal or both. The polymer or compound (binding partner) is preferably linked to an amino, carboxyl or thio group and may be linked by N-termini or C-termini of side chains of any amino acid residue. The polymer or compound (binding partner) may be conjugated to the side chain of any suitable residue. The polymer or compound (binding partner) may be conjugated via a spacer. The spacer may be a natural or unnatural amino acid, succinic acid, lysyl, glutamyl, asparagyl, glycyl, beta-alanyl, gamma-amino butanoyl. The polymer or compound (binding partner) may be conjugated via an ester, a sulphonyl ester, a thioester, an amide, a carbamate, a urea, a sulphonamide. A person skilled in the art is aware of suitable means to prepare the described conjugate.

"Fragment" means a segment of a protein, typically selected from SEQ ID Nos: 1 to 16 and 353-355, and particularly from a region of those proteins selected SEQ ID NOS: 17 to 70. In one embodiment, the fragment is typically 3 to 37 contiguous amino acids in length. In one embodiment, the fragment is typically 5 to 37 contiguous amino acids in length. In one embodiment, the fragment is typically 5 to 37 contiguous amino acids in length. The fragment generally having a charge of between −9 and +3; typically a c-terminal amino acid that typically is not cysteine (C) or methionine (M); and typically an n-terminal amino acid that typcially is not cysteine (C), histidine (H), proline (P) or threonine (T). The charge of a peptide, fragment or region is determined using the method of Cameselle, J. C., Ribeiro, J. M., and Sillero, A. (1986). Derivation and use of a formula to calculate the net charge of acid-base compounds. Its application to amino acids, proteins and nucleotides. Biochem. Educ. 14, 131-136.

The term "natural" as applied to a peptide means a peptide that includes (a) a fragment of a plant protein, typically rice or pea protein, or variants of pea protein including lentil, sweet pea, or chick pea or variants of rice protein including oat, grass, corn, wild rice and bananas, or (b) a variant of the fragment of a plant protein, for example a fragment of a homolog of the plant protein. The peptides or fragments of the invention may be isolated from plant proteins or made synthetically.

"C-terminal domain" as applied to a fragment means the first three amino acids at the c-terminus of the fragment.

"N-terminal domain" as applied to a fragment means the last three amino acids at the n-terminus of the fragment.

"Bioactive" as applied to a peptide or fragment means having a health promoting effect when administered a mammal, for example one or more of glucose transport promoting, anti-bacterial, anti-inflammatory, or cellular growth or proliferation promoting. In one embodiment, the term "bioactive" means anti-inflammatory.

"Glucose transport promoting" or "glucose transport promoting activity" as applied to a peptide or variant or fragment means a peptide, variant or fragment that is capable of increasing GLUT4 translocation into skeletal muscle compared with an untreated control when employed at a concentration of 2 µM in the following in-vitro assay. L6-GLUT4myc cells were grown in 10% FBS and 2 µg/ml blasticidin. Cells were grown for 48-72 hours before being seeded in 24-well plates at 15,000 cells per well in 2% FBS and allowed to differentiate for 6 to 8 days prior to experimentation. L6-GLUT4myc cells were serum-starved for three hours prior to incubation with 100 nM of insulin for 30 mins, or 200, 20, 2.0 and 0.2 µM of SP, and 2, 1, 0.5 and 0.25 mg/ml of peptide composition for 3 hours respectively. A 3 hour incubation period was selected based on previous findings identifying that incubation with branch chain amino acid containing di-peptides for 3 hours increases glucose uptake in L6 myotubes 1. Treatments were staggered in order to determine GLUT4myc translocation at the same time point. The quantity of myc-tagged GLUT4 at the cell surface was measured by antibody-coupled colorimetric assay. Briefly, after incubation with either insulin for 30 mins or synthetic peptide or peptide composition for 3 hours respectively, L6-GLUT4myc cells were fixed via incubation with 3% paraformaldehyde (PFA). A 0.1 M glycine solution was then added to quench PFA and cells were blocked with 5% goat serum. The myotube monolayer was exposed to anti-myc antibody and then incubated with peroxidase conjugated donkey anti-mouse IgG. 1 mL of o-phenylenediamine dihydrochloride (OPD) reagent was added to each well and this reaction was stopped by adding 250 µl/well of 3 M HCL. To determine GLUT4 translocation to cell surface, a measured aliquot of each condition was determined spectrophotometrically on a plate reader using absorbance at 492 nm. Preferably the peptide or fragment is capable of increasing GLUT4 translocation compared with an untreated control by at least 50% (i.e a relative unit increase in GLUT4 translocation of 1% to 1.5%).

"Antibacterial" or "antibacterial activity" as applied to a peptide or fragment means a peptide or fragment that is capable of visibly inhibiting the growth of a bacteria in the following agar-plate based growth inhibition assay: Peptide stock=5 mg/mL dissolved in DMSO. Bacterial inoculums were adjusted to McFarland 0.5 standard and MHA plates swabbed. Blank disks were placed in the plates and 10 µL of each compound (at 64 µg/mL—maximum concentration tested) added. Plates were incubated at 37° C. for 16-18 hours. Appropriate controls (DMSO; Mueller-Hinton media alone; and two antibiotic discs—ciprofloxacin and tetracycline) were also performed.

"Anti-inflammatory" as applied to a peptide or fragment means a peptide or fragment that is capable of significantly reducing the secretion of TNFα by LPS-stimulated J774.2 macrophages (compared with untreated LPS-stimulated J774.2 macrophages) when the macrophages are treated with 100 µM of the peptide or fragment. J774.2 macrophages were treated with 100 µM of synthetic peptide for 24 hours and then stimulated with (A) LPS (10 ng/ml) for five hours or (B) LPS (10 ng/ml) for 5 hours followed by ATP (5 mM) for one hour. Supernatant was collected and levels of TNFα were determined by ELISA.

"Cellular growth promoting" or "cellular growth or proliferation promoting" as applied to a peptide or fragment means a peptide or fragment that is capable of increasing elastin production or cellular proliferation of human skin treated with a 20 µM solution of peptide or fragment in the following assay. Skin explants were prepared from abdominal plastic surgery.

Some explants were delipidated with alcohol to obtain a dehydrated skin. These explants were maintained in maintenance medium supplied by the provider Biopredic International for 5 days. Test items are applied twice per day with 5 µL, per explant. At the end of the test, viabilities controls are realized with the MTT on two explants, the third explant is fixed in the formaldehyde 4% for histology and cell staining. For each time of analysis (D1 and D5), histologies on delipidated explants, treated explants with test items, the DMSO 0.3% control and water control, are performed. After receipt in the laboratory, each skin explant in the maintenance medium is delipidated with 5 µL, alcohol during 3 hours. After 3 hours, all skin explants are treated two per day with test items, and they are incubated at 37° C.+/−2° C., 5% CO2 for 1 day or 5 days. Integrity of the system is realized at day 1 and day 5 with a viability control with MTT. Histology is realized by the laboratory Gredeco and the immunostaining to elastin and Ki67 are realized by the same laboratory. Immunostaining to filaggrin is realized by the laboratory Intertek. The detection of elastin (rabbit monoclonal antibody, clone P15502, LSBio) is performed using an immunoperoxidase technique two layers (ABC kit, Vector Laboratories) and revealed by AEC (3-amino-9-ethyl-carbazole). The immunohistochemical staining intensity in the elastic fibers is evaluated using a semi-quantitative histological score. Epithelial proliferation was analyzed by immunohistochemistry using anti-Ki67 antibody. Immunodetection was performed using an indirect immunoperoxidase technique three layers, amplified (DAKO kit) and revealed by AEC (3-Amino-9-ethylcarbazole). Counting the number of labeled cells (keratinocytes of the basal layer of the epidermis) is performed and provides the total number of basal cells to calculate the % of labeled cells. The specific staining of filaggrin is performed with an immunoperoxidase staining (ABC kit, Fisher). The intensity of immunohistochemical marker in the epidermis is evaluated relative to the negative control of the solvent (Water or DMSO 0.3%).

"Enriched in peptides having a molecular weight of less than 10 KD" as applied to a composition of the invention means that the dry weight % of peptides in the composition having a molecular weight of less than 10 KD is greater than the dry weight % of polypeptide/protein in the composition having a molecular weight of 10 KD or greater.

"Homolog" of a reference protein should be understood to mean a protein from a different species of plant having at least 60% sequence homology with the reference protein. Thus, for example, homologs of pea protein P13918 include:

>gi|137584|sp|P08438.1|VCL_VICFA RecName: Full=Vicilin; Flags: Precursor [*Vicia faba*]
>gi|22057|emb|CAA68559.1| vicilin [*Vicia faba* var. *minor*] >gi|383931031|gb|AFH56916.1| vicilin [*Vicia faba*]
>gi|502105533|ref|XP_004492829.1| PREDICTED: vicilin-like isoform X1 [*Cicer arietinum*] ChickPea
>gi|29539109|emb|CAD87730.1| allergen Len c 1.0101 [*Lens culinaris*] Lentil A "variant" of an anti-inflammatory fragment shall be taken to mean a fragment having an amino acid sequence that is substantially identical to the anti-inflammatory fragment, and which has anti-inflammatory activity as defined above. Thus, for example, the term should be taken to include fragments that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Generally, the variant will have at least 70% amino acid sequence homology, preferably at least 80% sequence homology, more preferably at least 90% sequence homology, and ideally at least 95%, 96%, 97%, 98% or 99% sequence homology with the parent anti-inflammatory fragment.

In this specification, the term "sequence identity" should be understand to comprise both sequence identity and similarity, i.e. a variant (or homolog) that shares 70% sequence identity with a reference sequence is one in which any 70% of aligned residues of the variant (or homolog) are identical to or conservative substitutions of the corresponding residues in the reference sequence across the entire length of the sequence. Sequence identity is the amount of characters which match exactly between two different sequences. Hereby, gaps are not counted and the measurement is relational to the shorter of the two sequences. In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence. This alignment and the percent homology or sequence identity can be determined using software programs known in the art, for example, one alignment program is BLAST, using default parameters. Details of these programs can be found at the following Internet address: <www.ncbi.nlm.nih.gov/blast/Blast.cgi>

Variants of SEQ ID NO: 109 (anti-inflammatory peptide (I_37)

Variants of SEQ ID NO: 109 (RGPQQYAEWQINEK) including variants having 1, 2 or 3 conservative amino acid substitutions, 1, 2 to 3 non-conservative amino acid substitutions, 1-2 amino acid additions, 1, 2 or 3 amino acid deletions, are provided below:

One conservative amino acid substitution:

```
RGPQQYAEWQINER,    (SEQ ID NO: 268);
RGPQQYAEWQINDK,    (SEQ ID NO: 269)
RGPQQFAEWQINEK,    (SEQ ID NO: 270);
KGPQQYAEWQINEK,    (SEQ ID NO: 271);
RGPEQYAEWQINEK,    (SEQ ID NO: 272);
RGPQEYAEWQINEK,    (SEQ ID NO: 273);
RGPQQYADWQINEK,    (SEQ ID NO: 274);
RGPQQYAEYQINEK,    (SEQ ID NO: 275).
```

Two conservative amino acid substitutions:

```
KGPEQYAEWQINEK,    (SEQ ID NO: 276);
KGPQEYAEWQINEK,    (SEQ ID NO: 277);
KGPQQFAEWQINEK,    (SEQ ID NO: 278);
RGPEQFAEWQINEK,    (SEQ ID NO: 279);
KGPQQYAEWQINER,    (SEQ ID NO: 280);
RGPQQYAEWQINDR,    (SEQ ID NO: 281);
RGPQQYADWQINDK,    (SEQ ID NO: 282);
RGPQQFAEWQINER,    (SEQ ID NO: 283).
```

Three conservative amino acid substitutions:

```
RGPQQYAEWQVNEK,    (SEQ ID NO: 284);
RGPQQFAEWQINEK,    (SEQ ID NO: 285);
KGPQQFAEWQINER,    (SEQ ID NO: 286);
KGPQQFAEWQVNEK,    (SEQ ID NO: 287);
KGPQQFAEWQVNDK,    (SEQ ID NO: 288);
RGPQQYADWQINDR,    (SEQ ID NO: 289);
KGPQQYADWQINDK,    (SEQ ID NO: 290);
RGPQQFADYQINEK,    (SEQ ID NO: 291).
```

One non-conservative amino acid substitution

```
RGPQQYARWQINEK,    (SEQ ID NO: 292);
RGPQQYAEWQINEE,    (SEQ ID NO: 293);
HGPQQYAEWQINEK,    (SEQ ID NO: 294);
RGPYQYAEWQINEK,    (SEQ ID NO: 295);
RGPQQYMEWQINEK,   (SEQ ID NO: 296);
RGPQQYAEWCINEK,    (SEQ ID NO: 297);
RGPQPYAEWQINEK,    (SEQ ID NO: 292).
```

Two non-conservative amino acid substitution

```
RGGQQYAEWQINED,    (SEQ ID NO: 299);
RGPQQYARWKINEK,    (SEQ ID NO: 300);
RGGQQYAETQINEK,    (SEQ ID NO: 301);
RGPLQYAEWQNNEK,    (SEQ ID NO: 302);
EGPQQYAEWQINED,    (SEQ ID NO: 303);
RGPQQYAEWQINLL,    (SEQ ID NO: 304);
RGPQQGGEWQINEK,    (SEQ ID NO: 305).
```

Three non-conservative amino acid substitution

```
RGPQQYAEWQIGGG,    (SEQ ID NO: 306);
RGPQQKYEWQINEK,    (SEQ ID NO: 307);
RGPQAQYEWQINEK,    (SEQ ID NO: 308);
RPHQQYAEWQINEK,    (SEQ ID NO: 309);
RGPQHHHEWQINEK,    (SEQ ID NO: 310);
RGPPQYAPPQINEK,    (SEQ ID NO: 311);
RGPQCYYEWCINEK,    (SEQ ID NO: 312);
RGPTQYAEGQINEG,    (SEQ ID NO: 313).
```

One or two amino acid additions

```
RGPQQYAEWQINEKG,    (SEQ ID NO: 314);
RGPQQYAEWQINEKY,    (SEQ ID NO: 315);
RGPQQYAFTEWQINEK,  (SEQ ID NO: 316);
RGPQSQYAEWQINEKPM, (SEQ ID NO: 317);
RGPQQYAEWQINEKKK,  (SEQ ID NO: 318);
RRRRGPQQYAEWQINEK  (SEQ ID NO: 291).
```

The term "variant" typically encompasses fragments of the peptides of the invention. "Fragment of a peptide of the invention" or "peptide fragment" means a fragment of one of the peptides of the invention having at least 3, 4, 5, 6, 7, 8, 9, 10, 11, 12, 13, 14, 15, 16, 17, 18, 19, 20, 21 or 22 amino acids and that typically has a bioactivity, for example anti-inflammatory activity, cellular growth or proliferation promotion activity, glucose transport promoting activity, or anti-bacterial activity. In one embodiment, the fragment consists of at least 30%, 40%, 50%, 60%, 70%, 80%, or 90% of the reference sequence. Examples of fragments of the invention are provided in SEQ ID NOS 320-330.

```
RGPQQYAEWQINE,   (SEQ ID NO: 320);
RGPQQYAEWQIN,    (SEQ ID NO: 321);
RGPQQYAEWQI,     (SEQ ID NO: 322);
GPQQYAEWQINEK,   (SEQ ID NO: 323);
PQQYAEWQINEK,    (SEQ ID NO: 324);
QQYAEWQINEK,     (SEQ ID NO: 325);
QQYAEWQI,        (SEQ ID NO: 326);
PQQYAEWQINE,     (SEQ ID NO: 327);
PQQYAEWQIN,      (SEQ ID NO: 328);
RGPQQYA,         (SEQ ID NO: 329);
EWQINEK          (SEQ ID NO: 330.)
```

"Inflammatory disorder" means an immune-mediated inflammatory condition that affects humans and is generally characterised by dysregulated expression of one or more cytokines.

Examples of inflammatory disorders include skin inflammatory disorders, inflammatory disorders of the joints, inflammatory disorders of the cardiovascular system, certain autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves disease, Guillain-Barre disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation and bronchitis.

In this specification, the term "Metabolic disorder" should be understood to include pre-diabetes, diabetes; Type-1 diabetes; Type-2 diabetes; metabolic syndrome; obesity; diabetic dyslipidemia; hyperlipidemia; hypertension; hypertriglyceridemia; hyperfattyacidemia; hypercholerterolemia; hyperinsulinemia, and MODY.

"Man-made" as applied to comestible products should be understood to mean made by a human being and not existing in nature.

"Maintaining or restoring gut health": means reducing and/or regulating the pro-inflammatory response in the gut and more specifically the epithelial cells. The healthy microbiome offers some protection against pathogenic viruses and bacteria, and their presence is needed to guide the development of our immune system. It has been shown that these bacteria can react to human signals of stress, sickness, or age which can be manifested by inflammation and as a consequence switch on their virulence genes and cause or contribute to disease. Having the ability to reduce and maintain at healthy levels the inflammatory response can help maintain the healthy bacteria. Digestive problems, which comprise the number one health problem in North America, appear to be occurring with more frequency in recent years. One way to maintain digestive health is to maintain proper inflammation and intestinal flora.

"Maintaining or restoring muscle health" means helping retain or restore mammalian muscle health resulting from damage incurred during exercise. By lowering inflammation the peptides promote recovery from injuries during exercise, and relieve muscle soreness/pain and injury connected with exercise. They can also be used to decrease and prevent muscle cramping, and to allow a faster recovery from muscle cramping. Cramping can result from physical stress, mental stress, and or Repetitive Strain Injury stress. By lowering inflammation the peptides help reduce Myopathy of the muscle, and help prevent Sarcopenia in mammals, promote recovery from injuries during exercise, and relieve muscle soreness/pain and injury connected with exercise. They can also be used to decrease and prevent muscle cramping, and to allow a faster recovery from muscle cramping. Cramping can result from physical stress, mental stress, and or Repetitive Strain Injury stress. By lowering inflammation the peptides help reduce Myopathy of the muscle, and help prevent Sarcopenia in mammals.

In this specification, the term "composition" should be understood to mean something made by the hand of man, and not excludes naturally occurring compositions. Exemplary compositions include foods, beverages, nutritional supplements, personal care compositions, and pharmaceutical compositions.

In this specification, the term "substantially all" as applied to a list of peptides or fragments should be understood to mean at least 60%, 70%, 80%, 90% or 95% of the peptides or fragments.

In this specification, the term "personal care composition" should be understood to mean a composition formulated for use by humans in cleaning or treating the human body, particularly the skin, teeth, nails, feet and hair. Examples include shampoo, conditioner, skin creams and lotions, powders, dentrifice, shower gel or creams, body lotion, deodorant, and anti-perspirant.

In this specification, the term "nutritional supplement" should be understood to mean a product formulated for ingestion by a mammal and intended to confer a health benefit on the recipient. The supplement can take any form, for example a solid, liquid, or powder. Examples of supplements include powders, tablets, capsules, and drinks.

BRIEF DESCRIPTION OF THE FIGURES

FIG. 1 is SEQ ID NO: 339, FIG. 2 is SEQ ID NO: 352, FIG. 3 is SEQ ID NO: 341, FIG. 4 is SEQ ID NO: 351, FIG. 5 is SEQ ID NO: 144, FIG. 6 is SEQ ID NO: 93, FIG. 7 is SEQ ID NO: 320, FIG. 8 is SEQ ID NO: 92, FIG. 9 is SEQ ID NO: 75, FIG. 10 is SEQ ID NO: 76, FIG. 11 is SEQ ID NO: 349, FIG. 12 is SEQ ID NO: 350, FIG. 13 is SEQ ID NO: 105, FIG. 14 is SEQ ID NO: 177, FIG. 15 is SEQ ID NO: 345, FIG. 16 is SEQ ID NO: 353, FIG. 17 is SEQ ID NO: 344, FIG. 18 is SEQ ID NO: 346.

FIG. 26 is SEQ ID NO: 85, FIG. 27 is SEQ ID NO: 91, FIG. 28 is SEQ ID NO: 420.

DETAILED DESCRIPTION OF THE INVENTION

Example 1—Inflammatory Response

TNF-α is secreted by macrophages in response to stimulation by endotoxins such as lipopolysaccharides (LPS). TNF-α is thought to be involved in systemic inflammation and dysregulation of TNF-α production is thought to be involved in many diseases. The Biolegend assay is a sandwich ELISA kit that is designed for the accurate quantitation of human TNF-α from cell culture supernatant, serum or plasma.

THP-1 monocytes were seeded in a 96 well plate at 10,000 cells per well in RPMI containing 10% fetal calf serum (FCS), 1% Pen/strep, 1% L-glutamine, 100 nM PMA and allowed to differentiate for 72 h prior to experimentation.

Following differentiation the cells were incubated with 100 ng/ml, 10 ng/ml or 1 ng/ml synthetic peptide for 24 h respectively.

Following treatment the cells were stimulated with 10 ng/ml LPS for 5 h and the quantity of TNF-α in the supernatant determined using the Biolegend assay ELISA kit.

Results were calculated as a percentage of the untreated control. An increase in optical density reading indicates greater quantity of TNF-α release into cell culture supernatant.

The results are provided in FIGS. 1 to 21 and summarised in Table 1 below. All experiments were prepared in duplicate on three plates (6 wells/conditions). Significance was calculated using Students t-test (*$p<0.05$ compared to control, $p<0.01$ compared to control, * $p<0.001$ compared to control).

TABLE 1

Figure 1:
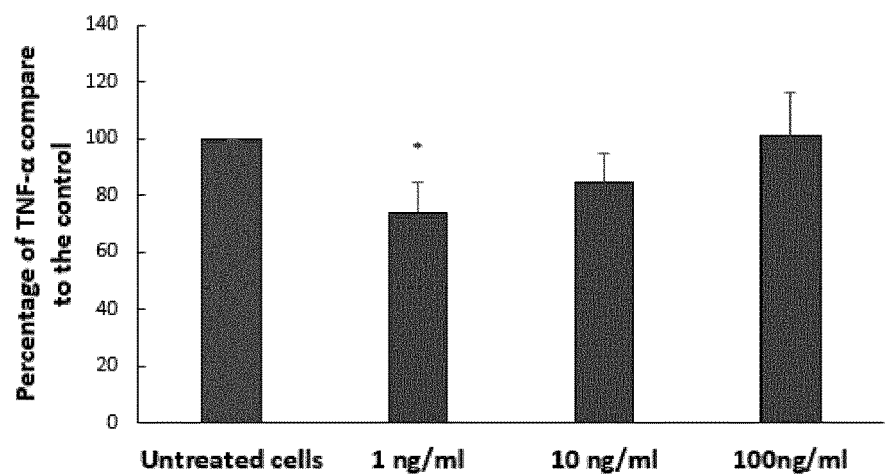
FIGS. 1 to 18: The effect of eighteen synthetic peptides of the invention on TNF-secretion in THP1 cells. All experiments were prepared in duplicate on three plates (6 wells/conditions). Significance was calculated using Students t-test (*p<0.05 compared to control, p<0.01 compared to control, * p<0.001 compared to control). The figures correspond with the following SEQ ID Nos.
Figure 2:
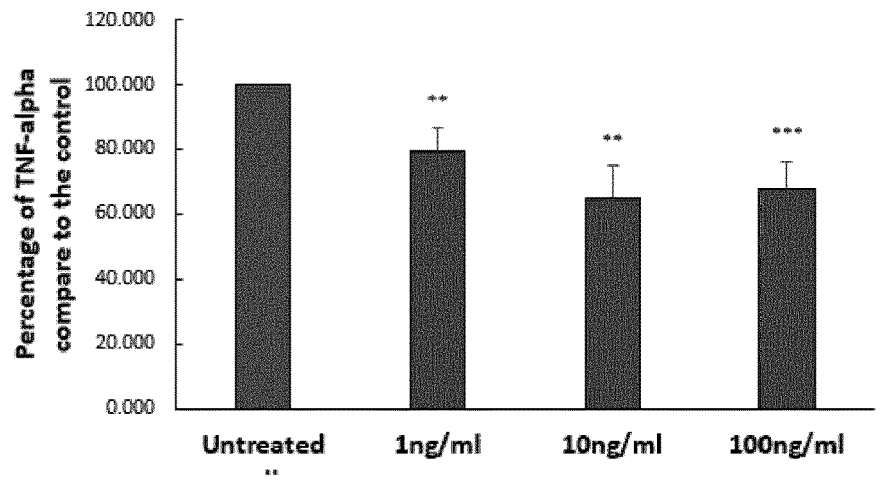
Figure 3:
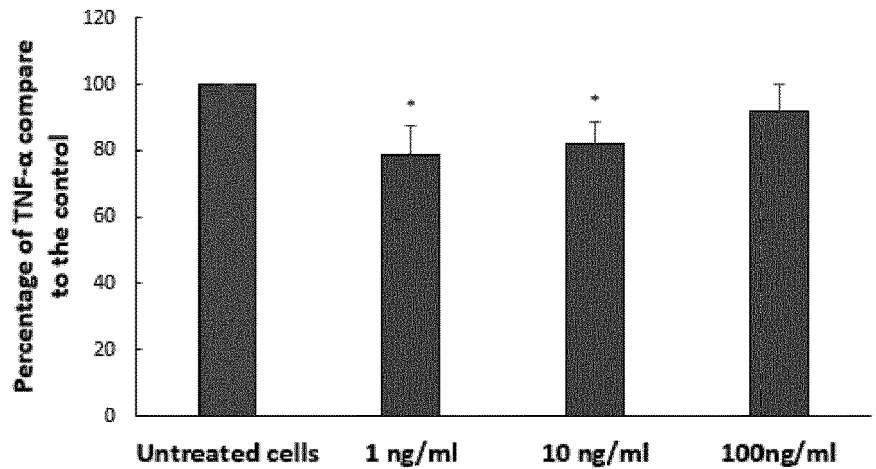
Figure 4:
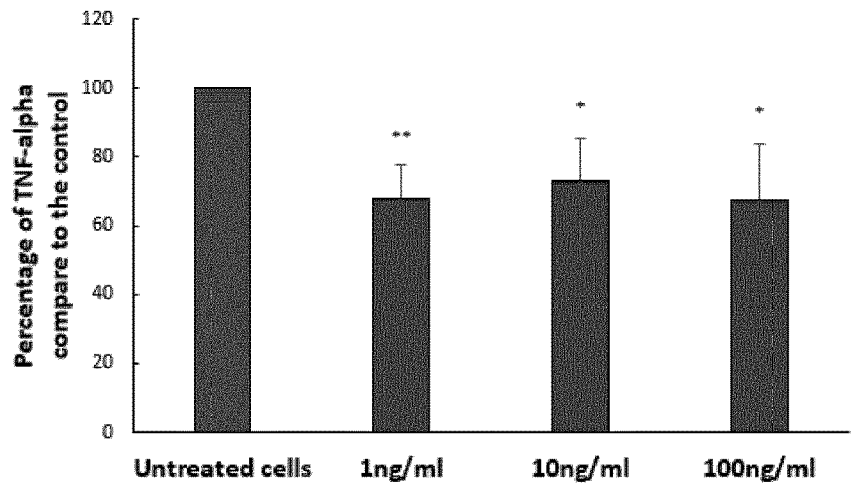
Figure 5:
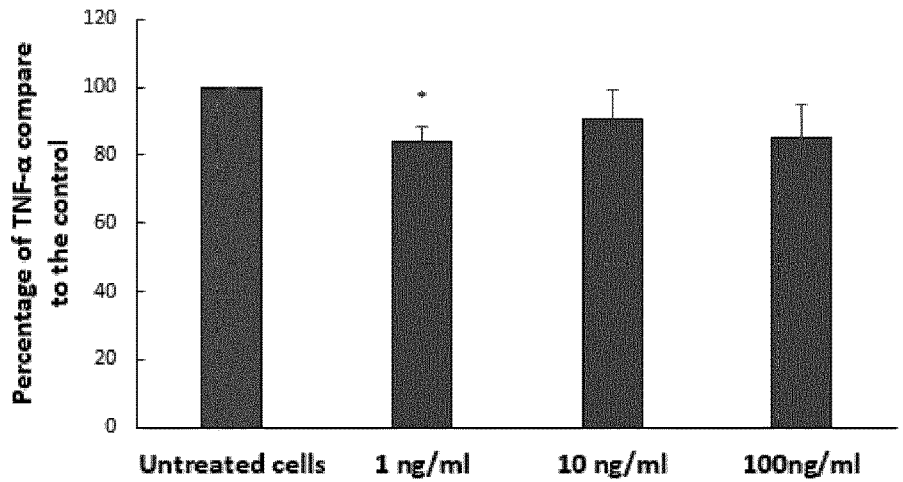
Figure 6:
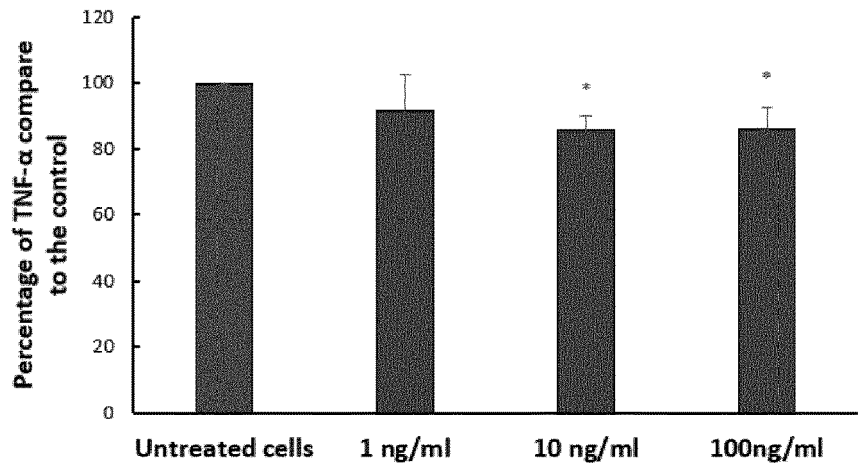
Figure 7:
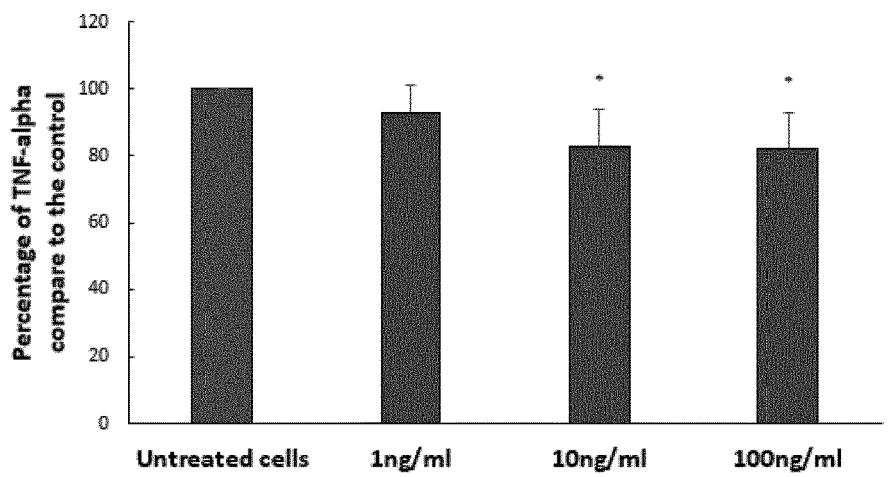
Figure 8:
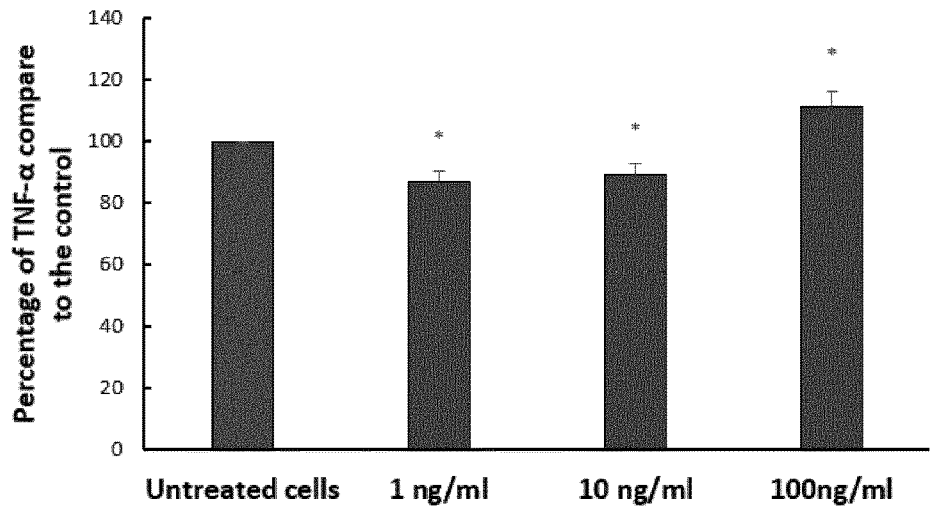
Figure 9:
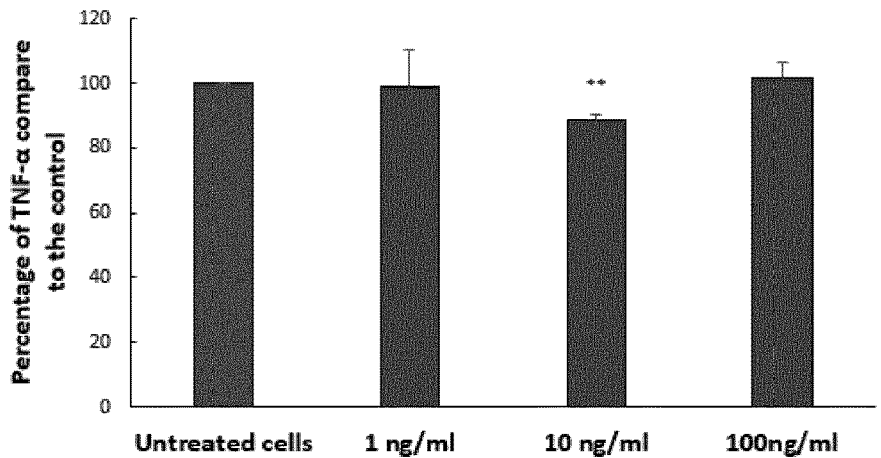
Figure 10:
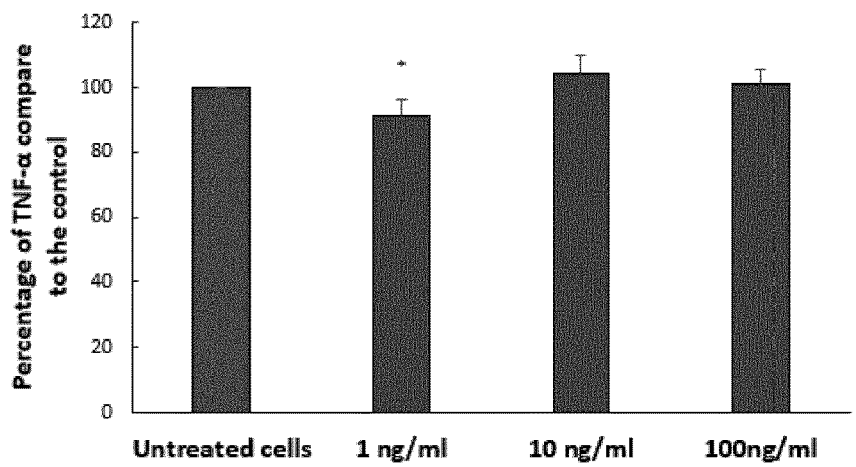
Figure 11:
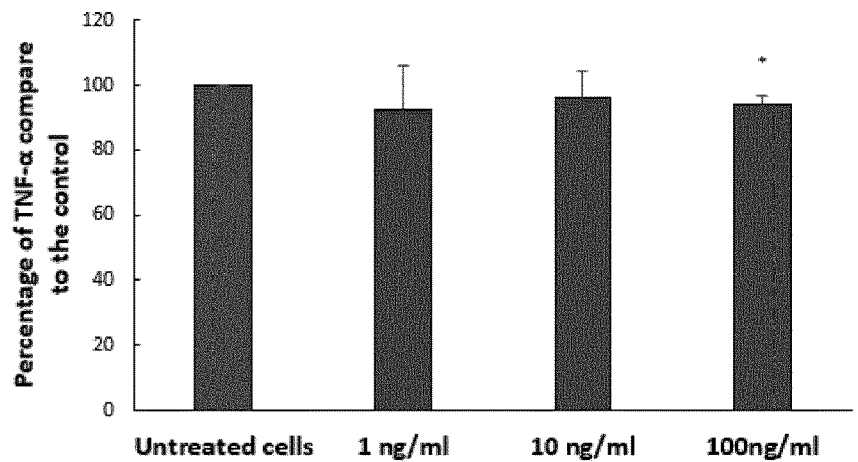
Figure 12:
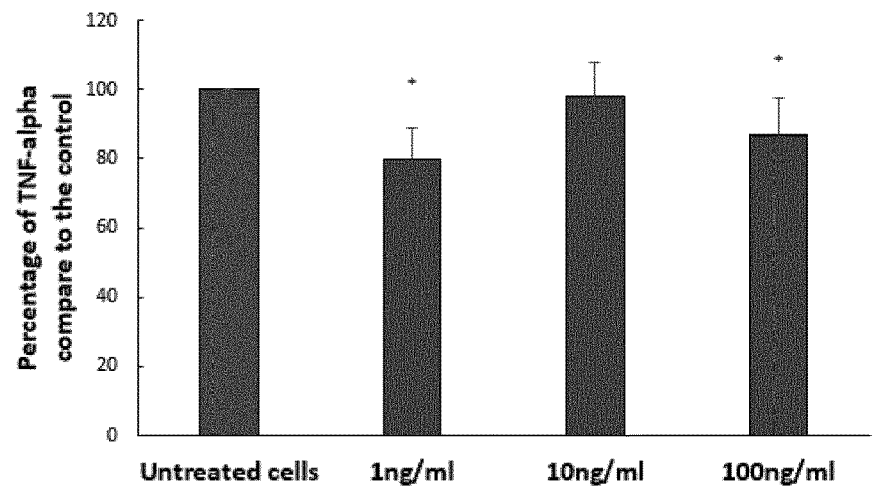
Figure 13:
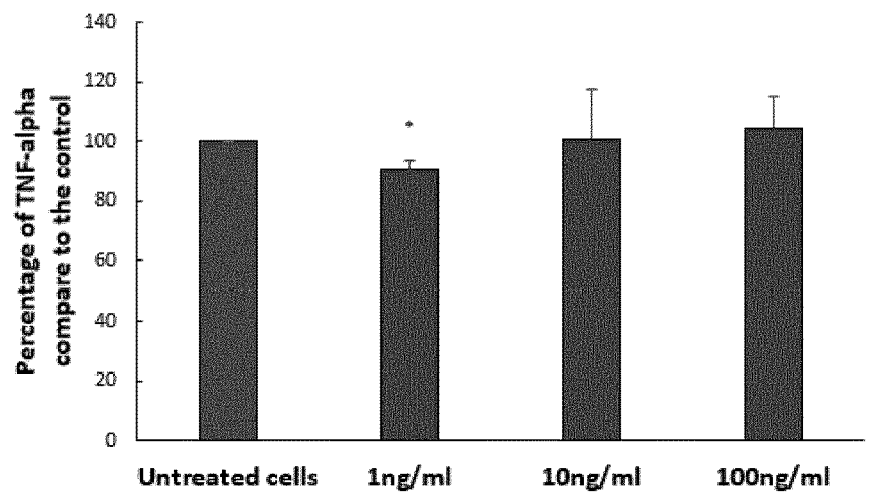
Figure 14:
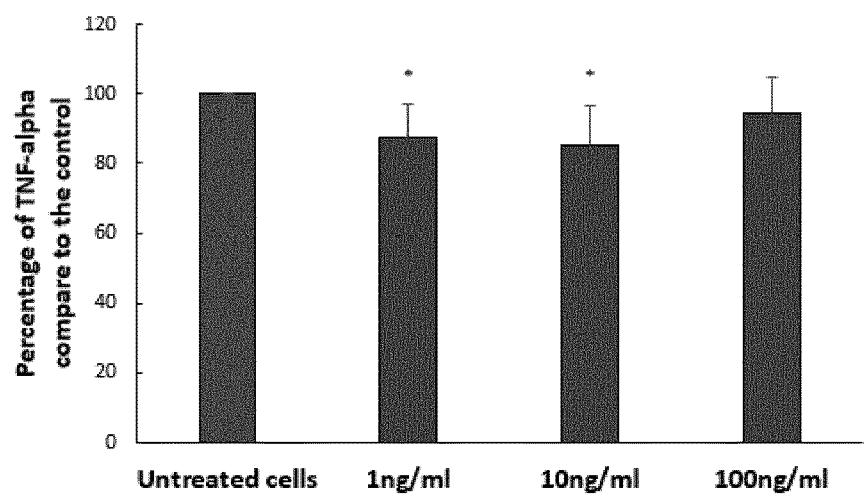
Figure 15:
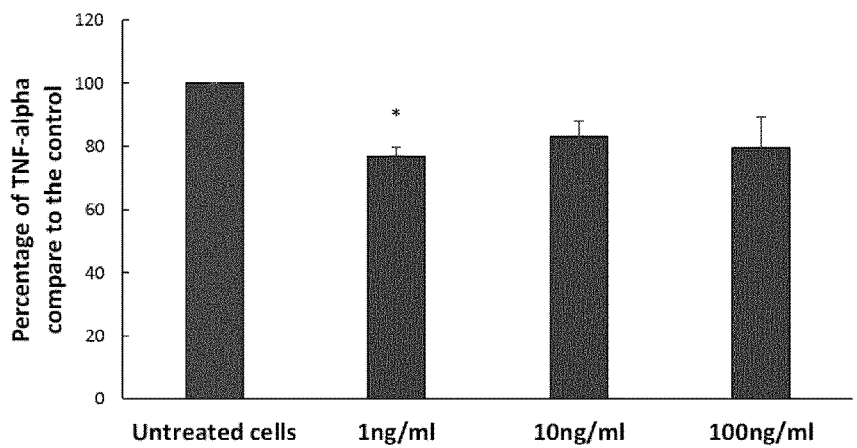
Figure 16:
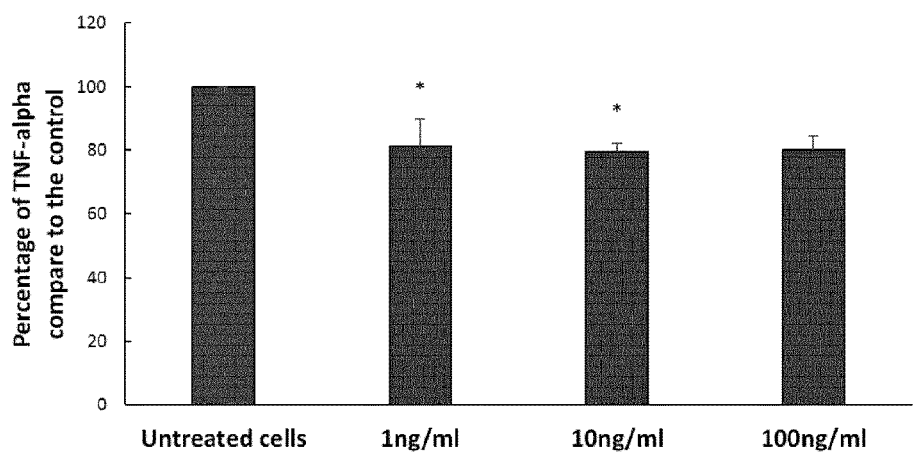
Figure 17:
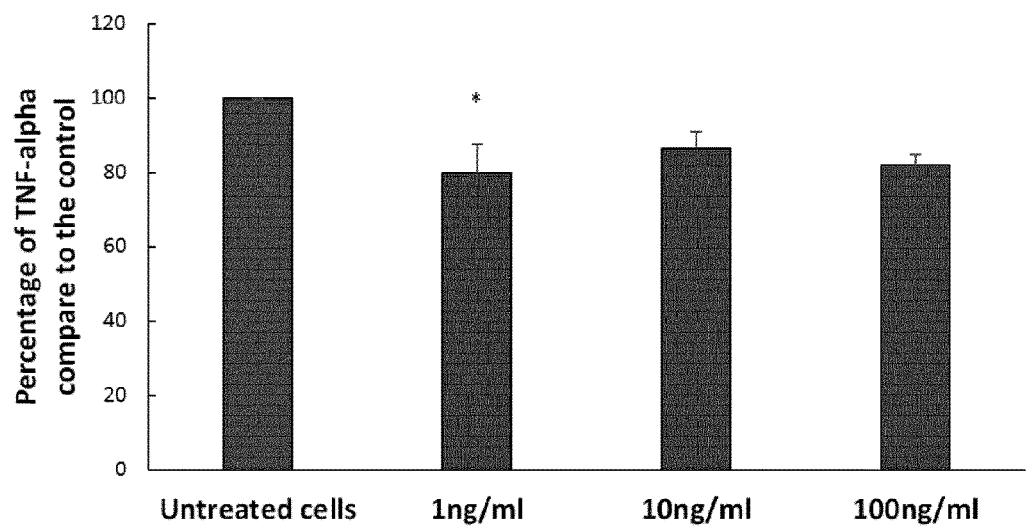
Figure 18:
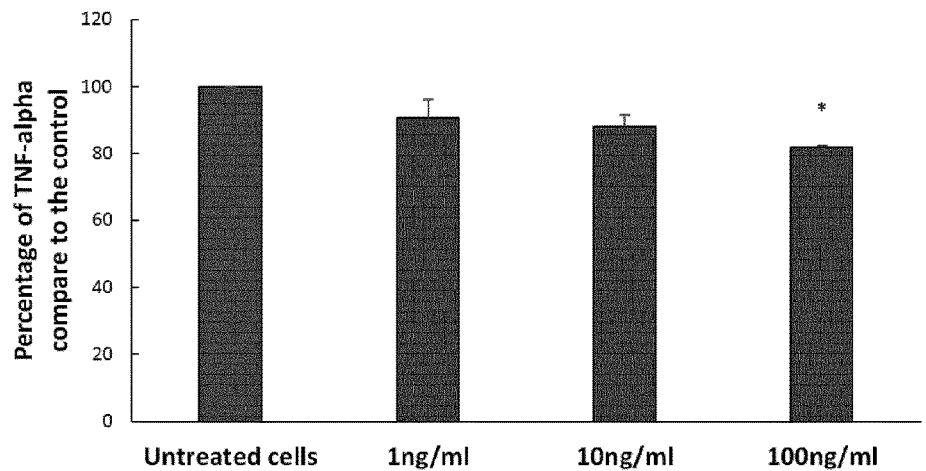
Figure 26:
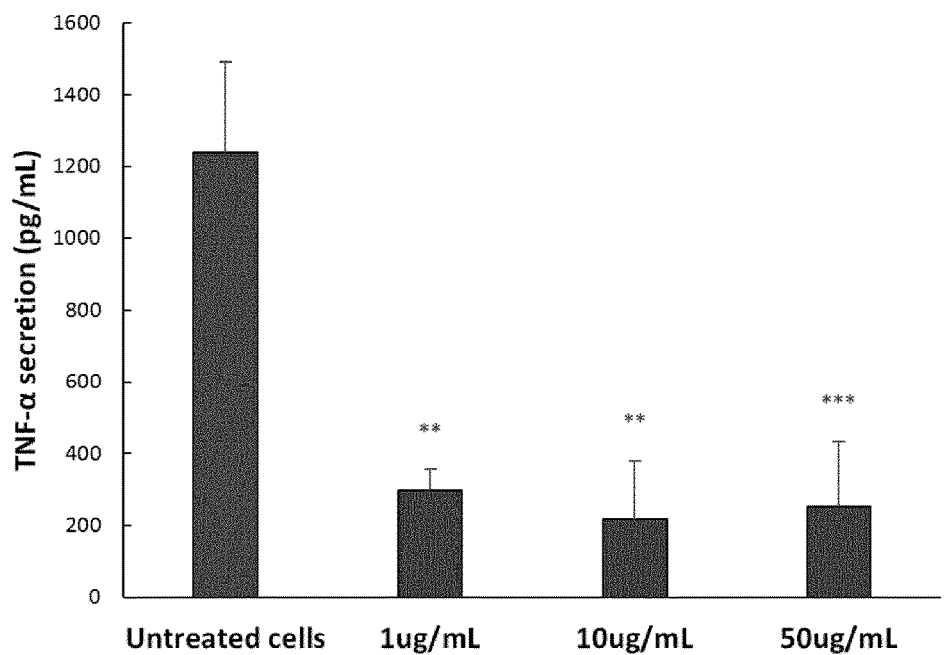
FIGS. 26 to 28. The effect of three synthetic peptides of the invention on TNF-secretion in THP1 cells. All experiments were prepared in duplicate on three plates (6 wells/conditions). Significance was calculated using Students t-test (*$p<0.05$ compared to control, $p<0.01$ compared to control, * $p<0.001$ compared to control). The figures correspond with the following SEQ ID Nos.
Figure 27:
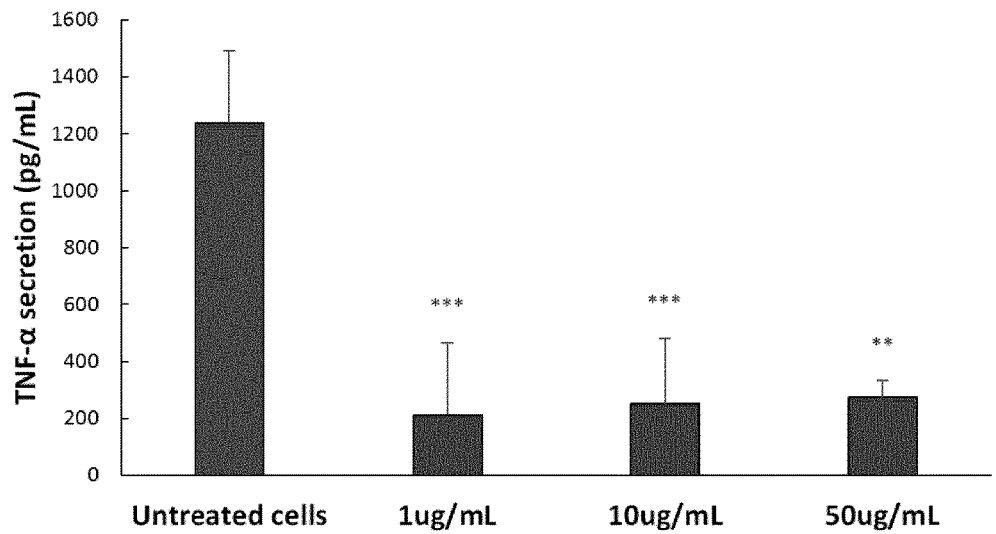
Figure 28:
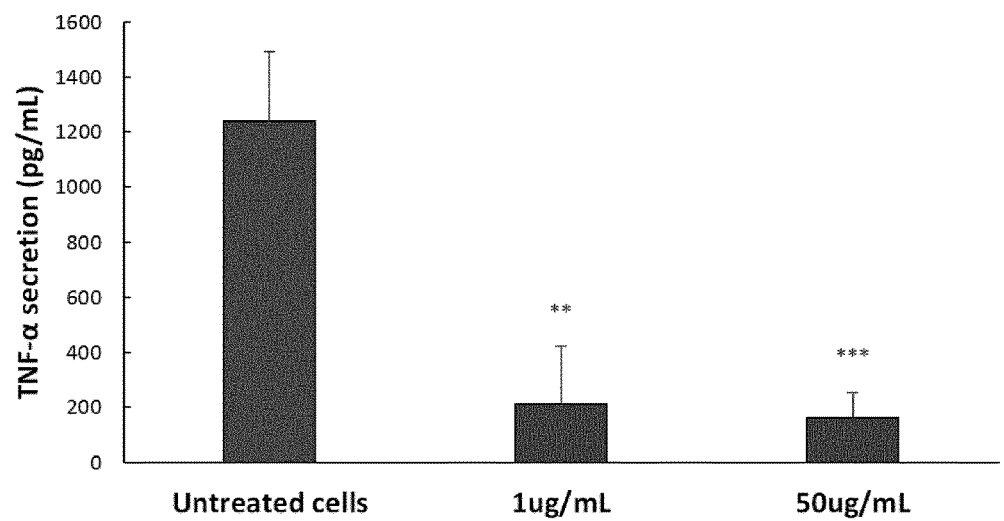

| FIG. NUMBER | SEQ ID | TNF-α DECREASE |
|---|---|---|
| FIG. 1 | 339 | 26% |
| FIG. 2 | 352 | 23% |
| FIG. 3 | 341 | 21% |
| FIG. 4 | 351 | 18% |
| FIG. 5 | 144 | 16% |
| FIG. 6 | 93 | 14% |
| FIG. 7 | 320 | 13% |
| FIG. 8 | 92 | 13% |
| FIG. 9 | 75 | 11% |
| FIG. 10 | 76 | 9% |
| FIG. 11 | 349 | 6% |
| FIG. 12 | 350 | |
| FIG. 13 | 105 | 9% |
| FIG. 14 | 177 | |
| FIG. 15 | 345 | 23% |
| FIG. 16 | 353 | 20% |
| FIG. 17 | 344 | 20% |
| FIG. 18 | 346 | 18% |
| FIG. 26 | 85 | 80% |
| FIG. 27 | 91 | 80% |
| FIG. 28 | 420 | 80% |

Example 2—Inflammatory Response

The effect of six synthetic peptides of the invention, SP1 to SP6 (SEQ ID NO: 108, 109, 110, 111, 85 and 91) and four peptide compositions on the inflammatory response in vitro using a cell line was determined.

Peptide composition I_1_HR (Rice) contained the followings peptides (identified by SEQ ID): 116, 197, 207, 112, 211, 158, 201, 203, 114, 183, 130, 113, 182, 167, 166, 152, 220, 213, 215, 154, 219, 218, 165, 123, 185, 190, 209, 181, 198, 200, 147, 172, 184, 124, 153, 205, 115, 196, 151, 161, 160, 216, 210, 208, 146, 133, 204, 212, 206.

Peptide composition I_2_HR (Rice) contained the followings peptides (identified by SEQ ID): 189, 177, 174, 129, 176, 202, 193, 195, 194, 192, 182, 128, 220, 127, 134, 136, 135, 180, 179, 178, 219, 218, 145, 120, 175, 190, 149, 126, 187, 191, 121, 122, 159, 132, 162, 137, 150, 186, 188, 164, 118, 125, 163, 157, 156, 117.

Peptide composition E_1_HR (Pea) contained the followings peptides (identified by SEQ ID):74, 76, 106, 102, 101, 100, 92, 96, 83, 89, 90, 104, 82, 75, 79, 78, 77, 99, 103, 72, 86, 105, 94, 93, 81, 97, 80, 88, 85, 87, 71, 107, 73, 84, 98, 95.

Peptide composition E_2_HR contained homologs of the peptides of the invention.

A J774.2 mouse macrophage cell line was treated with 100 μM of each synthetic peptide (SP) and 0.5 mg/ml of each peptide composition and the effect on two pro-inflammatory markers—tumour necrosis factor α (TNFα) and interleukin-1β (IL-1β) was determined after inflammation was induced using lipopolysaccharide (LPS) as an inflammatory stimulus. A one way anova was used with the dunnett test which is a multiple comparison and compares every mean with a single control mean.

Example 3—Synthetic Peptides: Cell Viability

Synthetic peptides were first diluted in a suitable solvent. Dimethyl sulfoxide (DMSO) was the solvent of choice for peptides with poor predicted water solubility. Final concentration of DMSO in each well: SP1 (1_155 HR)—0.3%, SP2 (1_374 HR)—0%, SP3 (E_155 HR)—0.3%, SP4 (E_54_HR)—1%, SP5 (E_41_HR)—1%, SP6 (E 788 HR)—0.3%, positive Control—0%. Cells were first treated with 100 μM of each SP for 24 hours before an alamar blue assay was performed. No viability issues were seen with any of the peptides.

Example 4—Peptide Compositions: Preparation and Toxicity

Figure 19:
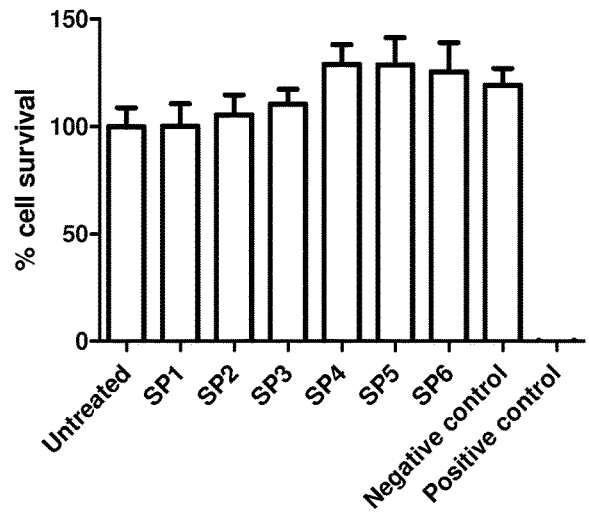
FIG. 19A-19B. Viability of J774.2 macrophages after treatment with synthetic peptides. J774.2 macrophages were treated 100 μM of synthetic peptide for 24 hours before an alamar blue assay was performed. Data are presented as an average of n=3+/−SEM.
Figure 20:
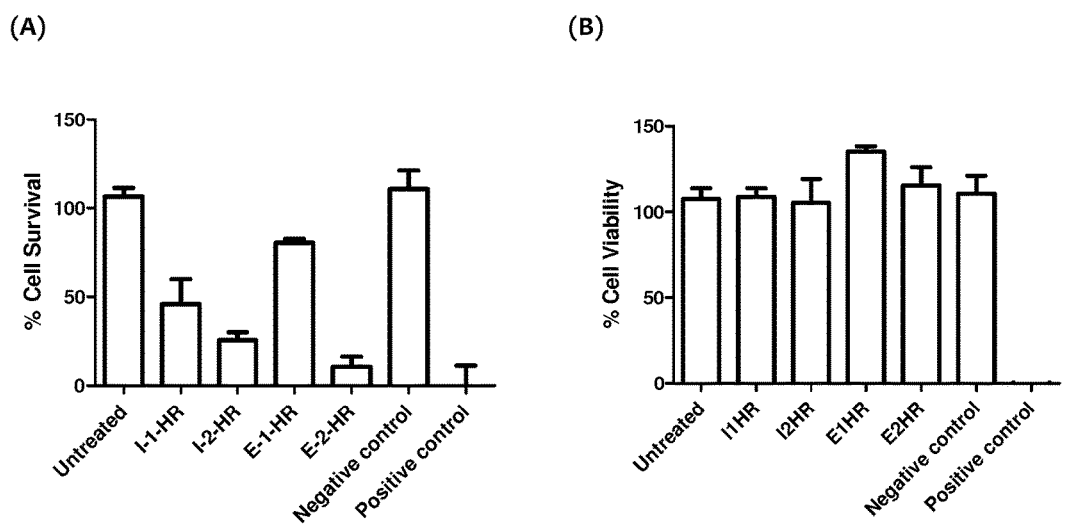
FIG. 20A-20B. The effects of peptide compositions on cell survival. J774.2 macrophages were treated with (FIG. 20A) 1 mg/ml or (FIG. 20B) 0.5 mg/ml of peptide compositions for 24 hours before an alamar blue assay was performed. Data is shown as (FIG. 20A) n=1+/−SEM and (FIG. 20B) n=3+/−SEM.
Figure 21:
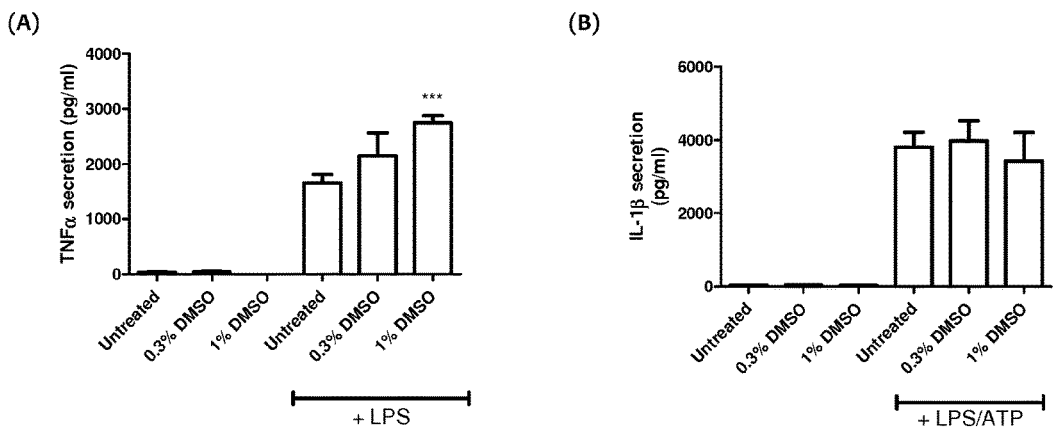
FIG. 21A-21B. The effect of DMSO vehicle on TNFα and IL-1β secretion from J774.2 macrophages. J774.2 macrophages were treated with a final concentration of 0.3% and 1% DMSO (equivalent to the amounts used to dissolve the peptides) for 24 hours and the effect on TNFα (FIG. 21A) and IL-1β (FIG. 21B) after stimulation was established. Data are presented as an average of n=3+/−SEM. (***$p<0.001$ w.r.t LPS).
Figure 22:
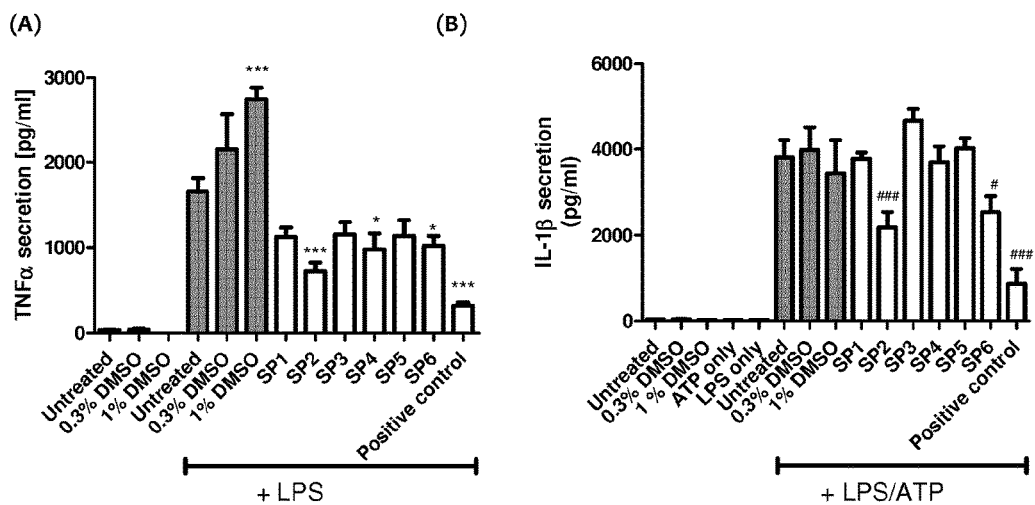
FIG. 22A-22B. The effect of six peptides of the invention on TNFα and IL-1β secretion from J774.2 macrophages. J774.2 macrophages were treated with 100 μM of synthetic peptide for 24 hours and then stimulated with (FIG. 22A) LPS (10 ng/ml) for five hours or (FIG. 22B) LPS (10 ng/ml) for 5 hours followed by ATP (5 mM) for one hour. Supernatant was collected and levels of (FIG. 22A) TNFα and (FIG. 22B) IL-1β were determined by ELISA. (*$p<0.001$ w.r.t LPS, $p<0.01$ w.r.t LPS, *$p<0.05$, +++$p<0.001$ w.r.t. LPS/ATP, ##$p<0.01$ w.r.t LPS/ATP and #$p<0.05$ w.r.t LPS/ATP). Final concentration of DMSO in well: SP1—0.3%, SP2—0%, SP3—0.3%, SP4—1%, SP5—1%, SP6—0.3%, Positive Control—0%. Data are presented as an average of n=3+/−SEM.
Figure 23:
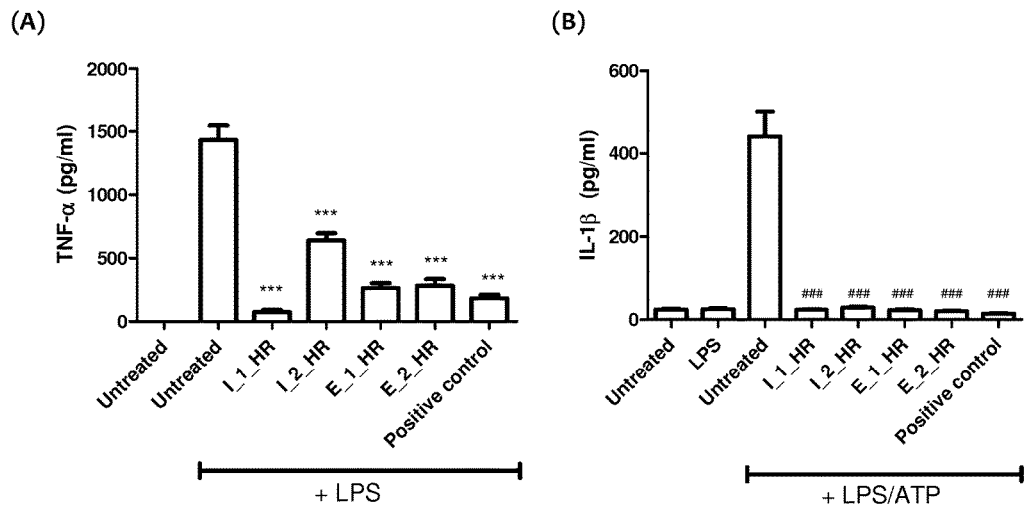
FIG. 23A-23B. The effect a peptide composition of the invention on TNFα and IL-1β secretion. J774.2 macrophages were treated with 0.5 mg/ml of peptide composition for 24 hours and then stimulated with (FIG. 23A) LPS (10 ng/ml) for five hours or (FIG. 23B) LPS (10 ng/ml) for 5 hours followed by ATP (5 mM) for one hour. Supernatant was collected and levels of (FIG. 23A) TNFα and (FIG. 23B) IL-1β were determined by ELISA. (***$p<0.001$ w.r.t untreated+LPS, ###$p<0.001$ w.r.t. untreated+LPS/ATP). Data are presented as an average of n=3+/−SEM.
Figure 24:
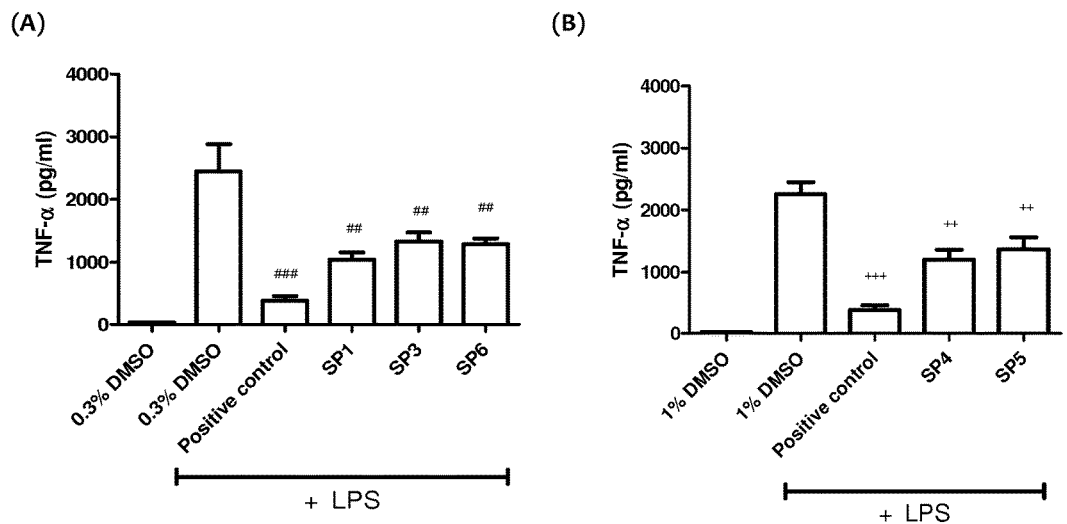
FIG. 24. The effects of synthetic peptides with DMSO vehicle on TNFα J774.2 macrophages were treated with 100 μM of synthetic peptide for 24 hours and then LPS (10 ng/ml) for five hours. Supernatant was collected and levels of TNFα were determined by ELISA. ###$p<0.001$ w.r.t 0.3% DMSO+LPS, ##$p<0.01$ w.r.t. 0.3% DMSO+LPS, +++$p<0.001$ w.r.t 1% DMSO+LPS, ++$p<0.01$ w.r.t 1% DMSO+LPS/ATP). Final concentration of DMSO in well: positive control—0%, SP1—0.3%, SP2—0%, SP3—0.3%, SP4—1%, SP5—1%, SP6—0.3%.
Figure 25:
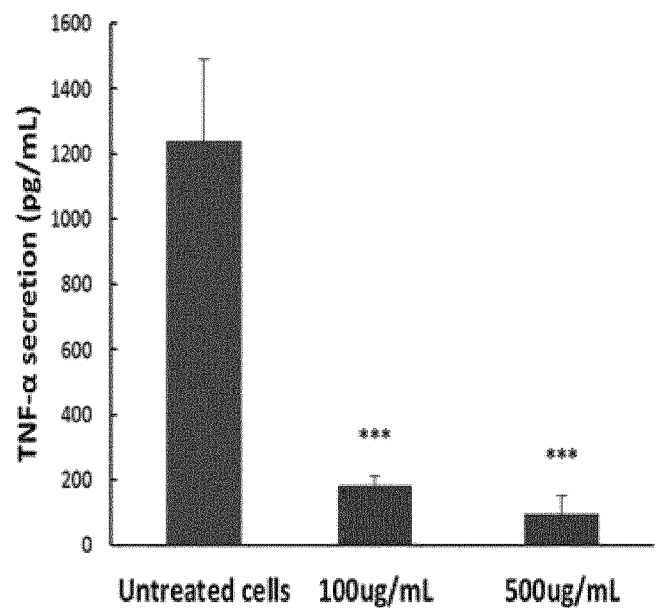
FIG. 25. THP-1 differentiated macrophages treated with a composition of rice peptides of the invention (I_2_HR) for 24 hrs. prior to LPS stimulation were compared to untreated cells. TNF-α secretion in I_2_HR treated cells is reduced by 92% vs. untreated cells. Significant results are observed at 100 ug/ml and 500 ug/ml concentrations of I_2_HR, indicating the potency of I_2_HR.

The peptide compositions were prepared by adjusting the pH to between 6-7 and sterile filtering. The effects of the peptide compositions on cell viability was determined. J774.2 macrophages were treated with 1 mg/ml and 0.5 mg/ml of each peptide composition, hydrogen peroxide to induce cell death as a positive control, and a peptide known to be non-toxic as a negative control. An alamar blue assay was then performed and cell survival is shown in FIG. 19 as a percentage of untreated (100%). As cell survival was compromised with 1 mg/ml of peptide, 0.5 mg/ml of peptide composition was used for further assays.

Example 5—Inflammatory Markers

The effect of the DMSO on TNFα and IL-1β secretion was determined. 1% DMSO significantly increased levels of TNFα (FIG. 3A. ***$p<0.001$ w.r.t LPS) and this was taken into account when analysing the effect of the peptides on TNFα. No significant effect was seen with regards DMSO and IL-1β secretion.

Example 6—Inflammatory Response

THP-1 differentiated macrophages were treated with a composition of rice peptides of the invention (I_2_HR) for 24 hrs. prior to LPS stimulation were compared to untreated cells. TNF-α secretion in I_2_HR treated cells is reduced by 92% vs. untreated cells. Significant results are observed at 100 ug/ml and 500 ug/ml concentrations of I_2_HR, indicating the potency of I_2_HR.

The invention is not limited to the embodiments hereinbefore described which may be varied in construction and detail without departing from the spirit of the invention.

SEQUENCE INFORMATION

```
PEA PROTEIN 1: P13918 - 1 -
MAATTMKASFPLLMLMGISFLASVCVSSRSDPQNPFIFKSNKFQTLFENENGHIRLLQKFDQRSKIFENLQNYRLLEYKSKPHTIFLPQHTDA
DYILVVLSGKAILTVLKPDDRNSFNLERGDTIKLPAGTIAYLVNRDDNEELRVLDLAIPVNRPGQLQSFLLSGNQNQQNYLSGFSKNILEASFN
TDYEEIEKVLLEEHEKETQHRRSLKDKRQQSQEENVIVKLSRGQIEELSKNAKSTSKKSVSSESEPFNLRSRGPIYSNEFGKFFEITPEKNPQLQ
DLDIFVNSVEIKEGSLLLPHYNSRAIVIVTVNEGKGDFELVGQRNENQQEQRKEDDEEEEQGEEEINKQVQNYKAKLSSGDVFVIPAGHPVA
VKASSNLDLLGFGINAENNQRNFLAGDEDNVISQIQRPVKELAFPGSAQEVDRILENQKQSHFADAQPQQRERGSRETRDRLSSV [SEQ
ID 1]

REGION: 253 to 274 - PFNLRSRGPIYSNEFGKFFEIT [SEQ ID 17]
PEPTIDE: SRGPIYSNEFGK [SEQ ID 71]

REGION: 110 to 126 - KPDDRNSFNLERGDTIK [SEQ ID 18]
PEPTIDE: NSFNLER [SEQ ID 72]

REGION: 134 to 160 - YLVNRDDNEELRVLDLAIPVNRPGQLQ [SEQ ID 19]
PEPTIDE: VLDLAIPVNR [SEQ ID 73]
PEPTIDE: DDNEELR [SEQ ID 74]

REGION: 331 to 381 - QEQRKEDDEEEEQGEEEINKQVQNYKAKLSSGDVFVIPAGHPVAVKASSNL [SEQ ID 20]
PEPTIDE: LSSGDVFVIPAGHPVAVK [SEQ ID 75]
PEPTIDE: EDDEEEEQGEEEINK [SEQ ID 76]

REGION: 175 to 242 - SGFSKNILEASFNTDYEEIEKVLLEEHEKETQHRRSLKDKRQQSQEENVIVKLSRGQIEELSKNAKST [SEQ
ID 21]
PEPTIDE: NILEASFNTDYEEIEKVLLEEHEKETQHR [SEQ ID 77]
PEPTIDE: NILEASFNTDYEEIEKVLLEEHEK [SEQ ID 78]
PEPTIDE: NILEASFNTDYEEIEK [SEQ ID 79]
PEPTIDE: RQQSQEENVIVK [SEQ ID 80]
PEPTIDE: QQSQEENVIVK [SEQ ID 81]
```

SEQUENCE INFORMATION

PEPTIDE: LSRGQIEELSK [SEQ ID 82]
PEPTIDE: GQIEELSK [SEQ ID 83]
PEPTIDE: VLLEEHEK [SEQ ID 84]

REGION: 35 to 108 - PFIFKSNKFQTLFENENGHIRLLQKFDQRSKIFENLQNYRLLEYKSKPHTIFLPQHTDADYILVVLSGKAILTV
[SEQ ID 22]
PEPTIDE: SKPHTIFLPQHTDADYILVVLSGK [SEQ ID 85]
PEPTIDE: PHTIFLPQHTDADYILVVLSGK [SEQ ID 86]
PEPTIDE: SNKFQTLFENENGHIR [SEQ ID 87]
PEPTIDE: SKIFENLQNYR [SEQ ID 88]
PEPTIDE: IFENLQNYR [SEQ ID 89]

REGION: 423 to 450 - QEVDRILENQKQSHFADAQPQQRERGSR [SEQ ID 23]
PEPTIDE: ILENQKQSHFADAQPQQR [SEQ ID 90]
PEPTIDE PGQLQSFLLSGNQNQQNYLSGFSK [SEQ ID 91]

PEA PROTEIN 2: P02856 - 2 -
DRRQELSNENVLVKVSRRQLEELSKNAKSSSRRSVSSESGPFNLRSEDPLYSNNSGKFFELTPEKNQQLQDLDLFVNSVDLKEGSLLLPNYNS
RALLVLVLVVNEGKGDFELVGQRNENQGKEN [SEQ ID 2]

REGION: 53 to 87 - NNSGKFFELTPEKNQQLQDLDLFVNSVDLKEGSLL [SEQ ID 24]
PEPTIDE: FFELTPEKNQQLQDLDLFVNSVDLK [SEQ ID 92]

REGION: 14 to 30 - KVSRRQLEELSKNAKSS [SEQ ID 25]
PEPTIDE: QLEELSK [SEQ ID 93]

PEA PROTEIN 3: P15838 - 3 -
MATKLLALSLSFCFLLLGGCFALREQPEQNECQLERLNALEPDNRIESEGGLIETWNPNNKQFRCAGVALSRATLQHNALRRPYYSNAPQEI
FIQQGNGYFGMVFPGCPETFEEPQESEQGEGRRYRDRHQKVNRFREGDIIAVPTGIVFWMYNDQDTPVIAVSLTDIRSSNNQLDQMPRR
FYLAGNHEQEFLRYQHQQGGKQEQENEGNNIFSGFKRDFLEDAFNVNRHIVDRLQGRNEDEEKGAIVKVKGGLSIISPPEKQARHQRGSR
QEEDEDEDEERQPRHQRGSRQEEEEDEDEERQPRHQRRRGEEEEEDKKERRGSQKGKSRRQGDNGLEETVCTAKLRLNIGPSSSPDIYNPE
AGRIKTVTSLDLPVLRWLKLSAEHGSLHKNAMFVPHYNLNANSIIYALKGRARLQVVNCNGNTVFDGELEAGRALTVPQNYAVAAKSLSD
RFSYVAFKTNDRAGIARLAGTSSVINNLPLDVVAATFNLQRNEARQLKSNNPFKFLVPARQSENRASA [SEQ ID 3]

REGION: 267 to 287- QRGSRQEEDEDEDEERQPRHQ [SEQ ID 26]
PEPTIDE: QEEDEDEDEER [SEQ ID 94]

REGION: 190 to 222- QEFLRYQHQQGGKQEQENEGNNIFSGFKRDFLE [SEQ ID 27]
PEPTIDE: YQHQQGGKQEQENEGNNIFSGFK [SEQ ID 95]

PEA PROTEIN 4: Q9M3X6 - 4 -
MATTIKSRFPLLLLLGIIFLASVVCVTYANYDEGSEPRVPAQRERGRQEGEKEEKRHGEWRPSYEKEEDEEEGQRERGRQEGEKEEKRHGE
WRPSYEKQEDEEEKQKYRYQREKEDEEEKQKYQYQREKKEQKEVQPGRERWEREEDEEQVDEEWRGSQRREDPEERARLRHREERTKR
DRRHQREGEEEERSSESQERRNPFLFKSNKFLTLFENENGHIRLLQRFDKRSDLFENLQNYRLVEYRAKPHTIFLPQHIDADLILVVLSGKAILT
VLSPNDRNSYNLERGDTIKLPAGTTSYLVNQDDEEDLRLVDLVIPVNGPGKFEAFDLAKNKNQYLRGFSKNILEASYNTRYETIEKVLLEEQE
KDRKRRQQGEETDAIVKVSREQIEELKKLAKSSSKKSLPSEFEPINLIRSHKPEYSNKFGKLFEITPEKKYPQLQDLDLFVSCVEINEGALMLPHY
NSRAIVVLLVNEGKGNLELLGLKNEQQEREDRKERNNEVQRYEARLSPGDVVIIPAGHPVAITASSNLNLLGFGINAENNERNFLSGSDDNV
ISQIENPVKELTFPGSVQEINRLIKNQKQSHFANAEPEQKEQGSQGKRSPLSSILGTFY [SEQ ID 4]

REGION: 284 to 317 - YNLERGDTIKLPAGTTSYLVNQDDEEDLRLVDLV [SEQ ID 28]
PEPTIDE: GDTIKLPAGTTSYLVNQDDEEDLR [SEQ ID 96]

REGION: 321 to 400 -
NGPGKFEAFDLAKNKNQYLRGFSKNILEASYNTRYETIEKVLLEEQEKDRKRRQQGEETDAIVKVSREQIEELKKLAKSS [SEQ ID 29]
PEPTIDE: RQQGEETDAIVK [SEQ ID 97]
PEPTIDE: VLLEEQEKDRK [SEQ ID 98]
PEPTIDE: NILEASYNTR [SEQ ID 99]
PEPTIDE: FEAFDLAK [SEQ ID 100]
PEPTIDE: EQIEELKK [SEQ ID 101]
PEPTIDE: EQIEELK [SEQ ID 102]
PEPTIDE: NKNQYLR [SEQ ID 103]

REGION: 503 to 549 - RYEARLSPGDVVIIPAGHPVAITASSNLNLLGFGINAENNERNFLSG [SEQ ID 30]
PEPTIDE: LSPGDVVIIPAGHPVAITASSNLNLLGFGINAENNER [SEQ ID 104]

REGION: 89 to 112 - HGEWRPSYEKQEDEEEKQKYRYQR [SEQ ID 31]
PEPTIDE: PSYEKQEDEEEKQK [SEQ ID 105]

REGION: 62 to 80 - PSYEKEEDEEEGQRERGRQ [SEQ ID 32]
PEPTIDE: EEDEEEGQR [SEQ ID 106]

PEA PROTEIN 5: D3VNE1 - 5 -
MAATPIKPLMLLAIAFLASVCVSSRSDQENPFIFKSNRFQTLYENENGHIRLLQKFDKRSKIFENLQNYRLLEYKSKPRTLFLPQYTDADFILVV
LSGKATLTVLKSNDRNSFNLERGDTIKLPAGTIAYLANRDDNEDLRVLDLTIPVNKPGQLQSFLLSGTQNQPSLLSGFSKNILEAAFNTNYEEI
EKVLLEQQEQEPQHRRSLKDRRQEINEENVIVKVSREQIEELSKNAKSSSKKSVSSESGPFNLRSRNPIYSNKFGKFFEITPEKNQQLQDLDIF
VNSVDIKEGSLLLPNYNSRAIVIVTVTEGKGDFELVGQRNENQGKENDKEEEQEEETSKQVQLYRAKLSPGDVFVIPAGHPVAINASSDLNLI
GFGINAENNERNFLAGEEDNVISQVERPVKELAFPGSSHEVDRLLKNQKQSYFANAQPLQRE [SEQ ID 5]

SEQUENCE INFORMATION

REGION: 75 to 104 - KSKPRTLFLPQYTDADFILVVLSGKATLTV [SEQ ID 33]
PEPTIDE: TLFLPQYTDADFILVVLSGK [SEQ ID 107]

RICE PROTEIN 7: Q6K508
**MATTTSLLSSCLCALLLAPLFSQGVDAWESRQGASRQCRFDRLQAFEPLRKVRSEAGDTE
YFDERNEQFRCAGVFVIRRVIEPQGLVVPRYSNTPALAYIIQGKGYVGLTFPGCPATHQQ
QFQLFEQRQSDQAHKFRDEHQKIHEFRQGDVVALPASVAHWFYNGGDTPAVVVYVYDIKS
FANQLEPRQKEFLLAGNNQRGQQIFEHSIFQHSGQNIFSGFNTEVLSEALGINTEASKRL
QSQNDQRGDIIRVKHGLQLLKPTLTQRQEEHRQYQQVQYREGQYNGLDENFCTIKARVNI
ENPSRADYYNPRAGRITLLNNQKFPILNLIGMGAARVNLYQNALLSPFWNINAHSVVYII
QGSVRVQVANNQGRSVFNGVLHQGQLLIIPQNHAVIKKAEHNGCQYVAIKTISDPTVSWV
AGKNSILRALPVDVIANAYRISRDEARRLKNNRADEIGPFTPRFPQKSQRGYQFLTEGLS
LIGM** [SEQ ID 6]

PEPTIDE: GYVGLTFPGCPATHQQQFQLFEQR [SEQ ID 108]

RICE PROTEIN 8: Q6K7K6
**MASMSTILPLCLGLLLFFQVSMAQFSFGGSPLQSPRGFRGDQDSRHQCRFEHLTALEATH
QQRSEAGFTEYYNIEARNEFRCAGVSVRRLVVESKGLVLPMYANAHKLVYIVQGRGVFGM
ALPGCPETFQSVRSPFEQEVATAGEAQSSIQKMRDEHQQLHQFHQGDVIAVPAGVAHWLY
NNGDSPVVAFTVIDTSNNANQLDPKRREFFLAGKPRSSWQQQSYSYQTEQLSRNQNIFAG
FSPDLLSEALSVSKQTVLRLQGLSDPRGAIIRVENGLQALQPSLQVEPVKEEQTQAYLPT
KQLQPTWLRSGGACGQQNVLDEIMCAFKLRKNIDNPQSSDIFNPHGGRITRANSQNFPIL
NIIQMSATRIVLQNNALLTPHWTVNAHTVMYVTAGQGHIQVVDHRGRSVFDGELHQQQIL
LIPQNFAVVVKARREGFAWVSFKTNHNAVDSQIAGKASILRALPVDVVANAYRLSREDSR
HVKFNRGDEMAVFAPRRGPQQYAEWQINEK** [SEQ ID 7]

PEPTIDE: RGPQQYAEWQINEK [SEQ ID 109]

PEA PROTEIN 6: P13919
**MATTIKSRFPLLLLLGIIFLASVVSVTYANYDEGSEPRVPAQRERGRQEGEKEEKRHGEW
RPSYEKEEDEEEGQRERGRQEGEKEEKRHGEWGPSYEKQEDEEEKQKYRYQREKEDEEEK
QKYQYQREKKEQKEVQPGRERWEREEDEEQVDEEWRGSQRREDPEERARLRHREERTKRD
RRHQREGEEEERSSESQERRNPFLFKSNKFLTLFENENGHIRLLQRFDKRSDLFENLQNY
RLVEYRAKPHTIFLPQHIDADLILVVLSGKAILTVLSPNDRNSYNLERGDTIKLPAGTTS
YLVNQDDEEDLRLVDLVIPVNGPGKFEAFDLAKNKNQYLRGFSKNILEASYNTRYETIEK
VLLEEQEKDRKRRQQGEETDAIVKVS** [SEQ ID 8]

PEPTIDE: LVDLVIPVNGPGKFEAFDLAK [SEQ ID 110]

PEA PROTEIN 7: P02855
**MATTIKSRFPLLLLLGIIFLASVVSVTYANYDEGSEPRVPAQRERGRQEGEKEEKRHGEW
RPSYEKEEDEEEGQRERGRQEGEKEEKRHGEWGPSYEKQEDEEEKQKYRYQREKEDEEEK
QKYQYQREKKEQKEVQPGRERWEREEDEEQVDEEWRGSQRREDPEERARLRHREERTKRD
RRHQREGEEEERSSESQERRNPFLFKSNKFLTLFENENGHIRLLQRFDKRSDLFENLQNY
RLVEYRAKPHTIFLPQHIDADLILVVLSGKAILTVLSPNDRNSYNLERGDTIKLPAGTTS
YLVNQDDEEDLRLVDLVIPVNGPGKFEAFDLAKNKNQYLRGFSKNILEASYNTRYETIEK
VLLEEQEKDRKRRQQGEETDAIVKVS** [SEQ ID 9]

PEPTIDE: KNPQLQDLDIFVNYVEIK [SEQ ID 111]

RICE PROTEIN 1: P14323 - 1 -
**MASSVFSRFSIYFCVLLLCHGSMAQLFNPSTNPWHSPRQGSFRECRFDRLQAFEPLRKVRSEAGVTEYFDEKNELFQCTGTFVIRRVIQPQG
LLVPRYTNIPGVVYIIQGRGSMGLTFPGCPATYQQQFQQFSSQGQSQSQKFRDEHQKIHQFRQGDIVALPAGVAHWFYNDGDAPIVAVY
VYDVNNNANQLEPRQKEFLLAGNNNRAQQQQVYGSSIEQHSGQNIFSGFGVEMLSEALGINAVAAKRLQSQNDQRGEIIHVKNGLQLLK
PTLTQQQEQAQAQDQYQQVQYSERQQTSSRWNGLEENFCTIKVRVNIENPSRADSYNPRAGRITSVNSQKFPILNLIQMSATRVNLYQN
AILSPFWNVNAHSLVYMIQGRSRVQVVSNFGKTVFDGVLRPGQLLIIPQHYAVLKAEREGCQYIAIKTNANAFVSHLAGKNSVFRALPVD
VVANAYRISREQARSLKNNRGEEHGAFTPRFQQQYYPGLSNESESETSE** [SEQ ID 10]

REGION: 138 to 159 - SQSQKFRDEHQKIHQFRQGDIV [SEQ ID 34]
PEPTIDE: DEHQKIHQFR [SEQ ID 112]
PEPTIDE: FRDEHQK [SEQ ID 113]

REGION: 336 to 358 - VNSQKFPILNLIQMSATRVNLYQ [SEQ ID 35]
PEPTIDE: FPILNLIQMSATR [SEQ ID 114]

REGION: 423 to 462 - YIAIKTNANAFVSHLAGKNSVFRALPVDVVANAYRISREQ [SEQ ID 36]
PEPTIDE: TNANAFVSHLAGK [SEQ ID 115]
PEPTIDE: ALPVDVVANAYR [SEQ ID 116]

REGION: 175 to 205 - APIVAVYVYDVNNNANQLEPRQKEFLLAGNN [SEQ ID 37]
PEPTIDE: YVYDVNNNANQLEPRQKEFL [SEQ ID 117]
PEPTIDE: VYVYDVNNNANQLEPRQKEFL [SEQ ID 118]

REGION: 318 to 334 - ENPSRADSYNPRAGRIT [SEQ ID 38]
PEPTIDE: ADSYNPR [SEQ ID 119]

| SEQUENCE INFORMATION |
| --- |

```
REGION: 265 to 296 - GLQLLKPTLTQQQEQAQAQDQYQQVQYSERQQ [SEQ ID 39]
PEPTIDE: KPTLTQQQEQAQAQDQ [SEQ ID 120]
PEPTIDE: QAQAQDQYQQVQY [SEQ ID 121]
PEPTIDE: QAQDQYQQVQY [SEQ ID 122]

REGION: 45 to 62 - CRFDRLQAFEPLRKVRSE [SEQ ID 40]
PEPTIDE: LQAFEPLR [SEQ ID 123]

REGION: 361 to 408 - ILSPFWNVNAHSLVYMIQGRSRVQVVSNFGKTVFDGVLRPGQLLIIPQ [SEQ ID 41]
PEPTIDE: SRVQVVSNFGK [SEQ ID 124]
PEPTIDE: WNVNAHSLVY [SEQ ID 125]
PEPTIDE: NVNAHSLVY [SEQ ID 126]
PEPTIDE: IQGRSRVQVVSNFGK [SEQ ID 127]
PEPTIDE: GKTVFDGVLRPGQL [SEQ ID 128]
PEPTIDE: FGKTVFDGVLRPGQL [SEQ ID 129]

REGION: 476 to 499 - AFTPRFQQQYYPGLSNESESETSE [SEQ ID 42]
PEPTIDE: FQQQYYPGLSNESESETSE [SEQ ID 130]
PEPTIDE: QQYYPGLSN [SEQ ID 131]
PEPTIDE: QQQYYPGLSN [SEQ ID 132]

RICE PROTEIN 2: P07728 - 2 -
MASINRPIVFFTVCLFLLCNGSLAQQLLGQSTSQWQSSRRGSPRECRFDRLQAFEPIRSVRSQAGTTEFFDVSNEQFQCTGVSVVRRVIEPR
GLLLPHYTNGASLVYIIQGRGITGPTFPGCPESYQQQFQQSGQAQLTESQSQSQKFKDEHQKIHRFRQGDVIALPAGVAHWCYNDGEVPV
VAIYVTDLNNGANQLDPRQRDFLLAGNKRNPQAYRREVEERSQNIFSGFSTELLSEALGVSSQVARQLQCQNDQRGEIVRVEHGLSLLQPY
ASLQEQEQGQVQSRERYQEGQYQQSQYGSGCSNGLDETFCTLRVRQNIDNPNRADTYNPRAGRVTNLNTQNFPILSLVQMSAVKVNLY
QNALLSPFWNINAHSVVYITQGRARVQVVNNNGKTVFNGELRRGQLLIIPQHYAVVKKAQREGCAYIAFKTNPNSMVSHIAGKSSIFRAL
PNDVLANAYRISREEAQRLKHNRGDEFGAFTPIQYKSYQDVYNAAESS [SEQ ID 11]

REGION: 332 to 362 - PRAGRVTNLNTQNFPILSLVQMSAVKVNLYQ [SEQ ID 43]
PEPTIDE: VTNLNTQNFPILSLVQMSAVK [SEQ ID 133]

REGION: 375 to 406 - HSVVYITQGRARVQVVNNNGKTVFNGELRRGQ [SEQ ID 44]
PEPTIDE: ITQGRARVQVVNNNGKTVF [SEQ ID 134]
PEPTIDE: ITQGRARVQVVNNNGKTVFNGE [SEQ ID 135]
PEPTIDE: ITQGRARVQVVNNNGKTVFNG [SEQ ID 136]
PEPTIDE: RVQVVNNNGKTVF [SEQ ID 137]

REGION: 440 to 471 - HIAGKSSIFRALPNDVLANAYRISREEAQRLK [SEQ ID 45]
PEPTIDE: RALPNDVLANAYRISREE [SEQ ID 138]
PEPTIDE: SIFRALPNDVLANAYR [SEQ ID 139]
PEPTIDE: SIFRALPNDVLANAY [SEQ ID 140]
PEPTIDE: SIFRALPNDVLAN [SEQ ID 141]
PEPTIDE: SSIFRALPNDVLANAYR [SEQ ID 142]
PEPTIDE: SIFRALPNDVLANAYRISREE [SEQ ID 143]
PEPTIDE: SIFRALPND [SEQ ID 144]

REGION: 180 to 208 - VPVVAIYVTDLNNGANQLDPRQRDFLLAG [SEQ ID 46]
PEPTIDE: IYVTDLNNGANQLDPRQRD [SEQ ID 145]

RICE PROTEIN 3: P07730 - 2 -
MASINRPIVFFTVCLFLLCDGSLAQQLLGQSTSQWQSSRRGSPRGCRFDRLQAFEPIRSVRSQAGTTEFFDVSNELFQCTGVSVVRRVIEPR
GLLLPHYTNGASLVYIIQGRGITGPTFPGCPETYQQQFQQSGQAQLTESQSQSHKFKDEHQKIHRFRQGDVIALPAGVAHWCYNDGEVPV
VAIYVTDINNGANQLDPRQRDFLLAGNKRNPQAYRREVEEWSQNIFSGFSTELLSEAFGISNQVARQLQCQNDQRGEIVRVERGLSLLQPY
ASLQEQEQGQMQSREHYQEGGYQQSQYGSGCPNGLDETFCTMRVRQNIDNPNRADTYNPRAGRVTNLNSQNFPILNLVQMSAVKVN
LYQNALLSPFWNINAHSIVYITQGRAQVQVVNNNGKTVFNGELRRGQLLIVPQHYVVVKKAQREGCAYIAFKTNPNSMVSHIAGKSSIFR
ALPTDVLANAYRISREEAQRLKHNRGDEFGAFTPLQYKSYQDVYNVAESS [SEQ ID 12]

REGION: 311 to 362 - TFCTMRVRQNIDNPNRADTYNPRAGRVTNLNSQNFPILNLVQMSAVKVNLYQ [SEQ ID 47]
PEPTIDE: VTNLNSQNFPILNLVQMSAVK [SEQ ID 146]
PEPTIDE: QNIDNPNR [SEQ ID 147]
PEPTIDE: ADTYNPR [SEQ ID 148]
PEPTIDE: NIDNPNRADTYNPRAGRVTNL [SEQ ID 149]
PEPTIDE: RVRQNIDNPNRADTYNPRAGRVTNL [SEQ ID 150]

REGION: 427 to 499 -
YIAFKTNPNSMVSHIAGKSSIFRALPTDVLANAYRISREEAQRLKHNRGDEFGAFTPLQYKSYQDVYNVAESS [SEQ ID 48]
PEPTIDE: TNPNSMVSHIAGKSSIFR [SEQ ID 151]
PEPTIDE: HNRGDEFGAFTPLQYK [SEQ ID 152]
PEPTIDE: SYQDVYNVAESS [SEQ ID 153]
PEPTIDE: ISREEAQR [SEQ ID 154]
PEPTIDE: SIFRALPTDVLANAYRISREE [SEQ ID 155]
PEPTIDE: YRISREEAQRLKHNRGDEF [SEQ ID 156]
PEPTIDE: YRISREEAQRLKHNRGDE [SEQ ID 157]
```

SEQUENCE INFORMATION

REGION: 143 to 178 - SQSHKFKDEHQKIHRFRQGDVIALPAGVAHWCYNDG [SEQ ID 49]
PEPTIDE: FKDEHQKIHR [SEQ ID 158]
PEPTIDE: QGDVIALPAGVAHW [SEQ ID 159]

REGION: 381 to 409 - TQGRAQVQVVNNNGKTVFNGELRRGQLLI [SEQ ID 50]
PEPTIDE: TVFNGELRR [SEQ ID 160]
PEPTIDE: TVFNGELR [SEQ ID 161]
PEPTIDE: QVQVVNNNGKTVF [SEQ ID 162]

REGION: 101 to 124 - NGASLVYIIQGRGITGPTFPGCPE [SEQ ID 51]
PEPTIDE: YIIQGRGITGPTF [SEQ ID 163]
PEPTIDE: VYIIQGRGITGPTF [SEQ ID 164]

REGION: 46 to 66 - CRFDRLQAFEPIRSVRSQAGT [SEQ ID 52]
PEPTIDE: LQAFEPIRSVR [SEQ ID 165]

REGION: 253 to 292 - QNDQRGEIVRVERGLSLLQPYASLQEQEQGQMQSREHYQE [SEQ ID 53]
PEPTIDE: GLSLLQPYASLQEQEQGQMQSR [SEQ ID 166]
PEPTIDE: GEIVRVER [SEQ ID 167]
PEPTIDE: RGLSLLQPYASLQ [SEQ ID 168]
PEPTIDE: RGLSLLQPYASLQEQ [SEQ ID 169]
PEPTIDE: RGLSLLQPYASLQEQE [SEQ ID 170]
PEPTIDE: RGLSLLQPYASLQE [SEQ ID 171]

REGION: 199 to 233 - PRQRDFLLAGNKRNPQAYRREVEEWSQNIFSGFST [SEQ ID 54]
PEPTIDE: RNPQAYR [SEQ ID 172]
PEPTIDE: FLLAGNKRNPQAY [SEQ ID 173]
PEPTIDE: EVEEWSQNIF [SEQ ID 174]
PEPTIDE: LAGNKRNPQAYR [SEQ ID 175]
PEPTIDE: FLLAGNKRNPQA [SEQ ID 176]

RICE PROTEIN 4: Q0D750 - 3 -
MASNKVVFSVLLLAVVSVLAATATMAEYHHQDQVVYTPGPLCQPGMGYPMYPLPRCRALVKRQCVGRGTAAAAEQVRRDCCRQLAAV
DDSWCRCEAISHMLGGIYRELGAPDVGHPMSEVFRGCRRGDLERAAASLPAFCNVDIPNGGGVCYWLARSGY [SEQ ID 13]

REGION: 102 to 124 - GGIYRELGAPDVGHPMSEVFRGC [SEQ ID 55]
PEPTIDE: ELGAPDVGHPMSE [SEQ ID 177]

RICE PROTEIN 5: P14614 - 4 -
MATIAFSRLSIYFCVLLLCHGSMAQLFGPNVNPWHNPRQGGFRECRFDRLQAFEPLRRVRSEAGVTEYFDEKNEQFQCTGTFVIRRVIEPQ
GLLVPRYSNTPGMVYIIQGRGSMGLTFPGCPATYQQQFQQFLPEGQSQSQKFRDEHQKIHQFRQGDIVALPAGVAHWFYNEGDAPVVA
LYVFDLNNNANQLEPRQKEFLLAGNNNREQQMYGRSIEQHSGQNIFSGFNNELLSEALGVNALVAKRLQGQNDQRGEIIRVKNGLKLLRP
AFAQQQEQAQQQEQAQAQYQVQYSEEQQPSTRCNGLDENFCTIKARLNIENPSHADTYNPRAGRITRLNSQKFPILNLVQLSATRVNLY
QNAILSPFWNVNAHSLVYIVQGHARVQVVSNLGKTVFNGVLRPGQLLIIPQHYVVLKKAEHEGCQYISFKTNANSMVSHLAGKNSIFRAM
PVDVIANAYRISREQARSLKNNRGEELGAFTPRYQQQTYPGFSNESENEALE [SEQ ID 14]

REGION: 372 to 397 - HSLVYIVQGHARVQVVSNLGKTVFNG [SEQ ID 56]
PEPTIDE: IVQGHARVQVVSNLGK [SEQ ID 178]
PEPTIDE: IVQGHARVQVVSNL [SEQ ID 179]
PEPTIDE: IVQGHARVQVVSN [SEQ ID 180]

REGION: 464 to 486 - ARSLKNNRGEELGAFTPRYQQQT [SEQ ID 57]
PEPTIDE: NNRGEELGAFTPR [SEQ ID 181]
PEPTIDE: GEELGAFTPR [SEQ ID 182]

REGION: 337 to 359 - LNSQKFPILNLVQLSATRVNLYQ [SEQ ID 58]
PEPTIDE: FPILNLVQLSATR [SEQ ID 183]

REGION: 210 to 293 -
QMYGRSIEQHSGQNIFSGFNNELLSEALGVNALVAKRLQGQNDQRGEIIRVKNGLKLLRPAFAQQQEQAQQQEQAQAQYQVQYS [SEQ ID 59]
PEPTIDE: SIEQHSGQNIFSGFNNELLSEALGVNALVAK [SEQ ID 184]
PEPTIDE: LQGQNDQR [SEQ ID 185]
PEPTIDE: SGFNNELLSEALGVNALVAK [SEQ ID 186]
PEPTIDE: PAFAQQQEQAQQQEQAQAQY [SEQ ID 187]
PEPTIDE: VAKRLQGQNDQRGEI [SEQ ID 188]
PEPTIDE: ALVAKRLQGQNDQRGEI [SEQ ID 189]
PEPTIDE: LQGQNDQRGEIIR [SEQ ID 190]

REGION: 24 to 47 - AQLFGPNVNPWHNPRQGGFRECRF [SEQ ID 60]
PEPTIDE: PNVNPWHNPRQGGF [SEQ ID 191]

REGION: 164 to 186 - GVAHWFYNEGDAPVVALYVFDLN [SEQ ID 61]
PEPTIDE: FYNEGDAPVVALY [SEQ ID 192]
PEPTIDE: FYNEGDAPVV [SEQ ID 193]

| SEQUENCE INFORMATION |
| --- |

PEPTIDE: FYNEGDAPVVAL [SEQ ID 194]
PEPTIDE: FYNEGDAPVVA [SEQ ID 195]

REGION: 424 to 463 - YISFKTNANSMVSHLAGKNSIFRAMPVDVIANAYRISREQ [SEQ ID 62]
PEPTIDE: TNANSMVSHLAGK [SEQ ID 196]
PEPTIDE: AMPVDVIANAYR [SEQ ID 197]

RICE PROTEIN 6: Q0DEV5 - 5 -
**MSALTTSQLATSATGFGIADRSAPSSLLRHGFQGLKPRSPAGGDATSLSVTTSARATPKQQRSVQRGSRRFPSVVVYATGAGMNVVFVGA
EMAPWSKTGGLGDVLGGLPPAMAANGHRVMVISPRYDQYKDAWDTSVVAEIKVADRYERVRFFHCYKRGVDRVFIDHPSFLEKVWGK
TGEKIYGPDTGVDYKDNQMRFSLLCQAALEAPRILNLNNNPYFKGTYGEDVVFVCNDWHTGPLASYLKNNYQPNGIYRNAKVAFCIHNIS
YQGRFAFEDYPELNLSERFRSSFDFIDGYDTPVEGRKINWMKAGILEADRVLTVSPYYAEELISGIARGCELDNIMRLTGITGIVNGMDVSE
WDPSKDKYITAKYDATTAIEAKALNKEALQAEAGLPVDRKIPLIAFIGRLEEQKGPDVMAAAIPELMQEDVQIVLLGTGKKKFEKLLKSMEE
KYPGKVRAVVKFNAPLAHLIMAGADVLAVPSRFEPCGLIQLQGMRYGTPCACASTGGLVDTVIEGKTGFHMGRLSVDCKVVEPSDVKKV
AATLKRAIKVVGTPAYEEMVRNCMNQDLSWKGPAKNWENVLLGLGVAGSAPGIEGDEIAPLAKENVAAP** [SEQ ID 15]

REGION: 571 to 608 - KGPAKNWENVLLGLGVAGSAPGIEGDEIAPLAKENVAA [SEQ ID 63]
PEPTIDE: NWENVLLGLGVAGSAPGIEGDEIAPLAK [SEQ ID 198]
PEPTIDE: NVLLGLGVAGSAPGIEGDE [SEQ ID 199]
PEPTIDE: NWENVLLGLGVAGSAPGIEGDEIAPLAK [SEQ ID 200]

REGION: 458 to 488 - RAVVKFNAPLAHLIMAGADVLAVPSRFEPCG [SEQ ID 64]
PEPTIDE: FNAPLAHLIMAGADVLAVPSR [SEQ ID 201]
PEPTIDE: FNAPLAHLIM [SEQ ID 202]
PEPTIDE: FNAPLAHLIMAGADVLAVPSR [SEQ ID 203]

REGION: 545 to 566 - KRAIKVVGTPAYEEMVRNCMNQ [SEQ ID 65]
PEPTIDE: VVGTPAYEEMVR [SEQ ID 204]

REGION: 93 to 147 - APWSKTGGLGDVLGGLPPAMAANGHRVMVISPRYDQYKDAWDTSVVAEIKVADRY [SEQ ID 66]
PEPTIDE: TGGLGDVLGGLPPAMAANGHR [SEQ ID 205]
PEPTIDE: YDQYKDAWDTSVVAEIK [SEQ ID 206]
PEPTIDE: DAWDTSVVAEIK [SEQ ID 207]
PEPTIDE: VMVISPR [SEQ ID 208]

REGION: 305 to 413 -
INWMKAGILEADRVLTVSPYYAEELISGIARGCELDNIMRLTGITGIVNGMDVSEWDPSKDKYITAKYDATTAIEAKALNKEALQAEAGLPVDR
KIPLIAFIGRLEEQK [SEQ ID 67]
PEPTIDE: LTGITGIVNGMDVSEWDPSKDK [SEQ ID 209]
PEPTIDE: VLTVSPYYAEELISGIAR [SEQ ID 210]
PEPTIDE: EALQAEAGLPVDRK [SEQ ID 211]
PEPTIDE: YDATTAIEAK [SEQ ID 212]
PEPTIDE: IPLIAFIGR [SEQ ID 213]
PEPTIDE: AGILEADR [SEQ ID 214]
PEPTIDE: IPLIAFIGR [SEQ ID 215]

REGION: 158 to 202 - RGVDRVFIDHPSFLEKVWGKTGEKIYGPDTGVDYKDNQMRFSLLC [SEQ ID 68]
PEPTIDE: VFIDHPSFLEK [SEQ ID 216]
PEPTIDE: GPDTGVDYKDNQM [SEQ ID 217]
PEPTIDE: IYGPDTGVDYKDNQMR [SEQ ID 218]
PEPTIDE: IYGPDTGVDYK [SEQ ID 219]

REGION: 206 to 226 - LEAPRILNLNNNPYFKGTYGE [SEQ ID 69]
PEPTIDE: ILNLNNNPYFK [SEQ ID 220]

PROTEIN P02855
PEPTIDE: KNPQLQDLDI [SEQ ID 356]

PROTEIN P07730
PEPTIDE: GQSTSQWQSSR [SEQ ID 357]
PEPTIDE: QSTSQWQSSR [SEQ ID 358]

PROTEIN P07728
PEPTIDE: QSTSQWQSSR (also in P07730) [SEQ ID 359]

PROTEIN P13918
PEPTIDE: EEEQGEEEINK [SEQ ID 360]

PROTEIN P14323
PEPTIDE: PSTNPWHSPR [SEQ ID 361]
PEPTIDE: AQAQDQYQQVQYSE [SEQ ID 362]
PEPTIDE: SEAGVTEYFDEKNELFQCTGTFVIRR [SEQ ID 363]
PEPTIDE: QAQAQDQYQQVQYSE [SEQ ID 363]
PEPTIDE: GSMGLTFPGCPAT (also in P14614) [SEQ ID 365]
PEPTIDE: GSMGLTFPGCPATY (also in P14614) [SEQ ID 366]

SEQUENCE INFORMATION

PROTEIN P14614
PEPTIDE: LGAFTPRY [SEQ ID 367]
PEPTIDE: LGAFTPRYQQ [SEQ ID 368]
PEPTIDE: ALGVNALVAKRLQGQN [SEQ ID 369]
PEPTIDE: LGAFTPRYQ [SEQ ID 370]
PEPTIDE: GSMGLTFPGCPAT (also in P14323) [SEQ ID 371]
PEPTIDE: GSMGLTFPGCPATY (also in P14323) [SEQ ID 372]

PROTEIN P15838
PEPTIDE: SNNPFKFLVPARQS [SEQ ID 373]

PROTEIN Q6K508
PEPTIDE: CAGVFVIRR [SEQ ID 374]

PROTEIN Q6K7K6
PEPTIDE: GSPLQSPRGF [SEQ ID 375]
PEPTIDE: RSSWQQQSY [SEQ ID 376]
PEPTIDE: SFGGSPLQSPR [SEQ ID 377]
PEPTIDE: YLPTKQLQPTW [SEQ ID 378]
PEPTIDE: GKPRSSWQQQ [SEQ ID 379]
PEPTIDE: FGGSPLQSPRG [SEQ ID 380]

PROTEIN Q9M3X6
PEPTIDE: LNLLGFGINAENNE [SEQ ID 381]

ADDITIONAL PEPTIDES [SEQ ID 381 - 417]
LRGFSK [381]
GALMLPHYN
GALMLPHYNSR
VFDGVLRPG
LQSQND
LQSQNDQRGEI
QSQNDQRGEIIHVK
RGEIIHVK
RLQSQNDQ
RLQSQNDQRG [SEQ ID 390]
RLQSQNDQRGEIIH
MPMP
PMPL
LEPDNR
GIARLAGTSSVIN
RSQNIF
PNSM
GHPM
HPMS
FLPQHTD [SEQ ID 400]
EWQINEK
GPQQYAEWQINEK
PQQYAEWQ
RGPQQYA
HNPR
WHN
WDP
HPSF
PGQLQSFLLSGNQNQQNYLSGF
QLQSFLLSGNQNQQNYLSGFSK [SEQ ID 410]
QSFLLSGNQNQQ
PGQLQSFLLSGN
QSFLLSGNQ
QNQQNYLSGFSK
YLRGFS
PVEMPTLLYPS
RGPQQYAEWQINE [SEQ ID 417]
TVFDGVLRPGQL
LDALEPDNR
RLQSQNDQRGEIIHVK [SEQ ID 420]
VLDLAIPVNRPGQL
HGPVEMPYTLLYPSSK [SEQ ID 422]
GYYGEQQQQPGMTR [SEQ ID 423] PROTEIN: P29835 - 5 - RICE
SEEGYYGEQQQQPGMTR [SEQ ID 424] PROTEIN: P29835 - 5 - RICE

PROTEIN: P29835 - 5 - RICE
MASKVVFFAAALMAAMVAISGAQLSESEMRFRDRQCQREVQDSPLDACRQVLDRQLTGRERFQPMFRRPGALGLRMQCCQQLQDVSRE
CRCAAIRRMVRSYEESMPMPLEQGWSSSSSEYYGGEGSSSEQGYYGEGSSEEGYYGEQQQQPGMTRVRLTRARQYAAQLPSMCRVEPQQC
SIFAAGQY [SEQ ID 353]

| SEQUENCE INFORMATION |
|---|
| PROTEIN: P02857 - 1 - PEA<br>MAKLLALSLSFCFLLLGGCFALREQPQQNECQLERLDALEPDNRIESEGGLIETWNPNNKQFRCAGVALSRATLQRNALRRPYYSNAPQEIFIQ<br>QGNGYFGMVFPGCPETFEEPQESEQGEGRRYRDRHQKVNRFREGDIIAVPTGIVPMYNDQDTPVIAVSLTDIRSSNNQLDQMPRRFYLAG<br>NHEQEFLQYQHQQGGKQEQENEGNNIFSGFKRDYLEDAFNVNRHIVDRLQGRNEDEEKGAIVKVKGGLSIISPPEKQARHQRGSRQEEDED<br>EEKQPRHQRGSRQEEEEDEDEERQPRHQRRRGEEEEEDKKERGGSQKGKSRRQGDNGLEETVCTAKLRLNIGPSSSPDIYNPEAGRIKTVTSL<br>DLPVLRWLKLSAEHGSLHKNAMFVPHYNLNANSIIYALKGRARLQVVNCNGNTVFDGELEAGRALTVPQNYAVAAKSLSDRFSYVAFKTNDR<br>AGIARLAGTSSVINNLPLDVVAATFNLQRNEARQLKSNNPFKFLVPARESENRASA [SEQ ID 354]<br><br>PROTEIN: P09918 - 14 - *Pisum sativum*<br>MFSGVTGILNRGHKIKGTVVLMRKNVLDINSLTTVGGVIGQGFDILGSTVDNLTAFLGRSVSLQLISATKPDATGKGKLGKATFLEGIISSLPTLG<br>AGQSAFKIHFEWDDDMGIPGAFYIKNFMQTEFFLVSLTLDDIPNHGSIYFVCNSWIYNAKHHKIDRIFFANQTYLPSETPAPLVHYREEELNNLR<br>GDGTGERKEWERIYDYDVYNDLGNPDSGENHARPVLGGSETYPYPRRGRTGRKPTRKDPNSESRSDYVYLPRDEAFGHLKSSDFLTYGLKAVS<br>QNVVPALESVFFDLNFTPNEFDSFDEVHGLYEGGIKLPTNILSQISPLPVLKEIFRTDGENTLKYPPPKVIQVSRSGWMTDEEFAREMLAGVNPN<br>VICCLQEFPPRSKLDSQIYGDHTSKISKEHLEPNLEGLTVEEAIQNKKLFLLDHHDSIMPYLRRINSTSTKAYATRTILFLNNNQNLKPLAIELSLPHP<br>QGDEHGAVSYVYQPALEGVESSIWLLAKAYVIVNDSCYHQLVSHWLNTHAVVEPFVIATNRHLSCLHPIYKLLYPHYRDTMNINSLARLSLVND<br>GGIIEKTFLWGRYSMEMSSKVYKNWVFTEQALPADLIKRGMAIEDPSSPCGVKLVVEDYPYAVDGLEIWAIIKTWVQDYVSLYYTSDEKLRQD<br>SELQAWWKELVEVGHGDKKNEPWWPKMQTREDLIEVCSIVIWTASALHAAVNFGQYSYGGLILNRPTLSRRFMPEKGSAEFEELVKSPQKA<br>YLKTITPKFQTLIDLSVIEILSRHASDELYLGERDNPNWTSDKRALEAFKKFGNKLAEIEKKLTQRNNDEKLRNRHGPVEMPYTLLYPSSKEGLTFR<br>GIPNSISI [SEQ ID 355]<br><br>BACTERIAL PROTEIN 1: P0C1U8 - 5 -<br>MKGKFLKVSSLFVATLTTATLVSSPAANALSSKAMDNHPQQTQSSKQQTPKIQKGGNLKPLEQREHANVILPNNDRHQITDTTNGHYAPV<br>TYIQVEAPTGTFIASGVVVGKDTLLTNKHVVDATHGDPHALKAFPSAINQDNYPNGGFTAEQITKYSGEGDLAIVKFSPNEQNKHIGEVVK<br>PATMSNNAETQVNQNITVTGYPGDKPVATMWESKGKITYLKGEAMQYDLSTTGGNSGSPVFNEKNEVIGIHWGGVPNEFNGAVFINEN<br>VRNFLKQNIEDIHFANDDQPNNPDNPDNPNNPDNPNNPDEPNNPDNPNNPDNPDNGDNNNSDNPDAA [SEQ ID 16]<br><br>REGION: 92 to 117 - YIQVEAPTGTFIASGVVVGKDTLLTN [SEQ ID 70]<br>PEPTIDE: APTGTFIASGVVVGKD [SEQ ID 221] |
| Homologs of Pea protein 1 (SEQ ID 1) |
| >gi\|137584\|sp\|P08438.1\|VCL_VICFA RecName: Full = Vicilin; Flags: Precursor [*Vicia faba*]>gi\|22057\|<br>emb\|CAA68559.1\|vicilin [*Vicia faba* var. minor]>gi\|383931031\|gb\|AFH56916.1\| vicilin [*Vicia faba*]<br>MAATTLKDSFPLLTLLGIAFLASVCLSSRSDQDNPFVFESNRFQTLFENENGHIRLLQKFDQHSKLLENLQNYRLLEYKSKPHTIFLPQQTDADFIL<br>VVLSGKAILTVLLPNDRNSFSLERGDTIKLPAGTIGYLVNRDDEEDLRVLDLVIPVNRPGEPQSFLLSGNQNQPSILSGFSKNILEASFNTDYKEIEK<br>VLLEEHGKEKYHRRGLKDRRQRGQEENVIVKISRKQIEELNKNAKSSSKKSTSSESEPFNLRSREPIYSNKFGKFFEITPKRNPQLQDLNIFVNYVEI<br>NEGSLLLPHYNSRAIVIVTVNEGKGDFELVGQRNENQQGLREEYDEEKEQGEEEIRKQVQNYKAKLSPGDVLVIPAGYPVAIKASSNLNLVGFGI<br>NAENNQRYFLAGEEDNVISQIHKPVKELAFPGSAQEVDTLLENQKQSHFANAQPRERERGSQEIKDHLYSILGSF [SEQ ID 222]<br><br>>gi\|502105533\|ref\|XP_004492829.1\| PREDICTED: vicilin-like isoform X1 [*Cicer arietinum*] ChickPea<br>MAIKARFPLLVLLGIVPLASVCAKSDKENPFFFKSNNCQTLFENENGHVRLLQRFDKRSQLFENLQNYRLMEYNSKPHTLFLPQHNDADFILVVL<br>RGRAILTVLNPNDRNTFKLERGDTIKLPAGTIAYLANRDDNEDLRVLDLAIPVNRPGQFQSFSLSGNENQQSYFQGFSKKILEASFNSDYEEIERV<br>LLEEQEQKPEQRRGHKGRQQSQETDVIVKISREQIEELSKNAKSNCKKSVSSESEPFNLRSRSPIYSNRFGNFFEITPEKNPQLKDLDIFVNSVEIK<br>EGSLLLPHFNSRATVILVVNEGKGEVELVGLRNENEQENKKEDEEEEEDRNVQVQRFQSKLSSGDVVVIPASHPFSINASSDLFLLGFGINAQN<br>NQRRNFLAGEEDNVISQIQRPVKEVAFPGSAEEVDRLLKNQRQSHFANAQPQQKRKGSQRIRSPF [SEQ ID 223]<br><br>>gi\|29539109\|emb\|CAD87730.1\| allergen Len c 1.0101 [Lens culinaris] Lentil<br>SRSDQENPFIFKSNRFQTIYENENGHIRLLQRFDKRSKIFENLQNYRLLEYKSKPHTIFLPQFTDADFILVVLSGKAILTVLNSNDRNSFNLERGDTI<br>KLPAGTIAYLANRDDNEDLRVLDLAIPVNRPGQLQSFLLSGTQNQPSFLSGFSKNILEAAFNTEYEEIEKVLLEEQEQKSQHRRSLRDKRQEITNE<br>DVIVKVSREQIEELSKNAKSSSKKSVSSESEPFNLRSRNPIYSNKFGKFFEITPEKNPQLDLDIFVNSVEIKEGSLLLPNYNSRAIVIVTVNEGKGDF<br>ELVGQRNENQQEQREENDEEEGQEEETTKQVQRYRARLSPGDVLVIPAGHPVAINASSDLNLIGFGINAKNNQRNFLAGEEDNVISQIQRPV<br>KELAFPGSSREVDRLLTNQKQSHFANAQPLQIE [SEQ ID 224] |
| Homologs of Pea protein 2 (SEQ ID 2) |
| >gi\|29539111\|emb\|CAD87731.1\| allergen Len c 1.0102 [*Lens culinaris*]<br>SRSDQENPFIFKSNRFQTIYENENGHIRLLQKFDKRSKIFENLQNYRLLEYKSKPHTLFLPQYTDADFILVVLSGKAVLTVLNSNDRNSFNLERGDT<br>IKLPAGTIAYLANRDDNEDLRVLDLAIPVNNPGQLESFLLSGTQNQPSFLSGFNKSILEAAFNTDYEEIEKVLLEDEQEPQHRRSLRDRRQEINK<br>ENVIVKVSREQIKELSKNAKSSSKKSVSSESEPFNLRSRNPIYSNKFGKFFEITPEKNPQLDLDIFVNSVEIKEGSLLLPNYNSRAIVIVTVNEGKGY<br>FELVGQRNENQREENDDEEEQEEETSTQVQRYRAKLSPGDVFVVPAGHPVAINASSDLNLIGFGINAKNNQRNFLAGEEDNVISQIQRPVKEL<br>AFPGSSREVDRLLTNQKQSHFANAQPLQIE [SEQ ID 225]<br><br>>gi\|1297072\|emb\|CAA96514.1\| vicilin precursor [*Vicia narbonensis*]<br>MAAITMKVSFPLLMLLGISFLASVCVSSRSDQDNPFIFKSNRFQTLFENDNGHIRLLQKFDERSKILENLQNYRLLEYKSKPRTIFLPQQTNADFIL<br>VVLSGKAILTVLKPDDRNSFNLERGDTIKLPAGTIAYLVNKDDNEDLRVLDLAIPVNGPDQLQSFLLSGSENQQSILSGFSKSVLEASFNTGYEEIE<br>KVLLEEREKETQHRRSLRDKRQHSQDEDVIVKLSRGQIEELSRNAKSSSKKSVSSESEPFNLRSRNPIYSNKFGKFFEITPEKNPQLDLDVLVNSV<br>EIKEGSLLLPHYNSRAIVIVTVNDGKGDFEIVGQRNENRQGQRKEDDEEEEQGDENTNTQVQNYKAKLSRGDVFVIPAGHPVSIKASSNLDLLG<br>FGINAKNNQRNFLAGEEDNVISQIDRPVKELAFPGSAQEVDRLLENQKQSHFANAQPQQRERGSHETRDHLSSILDAF [SEQ ID 226]<br><br>>gi\|28629838\|gb\|AAO45103.1\| beta-conglycinin alpha' subunit [*Glycine max*]<br>QYGHVRVLQRFNKRSQQLQNLRDYRILEFNSKPNTLLLPHHADADYLIVILNGTAILTLVNNDDRDSYNLQSGDALRVPAGTTYYVVNPDNDE<br>NLRMITLAIPVNKPGRFESFFLSSTQAQQSYLQGFSKNILEASYDTKFEEINKVLFGREEGQQQGEERLQESVIVEISKKQIRELSKHAKSSSRKTIS<br>SEDKPFNLRSRDPIYSNKLGKLFEITPEKNPQLRDLDVFLSVVDMNEGALFLPHFNSKAIVVLVINEGEANIELVGIKEQQRQQQEEPLEVRK<br>YRAELSEQDIFVIPAGYPVVVNATSDLNFFAFGINAENNQRNFLAGSKDNVISQIPSQVQELAFPGSAKDIENLIKSQSESYFVDAQPQQKEEGN<br>KGRKGPLSSILRAFY [SEQ ID 227] |

SEQUENCE INFORMATION

Homologs of Pea protein 3 (SEQ ID 3)

```
>gi|483449|emb|CAA83677.1| legumin A [Vicia sativa]
MAKLLALSLSFCFLLFSSCFALREQSQQNECQLERINALEPDNRIESEGGLIETWNPNNRQFRCARVALSRATLQRNALRPPYYSNAPQEIYIQQ
GNGYFGMVFPGCPETHEEPQQSEQGEGRRYRDSHQKVNRFREGDIIAVPTGIAFWMYNDQDTPVIAISLTDTGSSNNQLDQMPRRFYLAG
NQEQEFLRYQHQQGGKQEQDNDGNNIFSGFKRDFLEDAFNVNRHIVDRLQGRNEDEEKGAIVKVKGGLSIIAPPERQARHERGSRQEEDED
EKEEQRPSHHKSRRDEDEDDKEKRHSQKGQSRRQGDNGLEETVCTAKLRANIGSSPSPDIYNPQAGRIKTVTSLDLPVLRWLKLSAEHGSLHK
NAMFVPHYNLNANSVIYALKGRARLQVVNCNGNTVFDGELEAGRALTVPQNYAVAAKSLSERFTYVAFKTDDRASIARLAGTSSVIDDLPLDV
VAATFNMQRNEARQLKSNNPFKFLVPPRQSEMRASA [SEQ ID 228]

>gi|657379551|gb|KEH23931.1| legumin A2 [Medicago truncatula]
MAKLLALSLSLCFLLFSGCFAIREHQPHQKQQPQQNECQLEQLNALEPDNRIESEGGIIETWNPNNRQFRCAGVALSRCTLQRNSLRRPFYSNA
PQEIFIQQGSGYFGMVFPGCPETFEEPQESEQRESRRIRESEQGESRRIRESEQGEGRRFRDSHQKVNRFREGDLIAVPTGTVFWMYNDQDTP
VIAVSLIDTGSFQNQLDEMPRRFYLAGNQEQEFLQYQQQQVRGRGEQRRGREQQENEGGNIFSGFKRDFLEDALNVNRHIVDRLQGRNEDE
EKGAIVKVRGGLSFVTPPERQSRHQGGSIIEEDEDEEDEWRRPHHQKSRRGEEEERPCRRGQKCERSNGLEETICTARLRQNIGSSSSPDIYNPE
AGRIKTVTSFDLPALRWLRLSAEHGTLHRNAMFVPHYNLNANSAIYALRGRARLQVVNCNGNTVFDGELEAGRVLIVPQNFAVAAKSMSDRF
QYVSFKTNDNAAIARLAGTQSTLSGVPMDVLAATYNMDRNEARQLKNNNLYKFLVPPRESERRAAA [SEQ ID 229]

>gi|206712292|emb|CAR78996.1| legumin storage protein 5 [Lotus japonicus]
MAYKLFALSLSFCFLLFGGCFAIRQQSQQQNECQLERLNALKPDNRIESEAGYIETWNPTNNQFRCAGVALSRCTLRRNGLKRPSYSNAPQEIFI
QQGSGIFGMIFPGCPETVEEPFESDQQGRRDRHQKVNRFREGDVIAVPPGVVFWMYNEEETPVIAVSLIDTGSYLNQLDQMPRRFYLSGNQ
EQEFLQYQRQEVRGREEENQGGNIFSGFGGEFLEDALNIDRNIVHKLQGRDEEQDKGAIVRVKGGLSVITPPERQSHRRGSEEEEDEEEDRPS
RHQSRGGSRRNGLEETICTVRLRMNIGKSSSPDIFNPQAGRIKTATGFDFPALRFLKLSAEHGSLNRNAMVVPHYNLNANSIIYALRGRAWIQV
VNCKGNRIFDGELEEGQVLIVPQNFVVAARSMSDKFNYVAFKTNDMPTMAKLAGATSEIQAMPLEVIQNAFNLEREQAKQVKFNNRFNFLV
PPREQSQRRASA [SEQ ID 230]
```

Homologs of Pea protein 4 (SEQ ID 4)

```
>gi|164512526|emb|CAP06312.1| cvc [Pisum abyssinicum]
MATTVESRFPLLLFPGIIFLASVCVTYANYDEGSETRVPGQRERGRQEGEKEEKRHGEWRPSYEKEEDEEEKQKYRYQREKEDEEEKQKYRYQR
EKKEEKEVQPGRERWEREEDEEQVDEEWRGSQRRQDPEERARLRHREERTKRDRRHKREGEEEERSSESQEQRNPFLFKSNKFLTLFENENG
HIRRLQRFDKRSDLFENLQNYRLVEYRAKPHTIFLPQHIDADLILVVLNGKAILTVLSPNDRNSYNLERGDTIKIPAGTTSYLVNQDDEEDLRVVD
FVIPVNRPGKFEAFGLSENKNQYLRGFSKNILEASLNTKYETIEKVLLEEQEKKPQQLRDRKRRQQGGERDAIIKVSREQIEELRKLAKSSSKKSLPS
EFEPFNLRSHKPEYSNKFGKLFEITPEKKYPQLQDLDILVSCVEINKGALMLPHYNSRAIVVLLVNEGKGNLELLGLKNEQQEREDRKERNNEVQ
RYEARLSPGDVVIIPAGHPVAISASSNLNLLGFGTNAENNQRNFLSGSDDN [SEQ ID 231]

>gi|164512538|emb|CAP06318.1| cvc [Lathyrus annuus]
MATTIKSRFPLLLLLGIIFLASVCVTWANYDEGSEPRVPGQRERGRQEGEKEEKRHGEWRPSYEEYDEGLEPKVPGKRERGRQEGEKEEKRHE
EWRPSYEKEEDEEEKQKYNYQREKKEHKEVQPGRERWERKQDEKQVEEDEEPGEEQWRGSKRHEDPEERARLRHREEKTKSYVEDNEETSS
KEGRNPFLFKSNKFLTLFENENGHIRRLQRFDERSDIFENLQNYRLVEYRAKPHTMFLPQHIDADLILVVLNGKAILTVLSPNDRNSYNLERGDT
VKLPAGTTSYLVNQDDEEDLRVVDLAIPVNRPGKFEAFGLSANKNQYLRGFSKNILEASLNTKYETIEKVLLEERRDQKGRQQGQETNAIVKVSR
EQIEELRKLAKSSSKKSLLSESEPLNLRSQNPKYSNKFGKFFEITPQKKYPQLQDLDVSISCVEINKGALLLPHYNSRSIGILLVNEGKGNLELVGFKN
EQQRQRENEETNKKLQRYEARLSSGDVVVIPEGHPVAISASSNLNLLGFGINAANNQRNFLTGSDDN [SEQ ID 232]

>gi|164512558|emb|CAP06328.1| cvc [Vicia villosa]
MATTIKSRFPVLLLLGIIFLTSVCVTYANYDEGREPSVPGQRERGRQEGEKEEKRHGEWRPSEEDEEEKYKYEEGRVPGQRERGRQEGEKEEKR
HGKWRPSEEEDEEEKYRYEEGSEPRGPGQRETGRQEGEKEKQRPEREPSYEKEEDEEEKQKYQYHREKKEQREVRPGRERFERHEDEEQWRG
IQRHEDPEERARERYRAEIAKRQVEEEREDIPHEREQRNPFLFKSNKFLTLFENENGYIRRLQRFDKRSDLFENLQNYRLVEYRAKPHTIFLPQ
HIDADLIIVVLSGRAILTVLSPDDRNSYNLERGDTIKLPAGTTSYLVNQDDEEDLRVVDLAIPVNRPGKVESFLLSGNKNQYLRGFSKNILEASFNT
NYETIERVLLEEQDKESQQSIGQKRRSQRQETNALVKVSREQLEDLKRLAKSSSQEGLSSQFEPINLRSQNPKYSNKFGKVFEITPEKKYPQLQDL
DLFVSSVDIKEGALMLPHYNSRAIVVLLVNEGRGNLELVGLKNEQQEQREKEDEQQERNNQVQRYEARLSPGDVVIIPAGHPVAVRASSDLNL
LAFGINAENNQRNFLAGSDDN [SEQ ID 233]
```

Homologs of Pea protein 5 (SEQ ID 5)

```
>gi|357507721|ref|XP_003624149.1| Provicilin [Medicago truncatula]
>gi|87162569|gb|ABD28364.1| Cupin, RmlC-type[Medicago truncatula]
>gi|355499164|gb|AES80367.1| vicilin 47 kDa protein [Medicago truncatula]
MAIKAPFQLLMLLGIFFLASVCVSSRDDRHDQENPFFFNANHFQTLFENENGHIRLLQRFDKRSKIFENLQNYRLLEYHSKPHTLFLPQHNDAD
FILAVLSGKAILTVLNPDNRNSFNLKLPAGSIAYLANRLDLAIPVNRPGKFQSFSLSGSQNQQSFFSGFSKNILEAAFNANY
EEIERVLIEEHEQEPQHRRGLRKDRRQQSQDSNVIVKVSREQIEELSRHAKSSRRSGSSESAPFNLRSREPIYSNEFGNFFEITPEKNPQLKDLIL
VNYAEIREGSLLLPHFNSRATVIVVVDEGKGEFELVGQRNENQQEQREEDEQQEEERSQQVQRYARLSPGDVYVIPAGHPTVVSASSDLLL
GFGINAAENNERNFLAGEEDNVISQIERPVKEVAFPGSAQDVESLLKNQRQSYFANAQPQQREREEGRSQRQRELISSILGVF [SEQ ID 234]

>gi|164512560|emb|CAP06329.1| convicilin [Vicia peregrina]
MATTFKSRFSLLLLLGIIFLAFVCVTCANYDEGSEPRVPGQRERGRQEGEKEEQSRERHPQREPSREKEEDEEEKQKYDEGTEPRVPGQRERGR
QEGEKEEQRRERHPGQREPSQEEDEERREESDRRQEGSSKSEEQRNPFLFKSNKFLTLFQNGNGHIRLLQRFDKRSDLFENLQNYRLLEYRAKPH
TIFLPQHIDADLILVVLSGRAILTVLSPDDRNSYNLERGDTIKLPAGTTSYPLNQDDEEDLRVVDLAISVNRPGKVESFNLSGNKNQYLRGFSENIL
EASFNTKYETIEKVLLEEQDKESQQPRGQRLQRQETNALVKVSREQVEELKRLARTSSKKGVSSEFEPFNLRSHGPKYSNKFGKFFEITPEKKYPQ
LQDLDISVSSVEINEGALFLPHYNSRAIVVVLVDEGKGNLELVGFKNEQQEQREKEDEQEERNKQVQRYEAKLSPGDVVIIPAGHPVAVSASSN
LNLLGFGINAENNQRNFLTGSDDN [SEQ ID 235]

>gi|164512562|emb|CAP06330.1| convicilin [Vicia lutea]
MATTIKLRFPLLLLLGVILLASVCVTCANYDEGSEPRVPGRPEGEKEEKHRGKLRPSYEKEEDEGEKQRYHYEKKEQKEAQPRREKKEQKEEEKQ
VEEESRESQRYEDPGERARERYRAEIIKRQVEKEREERDRHQREGEEEEGSSKSRNPFLFKSNNFLTLFENENGHIRLLQRFDKRSDLFENLQNY
RLVEYRAKPHTIFLPQHIDADLILVVLSGKAILTVLSPNNRNSYNLKRGDTIKLPAGTTSYLLNSDDEEDLRMVDLAISVNRPGKVESFNLSGNKN
```

| SEQUENCE INFORMATION |
| --- |
| QYLRGFSKNILEASFNTKYETIEKVLLEEQDKESQQSIGQKRISQRQETNALVKVSREQIEEPKRLARSSSRKGVSSEFEPINLRSQRPKYSNKFGKF<br>YEISPEKKYPQLQDLDVSVSSVEINEGALLLPHYNSRAIVTVLVNEGKGNLELIGFQNEQQGQREKEDEQQHERNKQVQRYDARLSSGDVVIIP<br>AGHPVAVSASSNLDLLGFGINAENSQRNFLTGSDDN [SEQ ID 236] |
| Homologs of Rice protein 1 (SEQ ID 6) |
| >gi\|573919041\|ref\|XP_006647142.1\| PREDICTED: glutelin type-B 4-like [*Oryza brachyantha*]<br>MATTTFSRFSIYFCVLLLCHGSMAQLFSPTLNPWHSSRRGGSRDCRFDRLQAFEPLRRVRSEAGVTEYFDERNEQFQCTGTFVIRRVIEPQGLL<br>VPRYTNTPGVVYIMQGRGSMGLTFPGCPATYQQQFQQFLPEGQSQSQKFRDEHQKIHQFRQGDIVALPAGVAHWFYNEGDTPVVALYVFD<br>INNSANQLEPRQKDFLLAGNNNREQQVYGRSIEKHSGQNIFSGFNHELLSEALGISTLAAKRLQGQNDHRGEIIRVRNGLQLLKPTFTQQQEQ<br>AQSQYQVQYSEKQQESTRCNGLDENFCTINARLNIENPSRADTYNPRAGRITHLNNQKFPILNLVQMSATRVNLYQNAILSPYWNVNAHSLV<br>YMVQGHARVQVVSNLGKTVFNSVLRPGQLLIIPQHYVVLKKAEREGCQYIAFKTNANSIVSQLAGKNSILRAMPVDVVANAYRISREQARDLK<br>NNRGEELGAFTPKFEQQSYPGLSNESESEASE [SEQ ID 237] |
| >gi\|2764800\|emb\|CAA54153.1\| 12s globulin [*Avena sativa*]<br>MATTSFPSVLFYSCIFLLYNGSMAQLFGQSFTPWQSSRQGGLKGCKFDRLQAFEPLRQVRSQAGVTEYFDEQNEQFRCTGVFVIRRVIEPQGL<br>LLPQYHNAPGLVYILQGRGYTGLTFPGCPATFQQQFQPFDQAQDQSQSHLKDEHQRVHRFKQGDVIALPAGIVHWGYNDGDAPVVAIYVF<br>DVNNNANQLEPRQKEFLLAGNNKEDQQFGQNIFSGFNIQLLSEALGISQQAAQRIQSQKEQRGEIIRVTQALQFLKPTMSQQELVEHQAYQP<br>IQSQEGQSTQYQVGQSTQYQEGQSTQYQAGQSQDRSFNGLEENFCSLEARQNIGNPKRADTHNPRAGRITRLHGQNFPILNLVQMSATRV<br>NLYQNAILSPFWNINAHSVVYMIQGHAQVQVVNNNGQTVFNDRLRQGQLLIVPQHYVVLKKAEREGCQYISFKTNPNSMVSHIAGKSSILRA<br>LPVDVLANAYRISRQEARNLKNNRGQESGVFTPKFTQTSFQPYPEGEDESSLTNKASE [SEQ ID 238] |
| >gi\|357130026\|ref\|XP_003566659.1\| PREDICTED: 12S seed storage globulin 1-like [*Brachypodium distachyon*]<br>>gi\|357130028\|ref\|XP_003566660.1\| PREDICTED: 12S seed storage globulin 1-like [*Brachypodium distachyon*]<br>MAHTSFSSVLSYFCIFLLFHGSMAQVPGQGSTWQSPRQGGSRECSFDRLQTIEPLTQVRSQAGLTEYFDEQNEQFRCAGVSVIRRVIEPRGLLL<br>PRYHNTPGLVYILEGSSGFVGLAFPGCPETFLEQFQQSRQTQSTLGQSQCQSQSQLDVHQRVHQFTQGDVVALPAGVAHWFYNGGDAPV<br>VAVYVFDVNNNANQLEPRQKEFLLAGNYNGVLQSGRNILNGLNAQLLSQAFGINEQTSRIIQNQNDGRGEIVRVEYGLQFLTPVVTQQQQK<br>QPFLPIEPQEGQSSRNGLEENFCSLEPRQNIEDPNRADTYNPRAGSIARLNGQNPILNLVQMSATRVNLQKNAIVSPFWNINAHSVVYVIQG<br>QASVQVVNNQGRNVFNGLLRRGQLLIIPQNYVVLKKAESEGYQYIAFKTNANSMVSHIAGKNSILRALPVDVIANAYRISRQEAQNLKNNRGE<br>EIGVLTPNFPQSSCQSYPIGDVDSSSTPKAQE [SEQ ID 239] |
| Homologs of Rice protein 2 (SEQ ID 7) |
| >gi\|222622792\|gb\|EEE56924.1\| hypothetical protein OsJ_06602 [*Oryza sativa Japonica* Group]<br>MAQFSFGGSPLQSPRGFRGDQDSRHQCRFEHLTALEATHQQRSEAGFTEYYNIEARNEFRCAGVSVRRLVVESKGLVLPMYANAHKLVYIQ<br>GRGVFGMALPGCPETFQSVRSPFEQEVATAGEAQSSIQKMRDEHQQLHQFHQGDVIAVPAGVAHWLYNNGDSPVVAFTVIDTSNNANQL<br>DPKRREFFLAGKPRSSWQQQSYSYQTEQLSRNQNIFAGFSPDLLSEALSVSKQTVLRLQGLSDPRGAIIRVENGLQALQPSLQVEPVKEEQTQA<br>YLPTKQLQPTWLRSGGACGQQNVLDEIMCAFKLRKNIDNPQSSDIFNPHGGRITRANSQNFPILNIIQMSATRIVLQNNALLTPHWTVNAHT<br>VMYVTAGQGHIQVVDHRGRSVFDGELHQQQILLIPQNFAVVVKARREGFAWVSFKTNHNAVDSQIAGKASILRALPVDVVANAYRLSREDS<br>RHVKFNRGDEMAVFAPRRGPQQYAEWQINEK [SEQ ID 240] |
| >gi\|218190679\|gb\|EEC73106.1\| hypothetical protein OsI_07091 [*Oryza sativa Indica* Group]<br>MAQFSFGGSPLQSPRGFRGDQDSRHQCRFEHLTALEATHQQRSEAGFTEYYNIEARNEFRCAGVSVRRLVVESKGLVLPMYANAHKLVYIQ<br>GRGVFGMALPGCPETFQSVRSPFEQEVATAGEAQSSMQKMRDEHQQLHQFHQGDVIAVPAGVAHWLYNNGDSPVVAFTVIDTSNNANQ<br>LDPKRREFFLAGKPRSSWQQQSYSYQTEQLSRNQNIFAGFNPDLLSEALSVSKQTVLRLQGLSDPRGAIIRVENGLQALQPSLQVEPVKEEQTQ<br>AYLPTKQLQPTWSRSGGACGQQNGLDEIMCAFKLRKNIDNPQSSDIFNPHGGRITRANSQNFPILNIIQMSATRIVLQNNALLTPHWTVNAH<br>TVMYVTAGQGRIQVVDHRGRSVFDGELHQQQILLIPQNFAVVVKARREGFAWVSFKTNHNAVDSQIAGKASILRALPVDVVANAYRLSREDS<br>RRVKFNRGDEMAVFAPRRGPQQYAEWQINEK [SEQ ID 241] |
| >gi\|573922051\|ref\|XP_006648611.1\| PREDICTED: glutelin type-A 1-like [*Oryza brachyantha*]<br>MVDMSIVVPVCLTIFLLSQVCIAQVSFDGSPLYSSRGFRGGSASQQQCRFEHLAALEVTHQEKSEAGSIEYYNTEARDEFRCARVSARRLVIESR<br>GLVLPVYANAHKLLYIVQGRGVFGMALPGCPETFQSVRSAFEMATGDAESSTRKLRDEHQKIHQFRQGDVIAVPPGVAHWLYNNGDSPVVA<br>FSVIDFGNNANQLDPKREFFLAGKPWGWQQVQYSYQSEQQSKHQNIFAGFNPDLLAEALSVSRQTAMRLQELNDQRGAIIRVEQGLQLAL<br>DPSFQAEQEQEEQPQEYLSSQQQQPTWSQRSGACVQNNGLDEIMCAFKVSKNINSAQSTDIFNPRGGRITRANSQNFPVLNIIQMSATRTV<br>LQNNALLTPHWTVNAHTVMYVTAGQGRIQVVDHRGRTVFDGELRQQQILLIPQNFAVAVKARHEGFSWVSFKTSHNAIDSQIAGKSILRA<br>LPVDVLAKAYMLSREESRTLKYNRADETLVFAPRPEIQLYAESEK [SEQ ID 242] |
| Homologs of Pea protein 6 (SEQ ID 8) |
| >gi\|164512534\|emb\|CAP06316.1\| cvc [*Pisum fulvum*]<br>MATTTKSRFPLLLLLGIIFLASVVCVTYANYDEGSEPRVPGRRERGRQEGEKEEKRHGEWRPSYEKEEDEEEGQRERGRQEGEKEEKRHGEWG<br>PSYEKQEDEEEKQKYRYQREKEDEEEKQKYRYQREKKEQKEVQPGRERWEREEDEEHVDEEWRGSQRHEDPEERARLRYREERTKRDRRHQ<br>REGEEEERSSESQERRNPFLFKSNKFQTLFENENGHIRLLQRFDKRSDLFENLQNYRLVEYRAKPHTIFLPQHIDADLILVVLSGKAILTVLSPNAR<br>NSYNLERGDTIKLPAGTTSYLVNQDEEDLRLVDLVIPVNGPGKFEAFDLSKNKNQYLRGFSKNILEASYNTKYETIEKVLLEEQEKTDAIVKVSRE<br>QIEELRKHAKSSSKKIFPSEFEPINLRNHKPEYSNKFGKLFEITPEKKYPQLQDLDIFVSCVEINEGALMLPHYNSRAIVVLLVNEGKGNLELLGLEN<br>EQQEREDRKERNNEVQRYEARLSPGDVVIIPAGHPVAITASSNLNLLAFGINAENNQRNFLSGSDDN [SEQ ID 243] |
| >gi\|164512526\|emb\|CAP06312.1\| cvc [*Pisum abyssinicum*]<br>MATTVESRFPLLLFPGIIFLASVCVTYANYDEGSETRVPGQRERGRQEGEKEEKRHGEWRPSYEKEEDEEEKQKYRYQREKEDEEEKQKYRYQR<br>EKKEEKEVQPGRERWEREEDEEQVDEEWRGSQRRQDPEERARLRHEERTKRDRRHKREGEEEERSSESQEQRNPFLFKSNKFLTLFENENG<br>HIRRLQRFDKRSDLFENLQNYRLVEYRAKPHTIFLPQHIDADLILVVLNGKAILTVLSPNDRNSYNLERGDTIKIPAGTTSYLVNQDDEEDLRVVD<br>FVIPVNRPGKFEAFGLSENKNQYLRGFSKNILEASLNTKYETIEKVLLEEQEKKPQQLRDRKRRQQGGERDAIIKVSREQIEELRKLAKSSSKKSLPS<br>EFEPFNLRSHKPEYSNKFGKLFEITPEKKYPQLQDLDILVSCVEINKGALMLPHYNSRAIVVLLVNEGKGNLELLGLKNEQQEREDRKERNNEVQ<br>RYEARLSPGDVVIIPAGHPVAISASSNLNLLGFGTNAENNQRNFLSGSDDN [SEQ ID 244] |

| SEQUENCE INFORMATION |
| --- |

>gi|164512558|emb|CAP06328.1| cvc [*Vicia villosa*]
MATTIKSRFPVLLLLGIIFLTSVCVTYANYDEGREPSVPGQRERGRQEGEKEEKRHGEWRPSEEDEEEKYKYEEGRVPGQRERGRQEGEKEEKR
HGKWRPSEEEDEEEKYRYEEGSEPRGPGQRETGRQEGEKEKQRPEREPSYEKEEDEEEKQKYQYHREKKEQREVRPGRERFERHEDEEQWRG
IQRHEDPEERARERYRAEIAKRQVEEEREERDIPHEREQRNPFLFKSNKFQTLFQNENGYIRRLQRFDKRSDLFENLQNYRLVEYRAKPHTIFLPQ
HIDADLIIVVLSGRAILTVLSPDDRNSYNLERGDTIKLPAGTTSYLVNQDDEEDLRVVDLAIPVNRPGKVESFLLSGNKNQYLRGFSKNILEASFNT
NYETIERVLLEEQDKESQQSIGQKRRSQRQETNALVKVSREQLEDLKRLAKSSSQEGLSSQFEPINLRSQNPKYSNKFGKVFEITPEKKYPQLQDL
DLFVSSVDIKEGALMLPHYNSRAIVVLLVNEGRGNLELVGLKNEQQEQREKEDEQQERNNQVQRYEARLSPGDVVIIPAGHPVAVRASSDLNL
LAFGINAENNQRNFLAGSDDN [SEQ ID 245]

| Homologs of Pea protein 7 (SEQ ID 9) |
| --- |

>gi|164512536|emb|CAP06317.1| cvc [*Lathyrus hirsutus*]
MAIIIKSRFPLLLLLGIIFLASVCATWANYDEGSEPRVPGQRERGRQEGEKAEKSHEKWRPSYEEEYDEGSEPRVPGKRERGRQEGEKEEKRHGE
WRPSHEEEYDEGSEPRVPTHGERGRQEGEKEEKRHEEWRPSYEKEEDEEEEKEKYKYQREKKEQKEVQPGREKWERKQDEKHVEEDEDQEEE
QWRGSKRREDPEERARLRYREERTKSNVEEETEERRNPFLFKNKFLTLFENENGHIRRLQRFDERSDIFENLQNYRLVEYKAKPHTMFLPQHID
ADLIIVLNGKAILTVLSPNDRNSYNLERGDTIKLPAGTTSYLVNQDDEEDLRVVDLAIPVNRPGKFEAFGLSANKNQYLRGFSKNILEAFLNTKY
ETIEKVLLEEQERRDRKGRQQGQETNAIVKVSREQIEELRKLAKSSSKKSLLSESEPINLRSQNPKYSNKFGKLFEITPEKKYPQLQDLDVSISCVEI
NEGAPLLPHYNSRAIVLLLVNEGKGNLELVGFKNEQQRQRENEERNKKVQRYEARLSPGDVVVIPAGHPVAISASLNLNLVGFGVNAENNQR
NFLTGSDDN [SEQ ID 246]

>gi|164512542|emb|CAP06320.1| cvc [*Lathyrus cicera*]
MATIIKSRFPLLLLLGIIFLASVCVTLANYDEGSEPRVPAQRERGRQEGEKEEKRHGEWRPSHEKEYDEGSEPRVPGRRERGRQEGEKEEKRHGE
WRPSYEKEYDEGSEPRVPGRRERGRQEGEKEEKRHGEWRPSYEKEYDEEEKQKYQYEREKEEQKEVQPGRERWERKEDEEKEEDQWRGSQ
RHEDPEERARLRYRKERTKKYVEEDTEETSSESQGRRNPFLFKNKFLTLFENENGYIRRLQRFDERSDIFENLQNYRLVEYRAKPHTIFLPQHIDA
DLILVILNGKAILTVLSPNDRNSYNLERGDTIKLPAGTTSYLVNEDDEEDLRVVDLVIPVNRPGKFEAFDLNQYLGGFSKSVLEASLNTKYETIEKVL
LEEQQKGQGETNAIVKVSREQIEELRKLAKSSSKKSLLSELEPVNLRSHSPKYSNKFGKFFEITPEKKYPQLQDLDVSISCVEINEGALLLPHYNSRA
IVVVLVNEGKGNLELLGVQNEDEQQERKERNKEVQRYEARLSPGDVVIIPSGHPVAVSASSNLNLLGFGINAENNQRNFLSGSDDN [SEQ ID
247]

>gi|164512544|emb|CAP06321.1| convicilin [*Lathyrus sativus*]
MATIIKSRFPLLLLLGIIFLASVCVTYANYDEGSEPRVPAQRERGRQEGEKEEKRHGEWRPSEKEYDEGSEPRVPGRRERGRQEGEKEEKRHGE
WRPSYEKEYDEEEKQKYQYEREKKEQKEVEPGRERWERKEDEEKEDQWRGSQRHEDPEERARLRYRKERTKKYVEEDTEETSSESQGRRNP
FLFKSNKFLTLFENENGYIRRLQRFDERSDLFENLQNYRLVEYRAKPHTIFLPQHIDADLILVILNGKAILTVLSPNDRNSYNLERGDTIKLPAGTTS
YLVNEDDEEDLRVVDLVIPVNRPGKFEAFDLNQYLGGFSKSVLKASLNTKYETIEKVLLEEQQKGQGETNAIVKVSREQIEELRKLAKSSSKKSLLS
ELEPVNLRSHSPKYSNKFGKFFEITPEKKYPQLQDLDVSISCVEINEGALLLPHYNSRAIVVLLVNEGKGNLELLGVQDEDEQQERKKRNKEVQRY
EARLSPSDVVIIPAGHPVAVSASSNLNLLGFGINAENNERNFLSGSDDN [SEQ ID 248]

| Homologs of Rice protein 3 (SEQ ID 10) |
| --- |

>gi|573918992|ref|XP_006647120.1| PREDICTED: glutelin type-B 2-like [*Oryza brachyantha*]
MATTVFSRFSTYFCVLLLCHGSMAQLFNPSTNPWHNPRQGSSRECRFDRLQPFEPLRKVRSEAGVTEYFDEKNELFQCTGTFVIRRVIQPQGLL
VPRYTNAPGLVYIIQGRGSIGLTFPGCPATYQQFQQFLPQEQSQSQKFRDEHQKIHQFRQGDIVALPAGVAHWFYNDGDAPVVAVYVYDV
KNSANQLEPRQREFLLGGNNMRAQQVYGSSAEQHSRQNIFSGFGVEILSEALGISTVTTKRLQSQNDQRGEIIHVKNGLQFLKPTLTQQQEQA
QAQYQEVQYSEQQQTSSRWNGLDENFCTIKARMNIENTSRADTYNPRAGRTTSLNSQKFPILNLVQMSATRVNLYQNAILSTFWNVAHSL
VYTIQGRARVQVVSNFGKTVFDGELRPGQLLIIPQHYVVLKKAQREGFRYIAIKTNANAFVSQLVGKNSVFRSLPVDVIANVYRISREQARSLKN
NRGEEHGAFAPRSQQQSYPGFSNQSESETSE [SEQ ID 249]

>gi|573919041|ref|XP_006647142.1| PREDICTED: glutelin type-B 4-like [*Oryza brachyantha*]
MATTTFSRFSIYFCVLLLCHGSMAQLFSPTLNPWHSSRRGGSRDCRFDRLQAFEPIRVRSEAGVTEYFDERNEQFQCTGTFVIRRVIEPQGLL
VPRYTNTPGVVYIMQGRGSMGLTFPGCPATYQQFQQFLPEGQSQSQKFRDEHQKIHQFRQGDIVALPAGVAHWFYNEGDTPVVALYVFD
INNSANQLEPRQKDFLLAGNNNREQQVYGRSIEKHSGQNIFSGFNHELLSEALGISTLAAKRLQGGNDHRGEIIRVRNGLQLLKPTFTQQQEQ
AQSQYQVQYSEKQQESTRCNGLDENFCTINARLNIENPSRADTYNPRAGRITHLNNQKFPILNLVQMSATRVNLYQNAILSPYWNVAHSLV
YMVQGHARVQVVSNLGKTVFNSVLRPGQLLIIPQHYVVLKKAEREGCQYIAFKTNANSIVSQLAGKNSILRAMPVDVVANAYRISREQARDLK
NNRGEELGAFTPKFEQQSYPGLSNESESEASE [SEQ ID 250]

>gi|109894635|gb|ABG47337.1| glutelin precursor [*Zizania latifolia*]
MNMATINGPTIFFTVCLFLLCHGSLAQLLGQSTSQWQSSHRGSSRQCRFDRLQAFEPVRSVRSQAGTTEFFDASNELFQCAGVSIVRRIIEPRG
LLLPQYTNGATIMYIIQGRGITGQTFPGCPESYQQFQQSMQAQLTGSQSQSQKFKDEHQKINRFRQGDVIALPAGVAHWCYNDGEVPVVA
IYVIDINNAANQLDPRQRDFLLAGNMRSPQAYRREVENQSQNIFSGFSAELLSEALGISTGVARQLQCQNDQRGEIVREHGLSLLQPYASLQE
QEQKQEQPRERYQVTQHQQSQYGGGCSNGLDETFCAMRIWQNIDNPNLADTYNPRAGRVTNLNSQKFPILNLIQMSAVKVNLYQNALLSP
FWNINSHSVVYTQGCARVQVVNNNGKTVFNGELRRGQLLIIPQHYVVVKKAQREGCAYIAFKTNPSMVSHIVGKSSIFRALPTDVLANAY
RISREDAQRLKHNRGDELGAFTPLQYKSYQDVSSVAASS [SEQ ID 251]

| Homologs of Rice protein 4 (SEQ ID 11) |
| --- |

>gi|531874314|gb|AGT59174.1| glutelin, partial [*Oryza sativa Indica* Group]
CRFDRLQAFEPIRSVRSQAGTTEFFDVSNEQFQCTGVSAVRRVIEPRGLLLPHYTNGASLVYIIQGRGITGPTFPGCPESYQQFQQSGQAQLT
ESQSQSHKFKDEHQKIHRFRQGDVIALPAGVAHWCYNDGEVPVVAIYVTDLNNGANQLDPRQRDFLLAGNKRNPQAYRREVEERSQNIFSG
FSTELLSEALGVSSQVARQLQCQNDQRGEIVREHGLSLLQPYASLQEQEQGQVQSRERYQEGQYQQSQYGSGCSNGLDETFCTMKVRQN1
DNPNRADTYNPRAGRVTNLNTQNFPILNLVQMSAVKVNLYQNALLSPFWNINAHSVVYITQGRARVQVVNNNGKTVFNGELRRGQLLIIPQ
HYAVVKKAQREGCAYIAFKTNPSMVSHIAGKSSIFRALPNDVLANAYRISREEAQRLKHNRGDEFGAFTPIQYKSYQDVYNAAESS [SEQ ID
252]

>gi|109894635|gb|ABG47337.1| glutelin precursor [*Zizania latifolia*]
MNMATINGPTIFFTVCLFLLCHGSLAQLLGQSTSQWQSSHRGSSRQCRFDRLQAFEPVRSVRSQAGTTEFFDASNELFQCAGVSIVRRIIEPRG
LLLPQYTNGATIMYIIQGRGITGQTFPGCPESYQQFQQSMQAQLTGSQSQSQKFKDEHQKINRFRQGDVIALPAGVAHWCYNDGEVPVVA
IYVIDINNAANQLDPRQRDFLLAGNMRSPQAYRREVENQSQNIFSGFSAELLSEALGISTGVARQLQCQNDQRGEIVREHGLSLLQPYASLQE

| SEQUENCE INFORMATION |
|---|
| QEQKQEQPRERYQVTQHQQSQYGGGCSNGLDETFCAMRIWQNIDNPNLADTYNPRAGRVTNLNSQKFPILNLIQMSAVKVNLYQNALLSP<br>FWNINSHSVVYVTQGCARVQVVNNNGKTVFNGELRRGQLLIIPQHYVVVKKAQREGCAYIAFKTNPNSMVSHIVGKSSIFRALPTDVLANAY<br>RISREDAQRLKHNRGDELGAFTPLQYKSYQDVSSVAASS [SEQ ID 253]<br><br>>gi\|472867\|emb\|CAA52764.1\| 11S globulin [*Avena sativa*]<br>MATTSFPSMLFYFCIFLLFHGSMAQLFGQSSTPWQSSRQGGLRGCRFDRLQAFEPLRQVRSQAGITEYFDEQNEQFRCTGVSVIRRVIEPQGL<br>VLPQYHNAPALVYILQGRGFTGLTFPGCPATFQQQFQPFDQSQFAQGQRQSQTIKDEHQRVQRFKQGDVVALPAGIVHWCYNDGDAPIVA<br>IYVFDVNNNANQLEPRQKEFLLAGNNKREQQSGNNIFSGLSVQLLSEALGISQQAAQRIQSQNDQRGEIIRVSQGLQFLKPIVSQQVPGEQQV<br>YQPIQTQEGQATQYQVGQSTQYQVGKSTPYQGGQSSQYQAGQSWDQSFNGLEENFCSLEARKNIENPQHADTYNPRAGRITRLNSKNFPIL<br>NIVQMSATRVNLYQNAILSPFWNINAHSVIYMIQGHARVQVVNNNGQTVFNDILRRGQLLIVPQHFVVLKKAEREGCQYISFKTNPNSMVSH<br>IAGKSSILRALPIDVLANAYRISRQEARLKNNRGEEFGAFTPKLTQKGFQSYQDIEEGSSSPVRASE [SEQ ID 254] |

| Homoiogs of Rice protein 5 (SEQ. ID 12) |
|---|
| >gi\|225959\|prf\|1404367A glutelin<br>MASTNRPIVFFTVCLFLLCDGSLAQQLLGQSTSQWQSSRRGSPRGCRFDRLQAFEPIRSVRSQAGTTEFFDVSNELFQCTGVSVVRRVIEPRGL<br>LLPHYTNGASLVYIIQGRGITGPTFPGCPETYQQQFQQSGQAGLTESQSQSHKFKDEHQKIHRFRQGDVIALPAGVAHWCYNDCEVPVVAIYV<br>TDINNGANQLDPRQRDFLLAGNKRNPQAYRREVEEWSQNIFSGFSTELLSEAFGISNQVARQLQCQNDQKGEIVRVERGLSLLQPYASLQEQ<br>EQGQMQSREHYQEGGYQQSQYGSGCPNGLDETFCVNKVRQNIDNPNRADTYNPRAGRVTNLSQNFPILNLVQMSAVKVNLYQNTDTWIS<br>MGQEENALLSPFWNINAHSIVYITQGRAQVQVLRRGQLLIVPQHYVVVKKAQREGCAYIAFKTNPNSMVSHIAGKSSIFRALPTDVLANAYRIS<br>REEAQRLKHNRGDEFGAFTPLQYKSYQDVYNVAESS [SEQ ID 255]<br><br>>gi\|573943558\|ref\|XP_006654150.1\| PREDICTED: glutelin type-A 3-like [*Oryza brachyantha*]<br>MKSSIVFSTICLVLLCHGSLAQLLSQSTSQWQSSRRGSPRQCRFDQLQAFEPIRWRSQAGVTEFYDVSNELFQCTGVSVVRRVIEPRGLLLPHY<br>SNGATLVYIIQGRGITGPTFPGCPETYQQQFQQSGEAQPFEGQSHKFRDEHQKIHRFRQGDVVALPAGVAHWCYNDGEVPIVAIYVTDIYNS<br>ANQLDPRHRDFFLAGNNKVAQQLYRSEARENSKNIFGGFSVELLSEALGISRGVARQLQCQNDQRGEIVRVEHGLALLQPYASVQEQQQEQV<br>QSRDYEQTQYQQKQPQGSCSNGLDETFCTMRLRQNIDNPNLADTYNPKAGRITYLNGQKFPILNLVQMSAVKVNLYQNAVLSPFWNINAHS<br>VVYITQGRARVQVVNNNGKTVFDGELRQGQLLIIPQHHVVLKKAQREGCSYIALKTNPNSIVSHIAGKNSIFRALPGDVVTNAYRISREEAKRIK<br>HNRGDESGVFAPSHAYRSYQDMSVAA [SEQ ID 256]<br><br>>gi\|721641733\|ref\|XP_010231907.1\| PREDICTED: 12S seed storage globulin 1-like [*Brachypodium distachyon*]<br>MAHTSFSSFLSYFCLFLLFHGSMAQVLGQVSTWQSSRQGGSRDCSFDRLQAIEPVTQVRSQAGLTEYFDEQNEQFRCAGVFVIRRVIEPRGLL<br>LPRYHNTPGLVYILQGNGFVGLTFPGCPETFREQFQQFRQTQSTLGQSQCQSQKLGDVHQRVHQFTQGDVVALPTGVAHWIYNGGDAPVV<br>IVYVFDVNNNANQLEPRQKEFLLGGNYNGVLQYGQNIFSGFNAQLLSQAFGINEQTSQRIQNQNDGRGDIIRVDNGLQFLKPVVTQQQPEQ<br>PFMPIQHQTGQSSRNGLEENFCSLEPRQNIEDPNRADTYNPRAGSITRLNGQNFPILNLVQMSATRVNLQKNAILSPFWNINAHSVVYVIQG<br>HALVQVVNNQGHNVFNGLLHRGQLLIIPQNYVVLKKAESEGYQYIAFKTNANSMVSHIAGKNSILRALPVDVIANAYRISRQEAQNLKNNRGE<br>ETGVLTPNFSQSTCQSYQTEDVQSLRPMSHWSE [SEQ ID 257] |

| Homologs of Rice protein 6 (SEQ ID 13) |
|---|
| >gi\|169244463\|gb\|ACA50505.1\| seed allergenic protein RAG2 [*Oryza sativa Japonica* Group]<br>MASNKVVFSALLLIIVSVLAATATMADHHKDQVVYSLGERCQPGMGYPMYSLPRCRAVVKRQCVGHGAPGGAVDEQLRQDCCRQLAAVD<br>DSWCRCSALNHMVGGIYRELGATDVGHPMAXVFPGCRRGDLERAAASLPAFCNVDIPNGTGGVCYWLGYPRTPRTGH [SEQ ID 258]<br><br>>gi\|5777592\|emb\|CAA44001.1\| low molecular weight globulin [*Oryza sativa*]<br>MASNKVVFSALLLIIVSVLRRDGTMADHHKDQVVYSLGERCQPGMGYPMYSLPRCRAVVKRQCVGHGAPGAVDEQLRQDCCRQLAAVDD<br>SWCRCSALNHMVGGIYRELGATDVGHPMAEVFPGCRRGDLERAAASLPAFCNVDIPNGTGGVCYWLGYPRTPRTGH [SEQ ID 259]<br><br>>gi\|115471175\|ref\|NP_001059186.1\| Os07g0214600 [*Oryza sativa Japonica* Group]<br>>gi\|23616954\|db\|BAC20657.1\|allergen RA16 [*Oryza sativa Japonica* Group]<br>>gi\|113610722\|dbj\|BAF21100.1\| Os07g0214600 [*Oryza sativa Japonica*Group]<br>>gi\|125557687\|gb\|EAZ03223.1\| hypothetical protein OsI_25372 [*Oryza sativa Indica* Group]<br>MASNKVVISALLVVVSVLAATTTMADHHQEQVVYTPGQLCQPGIGYPTYPLPRCRAFVKRQCVAPGTVDEQVRRGCCRQLAAIDSSWCRC<br>DALNHMLRI1YRESGAADAGHPMAEVFRGCRRGDIERAAASLPAFCNVDIPNGVGGVCYWLPGTGY [SEQ ID 260] |

| Homologs of Rice protein 7 (SEQ ID 14) |
|---|
| >gi\|115445309\|ref\|NP_001046434.1\| Os2g0248800 [*Oryza sativa Japonica* Group]<br>>gi\|37993738\|gb\|AAR06952.1\| glutelin type-B [*Oryza sativa Japonica* Group]<br>>gi\|47497729\|dbj\|BAD19794.1\| glutelin type-B [*Oryza sativa Japonica* Group]<br>>gi\|113535965\|dbj\|BAF08348.1\| Os02g0248800 [*Oryza sativa Japonica* Group]<br>>gi\|215768942\|dbj\|BAH01171.1\| unnamed protein product [*Oryza sativa Japonica* Group]<br>>gi\|2844317721gbIADB84627.11 glutelin [*Oryza sativa Japonica* Group]<br>MTISVFSRFSIYFCVLLLCNGSMAQLFDPATNQWQTHRQGSFRECRFERLQAFEPLQNVRSEAGVTEYFDETNELFQCTGTFVIRRVIQPQGLL<br>IPRYANTPGMVYIIQGRGSMGLTFPGCPATYQQQSQQFLFQGESQSQKFIDEHQKIHQFRQGDIVVLPTGVAHWFYNDGDTPVVALYVDI<br>NNSANQLEPRHREFLLAGKNNRVQQVYGRSIQQHSGQNIFNGFSVEPLSEALNINTVTTKRLQSQNDQRGEIIHVKNGLQLLKPTLTQRQEQE<br>QAQYQEVQYSEKPQTSSRWNGLEENLCTIKTRLNIENPSRADSYDPRAGRITSLDSQKFPILNIIQMSATRVNLYQNAILTPFWNVAHSLMYV<br>IRGRARVQVVSNFGKTVFDGVLRPEQLLIIPQNYVVLKKAQHEGCQYIAINTNANAFVSHLAGVDSVFHALPVDVIANAYCISREEARRLKNNR<br>GDEYGPFPPRLQQQIYPEFSNESKGETSE [SEQ ID 261]<br><br>>gi\|428674402\|gb\|AFZ41188.1\| glutelin, partial [*Oryza sativa Japonica* Group]<br>LLCHGSMAQIFSLGINPWQNPRQGGSRECRFDRLQAFEPLRKVRHEAGVTEYFDEKNEQFQCTGTLVIRRIIEPQGLLLPRYSNTPGLVYIIQGT<br>GVLGLTFPGCPATYQKQFRHFGLEGGSQRQGKKLRDENQKIHQFRQGDVVALPSGIPHWFYNEGDTPVVALFVDVNNNANQLEPRQKEFL<br>LAGNNIEQQVSNPSINKHSGQNIFNGFNTKLLSEALGVNIEVTRRLQSQNDRRGDIIRVKNGLRLIKPTITQQQEQTQDQYQQIQYHIREQRSTS |

SEQUENCE INFORMATION

KYNGLDENFCAIRARLNIENPNHADTYNPRAGRITNLNSQKFSILNLVQMSATRVNLYQNAILSPFWNINAHSLVYTIQGRARVQVVSNHGKA
VFNGVLRPGQLLIIPQNYVVMKKAELEGFQFIAFKTNPNAMVNHIAGKNSVLRAMPVDVIANAYRISRQEARSLKNNRGEEIGAFTPRYQQQ
KIHQEYSNPNESETQ [SEQ ID 262]

>gi|226510|prf|1515394A seed storage globulin
MATTRFPSLLFYSCIFLLCNGSMAQLFGQSFTPWQSSRQGGLRGCRFDRLQAFEPLRQVRSQAGITEYFDEQNEQFRCAGVSVIRRVIEPQGLL
LPQYHNAPGLVYILQGRGFTGLTFPGCPATFQQQFQPFDQARFAQGQSKSQNLKDEHQRVHHIKQGDVVALPAGIVHWCYNDGDAPIVAV
YVFDVNNNANQLEPRQKEFLLAGNNKREQQFGQNIFSGFSVQLLSEALGISQQAAQKIQSQNDQRGEIIRVSQGLQFLKPFVSQQGPVEHQA
YQPIQSQQEQSTQYQVGQSPQYQEGQSTQYQSGQSWDQSFNGLEENFCSLEARQNIENPKRADTYNPRAGRITHLNSKNFPTLNLVQMSA
TRVNLYQNAILSPYWNINAHSVMHMIQGRARVQVVNNHGQTVFNDILRRGQLLIIPQHYVVLKKAEREGCQYISFKTTPNSMVSYIAGKTSIL
RALPVDVLANAYRISRQESQNLKNNRGEEFGAFTPKFAQTGSQSYQDEGESSSTEKASE [SEQ ID 263]

Homologs of Rice protein 8 (SEQ ID 15)

>gi|83375868|gb|ABC17777.1| waxy [Oryza rufipogon]
MSALTTSQLATSATGFGIADRSAPSSLLRHGFQGLKPRSPAGGDATSLSVTTSARATPKQQRSVQRGSRRFPSVVVYATGAGMNVVFVGAEM
APWSKTGGLGDVLGGLPPAMAANGHRVMVISPRYDQYKDAWDTSVVAEIKVADRYERVRFFHCYKRGVDRVFVDHPSFLEKVWGKTGEKI
YGPDTGVDYKDNQMRFSLLCQAPRILNLNNNPYFKGTYGEDVVFVCNDWHTGPLASYLKNNYQPNGIYRNAKVAFCIHNISYQGRFAFEDYP
ELNLSERFRSSFDFIDGYDTPVEGRKINWMKAGILEADRVLTVSPYYAEELISGIARGCELDNIMRLTGITGIVNGMDVSEWDPSKDKYITAKYD
ATTAIEAKALNKEALQAEAGLPVDRKIPLIAFIGRLEEQKGPDVMAAAIPELMQENVQIVLLGTGKKKFEKLLKSMEEKYPGKVRAVVKFNAPLA
HLIMAGADVLAVPSRFEPCGLIQLQGMRYGTPCACASTGGLVDTVIEGKTGFHMGRLSVDCKVVEPSDVKKVAATLKRAIKVVGTPAYEEMV
RNCMNQDLSWKGPAKNWENVLLGLGVAGSAPGIEGDEIAPLAKENVAAP [SEQ ID 264]

>gi|297614332|gb|ADI48504.1| glycogen synthetase [Oryza officinalis]
MSALTTSQLATSATGFGIADRSAPSSLLRHGFQGLKPRSPAGGDASSLSVTTSARATPKQQRSVQRGSRRFPSVVVYATGAGMNVVFVGAEM
APWSKTGGLGDVLGGLPPAMAANGHRVMVISPRHDQYKDAWDTSVVAEIKVADRYERVRFFHCYKRGVDRVFIDHPSFLEKVWGKTGEKI
YGPDTGVDYKDNQMRFSLLCQAALEAPRILNLNNNPYFKGTYGEDVVFVCNDWHTGPLPSYLKNNYQPNGIYRNAKVAFCIHNISYQGRFAF
EDYPELNLSERFRSSFDFIDGYDTPVEGRKINWMKAGILESDRVLTVSPYYAEELISGIARGCELDNIMRLTGITGIVNGMDVSEWDPSKDKYIA
AKYDATTAIEAKALNKEALQAEAGLPVDRKIPLIAFIGRLEEQKGPDVMAAAIPELMQENVQIVLLGTGKKKFEKLLKSMEEKYPGKVRAVVKF
NAPLAHLIMAGADVLAVPSRFEPCGLIQLQGMRYGTPCACASTGGLVDTVIEGKTGFHMGRLSVDCKVVEPSDVQKVATTLKRAIKIVGTPAY
NEMVRNCMNQDLSWKGPAKNWENVLLGLGVAGSAPGVEGEEIAPLAKENVAAP [SEQ ID 265]

>gi|389620054|gb|AFK93486.1| granule-bound starch synthase [Hordeum vulgare subsp. vulgare]
MAALATSQLATSGTVLGVTDRFRRPGFQGLRPRNPADAALGMRTIGASAAPKQSRKAHRGSRRCLSVVVRATGSGMNLVFVGAEMAPWS
KTGGLGDVLGGLPPAMAANGHRVMVVSPRYDQYKDAWDTSVISEIKVADEYERVRFFHCYKRGVDRVFIDHPWFLEKVRGKTKEKIYGPDA
GTDYEDNQQRFSLLCQAALEAPRILNLNNPYFSGPYGEDVVFVCNDWHTGLLACYLKSNYQSNGIYRTAKVAFCIHNISYQGRFSFDDFAQL
NLPDRFKSSFDFIDGYDKPVEGRKINWMKAGILQADKVLTVSPYYAEELISDEARGCELDNIMRLTGITGIVNGMDVSEWDPTKDKFLAVNYDI
TTALEAKALNKEALQAEVGLPVDRKVPLVAFIGRLEEQKGPDVMIAAIPEILKEEDVQIILLGTGKKKFEKLLKSMEEKFPGKVRAVVRFNAPLAH
QMMAGADLLAVTSRFEPCGLIQLQGMRYGTPCVCASTGGLVDTIVEGKTGFHMGRLSVDCNVVEPADVKKVATTLKRAVKVVGTPAYQEM
VKNCMIQDLSWKGPAKNWEDVLLELGVEGSEPGIVGEEIAPLAMENVAAP [SEQ ID 266]

Homologs of GLUC (Staphylococcus aureus) protein 1 (SEQ ID 16)

>gi|446599182|ref|WP_000676528.1| glutamyl endopeptidase [Staphylococcus aureus]
>gi|253729369|gb|EES98098.1| trypsin [Staphylococcus aureus subsp. aureus TCH130]
>gi|341844549|gb|EGS85761.1| glutamyl endopeptidase [Staphylococcus aureus subsp. aureus 21259]
>gi|537390486|gb|AGU61109.1| Glutamyl endopeptidase precursor [Staphylococcus aureus subsp. aureus CN1]
>gi|564714561|gb|ETD14665.1| glutamyl endopeptidase [Staphylococcus aureus subsp. aureus KPL1845]
>gi|577466329|gb|EUG79766.1| glutamyl endopeptidase [Staphylococcus aureus M0139]
>gi|580560623|gb|EVF84961.1| glutamyl endopeptidase [Staphylococcus aureus COAS6020]
>gi|580687002|gb|EVH10169.1| glutamyl endopeptidase [Staphylococcus aureus UCIM6080]
>gi|751815683|gb|KIN24957.1| glutamyl endopeptidase [Staphylococcus aureus MRSA_CVM43477]
>gi|781884797|dbj|BAR08486.1| glutamyl endopeptidase precursor [Staphylococcus aureus subsp. aureus]
>gi|781887762|dbj|BAR11210.1| glutamyl endopeptidase precursor [Staphylococcus aureus subsp. aureus]
MKGKFLKVSSLFVATLTTATLVSSPAANALSSKAMDNHPQQSQSSKQQTPKIQKGGNLKPLEQREHANVILPNNDRHQITDTTNGHYAPVTYI
QVEAPTGTFIASGVVVGKDTLLTNKHVVDATHGDPHALKAFPSAINQDNYPNGGFTAEQITKYSGEGDLAIVKFSPNEQNKHIGEVVKPATMS
NNAETQVNQNITVTGYPGDKPVATMWESKGKITYLKGEAMQYDLSTTGGNSGSPVFNEKNEVIGIHWGGVPNEFNGAVFINENVRNFLKQ
NIEDIHFANDDQPNNPDNPNNPDNPNNPDEPNNPDNPNNPDNPDNGDNNNSDNPDAA [SEQ ID 267]

The invention claimed is:

1. A comestible powder composition comprising a peptide that is up to 50 amino acids in length and comprises the amino acid sequence of SEQ ID NO: 343 or 344.

2. The comestible powder composition of claim 1, wherein the peptide consists of the amino acid sequence of SEQ ID NO: 343 or 344.

3. The comestible powder composition of claim 1, wherein the peptide is up to 37 amino acids in length.

4. The comestible powder composition of claim 1, wherein the comestible powder composition is powdered milk.

5. A method of reducing inflammation in a mammal in need thereof, the method comprises orally administering to the mammal the comestible powder composition of claim 1.

* * * * *